US012478693B2

(12) United States Patent
Sarraf et al.

(10) Patent No.: US 12,478,693 B2
(45) Date of Patent: Nov. 25, 2025

(54) COMPOSITIONS AND METHODS FOR DETECTION OF TRAUMATIC BRAIN INJURY

(71) Applicant: Amydis, Inc., San Diego, CA (US)

(72) Inventors: Stella Sarraf, Beverly Hills, CA (US); Lyndsay M. Randolph, San Diego, CA (US); Suhail Rasool, San Diego, CA (US)

(73) Assignee: Amydis, Inc., Los Angeles, CA (US)

( * ) Notice: Subject to any disclaimer, the term of this patent is extended or adjusted under 35 U.S.C. 154(b) by 1127 days.

(21) Appl. No.: 16/973,028

(22) PCT Filed: May 31, 2019

(86) PCT No.: PCT/US2019/034977

§ 371 (c)(1),
(2) Date: Dec. 7, 2020

(87) PCT Pub. No.: WO2019/232422

PCT Pub. Date: Dec. 5, 2019

(65) Prior Publication Data

US 2021/0369873 A1 Dec. 2, 2021

Related U.S. Application Data

(60) Provisional application No. 62/733,025, filed on Sep. 18, 2018, provisional application No. 62/678,900, filed on May 31, 2018.

(51) Int. Cl.

| | |
|---|---|
| ***A61B 5/00*** | (2006.01) |
| ***A61B 3/12*** | (2006.01) |
| ***A61B 5/145*** | (2006.01) |
| ***A61B 8/00*** | (2006.01) |
| ***A61B 10/00*** | (2006.01) |
| ***A61K 49/00*** | (2006.01) |

(52) U.S. Cl.

CPC ............ *A61K 49/0021* (2013.01); *A61B 3/12* (2013.01); *A61B 5/14546* (2013.01); *A61B 5/4064* (2013.01)

(58) Field of Classification Search

CPC .. A61K 49/0021; A61B 3/12; A61B 5/14546; A61B 5/4064; G01N 33/582; G01N 2333/4709; G01N 2800/2871; G01N 33/6896

See application file for complete search history.

(56) References Cited

U.S. PATENT DOCUMENTS

| | | | |
|---|---|---|---|
| 5,043,013 | A | 8/1991 | Kluger et al. |
| 5,413,996 | A | 5/1995 | Bodor |
| 6,048,662 | A | 4/2000 | Bruhnke et al. |
| 6,541,454 | B1 | 4/2003 | Breuer et al. |
| 9,452,985 | B2 | 9/2016 | Kudo et al. |
| 10,005,745 | B2 | 6/2018 | Yang et al. |
| 10,370,345 | B2 | 8/2019 | Yang et al. |
| 10,934,264 | B2 | 3/2021 | Yang et al. |
| 11,718,596 | B2 | 8/2023 | Yang et al. |
| 2002/0036750 | A1 | 3/2002 | Eberl et al. |
| 2006/0115516 | A1 | 6/2006 | Pearson et al. |
| 2009/0163545 | A1 | 6/2009 | Goldfarb |
| 2012/0101371 | A1 | 4/2012 | Verdooner |
| 2012/0282169 | A1 | 11/2012 | Duan et al. |
| 2012/0302603 | A1 | 11/2012 | Yang et al. |
| 2013/0135580 | A1 | 5/2013 | Hartung et al. |
| 2015/0177262 | A1 | 6/2015 | Yang et al. |
| 2015/0344954 | A1 | 12/2015 | Patel et al. |
| 2016/0272619 | A1 | 9/2016 | Mcknight et al. |
| 2016/0326126 | A1 | 11/2016 | Yang et al. |
| 2017/0248616 | A1 | 8/2017 | Sarraf |
| 2018/0127828 | A1 | 5/2018 | Belli et al. |
| 2018/0327373 | A1 | 11/2018 | Yang et al. |
| 2019/0033328 | A1 | 1/2019 | Tokuda et al. |
| 2020/0123118 | A1 | 4/2020 | Yang et al. |
| 2020/0138351 | A1 | 5/2020 | Kerbage et al. |
| 2021/0371390 | A1 | 12/2021 | Yang et al. |
| 2022/0001033 | A1 | 1/2022 | Sarraf et al. |
| 2022/0370642 | A1 | 11/2022 | Sarraf et al. |
| 2024/0033380 | A1 | 2/2024 | Sarraf et al. |
| 2024/0165274 | A1 | 5/2024 | Sarraf et al. |
| 2024/0208916 | A1 | 6/2024 | Yang et al. |
| 2024/0325572 | A1 | 10/2024 | Sarraf |

FOREIGN PATENT DOCUMENTS

| | | |
|---|---|---|
| CN | 102046638 | 5/2011 |
| EP | 1431280 | 6/2004 |
| JP | 2008013446 | 1/2008 |
| JP | 2013534171 | 9/2013 |

(Continued)

OTHER PUBLICATIONS

Sharma et al. (Neurochem. Int. 108 (2017) 481-493).*
International Search Report and Written Opinion for International Application No. PCT/US2019/034977 dated Oct. 16, 2019. 10 pages.
Optos and Amydis Establish Clinical Alliance to Develop Early Diagnostic Test for Alzheimer's Disease. Globe Newswire 2018. 3 pages.
Antonsen et al., "Water Structure of PEG Solutions by Differential Scanning Calorimetry Measurements." J. M. Harris (ed.), Poly(Ethylene Glycol) Chemistry. Springer Science+Business Media New York 1992, pp. 15-28.
Ash, M., "Handbook of Pharmaceutical Additives. Third Edition, Endicott, NY: Synapse Information Resources." (2007) p. 673.

(Continued)

*Primary Examiner* — Frederick F Krass
*Assistant Examiner* — Melissa J Perreira
(74) *Attorney, Agent, or Firm* — Sheppard Mullin Richter & Hampton LLP

(57) ABSTRACT

The present disclosure relates generally to compositions and methods for determining whether a patient suffers from a traumatic brain injury (TBI) by detecting the presence of an amyloid beta protein in an eye of the patient. Also provided are compositions and methods for preparing a patient for diagnosis and treatment of traumatic brain injury (TB).

9 Claims, 9 Drawing Sheets

(56) References Cited

FOREIGN PATENT DOCUMENTS

| | | | |
|---|---|---|---|
| WO | WO-03020690 | 3/2003 | |
| WO | WO-2005040337 | 5/2005 | |
| WO | WO-2006057824 | 6/2006 | |
| WO | WO-2006059245 | 6/2006 | |
| WO | WO-2007139149 | 12/2007 | |
| WO | WO-2008016682 | 2/2008 | |
| WO | WO-2009117728 | 9/2009 | |
| WO | WO-2010033861 | 3/2010 | |
| WO | WO-2011072257 | 6/2011 | |
| WO | WO-2011082617 | 7/2011 | |
| WO | WO-2012008767 | 1/2012 | |
| WO | WO-2012024188 | 2/2012 | |
| WO | WO-2012061078 | 5/2012 | |
| WO | WO-2014138919 | 9/2014 | |
| WO | WO-2015143185 A1 * | 9/2015 | ........... A61B 5/0075 |
| WO | WO-2015188142 | 12/2015 | |
| WO | WO-2015188142 A1 * | 12/2015 | ........... A61B 3/0025 |
| WO | WO-2016040891 | 3/2016 | |
| WO | WO-2016055148 | 4/2016 | |
| WO | WO-2016153549 | 9/2016 | |
| WO | WO-2017004560 A1 * | 1/2017 | ........... G01N 33/582 |
| WO | WO-2020093008 | 5/2020 | |
| WO | WO-2021055639 | 3/2021 | |
| WO | WO-2022192714 | 9/2022 | |
| WO | WO-2023288109 | 1/2023 | |
| WO | WO-2024155678 | 7/2024 | |

OTHER PUBLICATIONS

Baertschi, S. W., Pharmaceutical stress testing, Second Edition, Chapter 3, Informa Healthcare, 2011, p. 49-141.
Berge et al. Pharmaceutical Salts. Journal of Pharmaceutical Sciences 66(1):1-19 (1977).
Buhimschi, IA et al. Protein misfolding, congophilia, oligomerization, and defective amyloid processing in preeclampsia. Sci. Transl. Med. 6(245):245ra92; pp. 1-14 (2014).
Cai, L. Radioligand Development for PET Imaging of ß-Amyloid (Aß)-Current Status. Current Medicinal Chemistry, 14(1):19-52 (2007).
Cao, K. et al. Amino Naphthalenyl-2-Cyano-Acrylate (ANCA) Probes Fluorescently Discriminate between Amyloid-ß and Prion Plaques in Brain. Journal of the American Chemical Society, 134 (42):17338-17341 (2012).
Carey, FA. Organic Chemistry, 6th Edition, McGraw Hill Chapter 1, pp. 1-9. 2006.
Carre et al., Fluorescent Molecular Rotors with Specific Hydrophilic Functions: Glucosamine and Inositol Derivatives. Journal of Fluorescence 8(1): 53-57 (1998).
CAS Registry No. 478016-48-7, located at stneasy.cas.org/tmp/20171006/1240090-1942032854-200/479739346.html last visited Oct. 6, 2017, 1 page.
CAS Registry No. 811462-20-1, located at stneasy.cas.org/tmp/20171006/1240090-1942032854-200/33392095.html last visited Oct. 6, 2017, 1 page.
CAS Registry No. 862649-67-0, located at stneasy.cas.org/tmp/20171006/1240090-1942032854-200/740546802.html last visited Oct. 6, 2017, 1 page.
CAS Registry No. 888490-95-7, located at stneasy.cas.org/tmp/20171006/1240090-1942032854-200/490202741.html Oct. 6, 2017, 1 page.
Chang et al., ANCA: A Family of Fluorescent Probes that Bind and Stain Amyloid Plaques in Human Tissue. ACS Chemical Neuroscience 2(5): 249-255 (2011).
Funke "Detection of Soluble Amyloid-ß Oligomers and Insoluble High-Molecular-Weight Particles in CSF: Development of Methods with Potential for Diagnosis and Therapy Monitoring of Alzheimer's Disease" IJAD, article 151645 (Year: 2011).
Furumoto, S. et al. Recent advances in the development of amyloid imaging agents. Current Topics in Medicinal Chemistry 2007, 7(18):1773-1789, XP008150930.
Geoffroy-Chapotot et al., Three-Dimensional Fluorescence Microscopy of Endothelial Cells Labeled with Coumarins. Journal of Fluorescence 10(2): 203-207 (2000).
Guan et al., Real-Time Monitoring of Alzheimer's-Related Amyloid Aggregation via Probe Enhancement-Fluorescence Correlation Spectroscopy, ACS Chemical Neuroscience 2015, vol. 6, No. 9, pp. 1503-1508, XP055252087.
He et al: "Identification of Binding Modes for Amino Naphthalene 2-Cyanoacrylate (ANCA) Probes to Amyloid Fibrils from Molecular Dynamics Simulations", Journal of Physical Chemistry Part B, vol. 121, 2017, pp. 1211-1221.
International Application No. PCT/US2015/021512 International Search Report and Written Opinion Mailed Aug. 18, 2015.
International Application No. PCT/US2015/049825 International Preliminary Report on Patentability Mailed Mar. 14, 2017.
International Application No. PCT/US2015/049825 International Search Report and Written Opinion Mailed Mar. 23, 2016.
International Preliminary Report on Patentability for International Application No. PCT/US2015/021512 dated Sep. 20, 2016, 9 pages.
International Search Report and Written Opinion for International Application No. PCT/US2019/059538 dated Mar. 2, 2020. 11 pages.
International Search Report and Written Opinion for International Application No. PCT/US2020/051325 dated Dec. 16, 2020. 7 pages.
International Search Report and Written Opinion for International Application No. PCT/US2022/020013 dated Aug. 11, 2022. 15 pages.
International Search Report and Written Opinion for International Application No. PCT/US2022/037387 dated Dec. 19, 2022. 18 pages.
Johnson et al., Traumatic brain injury and amyloid-ß pathology: a link to Alzheimer's disease? Nature Reviews Neuroscience, vol. 11, No. 5, pp. 361-370 (2010), XP055907506.
Jornada et al., Molecules. 2016, 21(1): 42. Published online Dec. 29, 2015. doi: 10.3390/molecules21010042.
Kittaka, Astushi, Drug discovery science, Medicinal chemistry, 2007, pp. 142-150.
Knowles, T.P.J. et al. The amyloid state and its association with protein misfolding diseases. Nature Reviews Molecular Cell Biology, 15(6):384-396 (2014).
Koronyo et al., Retinal amyloid pathology and proof-of-concept imaging trial in Alzheimer's disease, JCI Insight. 2017;2(16):e93621, doi.org/10.1172/jci.insight.93621.
Maruyama, M. et al. Imaging of Tau pathology in a tauopathy mouse model and in Alzheimer patients compared to normal controls. Neuron, 79:1094-1108 (2013).
Maruyama, M. et al. Imaging of Tau pathology in a tauopathy mouse model and in Alzheimer patients compared to normal controls. Neuron, Supplemental Information, 79:1-37 (2013).
Mathis, C.A. et al., Synthesis and evaluation of $^{11}C$-labeled 6-substituted 2-arylbenzothiazoles as amyloid imaging agents. Journal of Medicinal Chemistry, 46(13):2740-2754 (2003), XP-002285914.
Mircheva et al., "Properties of ß-carotene and retinoic acid in mixed monolayers with dipalmitoylphosphatidylcholine (DPPC) and Solutol." Colloids and Surfaces A: Physicochemical and Engineering Aspects, (2014), 460, pp. 209-218. dx.doi.org/10.1016/j.colsurfa.2013.12.046.
Moda, F. et al. Prions in the Urine of Patients with Variant Creutzfeldt-Jakob Disease, New England Journal of Medicine, 371 (6):530-539 (2014).
National Institutes of Health, National Center for Advancing Translational Sciences (NCATS), F751QVSOSX Methoxy PEG-12 Retinamide, located at drugs.ncats.io/substance/F751QVSOSX#details, accessed Aug. 29, 2022, printed Sep. 20, 2022. 2 pages.
Nelson et al., "Correlation of Alzheimer Disease Neuropathologic Changes With Cognitive Status: A Review of the Literature" J Neuropathol Exp Neurol, 71(5):362-381 (Year: 2012).
Nizynski et al., Amyloidogenesis of Tau protein. The Protein Society, Protein Science 2017, vol. 26, pp. 2126-2150.
Nozaki, M. et al., Medicinal chemistry, 1995, first edition, pp. 98-99, published by Kagaku-Dojin Publishing Company.

(56) References Cited

OTHER PUBLICATIONS

Pubchem, SID 322288298, Available Date: Jan. 24, 2017 [retrieved on Jul. 11, 2022], Retrieved from the Internet pubchem.ncbi.nlm.nih.gov/substance/322288298.
Pubchem, SID 381923871, Available Date: Apr. 9, 2019 [retrieved on Apr. 18, 2022], Retrieved from the Internet pubchem.ncbi.nlm.nih.gov/substance/381923871.
Purkey et al., "Evaluating the binding selectivity of transthyretin amyloid fibril inhibitors in blood plasma" PNAS 98(10):5566-5571 (Year: 2001).
Sanchorawala "Light-Chain (AL) Amyloidosis: Diagnosis and Treatment" ASN, Clin J Am Soc Nephrol, 1:1331-1341 (Year: 2006).
Shuto, Satoshi, Molecular theory of organic medicine, 2012, pp. 201-218.
Silva et al. Prion-like aggregation of mutant p53 in cancer, Trends in Biochemical Sciences, 39(6):260-267 (2014).
STN-478016-52-3, 2-Propenamide, 2-cyano-3-[4-[ethyl(phenylmethyl)amino]phenyl]-N-(2-methoxyethyl)-, entered Jan. 3, 2003. 1 page.
STN-RN1013518-60-9, 2-Propenamide, 2-cyano-N-(2-methoxyethyl)-3-[2-(4-morpholinyl)-3-quinolinyl) entered Apr. 10, 2008. (1 page).
STN-RN1164496-51-8, 2-Propenamide, 2-cyano-N-(2-methoxyethyl)-3-[5-(4-morpholinyl)-2-furanyl], entered Jul. 19, 2009. (1 page).
STN-RN347334-29-6, 2-Propenamide, 2-cyano-3-[4-(dimethylamino)phenyl]-N-(2-methoxyethyl), entered Jul. 22, 2001. (1 page).
STN-RN364768-44-5, 2-Propenamide, 2-cyano-N-(2-methoxyethyl)-3-[5-(4-morpholinyl)-2-furanyl], entered Oct. 26, 2001. (1 page).
STN-RN365234-08-8, 2-Propenarnide, 3-[3-bromo-4-(dimethylamino)phenyl]-2-cyano-N-(2-methoxyethyl), entered Oct. 29, 2001. (1 page).
STN-RN365550-20-5, 2-Propenamide, 2-cyano-N-(2-methoxyethyl)-3-[5-(1-piperidinyl)-2-furanyl], entered Oct. 31, 2001. (1 page).
STN-RN444317-74-2, 2-Propenamide, 2-cyano-3-[4-(diethylamino)-2-methoxyphenyl]-N-(2-methoxyethyl), entered Aug. 20, 2002. (1 page).
STN-RN473875-91-1, 2-Propenamide, 2-cyano-3-[4-(diethylamino)-2-hydroxyphenyl]-N-(2-methoxyethyl), entered Nov. 19, 2002. (1 page).
STN-RN474401-13-3, 2-Propenamide, 2-cyano-3-[4-(diethylamino)phenyl]-N-(2-methoxyethyl], entered Nov. 25, 2002. (1 page).
STN-RN478016-48-7, 2-Propenamide, 2-cyano-N-(2-methoxyethyl)-3-[4-(4-morpholinyl)phenyl], entered Jan. 3, 2003. (1 page).
STN-RN478016-72-7, 2-Propenamide, 2-cyano-3-[4-(diphenylamino)phenyl]-N-(2-methoxyethyl), entered Jan. 3, 2003. (1 page).
STN-RN502908-83-0, 2-Propenamide, 2-cyano-N-(2-methoxyethyl)-3-[2-(4-morpholinyl)-4-phenyl-5-thiazolyl], entered Apr. 14, 2003. (1 page).
STN-RN568557-51-7, 2-Propenamide, 2-cyano-N-(2-methoxyethyl)-3-(5-(4-morpholi nyl)-2-thienyl]-, entered Aug. 18, 2003. (1 page).
STN-RN775314-93-7, 2-Propenamide, 3-[5-chloro-2-(dimethylamino)-1-(4-fluorophenyl)-1H-imidazol-4-yl)-2-cyano-N-(2-methoxyethyl), entered Nov. 5, 2004. (1 page).
STN-RN811462-20-1, 2-Propenamide, 2-cyano-N-(2-methoxyethyl)-3-[2-methoxy-4-(4-morpholinyl)phenyl], entered Jan. 11, 2005. (1 page).
STN-RN862649-67-0, 2-Propenamide, 2-cyano-N-(2-methoxyethyl)-3-[4-(1-piperidinyl)phenyl], entered Sep. 8, 2005. (1 page).
Sutharsan et al., Rational Design of Amyloid Binding Agents Based on the Molecular Rotor Motif. ChemMedChem 5(1): 56-60 (2010).
Takata et al., "Detection of amyloid ß protein in the urine of Alzheimer's disease patients and healthy individuals" Neurosci Letters 435: 126-130 (Year: 2008).
Teiten et al., Specific Fluorescent Tracers. Imaging and Applications for Photodynamic Therapy. Comptes Rendus Biologies 325: 487-493 (2002).
U.S. Pharmacopeia Convention USP 30, Chemical Tests (467) Residual Solvents. Table 2. Class 2 Residual Solvents. pp. 1-10. Published Mar. 23, 2007. Accessed Apr. 20, 2017.
Wermuth, C.G., The practice of medicinal chemistry, 1998, Chapter 13: Conversion of molecules based on equivalent replacement, pp. 235-271, published by Technomics, Inc.
Yellapu et al., Design, synthesis, in silico, and in vitro evaluation of novel pyrimidine phosphonates with cytotoxicity against breast cancer cells, Medicinal Chemistry Research 2014, vol. 23, pp. 317-328.
Gallardo et al., "Amyloid structures: much more than just a cross-β fold," Current Opinion in Structural Biology, 2020, vol. 60, pp. 7-16.
International Search Report and Written Opinion for International Application No. PCT/US2024/011789 dated Apr. 26, 2024. 12 pages.
Petric et al., Dicyanovinylnaphthalenes for neuroimaging of amyloids and relationships of electronic structures and geometries to binding affinities, Proceedings of the National Academy of Sciences of the United States of America, 2012, vol. 109, No. 41, pp. 16492-16497.
Robert Tycko, "Amyloid Polymorphism: Structural Basis and Neurobiological Relevance," Neuron, Author manuscript, May 6, 2016.

* cited by examiner

COMPOSITIONS AND METHODS FOR DETECTION OF TRAUMATIC BRAIN INJURY

CROSS REFERENCE TO RELATED APPLICATIONS

This application is a U.S. National Stage Application under 35 U.S.C. § 371 of International Application No. PCT/US2019/034977, filed May 31, 2019, which application claims the benefit under 35 U.S.C. § 119 (e) of the U.S. Provisional Application Ser. No. 62/678,900, filed May 31, 2018 and 62/733,025, filed Sep. 18, 2018, the content of each of which is hereby incorporated into the present application by reference in its entirety.

BACKGROUND

Traumatic Brain Injury (TBI) is a chronic disease defined as damage to the brain caused by an external force, such as a bump, blow, jolt, rapid acceleration or deceleration, or penetration by a projectile. Injury leading to TBI may produce diminished or altered states of consciousness, resulting in temporary or permanent impairment in cognition, sensorimotor, and psychosocial function. A recent study showed that nearly 80 percent of military personnel who experienced both blast and non-blast related mild to severe TBIs suffered moderate to severe overall disability within a year after injury. Additionally, several studies have shown mild TBI to be associated with post-traumatic stress disorder (PTSD), depression, and other psychiatric and physical health problems three months after soldiers return home. In addition to these life-altering symptoms, recent studies have demonstrated that even after a single incident, TBI is recognized as a major risk factor for later development of age-related neurodegenerative diseases such as Alzheimer's disease (AD), Parkinson's disease (PD), and Chronic Traumatic Encephalopathy (CTE). A recent study on war veterans suggests that the overall risk of PD increases by 71% after any TBI, where even mild TBI can increase the risk by 56%. War veterans are also more likely to develop PD at least two years earlier than veterans who develop PD without a TBI.

The disease can be categorized as mild, moderate or severe, yet identifying mild versus severe TBIs has been problematic as physicians often refer to existing symptoms and subjective measures only to assess the severity. The diagnosis of mild TBI, the majority of all brain injuries, is often missed by physicians as the presenting symptoms are those similar to mental health disorders such as bipolar disorder or depression. As such, mild TBIs are under-reported and tend to be untreated. The Concussion Legacy Foundation estimates that only one in six mild TBIs (also known as concussions) are diagnosed.

Diagnosis can be further complicated by inconsistent diagnostic criteria that rely heavily on patients' self-reported symptoms rather than objective tests. The only way to definitively diagnose TBI is through a post-mortem examination of the brain using clinical assessment and standard neuroimaging techniques.

However, it has been generally established that plaques of the misfolded protein amyloid-beta (Aβ) have been found within hours or days following a single TBI, similar to the hallmark Aβ plaque pathology of AD. Studies in humans and swine shortly after TBI have demonstrated the long-term accumulation of Aβ in damaged axons, as well as other proteins involved in the production of Aβ peptides. Recent studies have found AR aggregates in the brains of up to a third of patients who die shortly after TBI, as well as in those who survive for a year or more. Furthermore, approximately one third of American troops who suffered brain injuries from bomb blasts showed immediate evidence of damaged nerve fibers in the brain, also known as Diffuse Axonal Injury (DAI). Even a mild TBI (mTBI) can have serious repercussions, inducing DAI and causing physical damage and dysfunction of injured axons. This, in turn with repetitive mild TBI (rmTBI)-involving multiple mild TBIs—can predispose an injured person for an exacerbated response and induce AR and tau pathologies. This evidence suggests that AR may be an acute biomarker for diagnosing TBI.

The current standard diagnosis for severe TBI or TBIs affecting infants and adults over the age of 60 years old requires invasive and costly procedures, such as intracranial pressure monitoring (ICP) and MRI. Diagnosing mild TBI is even more complicated as studies have shown that less than 10% of patients with minor head injuries have positive findings on computerized tomography (CT). Furthermore, the majority of TBI diagnostics are self-report tests, which are subjective and can be easily manipulated. Self-report tests are especially problematic as some soldiers may be reluctant to be diagnosed and manipulate test results in order to avoid the stigma of being injured or separated from their platoons. Additionally, the Pentagon found that 60 percent of soldiers who suffered from TBI symptoms refused help because they were worried about being treated differently or that their condition would prevent them from getting jobs as police officers and firefighters after they got out of service.

Most recently, a 2018 study reported that females had a significantly longer length of recovery than males post mild TBI. Symptom severity was also higher for females who did not use hormonal contraceptive (HC) as opposed to females who did, where this difference was associated with a lower subjective appraisal of symptom severity in females using HC. As the military's female personnel represent a significant portion of the troops and join at prime reproductive age, the impact of TBI is even more detrimental. There remains a major clinical need for an objective diagnostic for TBI.

SUMMARY

The present disclosure, in some embodiments, provides compositions and methods capable of diagnosing traumatic brain injuries (TBI) to reduce the risk of more permanent brain damages. Such methods can be quick and non-invasive. In an example, a non-invasive fluorescent diagnostic probe capable of detecting misfolded protein amyloid-beta (Ap) can be used in a simple ophthalmic exam to detect accumulation of the Aβ in a patient's retina. Such detection which can be made with retinal imaging, the instant inventors discovered, makes a fast and reliable diagnosis of TBI.

According to another embodiment of the disclosure, a rapid detection TBI kit is provided, which can include a fluorescent diagnostic probe and a portable retinal imaging device. The portable retinal imaging device can be used with an indirect ophthalmoscope or a smartphone to capture real time retinal images at the point of care.

The present disclosure, in one embodiment, provides a method for determining whether a patient suffers from a traumatic brain injury (TBI). The method can comprise detecting the presence of an amyloid beta protein in an eye of the patient. In some embodiments, the detection is for the amyloid beta protein in the retina of the eye.

In some embodiments, the patient has been inflicted with a physical impact on the head within 30 days, 25 days, 20 days, 15 days, 10 days, 5 days, or 2 days prior to the detection. In some embodiments, the physical impact was more than 1 day, 2 days, 3 days, 4 days, 5 days, 10 days, 15 days, 20 days, 25 days or 30 days prior to the detection. In some embodiments, the patient has been inflicted with a physical impact on the head within 24 hours prior to the detection.

In some embodiments, the patient has not suffered a direct physical or optical impact on the eyes. In some embodiments, the patient is not known or suspected for suffering from Alzheimer's disease. In some embodiments, the patient is a human under 40 years of age.

In some embodiments, the detection comprises contacting, in vivo, the amyloid beta protein with a probe. In some embodiments, the contact, upon activation by a light, causes emission of a detectable signal. In some embodiments, the detectable signal is an infrared signal. In some embodiments, the detectable signal is a fluorescent signal.

In some embodiments, the detection comprises imaging the amyloid beta protein with a probe ex vivo. In some embodiments, contacting the amyloid beta protein with a probe is conducted in vivo, and detecting and/or imaging is conducted ex vivo. In some embodiments, a sample comprising the amyloid beta protein is removed from the subject prior to detecting and/or imaging.

In some embodiments, the probe comprises a compound of formula Ic:

Ic

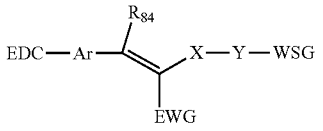

wherein

EDG is:

a) heterocycloalkyl of no more than 10 carbons optionally substituted with one or more $R_{17}$; or b) $—NR_{10}R_{11}$;

wherein each $R_{17}$ is independently halogen, $—OR_{18}$, $—NR_{19}R_{20}$, $C_1$-$C_{10}$ alkyl, $C_1$-$C_{10}$ heteroalkyl, cycloalkyl of no more than 10 carbons, heterocycloalkyl of no more than 10 carbons, arylene of no more than 10 carbons, or heteroarylene of no more than 10 carbons;

each of $R_{10}$, $R_{17}$, $R_{18}$, $R_{19}$ and $R_{20}$ is independently hydrogen, $C_1$-$C_{10}$ alkyl, $C_1$-$C_{10}$ heteroalkyl, cycloalkyl of no more than 10 carbons, heterocycloalkyl of no more than 10 carbons, arylene of no more than 10 carbons, or heteroarylene of no more than 10 carbons, each of which except for hydrogen is optionally substituted with one or more $R_{21}$;

each of $R_{21}$ is independently halogen, $—OR_{22}$, $—NR_{23}R_{24}$, $C_1$-$C_{10}$ alkyl, $C_1$-$C_{10}$ heteroalkyl, cycloalkyl of no more than 10 carbons, heterocycloalkyl of no more than 10 carbons, arylene of no more than 10 carbons, or heteroarylene of no more than 10 carbons, wherein the alkyl, heteroalkyl, cycloalkyl, heterocycloalkyl, arylene or heteroarylene is optionally substituted with one or more $R_{25}$;

each of $R_{22}$, $R_{23}$ and $R_{24}$ is independently hydrogen or $C_1$-$C_{10}$ alkyl; and each of $R_{25}$ is independently $C_1$-$C_{10}$ alkyl, $C_1$-$C_{10}$ heteroalkyl, cycloalkyl of no more than 10 carbons, heterocycloalkyl of no more than 10 carbons, arylene of no more than 10 carbons or heteroarylene of no more than 10 carbons;

Ar is arylene of no more than 14 carbon atoms or heteroarylene of no more than 14 carbon atoms, each optionally substituted with one or more $R_1$;

each $R_1$ is independently halogen, $—OR_2$, $—NR_3R_4$, $C_1$-$C_{10}$ alkyl, $C_1$-$C_{10}$ heteroalkyl, cycloalkyl of no more than 10 carbons, heterocycloalkyl of no more than 10 carbons, arylene of no more than 10 carbons, or heteroarylene of no more than 10 carbons wherein the alkyl, heteroalkyl, cycloalkyl, heterocycloalkyl, arylene, or heteroarylene is optionally substituted with one or more $R_5$;

$R_2$, $R_3$ and $R_4$ are independently hydrogen, $C_1$-$C_{10}$ alkyl, $C_1$-$C_{10}$ heteroalkyl, cycloalkyl of no more than 10 carbons, heterocycloalkyl of no more than 10 carbons, arylene of no more than 10 carbons, or heteroarylene of no more than 10 carbons, each of which except for hydrogen is optionally substituted with one or more $R_5$;

each $R_5$ is independently halogen, $—OR_6$, $—NR_7R_8$, $C_1$-$C_{10}$ alkyl, $C_1$-$C_{10}$ heteroalkyl, cycloalkyl of no more than 10 carbons, heterocycloalkyl of no more than 10 carbons, arylene of no more than 10 carbons, or heteroarylene of no more than 10 carbons;

$R_6$, $R_7$, $R_8$ and $R_{84}$ are independently hydrogen or $C_1$-$C_{10}$ alkyl;

EWG is selected from a group consisting of —F, —Cl, —Br, —CH═O, $NO_2$, $—CF_3$, $—CCl_3$, $—SO_3H$ and —CN;

WSG is:

i)

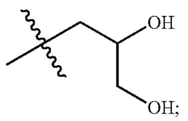 [SMILES: *CC(O)CO]

ii) polyethylene glycol, polypropylene glycol, co-polymer of polyethylene glycol and polypropylene glycol, or alkoxy derivatives thereof, iii)

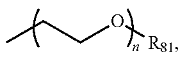

wherein n is an integer from 1-50 and $R_{81}$ is hydrogen, a $C_1$-$C_{10}$ alkyl, a $C_1$-$C_{10}$ alkenyl, or a $C_1$-$C_{10}$ alkynyl, wherein the alkyl, alkenyl, or alkynyl is optionally substituted with one or more $C_1$-$C_{10}$ alkyl, $C_1$-$C_{10}$ heteroalkyl, cycloalkyl of no more than 10 carbons, heterocycloalkyl of no more than 10 carbons, arylene of no more than 10 carbons, or heteroarylene of no more than 10 carbons;

iv)

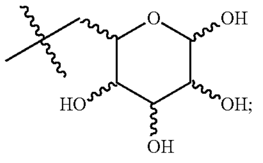 [SMILES: *CC1OC(O)C(O)C(O)C1O]

v)

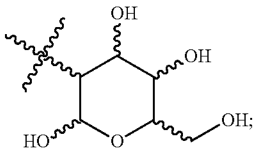

vi)

—($C_1$-$C_{10}$ alkyl)-$R_{33}$-$R_{37}$, wherein:

$R_{33}$ is heteroarylene of no more than 10 carbons; and $R_{37}$ is —($C_1$-$C_6$alkyl) (heterocycloalkyl of no more than 10 carbons);

vii)

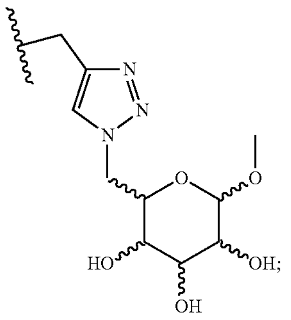 [SMILES: *Cc1cn(CC2OC(OC)C(O)C(O)C2O)nn1]

viii)

—($C_1$-$C_{10}$ heteroalkyl)-$R_{33}$-$R_{37}$, wherein:

$R_{33}$ is heteroarylene of no more than 10 carbons; and $R_{37}$ is —($C_1$-$C_6$alkyl)(heterocycloalkyl of no more than 10 carbons); or ix)

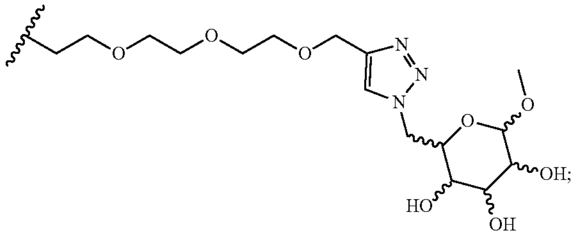 [SMILES: *CCOCCOCCOCc1cn(CC2OC(OC)C(O)C(O)C2O)nn1]

X is C═O or $SO_2$ or X and $R_{84}$ join to form a pyridinyl;

Y is NH or S.

In some embodiments, the probe comprises an antibody. In some embodiments, the antibody is specific to protein amyloid-beta (Aβ). In some embodiments, the antibody selectively binds to misfolded protein amyloid-beta (Aβ). The antibody can be labeled with a detectable marker, or can be detected by binding to a molecule associated with a detectable marker.

In some embodiments, the method further comprises determining that the patient suffers from TBI if an amyloid beta protein is detected in the eye. In some embodiments, the method further comprises instructing the patient to refrain from active physical activities. In some embodiments, the method further comprises administering to the patient an agent that treats or ameliorates TBI.

Also provided, in one embodiment, is a method for preparing a patient for diagnosis of traumatic brain injury (TBI), comprising administering to an eye of the patient a probe that specifically binds an amyloid beta protein. In some embodiments, the method further comprises detecting the binding of the probe to the amyloid beta protein in the eye. Examples of probes are as provided above.

In some embodiments, provided is a method for diagnosing traumatic brain injury (TBI), comprising administering to an eye of the patient a probe that specifically binds an amyloid beta protein, and detecting the binding of the probe to the amyloid beta protein ex vivo. In some embodiments, contacting the amyloid beta protein with the probe is conducted in vivo, and detecting is conducted ex vivo. In some embodiments, a sample comprising the amyloid beta protein and the probe is removed from the subject prior to detecting.

In some embodiments, the administration is intravenous administration or is localized in the retina of the eye. In some embodiments, the patient has been inflicted with a physical impact on the head within 30 days, 25 days, 20 days, 15 days, 10 days, 5 days, or 2 days prior to the detection. In some embodiments, the physical impact was more than 1 day, 2 days, 3 days, 4 days, 5 days, 10 days, 15 days, 20 days, 25 days or 30 days prior to the detection. In some embodiments, the patient has been inflicted with a physical impact on the head within 24 hours prior to the detection.

In some embodiments, the patient has not suffered a direct physical or optical impact on the eyes. In some embodiments, the patient is not known or suspected for suffering from Alzheimer's disease. In some embodiments, the patient is a human under 40 years of age.

Also provided are kits and packages, which comprise a probe that specifically binds an amyloid beta protein and a retinal imaging device. In some embodiments, the retinal imaging device comprises a laser light source. In some embodiments, the retinal imaging device further comprises a retina scanner. In some embodiments, the kit or package further comprises an ophthalmoscope.

Figure 1:
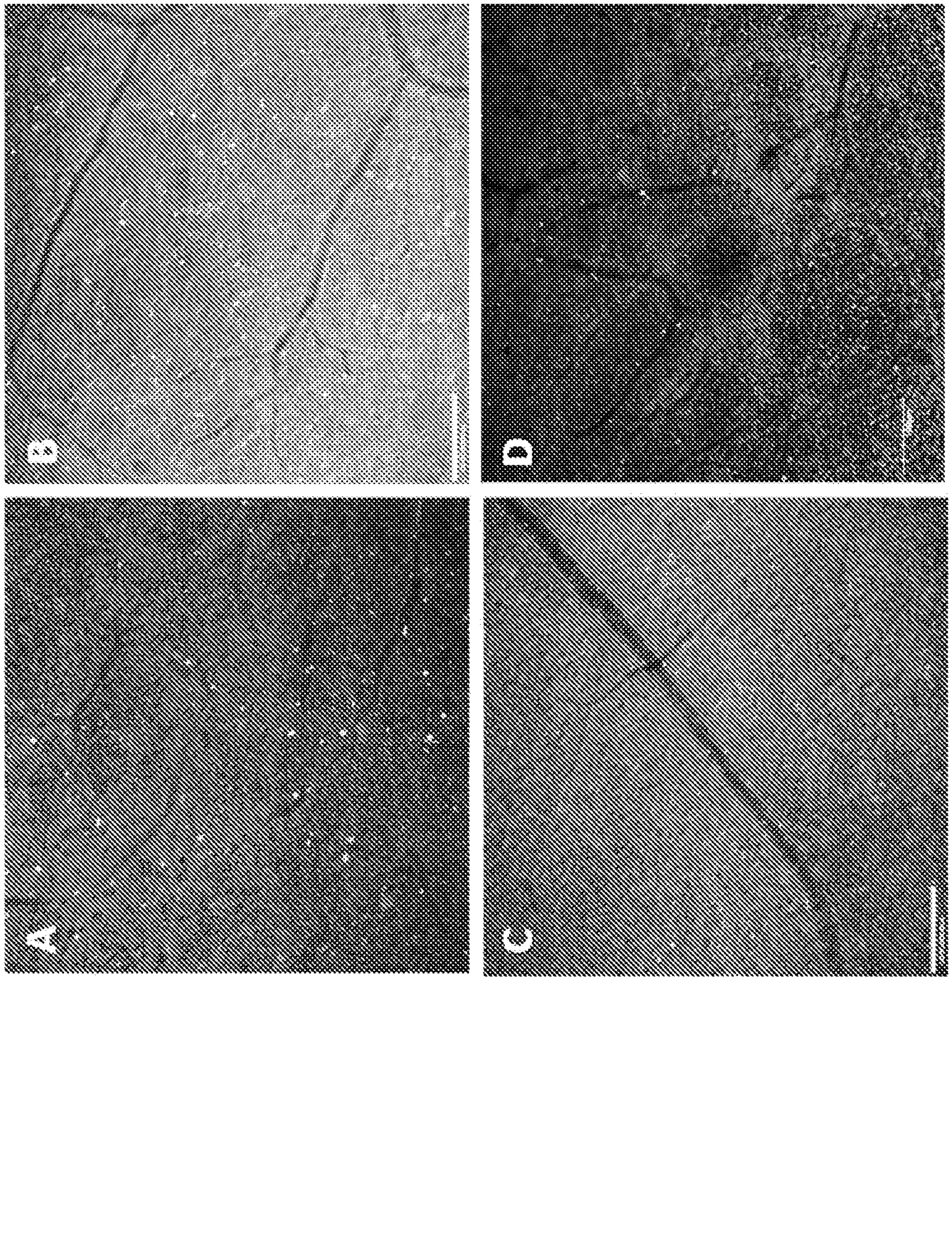
FIG. 1 presents ex vivo fluorescence images of the surface of flat mounted human retina (superior temporal region) stained with DAPI (4',6-diamidino-2-phenylindole) and Compound 1. A) AD patient with Braak stage V/VI. B) AD patient with Braak stage V/VI. C) Cognitively normal patient. D) Cognitively normal patient. Staining is as follows: blue=DAPI nuclear stain, red=autofluorescence, green/yellow=Compound 1 stained. Scale bar=100 μm.

It will be recognized that some or all of the figures are schematic representations for purpose of illustration.

DETAILED DESCRIPTION

Definitions

The following description sets forth exemplary embodiments of the present technology. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

The term "alkyl," by itself or as part of another substituent, represent a straight (i.e. unbranched) or branched chain, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like.

The term "heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, Si and S, and wherein the nitrogen and sulfur atoms may optionally be oxidized and the nitrogen heteroatom may optionally be quaternized. The heteroatom (s) O, N, P and S and Si may be placed at any interior position of the heteroalkyl group or at the position at which the alkyl group is attached to the remainder of the molecule. Examples include, but are not limited to, $-CH_2-CH_2-O-CH_3$, $-CH_2-CH_2-O-CH_2-CH_2-O-CH_3$, $-CH_2-CH_2-O-CH_2-CH_2-O-CH_2-CH_2-O-CH_3$, $-CH_2-CH_2-NH-CH_3$, $-CH_2-CH_2-N(CH_3)-CH_3$, $-CH_2-S-CH_2-CH_3$, $-CH_2-CH_2-S(O)-CH_3$, $-CH_2-CH_2-S(O)_2-CH_3$, $-CH=CH-O-CH_3$, $-Si(CH_3)_3$, $-CH_2-CH=N-OCH_3$, $-CH=CH-N(CH_3)-CH_3$, $O-CH_3$, $-O-CH_2-CH_3$, and $-CN$. Two or more heteroatoms may also be consecutive.

The terms "cycloalkyl" and "heterocycloalkyl," by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, tetrahydropyran, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. Examples of heterocycloalkyl include, but are not limited to glucose, mannose, allose, altrose, gulose, idose, galactose, and talose. Examples of heterocycloalkyl include, but are not limited to:

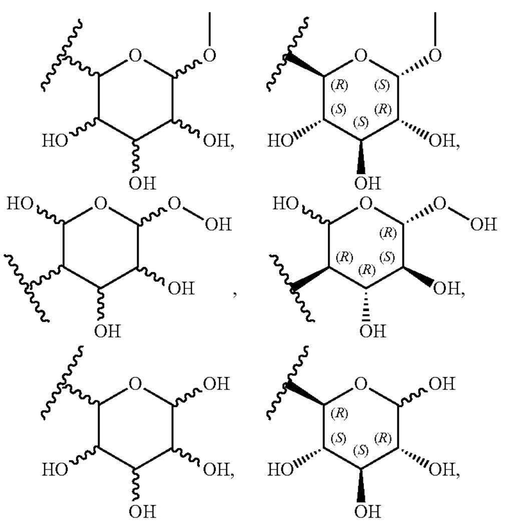

and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is meant to include, but not be limited to, fluoromethyl, difluoromethyl, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together (i.e. a fused ring aryl) or linked covalently. A fused ring aryl refers to multiple rings fused together wherein at least one of the fused rings is an aryl ring.

The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. Thus, the term "heteroaryl" includes fused ring heteroaryl groups (i.e. multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6, 5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, triazolyl, 1,2,3-triazolyl, 1,2,4-triazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

An "arylene" and a "heteroarylene," alone or as part of another substituent means a divalent radical derived from an aryl and heteroaryl, respectively.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

As used herein, the term "heteroatom" or "ring heteroatom" is meant to include oxygen (O), nitrogen (N), sulfur (S), phosphorus (P), and silicon (Si).

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g. arylalkyl, the last mentioned group contains the atom by which the moiety is attached to the rest of the molecule.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen.

Some of the compounds exist as tautomers. Tautomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

Any formula or structure given herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2H$ (deuterium, D), $^3H$ (tritium), C, $^{13}C$, $^{14}C$, $^{15}N$, $^{18}F$, $^{31}P$, $^{32}P$, $^{35}S$, $^{36}Cl$ and $^{125}I$. Various isotopically labeled compounds of the present disclosure, for example those into which radioactive isotopes such as $^3H$, $^{13}C$ and $^{14}C$ are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes "deuterated analogs" of compounds of Formula I in which from 1 to n hydrogens attached to a carbon atom is/are replaced by deuterium, in which n is the number of hydrogens in the molecule. Such compounds exhibit increased resistance to metabolism and are thus useful for increasing the half-life of any compound of Formula I when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}F$ labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compounds described herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound, and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Likewise, pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines (i.e., $NH_2$(alkyl)), dialkyl amines (i.e., HN(alkyl)$_2$), trialkyl amines (i.e., N(alkyl)$_3$), substituted alkyl amines (i.e., $NH_2$(substituted alkyl)), di(substituted alkyl) amines (i.e., HN(substituted alkyl)$_2$), tri (substituted alkyl) amines (i.e., N(substituted alkyl)$_3$), alkenyl amines (i.e., $NH_2$(alkenyl)), dialkenyl amines (i.e., HN(alkenyl)$_2$), trialkenyl amines (i.e., N(alkenyl)$_3$), substituted alkenyl amines (i.e., $NH_2$(substituted alkenyl)), di(substituted alkenyl) amines (i.e., HN(substituted alkenyl)$_2$), tri(substituted alkenyl) amines (i.e., N(substituted alkenyl)$_3$, mono-, di- or tri-cycloalkyl amines (i.e., $NH_2$(cycloalkyl), HN(cycloalkyl)$_2$, N(cycloalkyl)$_3$), mono-, di- or tri-arylamines (i.e., $NH_2$(aryl), HN(aryl)$_2$, N(aryl)$_3$), or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, haloalkoxy, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. Unless specified otherwise, where a group is described as optionally substituted, any substituents of the group are themselves unsubstituted. For example, in some embodiments, the term "substituted alkyl" refers to an alkyl group having one or more substituents including hydroxyl, halo, alkoxy, cycloalkyl, heterocyclyl, aryl, and heteroaryl. In other embodiments, the one or more substituents may be further substituted with halo, alkyl, haloalkyl, hydroxyl, alkoxy, cycloalkyl, heterocyclyl, aryl, or heteroaryl, each of which is substituted. In other embodiments, the substituents may be further substituted with halo, alkyl, haloalkyl, alkoxy, hydroxyl, cycloalkyl, heterocyclyl, aryl, or heteroaryl, each of which is unsubstituted.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

A "solvate" is formed by the interaction of a solvent and a compound. Solvates of salts of the compounds described herein are also provided. Hydrates of the compounds described herein are also provided.

Detection of Traumatic Brain Injuries (TBI)

It is contemplated that a traumatic brain injury (TBI), even a mild TBI, can quickly cause release and/or accumulation of amyloid-beta (Aβ) in the retina of a patient. Such presence of the Aβ in the retina, as the experimental examples show, can be detected with probes able to bind to the Aβ, which binding can then be detected by means such as laser-activated fluorescence scanning of the retina.

"Traumatic brain injury" (TBI) happens when a bump, blow, jolt, or other head injury causes damage to the brain. The TBI can lead to permanent brain damage or death. Half of all TBIs are from motor vehicle accidents. Military personnel in combat zones are also at risk. Symptoms of a TBI may not appear until days or weeks following the injury. A concussion is the mildest type. It can cause a headache or neck pain, nausea, ringing in the ears, dizziness, and tiredness. People with a moderate or severe TBI may have symptoms such as a headache that gets worse or does not go away, repeated vomiting or nausea, convulsions or seizures, inability to awaken from sleep, slurred speech, weakness or numbness in the arms and legs, and dilated eye pupils.

"Amyloid beta" (AB or Abeta) denotes peptides of about 36 to 43 amino acids that are involved in Alzheimer's disease (AD) as the main component of the amyloid plaques found in the brains of Alzheimer patients. The peptides derive from the amyloid precursor protein (APP; example GenBank Accession No: NP_000475), which is cleaved by beta secretase and gamma secretase to yield Aβ. Aβ molecules can aggregate to form flexible soluble oligomers which may exist in several forms. It is believed that certain misfolded oligomers (known as "seeds") can induce other Aβ molecules to also take the misfolded oligomeric form, leading to a chain reaction akin to a prion infection. The oligomers are toxic to nerve cells.

In accordance with one embodiment of the present disclosure, therefore, provided is a method for determining whether a patient suffers from a traumatic brain injury (TBI). The method entails detecting the presence of an amyloid beta protein in an eye of the patient. It is contemplated that the accumulation of the amyloid beta protein occurs mainly in the retina. Accordingly, the detection can primarily target amyloid beta protein in the retina of the eye.

Accumulation of the amyloid beta protein, it is contemplated, can start quickly following the physical impact on the head, which causes the TBI. It is understood that physical impact may not be the only cause of a TBI. Sound, light, and temperature may also cause TBI and thus are within the scope of the present disclosure. In some embodiments, the detection is carried out within 1 or 2 hours after the cause of the potential TBI. Alternatively, the detection can be carried out within 6, 12, 18, 24, 36 or 48 hours. In some embodiments, the detection is carried out at least 1, 2, 3, 4, 6, 8, 12, 18 or 24 hours after the cause of the potential TBI. In some embodiments, the detection is carried out at least 1, 2, 3, 4, 5, 6, 7, 8, 9, or 10 days after the cause of the potential TBI. In some embodiments, the detection is carried out within 3, 4, 5, 6, 7, 8, 9, or 10 days, or within 1, 2, 3, 4, or 5 weeks after the cause of the potential TBI.

In some embodiments, the patient may suffer from another disease or condition that causes accumulation of the amyloid beta protein. An example of such a disease is Alzheimer's disease (AD). It is contemplated, however, that a patient subject to the presently disclosed detection method does not suffer from such other diseases or conditions (e.g., AD). In some embodiments, the patient is young enough (e.g., younger than 70, 65, 60, 55, 50, 45 or 40 years old) to be reasonably not suspected to suffer from such a disease or condition.

It is possible that direct physical impact (or light, sound or temperature) on the eye may cause release or accumulation of the amyloid beta protein in the eye. In some embodiments, the patient of the method has not suffered from such a direct impact on the eyes.

In another embodiment, provided is a method for preparing a patient for diagnosis of traumatic brain injury (TBI), which method comprises administering to an eye of the patient a probe that specifically binds an amyloid beta protein. Types of patients suitable for such a method are described above, without limitation. Once the probe is administered to the eye of the patient, its binding to the amyloid beta protein may be detected with methods described herein, which binding indicates accumulation of the amyloid beta protein, an indication of a traumatic brain injury.

Amyloid Beta-Binding Probes and Detection

Detection of an amyloid beta protein can be made with probes that can selectively bind to the amyloid beta protein, which is herein referred to as amyloid beta-binding (Aβ-binding) probes. Such probes are known or can be readily developed or prepared.

In one embodiment, an Aβ-binding probe, when bound to an Aβ, can be detected through its emitted fluorescent signal, upon activation by a laser light. Examples of Aβ-binding fluorescent probes are provided in the section below.

An Aβ-binding probe can also be an antibody that specifically binds the Aβ. Antibodies against a protein or peptide can be routinely developed and prepared from animal sources or by methods such as phage display. Detection of the antibody can also be made by methods known in the art, such as probes that can bind to the antibody and can emit detectable signals. Non-limiting examples of antibodies include the 6E10 antibody as used herein and ab2539 available from Abcam (Cambridge, MA).

In situ detection of binding of an Aβ-binding probe to an Aβ in the retina of the patient can be facilitated with a retinal imaging device, which is preferably handheld or portable. The retinal imaging device can include a lens and an image sensor, and optionally a laser light source. When the light source emits laser light to the retina, if AR is accumulated there and has bound to an AD-binding probe, the accumulation can be readily detected and quantitated by the lens and image sensor that collects and senses a fluorescent signal.

Amyloid Sensitive Fluorescent Probe (ASF)

The present disclosure further provides small molecule fluorescent probes capable of binding to an amyloid beta (Aβ). In one embodiment, the probes may be selected from those compounds described in WO 2011/072257, WO 2015/143185 or WO 2017/004560, which are incorporated by reference in their entirety. In one embodiment, the probe may be curcumin or other compounds currently used to stain AD, such as thioflavins or congo red.

In one embodiment, the probe can be selected from compounds described in WO 2015/143185, which compounds are described below.

In certain embodiments, the disclosure provides a compound of Formula I or a salt or solvate thereof:

(Formula I)

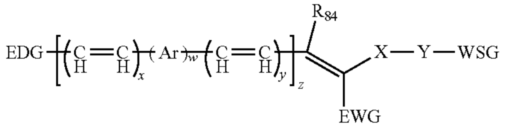

wherein

EDG is an electron donating group;

each Ar is independently $C_1$-$C_{14}$ arylene or $C_1$-$C_{14}$ heteroarylene, each optionally substituted with one or more $R_1$;

each $R_1$ is independently halogen, —$OR_2$, —$NR_3R_4$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene;

wherein the alkyl, heteroalkyl, cycloalkyl, heterocycloalkyl, arylene, or heteroarylene is optionally substituted with one or more $R_5$;

$R_2$, $R_3$ and $R_4$ are independently hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, each of which except for hydrogen is optionally substituted with one or more $R_5$;

each $R_5$ is independently halogen, —$OR_6$, —$NR_7R_8$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene;

$R_6$, $R_7$, $R_8$ and $R_{84}$ are independently hydrogen or $C_1$-$C_{10}$ alkyl;

$R_{84}$ is hydrogen or $C_1$-$C_{10}$ alkyl;

EWG is an electron withdrawing group;

WSG is a water soluble group;

X is C═O or $SO_2$ or X and $R_{84}$ join to form a pyridinyl;

Y is NH, or S;

each x is independently an integer from 0-10;

each w is independently an integer from 1-5;

each y is independently an integer from 0-10; and z is an integer from 1-10.

In certain embodiments, the compounds are of Formula II or a salt or a solvate thereof:

(Formula II)

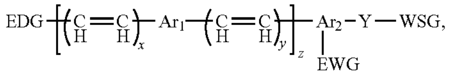

wherein

EDG is an electron donating group;

$Ar_2$ and each Art is independently $C_1$-$C_{14}$ arylene or $C_1$-$C_{14}$ heteroarylene;

each optionally substituted with one or more $R_{41}$;

each $R_{41}$ is independently halogen, —CN, —$OR_{42}$, —$NR_{43}R_{44}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene wherein the alkyl, heteroalkyl, cycloalkyl, heterocycloalkyl, arylene, or heteroarylene is optionally substituted with one or more $R_{45}$;

$R_{42}$, $R_{43}$ and $R_{44}$ are independently hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, each of which except for hydrogen is optionally substituted with one or more $R_{45}$;

each $R_{45}$ is independently halogen, —$OR_{46}$, —$NR_{47}R_{48}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene; and $R_{46}$, $R_{47}$ and $R_{48}$ are independently hydrogen or $C_1$-$C_{10}$ alkyl;

EWG is an electron withdrawing group;

Y is absent, O, NH, or S;

WSG is hydrogen or a water soluble group;

x is an integer from 0-10;

y is an integer from 0-10; and z is an integer from 1-10.

In certain embodiments, $R_{84}$ is hydrogen. In certain embodiments, $R_{84}$ is $C_1$-$C_{10}$ alkyl. In certain embodiments, $R_{84}$ is methyl, ethyl, propyl, butyl, pentyl, hexyl, heptyl, octyl, neptyl or decyl. In certain embodiments, $R_{84}$ is methyl.

The substituent EDG is an electron donor group, as known in the art. In certain embodiments, EDG is any atom or functional group that is capable of donating some of its electron density into a conjugated pi system, thus making the pi system more nucleophilic.

In certain embodiments,

EDG is —$OR_9$, —$NR_{10}R_{11}$, —$SR_{12}$, —$PR_{13}R_{14}$, —$NR_{15}C(O)R_{16}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{17}$;

each $R_{17}$ is independently halogen, —$OR_{18}$, —$NR_{19}R_{20}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene;

each of $R_9$, $R_{10}$, $R_{11}$, $R_{12}$, $R_{13}$, $R_{14}$, $R_{18}$, $R_{16}$, $R_{18}$, $R_{19}$ and $R_{20}$ is independently hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, each of which except for hydrogen is optionally substituted with one or more $R_{21}$ and wherein $R_{10}$ and $R_{11}$ are optionally joined together to form a heterocycloalkyl or heteroaryl optionally substituted with $R_{21}$;

each of $R_{21}$ is independently halogen, —$OR_{22}$, —$NR_{23}R_{24}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{25}$;

each of $R_{22}$, $R_{23}$ and $R_{24}$ is independently hydrogen or $C_1$-$C_{10}$ alkyl; and each $R_{25}$ is independently $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene.

In certain embodiments, the EDG is selected from a group consisting of

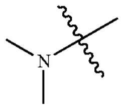,
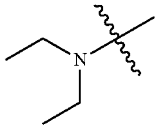,
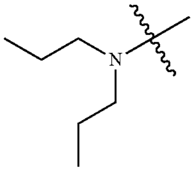,
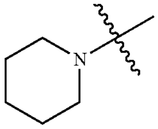,
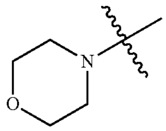,
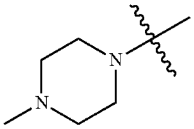, and
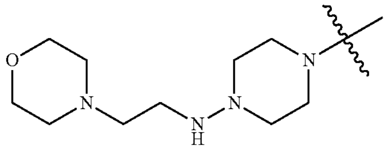.

In certain embodiments, the EDG is

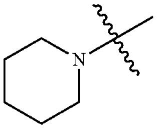.

In certain embodiments, EDG is

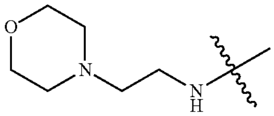.

EWG is an electron withdrawing group. In certain embodiments, the electron withdrawing group as used herein is any atom or group that is capable of drawing electron density from neighboring atoms towards itself, either by resonance or inductive effects.

In certain embodiments,

EWG is selected from a group consisting of halogen, —CN, —$NO_2$, —$SO_3H$, —$CR_{26}R_{27}R_{28}$, —$COR_{29}$, or —$COOR_{30}$;

each $R_{26}$, $R_{27}$ and $R_{28}$ is independently hydrogen or halogen;

$R_{29}$ is halogen, hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{31}$;

$R_{30}$ is hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{32}$; and each $R_{31}$ and $R_{32}$ is independently $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene.

In certain embodiments, the EWG is selected from a group consisting of —F, —Cl, —Br, —CH═O, $NO_2$, —$CF_3$, —$CCl_3$, —$SO_3$ and —CN. In certain embodiments, the EWG is F, Cl, or Br. In certain embodiments, the EWG is —CN.

WSG is a water soluble group. In certain embodiments, the WSG group serves to alter the solubility of the compounds in an aqueous systems.

In certain embodiments,

WSG is hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{33}$;

wherein each $R_{33}$ is independently halogen, —$OR_{34}$, —$NR_{35}R_{36}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{37}$;

each $R_{34}$, $R_{35}$ and $R_{36}$ is independently hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{37}$;

each $R_{37}$ is independently halogen, —$OR_{38}$, —$NR_{39}R_{40}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, —($C_1$-$C_6$alkyl)($C_1$-$C_{10}$heterocycloalkyl), $C_1$-$C_{10}$ arylene, or $C_1$-$C_{10}$ heteroarylene; and each of $R_{38}$, $R_{39}$ and $R_{40}$ is independently hydrogen or $C_1$-$C_{10}$ alkyl.

In certain embodiments, the WSG is

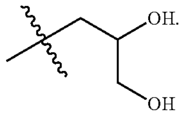.

In certain embodiments, WSG is polyethylene glycol, polypropylene glycol, co-polymer of polyethylene glycol and polypropylene glycol, or alkoxy derivatives thereof.

In certain embodiments, WSG is

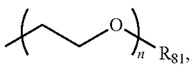, wherein n is an integer from 1-50 and $R_{81}$ is hydrogen, $C_1$-$C_{10}$ alkyl, a $C_1$-$C_{10}$ alkenyl, or a $C_1$-$C_{10}$ alkynyl wherein each wherein the alkyl, alkenyl, or alkynyl is optionally substituted with one or more $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene. In certain embodiments, $R_{81}$ is hydrogen. In certain embodiments, $R_{81}$ is methyl. In certain embodiments, $R_{81}$ is ethyl. In certain embodiments, $R_{81}$ is —$CH_2$—C≡CH. In certain embodiments, n is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In certain embodiments, n is an integer of value 1-10, 1-20, 1-30, 1-40, 1-50, 10-20, 10-30, 10-40, 10-50, 20-30, 20-40, 20-50, 30-40, 30-50, or 40-50. In certain embodiments, n is 1, 2, 3, 4, 5, 6, 7, 8, 9, or 10. In certain embodiments, and n is 3 or 6.

In certain embodiments, $R_{81}$ is hydrogen.

In certain embodiments, WSG is

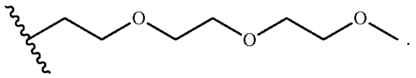 [SMILES: *CCOCCOCCOC]

In certain embodiments, WSG is

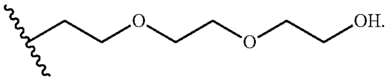 [SMILES: *CCOCCOCCO]

In certain embodiments, WSG is

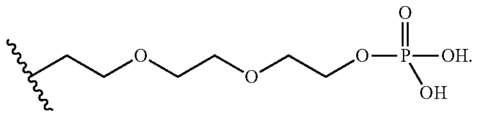 [SMILES: *CCOCCOCCOP(=O)(O)O]

In certain embodiments, WSG is

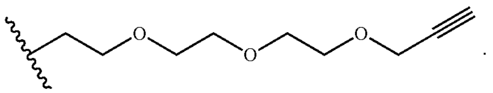 [SMILES: *CCOCCOCCOCC#C]

In certain embodiments, the WSG is

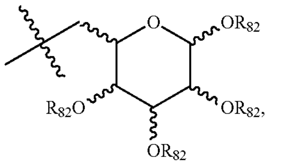

wherein each $R_{82}$ is independently hydrogen or $C_1$-$C_{10}$ alkyl.

In certain embodiments, each $R_{82}$ is independently a hydrogen, methyl, ethyl, propyl, or butyl.

In certain embodiments, the WSG is

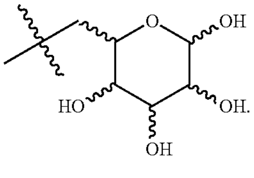 [SMILES: *CC1OC(O)C(O)C(O)C1O]

In certain embodiments, the WSG is

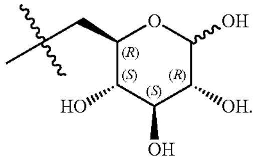

In certain embodiments, the WSG is

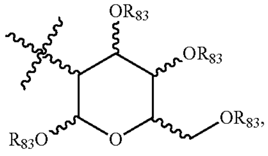

wherein each $R_{83}$ is hydrogen or $C_1$-$C_{10}$ alkyl. In certain embodiments, each $R_{83}$ is independently a hydrogen, methyl, ethyl, propyl, or butyl.

In certain embodiments, the WSG is

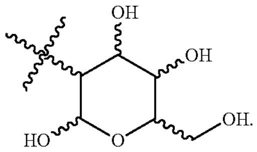

In certain embodiments, the WSG is

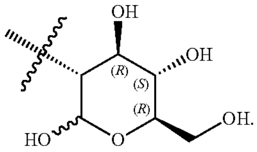

In certain embodiments, WSG is —($C_1$-$C_{10}$ alkylene)-$R_{33}$-$R_{37}$. In certain embodiments, WSG is —($C_1$-$C_{10}$ alkylene)-$R_{33}$-$R_{37}$ and $R_{33}$ is $C_1$-$C_{10}$ heteroarylene. In certain embodiments, WSG is —($C_1$-$C_{10}$ alkyl)-$R_{33}$-$R_{37}$, $R_{33}$ is $C_1$-$C_{10}$ heteroarylene and $R_{37}$ is —($C_1$-$C_6$alkyl)($C_1$-$C_{10}$heterocycloalkyl). In certain embodiments, WSG is —$CH_2$—$R_{33}$-$R_{37}$. In certain embodiments, WSG is —$CH_2$—$R_{33}$-$R_{37}$ and $R_{33}$ is triazole, imidazole, or pyrazole. In certain embodiments, WSG is —$CH_2$—$R_{33}$-$R_{37}$ and $R_{33}$ is triazole. In certain embodiments, WSG is —$CH_2$—$R_{33}$-$R_{37}$ and $R_{33}$ is 1,2,4-triazole. In certain embodiments, WSG is —$CH_2$—$R_{33}$-$R_{37}$ and $R_{33}$ is 1,2,3-triazole. In certain embodiments, WSG is —$CH_2$—$R_{33}$-$R_{37}$, $R_{33}$ is 1,2,3-triazole and $R_{37}$ is —($C_1$-$C_6$alkyl)($C_1$-$C_{10}$heterocycloalkyl). In certain embodiments, WSG is —$CH_2$—$R_{33}$-$R_{37}$, $R_{33}$ is 1,2,3-triazole and $R_{37}$ is —($C_1$alkyl)($C_1$-$C_{10}$heretocycloalkyl). In certain embodiments, WSG is —$CH_2$—$R_{33}$-$R_{37}$, $R_{33}$ is 1,2,3-triazole, $R_{37}$ is —($C_1$alkyl)($C_1$-$C_{10}$heretocycloalkyl), and $C_1$-$C_{10}$heretocycloalkyl is a tetrahydropyran derivative.

In certain embodiments, WSG is

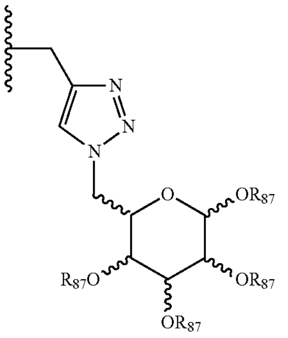

wherein each $R_{87}$ is hydrogen, $C_1$-$C_{10}$ alkyl, or —C(═O)$C_1$-$C_{10}$ alkyl. In certain embodiments, each $R_{87}$ is independently a hydrogen, methyl, ethyl, propyl, butyl, acetate, propionate, or butyrate. In certain embodiments, each $R_{87}$ is independently a hydrogen or methyl. In certain embodiments, each $R_{87}$ is independently a methyl or acetate.

In certain embodiments, WSG is

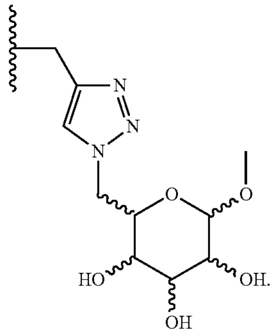 [SMILES: *Cc1cn(CC2OC(OC)C(O)C(O)C2O)nn1]

In certain embodiments, WSG is

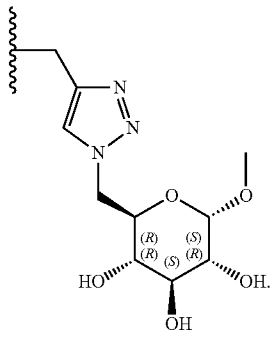

In certain embodiments, WSG is —($C_1$-$C_{10}$ heteroalkyl)-$R_{33}$-$R_{37}$. In certain embodiments, WSG is —($C_1$-$C_{10}$ heteroalkyl)-$R_{33}$-$R_{37}$ and $R_{33}$ is $C_1$-$C_{10}$ heteroarylene. In certain embodiments, WSG is —($C_1$-$C_{10}$ heteroalkyl)-$R_{33}$-$R_{37}$ and $R_{33}$ is $C_1$-$C_{10}$ heteroarylene and $R^{37}$ is —($C_1$-$C_6$alkyl)($C_1$-$C_{10}$heretocycloalkyl).

In certain embodiments, WSG is

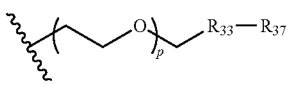

and p is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In certain embodiments, p is an integer of value 1-10, 1-20, 1-30, 1-40, 1-50, 10-20, 10-30, 10-40, 10-50, 20-30, 20-40, 20-50, 30-40, 30-50, or 40-50. In certain embodiments, p is 1, 2, 3, 4, 5, 6, 7, 8, 9, or 10. In certain embodiments, p is 3 or 6. In certain embodiments, p 3.

In certain embodiments, WSG is

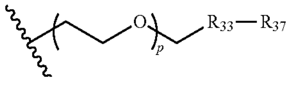

and $R_{33}$ is a $C_1$-$C_{10}$ heteroarylene. In certain embodiments, $R_{33}$ is a $C_5$ heteroarylene. In certain embodiments, $R_{33}$ is triazole, imidazole, or pyrazole. In certain embodiments, $R_{33}$ is triazole. In certain embodiments, $R_{33}$ is 1, 2, 4-triazole. In certain embodiments, $R_{33}$ is 1, 2, 3-triazole. In certain embodiments, $R_{33}$ is 1, 2, 3-triazole, and p is 3. In certain embodiments, $R_{33}$ is 1,2,3-triazole and $R_{37}$ is —($C_1$-$C_6$alkyl)($C_1$-$C_{10}$heretocycloalkyl). In certain embodiments, $R_{33}$ is 1,2,3-triazole and $R_{37}$ is —($C_1$alkyl)($C_1$-$C_{10}$heretocycloalkyl). In certain embodiments, $R_{33}$ is 1,2,3-triazole, $R_{37}$ is a tetrahydropyran derivative. In certain embodiments, $R_{33}$ is 1,2,3-triazole, and $R_{37}$ is

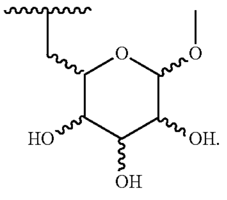 [SMILES: *CC1OC(OC)C(O)C(O)C1O]

In certain embodiments, WSG is

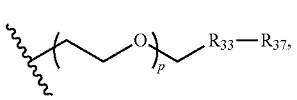

$R_{33}$ is 1,2,3-triazole, $R_{37}$ is

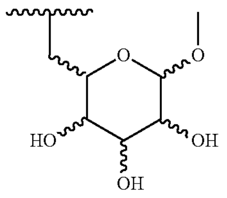 [SMILES: *CC1OC(OC)C(O)C(O)C1O]

and p is 3.

In certain embodiments, WSG is

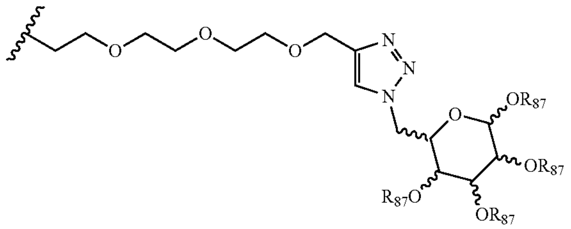

wherein each $R_{87}$ is hydrogen, $C_1$-$C_{10}$ alkyl, or —C(=O) $C_1$-$C_{10}$ alkyl. In certain embodiments, each $R_{87}$ is independently a hydrogen, methyl, ethyl, propyl, butyl, acetate, propionate, or butyrate. In certain embodiments, each $R_{87}$ is independently a hydrogen or methyl. In certain embodiments, each $R_{87}$ is independently a methyl or acetate.

In certain embodiments, WSG is

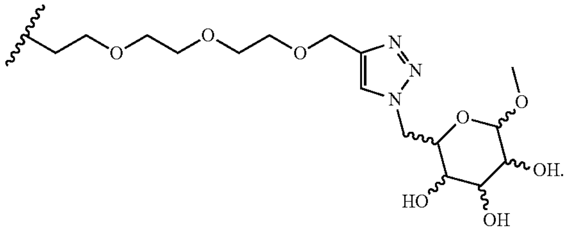 [SMILES: *CCOCCOCCOCc1cn(CC2OC(OC)C(O)C(O)C2O)nn1]

In certain embodiments, WSG is

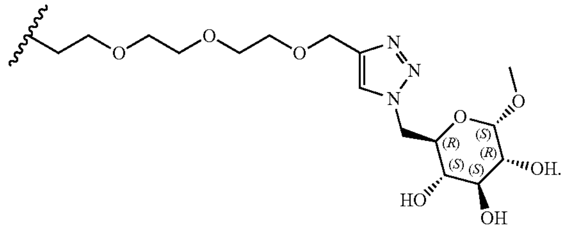

In certain embodiments, X is C=O or $SO_2$. In certain embodiments, X is C=O. In certain embodiments, X is $SO_2$.

In certain embodiments, Y is NH or S. In certain embodiments, Y is NH. In certain embodiments, Y is S.

The variable w in Formula I is an integer from 1-5. In certain embodiments, w is 1. In certain embodiments, w is 2. In certain embodiments, w is 3. In certain embodiments, w is 4. In certain embodiments, w is 5.

The variable x in Formula I is an integer from 0-10. In certain embodiments, x is 0. In certain embodiments, x is 1. In certain embodiments, x is 2. In certain embodiments, x is 3. In certain embodiments, x is 4. In certain embodiments, x is 5. In certain embodiments, x is 6. In certain embodiments, x is 7. In certain embodiments, x is 8. In certain embodiments, x is 9. In certain embodiments, x is 10.

The variable y in Formula I is an integer from 0-10. In certain embodiments, y is 0. In certain embodiments, y is 1. In certain embodiments, y is 2. In certain embodiments, y is 3. In certain embodiments, y is 4. In certain embodiments, y is 5. In certain embodiments, y is 6. In certain embodiments, y is 7. In certain embodiments, y is 8. In certain embodiments, y is 9. In certain embodiments, y is 10.

The variable z in Formula I is an integer from 1-10. In certain embodiments, z is 1. In certain embodiments, z is 2. In certain embodiments, z is 3. In certain embodiments, z is 4. In certain embodiments, z is 5. In certain embodiments, z is 6. In certain embodiments, z is 7. In certain embodiments, z is 8. In certain embodiments, z is 9. In certain embodiments, z is 10.

In certain embodiments, x is 0, w is 1, y is 0, z is 1, X is C=O, and Y is NH.

In certain embodiments, x is 0, w is 1, y is 0, z is 1, X is $SO_2$, and Y is NH.

In certain embodiments, x is 0, w is 2, y is 0, z is 1, X is C=O, and Y is NH.

In certain embodiments, x is 0, w is 2, y is 0, z is 1, X is $SO_2$, and Y is NH.

In certain embodiments, the disclosure provides a compound of Formula Ia:

(Formula Ia)

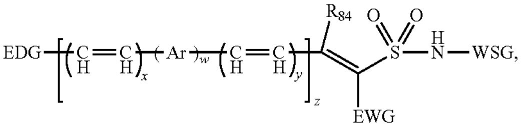

wherein EDG, Ar, $R_{84}$, x, w, y, z, EWG, and WSG are defined as above.

In certain embodiments, the disclosure provides a compound of Formula Ib:

(Formula Ib)

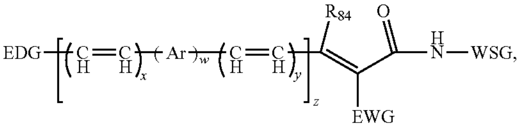

wherein EDG, Ar, $R_{84}$, x, w, y, z, EWG, and WSG are defined above.

In one aspect the disclosure provides a compound of Formula Ic:

(Formula Ic)

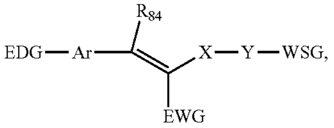

wherein EDG, Ar, $R_{84}$, X, Y, EWG, and WSG are defined above.

In certain embodiments, the compound of Formula (Ic), or a salt or solvate thereof Ic

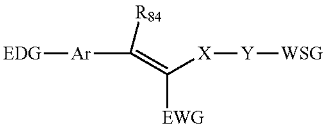

wherein

EDG is:

a) heterocycloalkyl of no more than 10 carbons optionally substituted with one or more $R_{17}$; or b) —$NR_{10}R_{11}$;

wherein each $R_{17}$ is independently halogen, —$OR_{18}$, —$NR_{19}R_{20}$, $C_1$-$C_{10}$ alkyl, $C_1$-$C_{10}$ heteroalkyl, cycloalkyl of no more than 10 carbons, heterocycloalkyl of no more than 10 carbons, arylene of no more than 10 carbons, or heteroarylene of no more than 10 carbons;

each of $R_{10}$, $R_{11}$, $R_{18}$, $R_{19}$ and $R_{20}$ is independently hydrogen, $C_1$-$C_{10}$ alkyl, $C_1$-$C_{10}$ heteroalkyl, cycloalkyl of no more than 10 carbons, heterocycloalkyl of no more than 10 carbons, arylene of no more than 10 carbons, or heteroarylene of no more than 10 carbons, each of which except for hydrogen is optionally substituted with one or more $R_{21}$;

each of $R_{21}$ is independently halogen, —$OR_{22}$, —$NR_{23}R_{24}$, $C_1$-$C_{10}$ alkyl, $C_1$-$C_{10}$ heteroalkyl, cycloalkyl of no more than 10 carbons, heterocycloalkyl of no more than 10 carbons, arylene of no more than 10 carbons, or heteroarylene of no more than 10 carbons, wherein the alkyl, heteroalkyl, cycloalkyl, heterocycloalkyl, arylene or heteroarylene is optionally substituted with one or more $R_{25}$;

each of $R_{22}$, $R_{23}$ and $R_{24}$ is independently hydrogen or $C_1$-$C_{10}$ alkyl; and each of $R_{25}$ is independently $C_1$-$C_{11}$ alkyl, $C_1$-$C_{10}$ heteroalkyl, cycloalkyl of no more than 10 carbons, heterocycloalkyl of no more than 10 carbons, arylene of no more than 10 carbons or heteroarylene of no more than 10 carbons;

Ar is arylene of no more than 14 carbon atoms or heteroarylene of no more than 14 carbon atoms, each optionally substituted with one or more $R_1$;

each $R_1$ is independently halogen, —$OR_2$, —$NR_3R_4$, $C_1$-$C_{10}$ alkyl, $C_1$-$C_{10}$ heteroalkyl, cycloalkyl of no more than 10 carbons, heterocycloalkyl of no more than 10 carbons, arylene of no more than 10 carbons, or heteroarylene of no more than 10 carbons wherein the alkyl, heteroalkyl, cycloalkyl, heterocycloalkyl, arylene, or heteroarylene is optionally substituted with one or more $R_5$;

$R_2$, $R_3$ and $R_4$ are independently hydrogen, $C_1$-$C_{10}$ alkyl, $C_1$-$C_{10}$ heteroalkyl, cycloalkyl of no more than 10 carbons, heterocycloalkyl of no more than 10 carbons, arylene of no more than 10 carbons, or heteroarylene of no more than 10 carbons, each of which except for hydrogen is optionally substituted with one or more $R_5$;

each $R_5$ is independently halogen, —$OR_6$, —$NR_7R_8$, $C_1$-$C_{10}$ alkyl, $C_1$-$C_{10}$ heteroalkyl, cycloalkyl of no more than 10 carbons, heterocycloalkyl of no more than 10 carbons, arylene of no more than 10 carbons, or heteroarylene of no more than 10 carbons;

$R_6$, $R_7$, $R_8$ and $R_{84}$ are independently hydrogen or $C_1$-$C_{10}$ alkyl;

EWG is selected from a group consisting of —F, —Cl, —Br, —CH═O, $NO_2$, —$CF_3$, —$CCl_3$, —$SO_3H$ and —CN;

WSG is:

i)

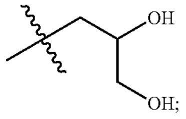 [SMILES: *CC(O)CO]

ii) polyethylene glycol, polypropylene glycol, co-polymer of polyethylene glycol and polypropylene glycol, or alkoxy derivatives thereof, iii)

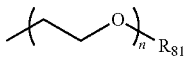

wherein n is an integer from 1-50 and $R_{81}$ is hydrogen, a $C_1$-$C_{10}$ alkyl, a $C_1$-$C_{10}$ alkenyl, or a $C_1$-$C_{10}$ alkynyl, wherein the alkyl, alkenyl, or alkynyl is optionally substituted with one or more $C_1$-$C_{10}$ alkyl, $C_1$-$C_{10}$ heteroalkyl, cycloalkyl of no more than 10 carbons, heterocycloalkyl of no more than 10 carbons, arylene of no more than 10 carbons, or heteroarylene of no more than 10 carbons;

iv)

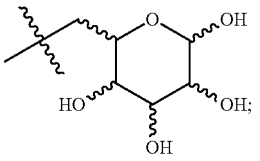 [SMILES: *CC1OC(O)C(O)C(O)C1O]

v)

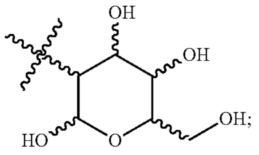

vi)

—($C_1$-$C_{10}$ alkyl)-$R_{33}$-$R_{37}$, wherein:

$R^{33}$ is heteroarylene of no more than 10 carbons; and $R_{37}$ is —($C_1$-$C_6$alkyl)(heterocycloalkyl of no more than 10 carbons);

vii)

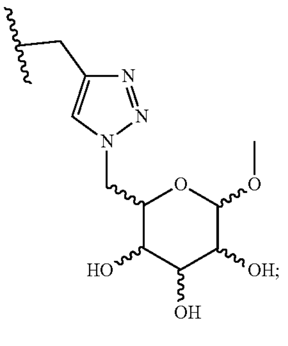 [SMILES: *Cc1cn(CC2OC(OC)C(O)C(O)C2O)nn1]

viii)

($C_1$-$C_{10}$ heteroalkyl)-$R_{33}$-$R_{37}$, wherein:

$R_{33}$ is heteroarylene of no more than 10 carbons; and $R_{37}$ is —($C_1$-$C_6$alkyl)(heterocycloalkyl of no more than 10 carbons); or ix)

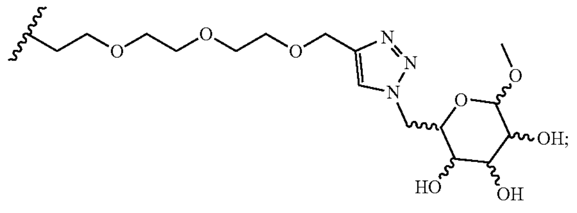 [SMILES: *CCOCCOCCOCc1cn(CC2OC(OC)C(O)C(O)C2O)nn1]

X is C═O or $SO_2$ or X and $R_{84}$ join to form a pyridinyl; Y is NH or S.

In certain embodiments, $R_{81}$ is hydrogen.

In certain embodiments, WSG is

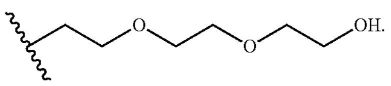 [SMILES: *CCOCCOCCO]

In certain embodiments, WSG is

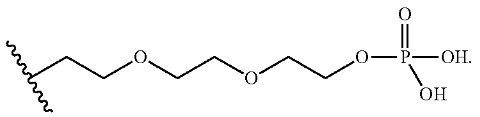 [SMILES: *CCOCCOCCOP(=O)(O)O]

In one aspect the disclosure provides a compound of Formula Id:

(Formula Id)

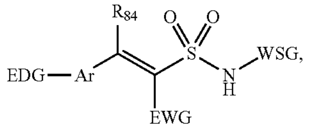

wherein EDG, $R_{84}$, Ar, EWG, and WSG are defined as above.

In one aspect the disclosure provides a compound of Formula Ie:

(Formula Ie)

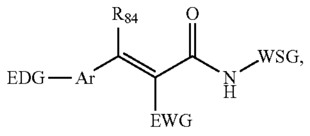

wherein EDG, $R_{84}$, Ar, EWG, and WSG are defined as above.

In some cases, the compound is selected from a group consisting of

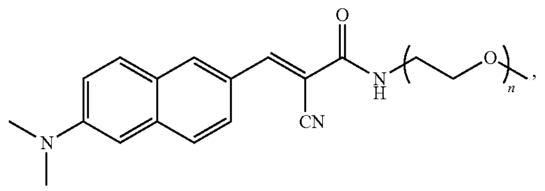

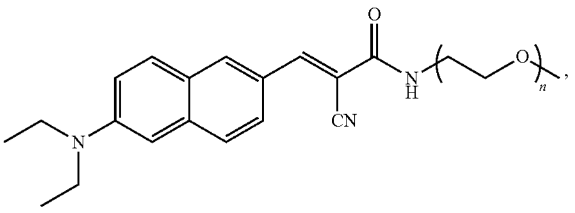

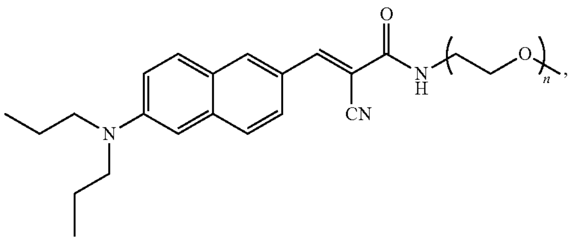

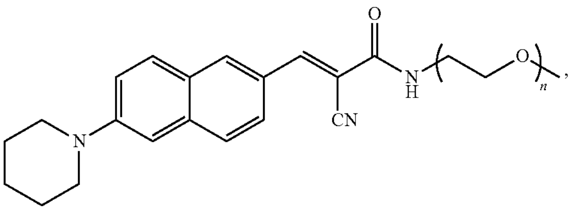

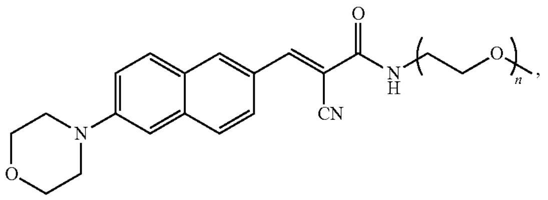

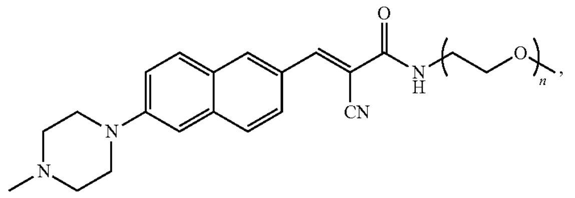

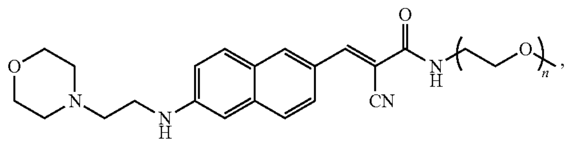

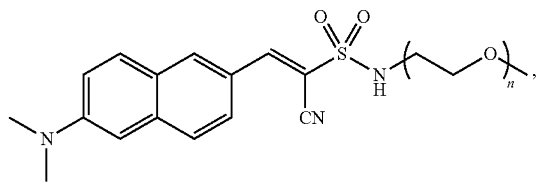

-continued
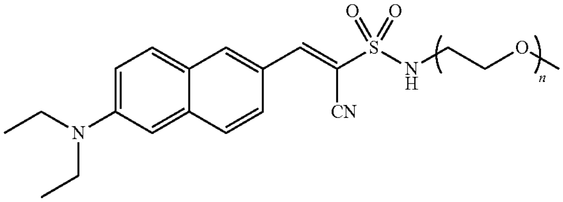,
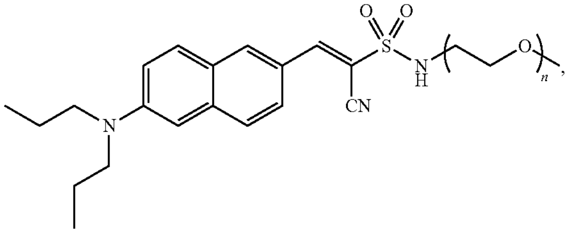,
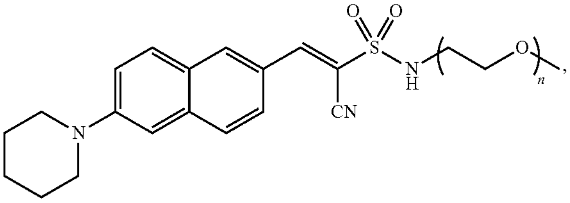,
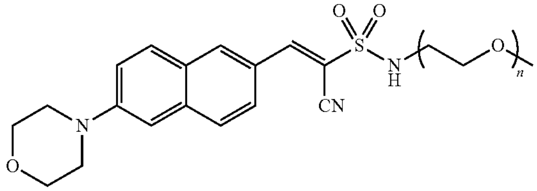,
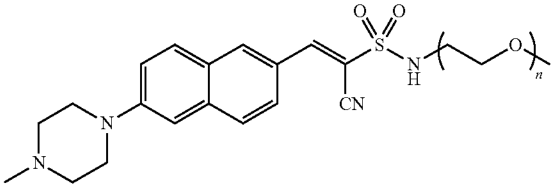,
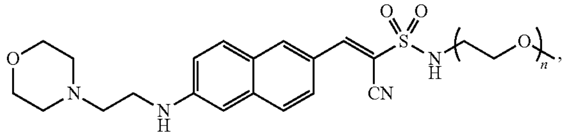,
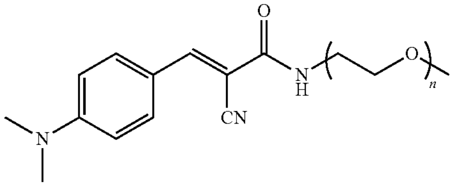,
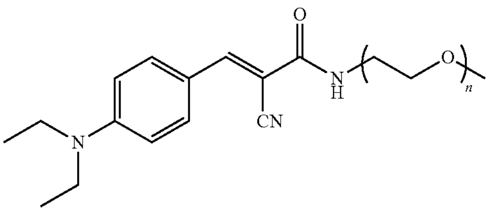,
-continued
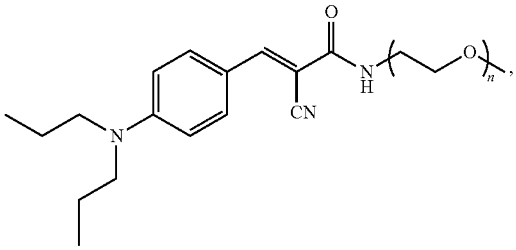,
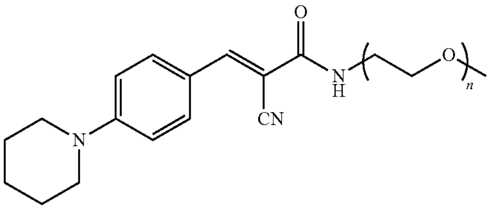,
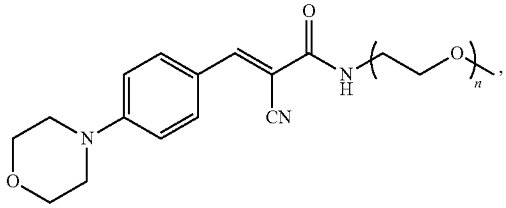,
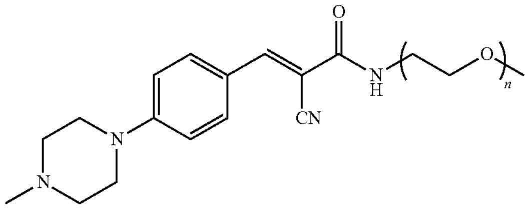,
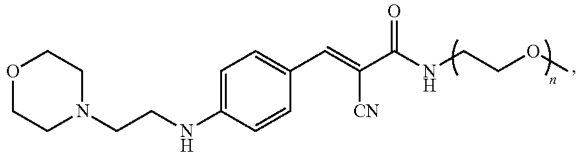,
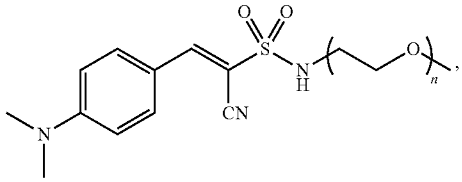,
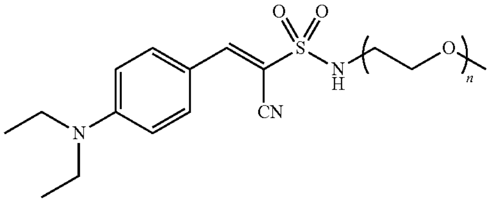,
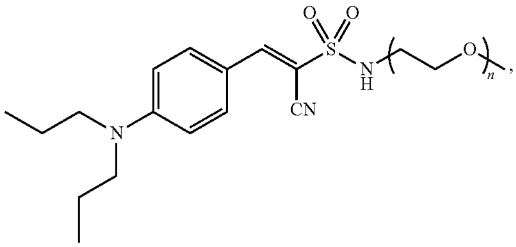, -continued
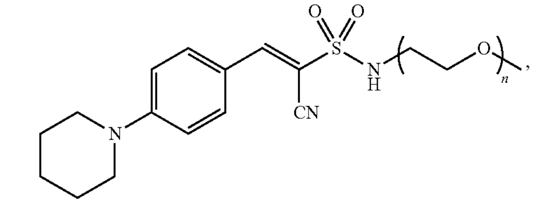
,
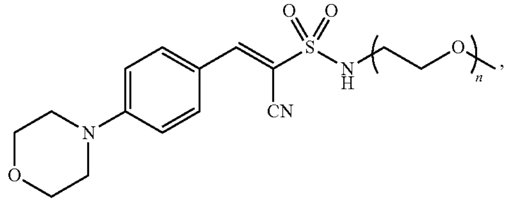
,
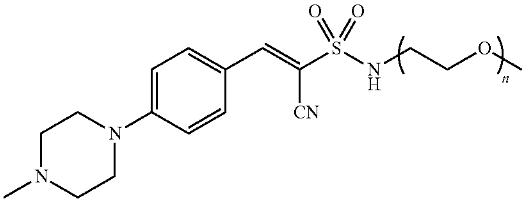
and
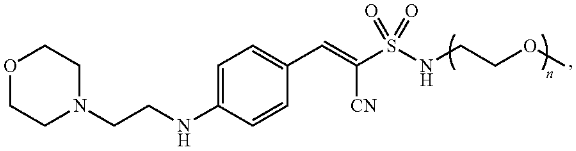
,
wherein n is an integer with value 1-50. In some cases, n is a integer of value 1-10, e.g. n is 1, 2, 3, 4, 5, 6, 7, 8, 9, or 10.
In certain embodiments, the compound is selected from a group consisting of
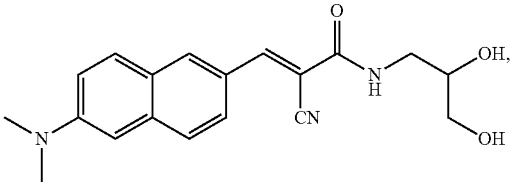
,
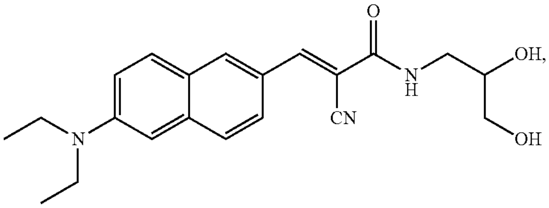
,
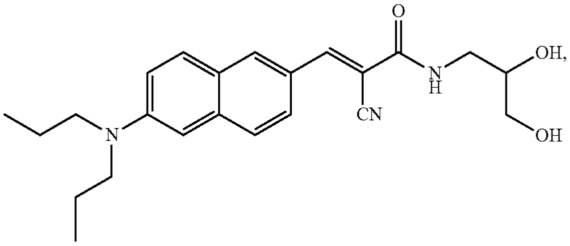
,
-continued
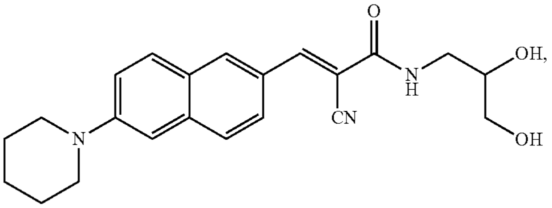
,
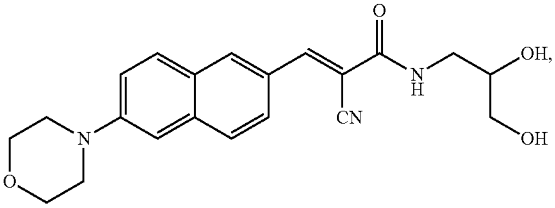
,
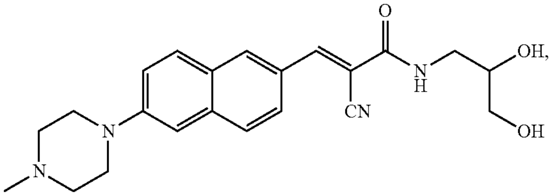
,
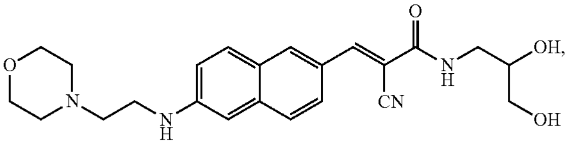
,
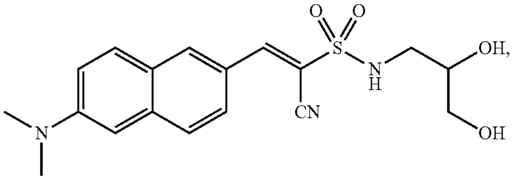
,
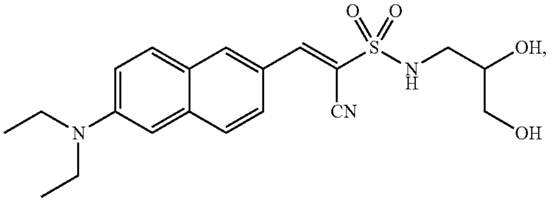
,
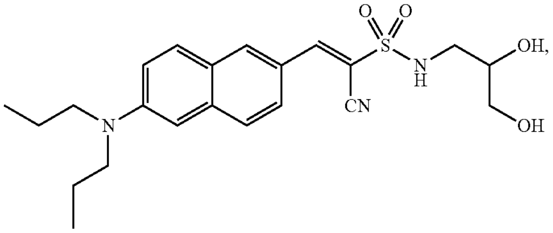
,
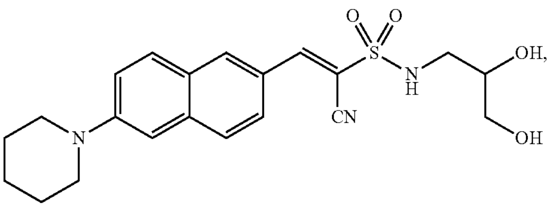
, -continued
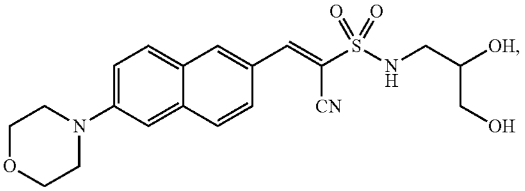
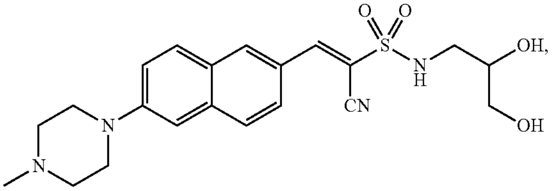
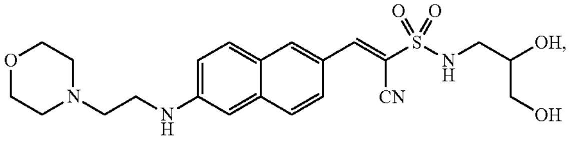
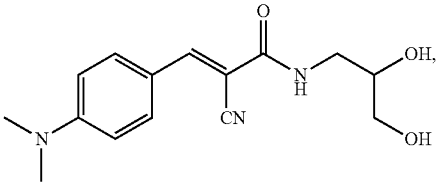
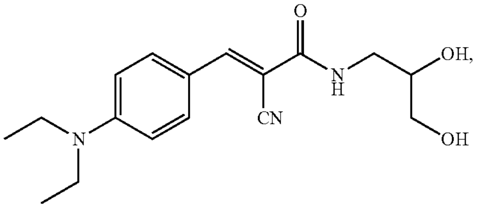
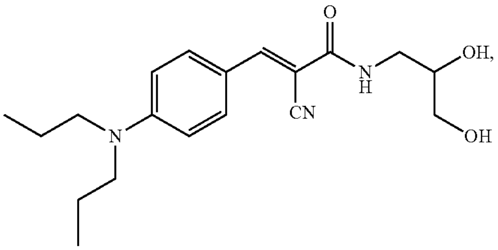
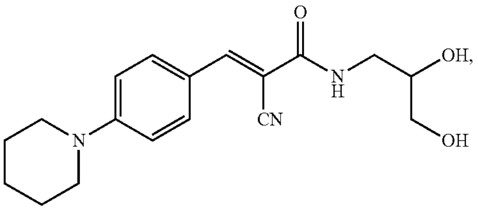
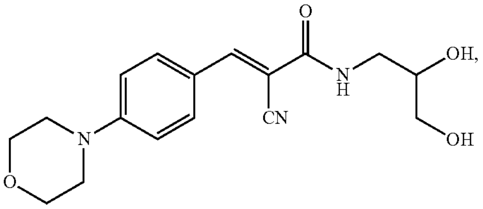
-continued
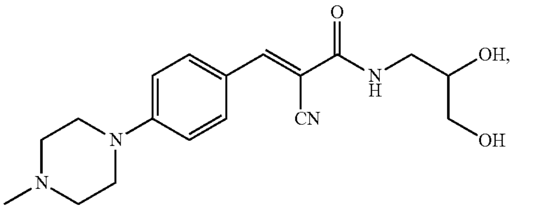
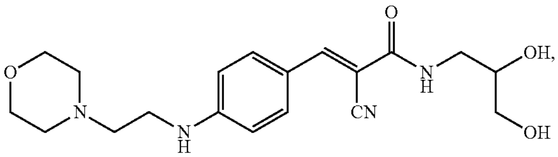
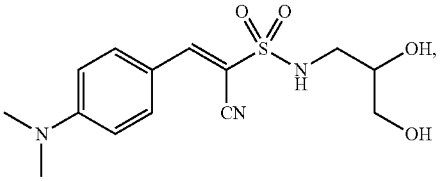
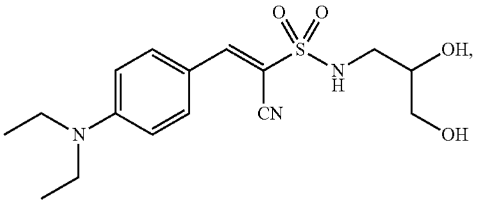
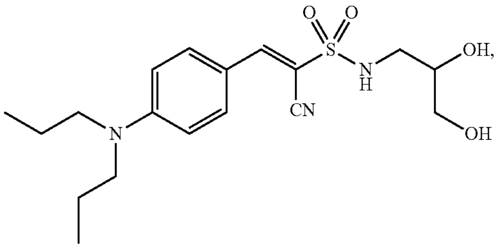
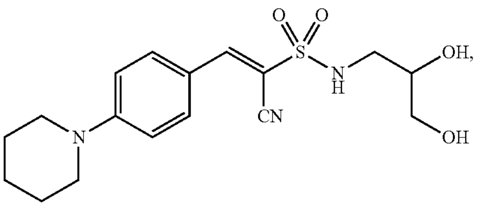
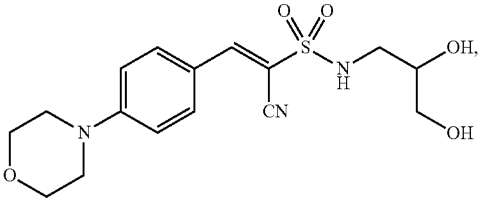

-continued
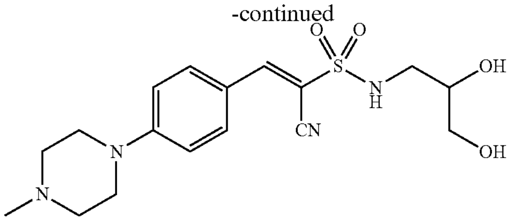
and
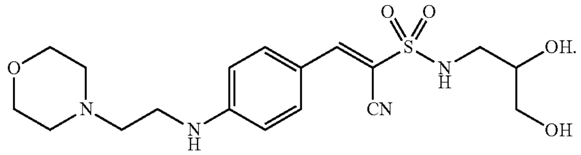 [SMILES: N#C/C(=C\c1ccc(NCCN2CCOCC2)cc1)S(=O)(=O)NCC(O)CO]
In certain embodiments, the compound is selected from a group consisting of
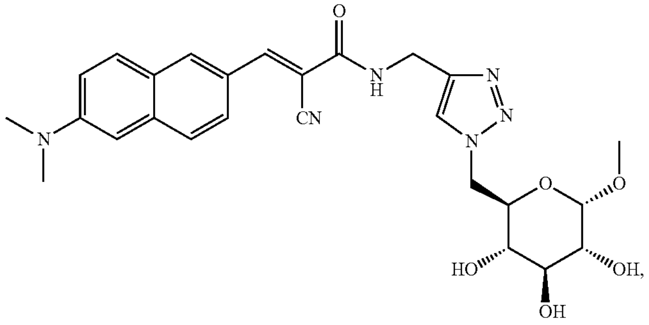
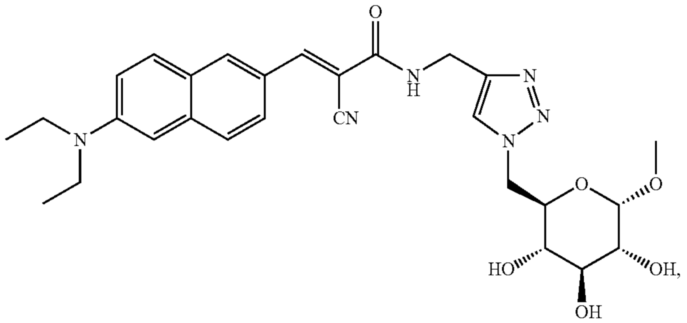
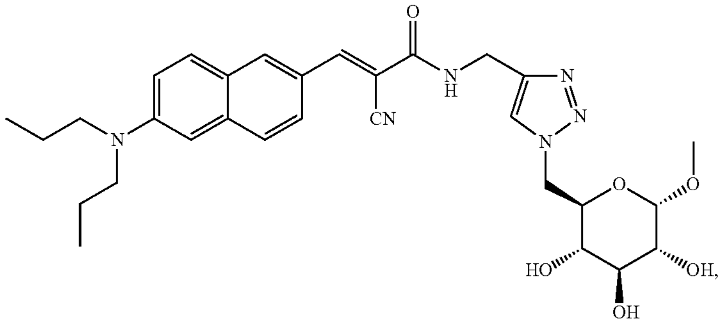
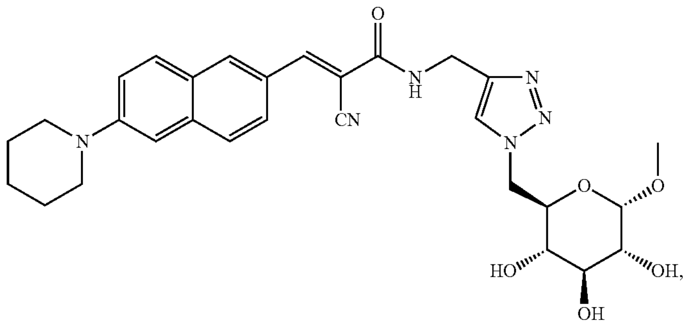

-continued
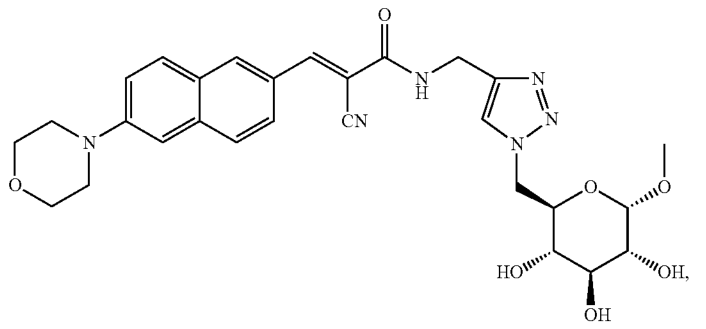
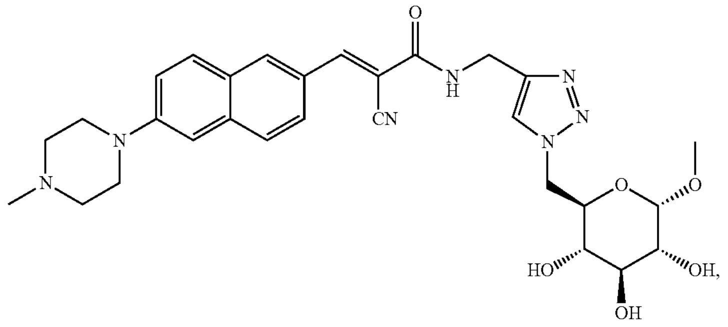
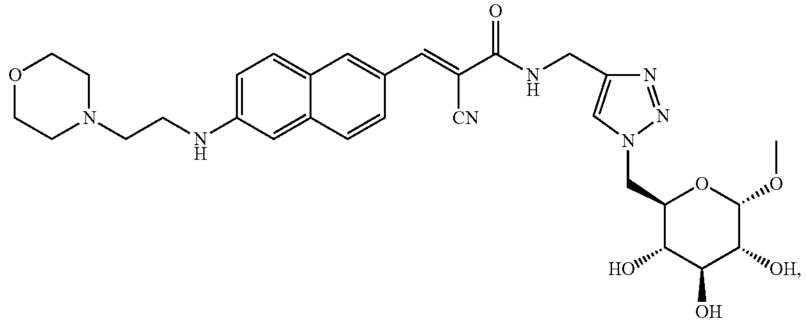
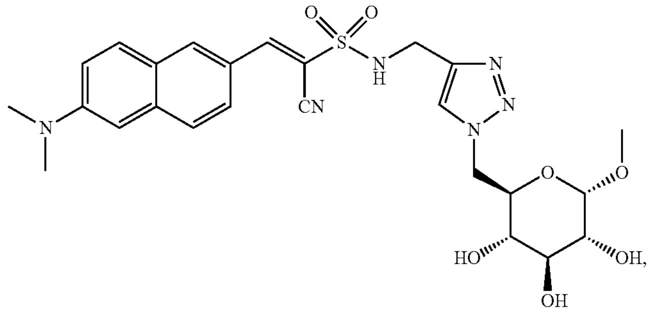
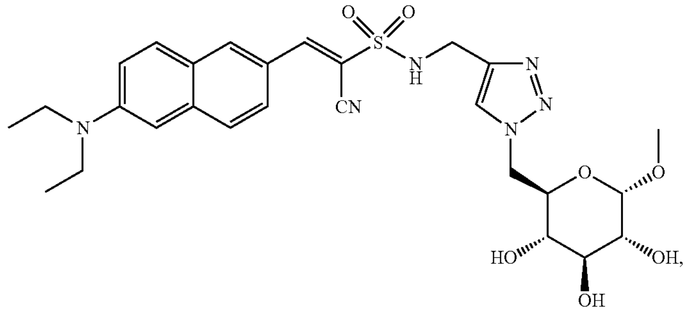

-continued
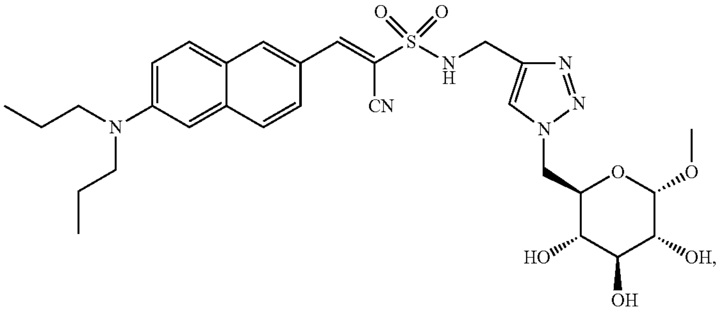
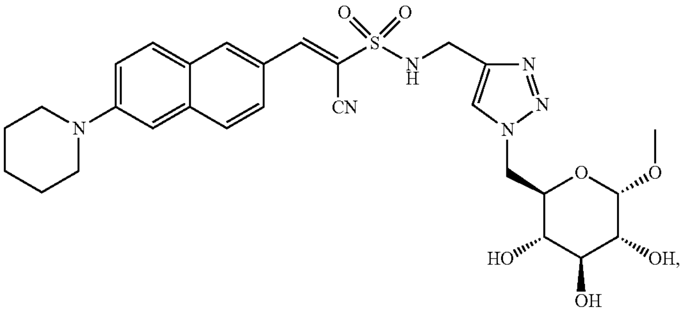
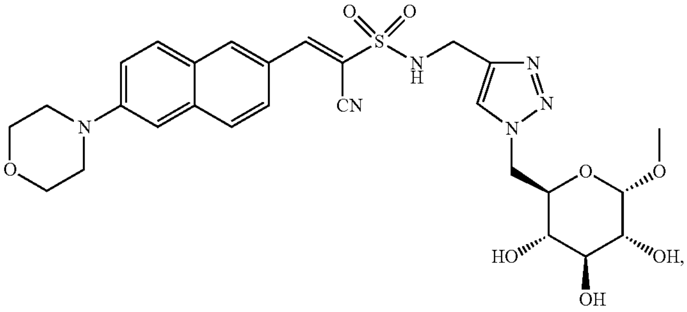
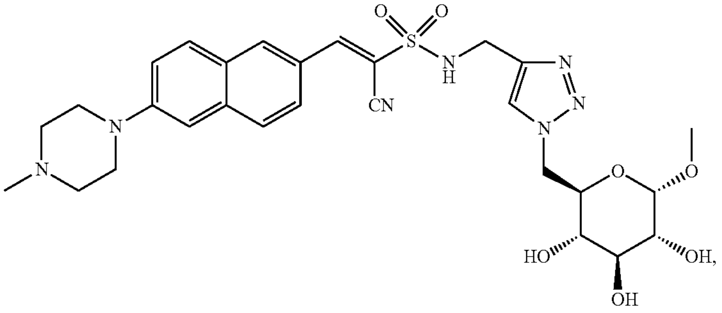
and
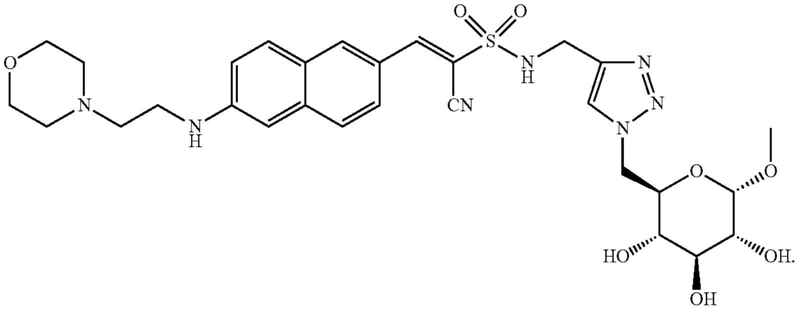

In certain embodiments, the compound is selected from a group consisting of
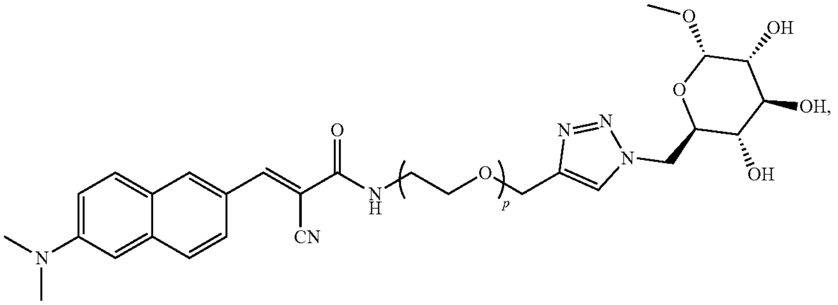
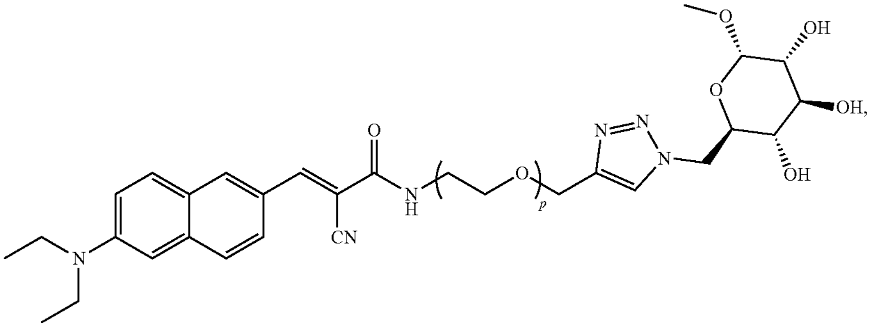
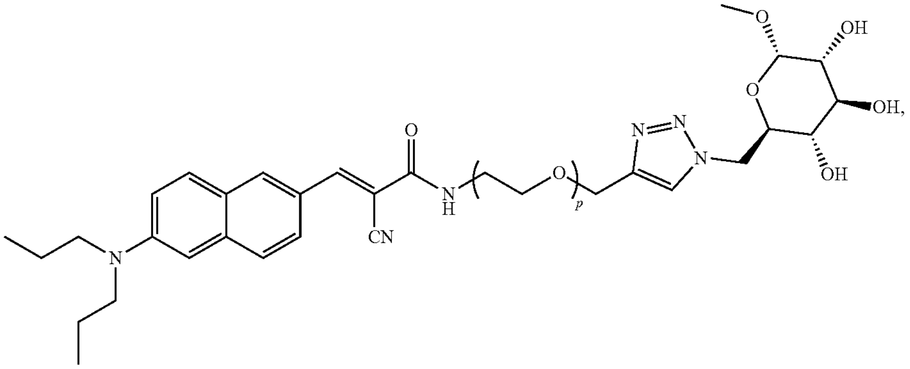
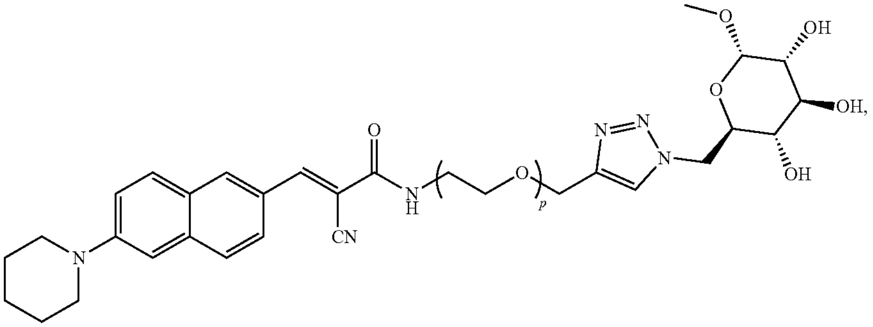
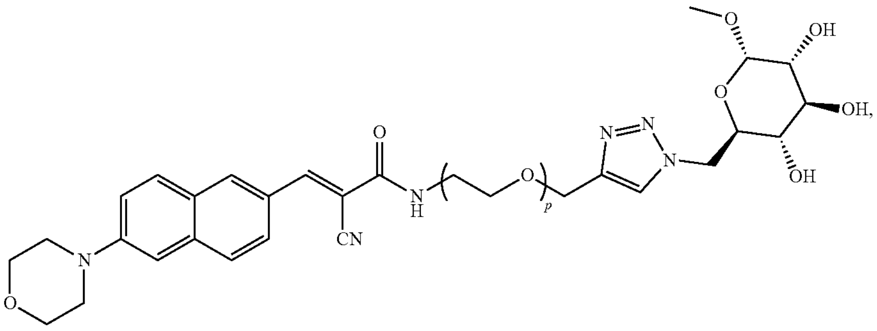

-continued
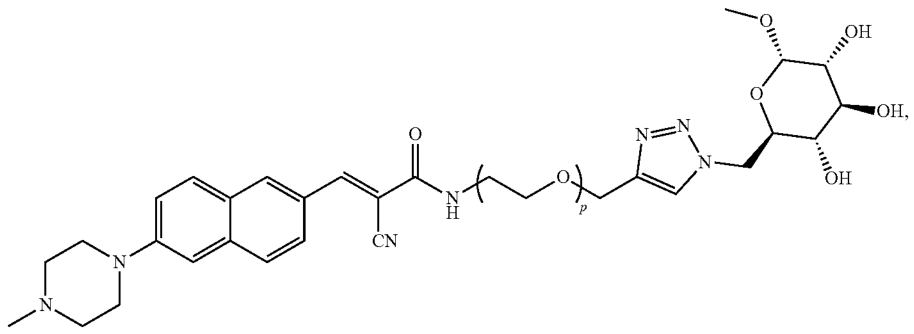
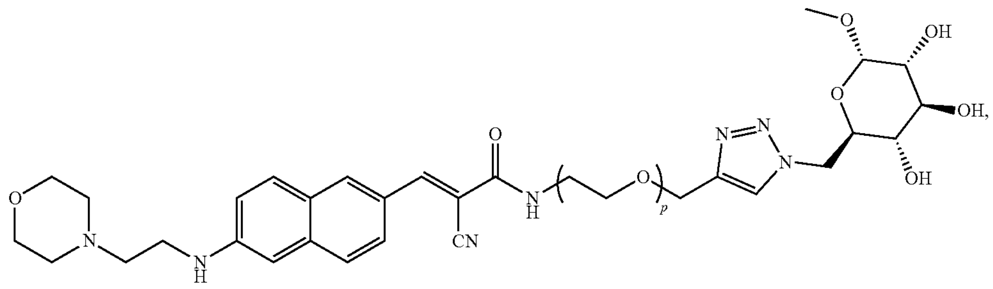
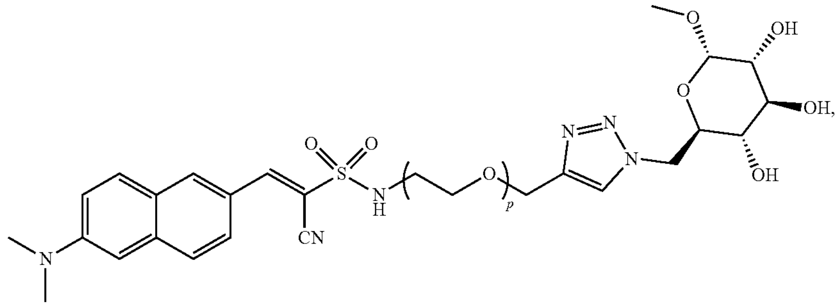
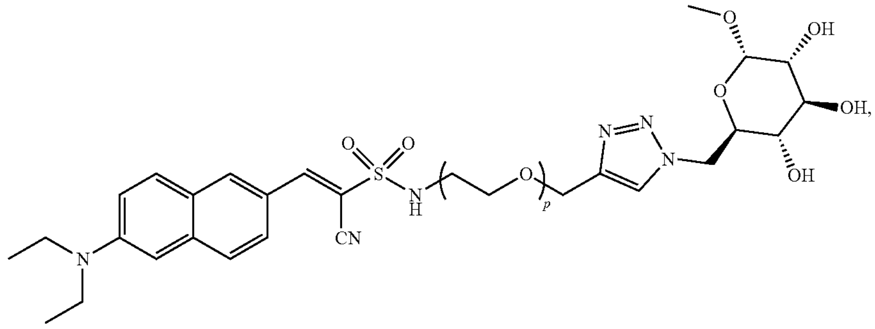
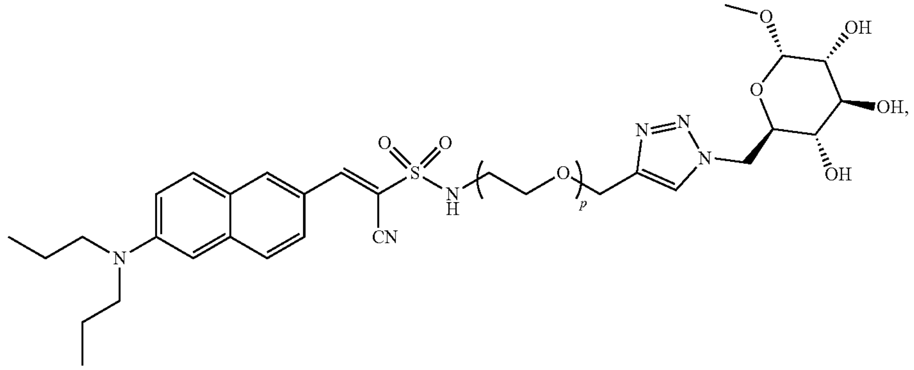

-continued
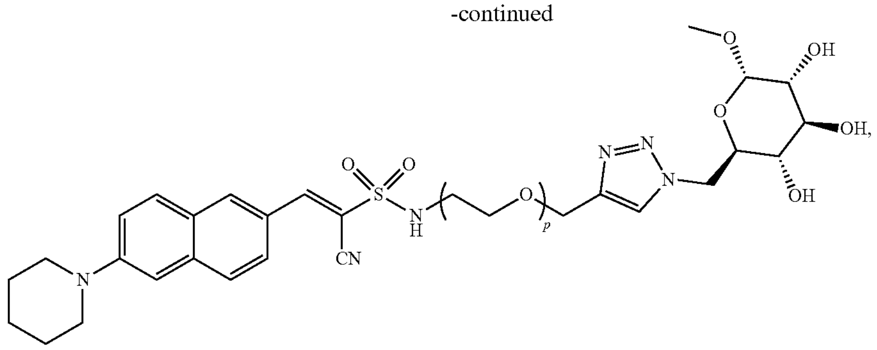
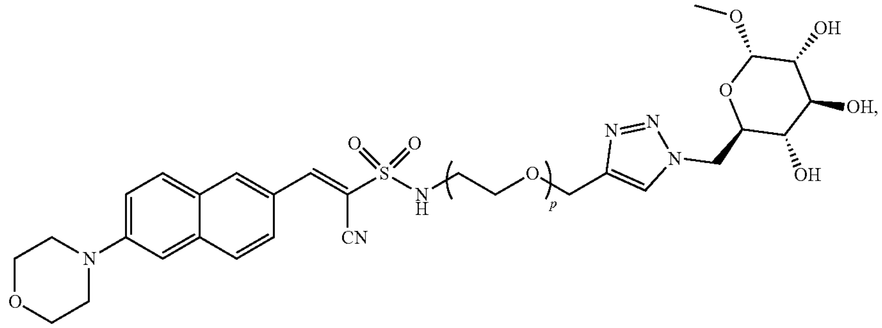
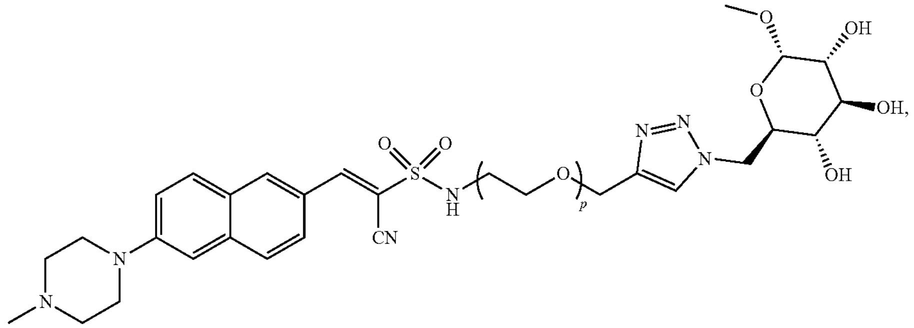
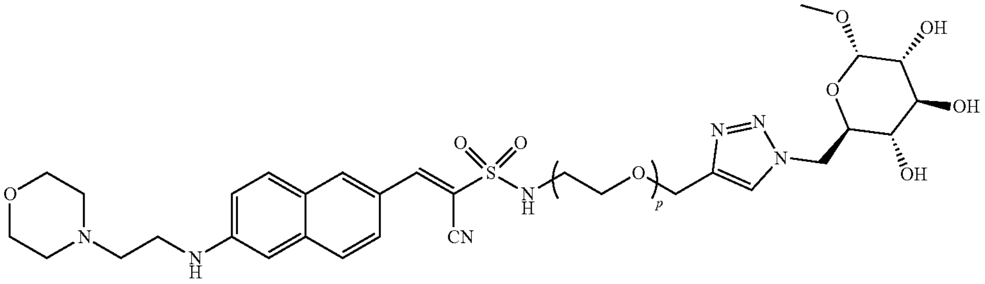
wherein p is an integer with value 1-50. In some cases, p is a integer of value 1-10, e.g. n is 1, 2, 3, 4, 5, 6, 7, 8, 9, or 10.
In certain embodiments, the compound is selected from a group consisting of
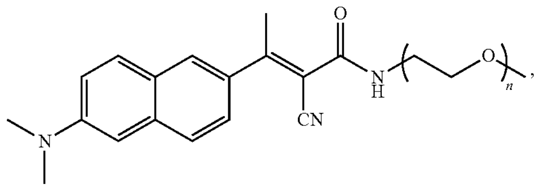
-continued
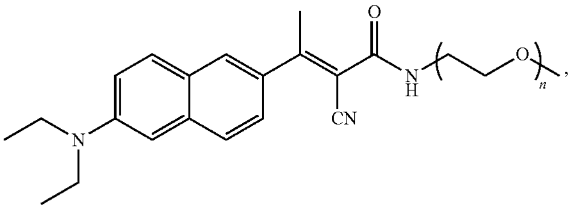

-continued
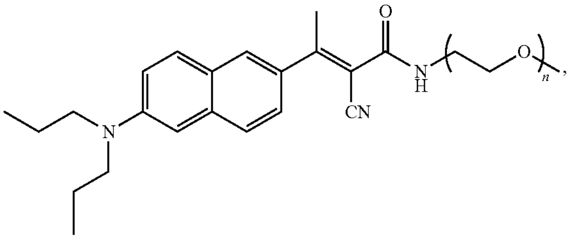,
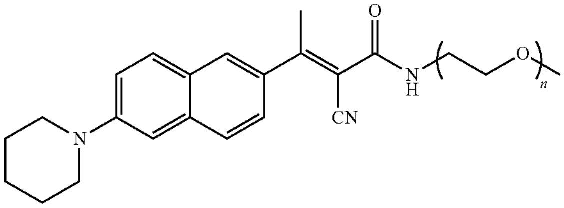,
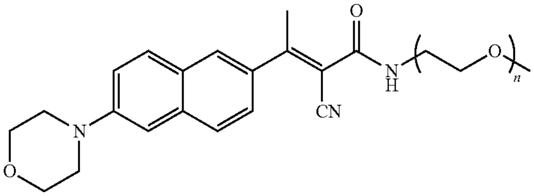,
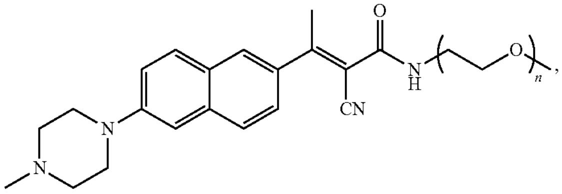,
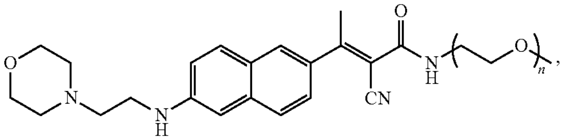,
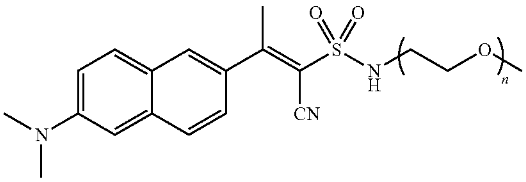,
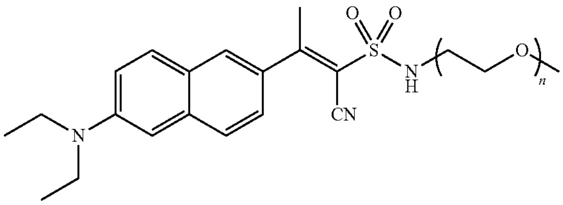,
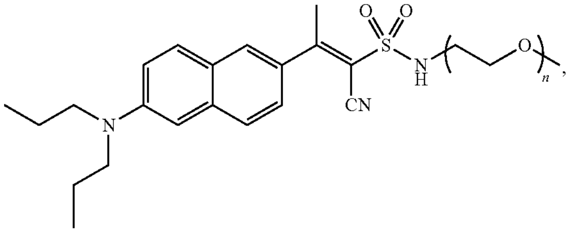,
-continued
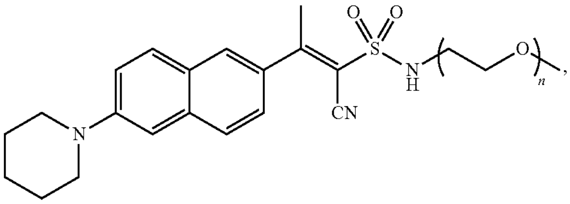,
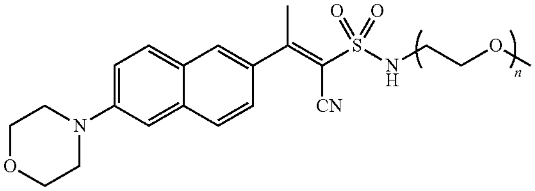,
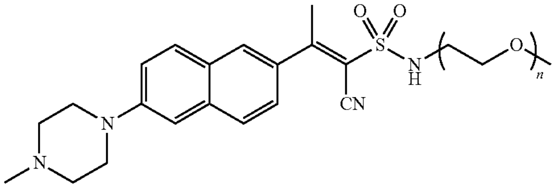,
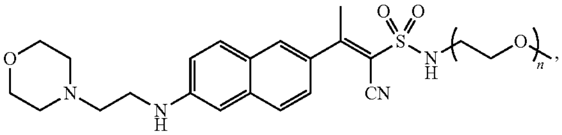,
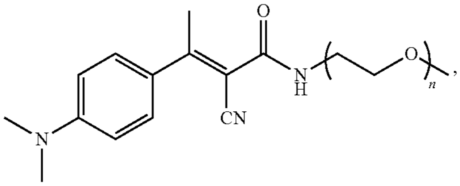,
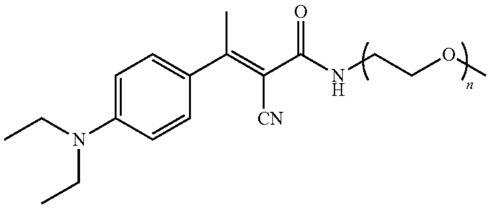,
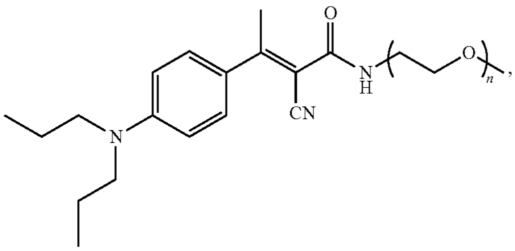,
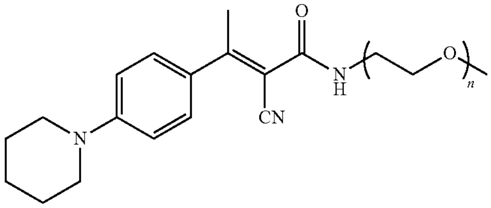, -continued
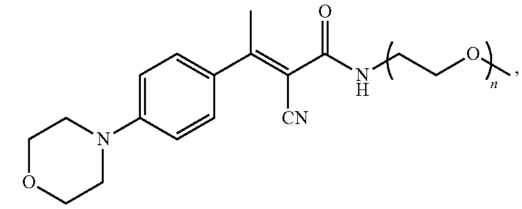,
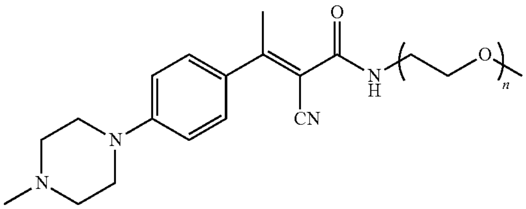,
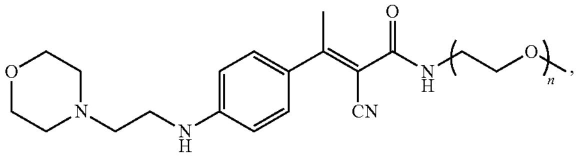,
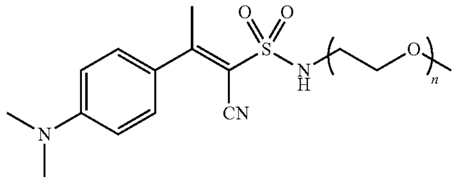,
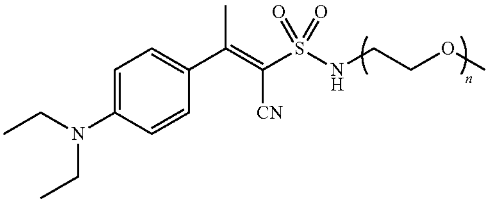,
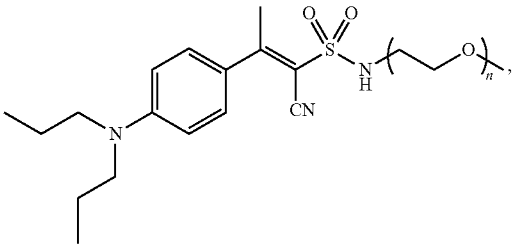,
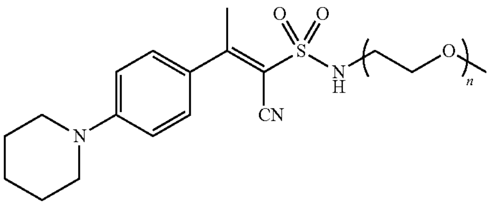,
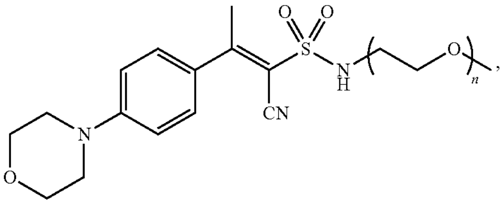,
-continued
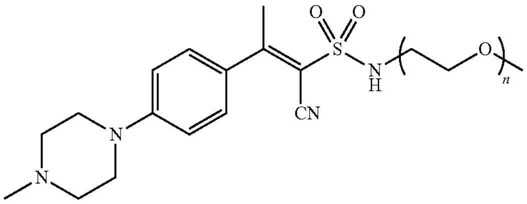 and
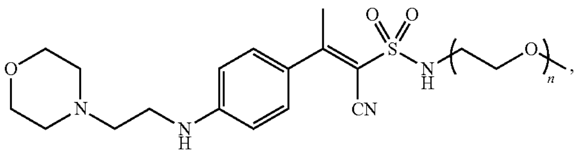,
wherein n is an integer with value 1-50. In some cases, n is a integer of value 1-10, e.g. n is 1, 2, 3, 4, 5, 6, 7, 8, 9, or 10.
In certain embodiments, the compound is selected from a group consisting of
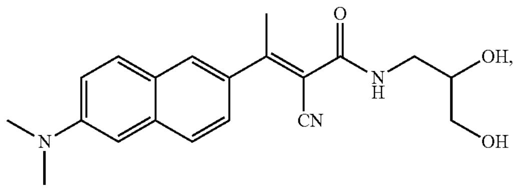,
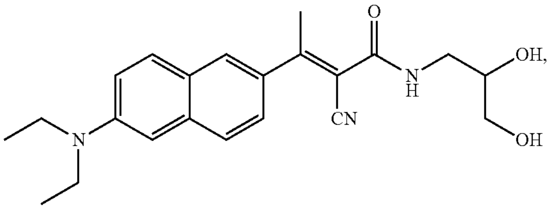,
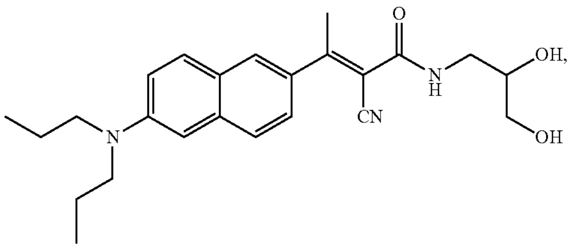,
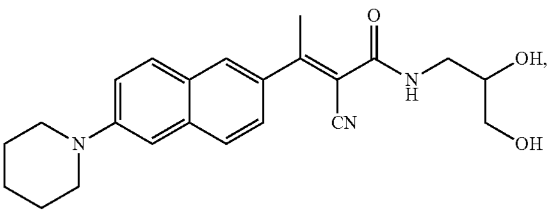,
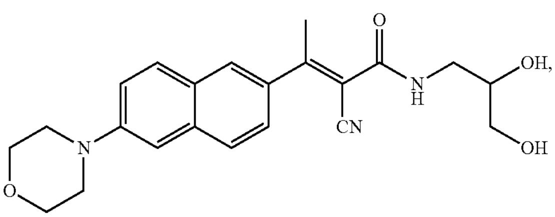

-continued
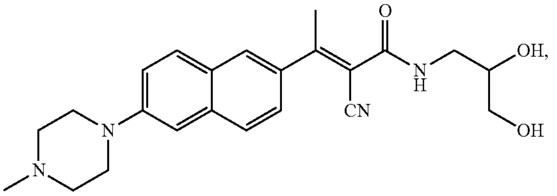
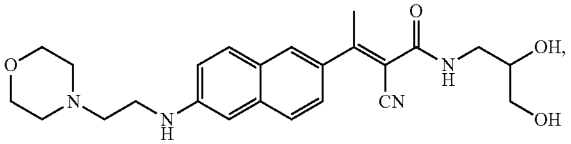
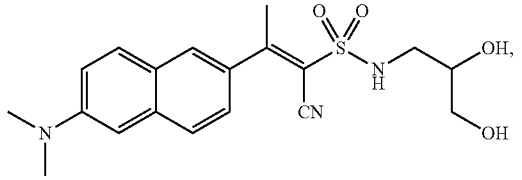
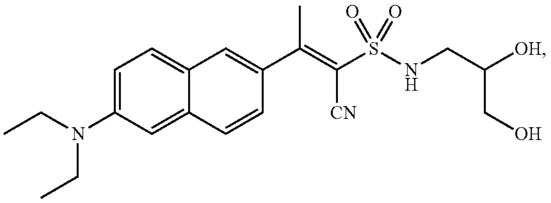
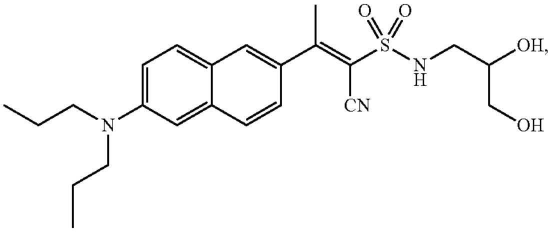
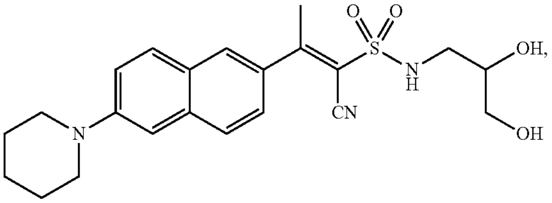
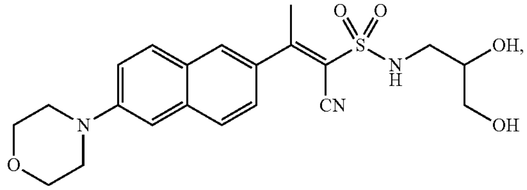
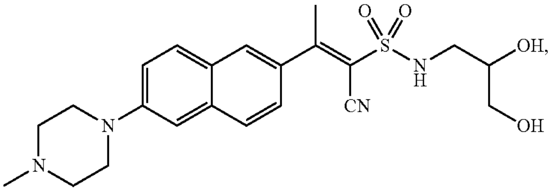
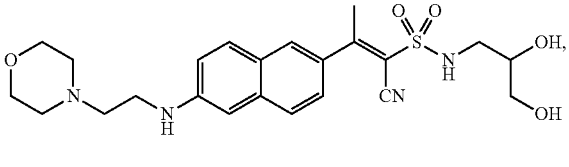
-continued
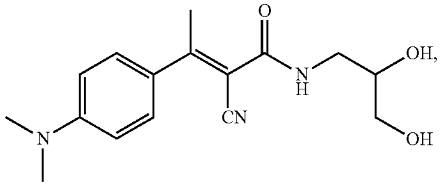
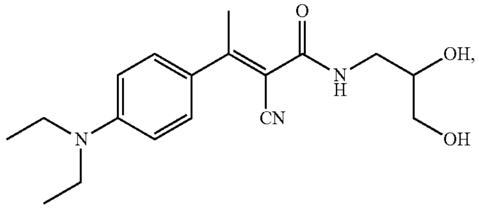
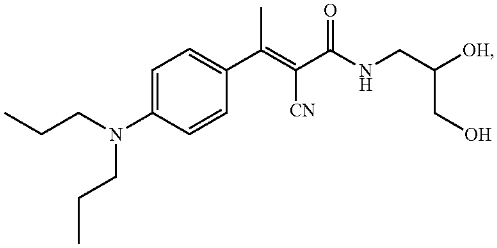
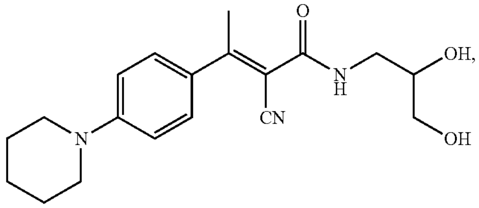
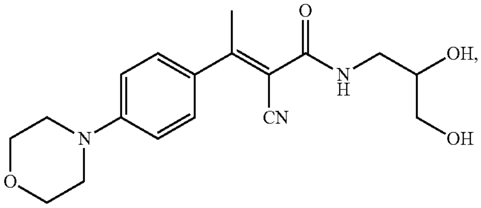
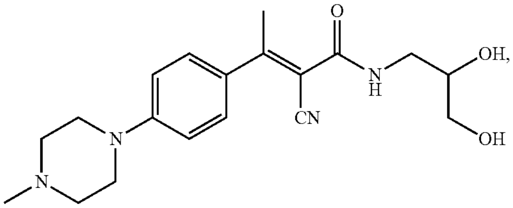
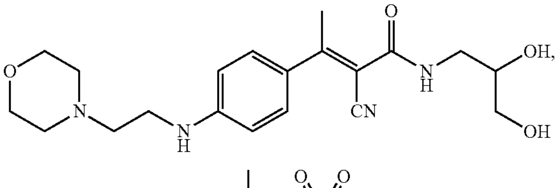
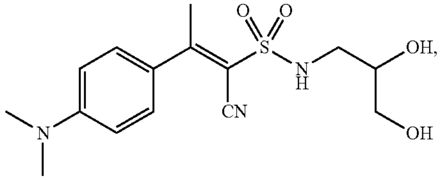

-continued
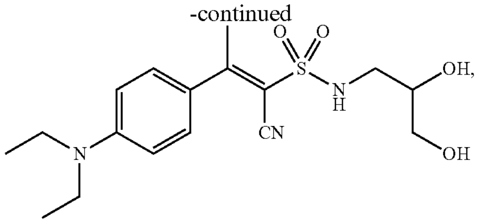
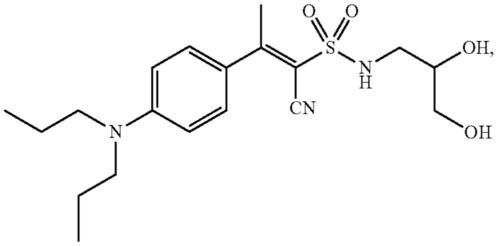
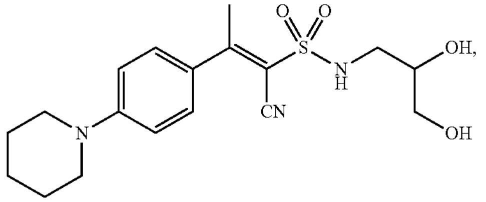
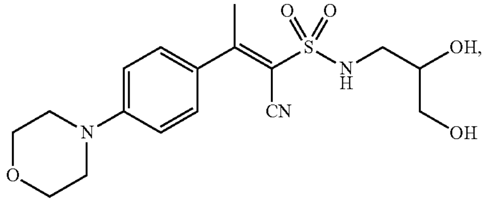
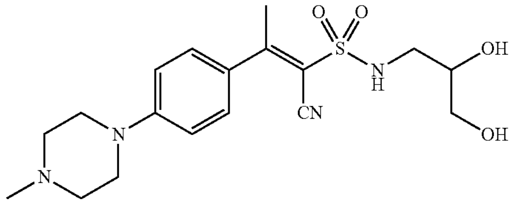
and
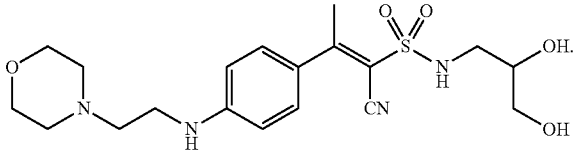 [SMILES: C/C(=C(/C#N)S(=O)(=O)NCC(O)CO)c1ccc(NCCN2CCOCC2)cc1]
In certain embodiments, the compound is selected from a group consisting of
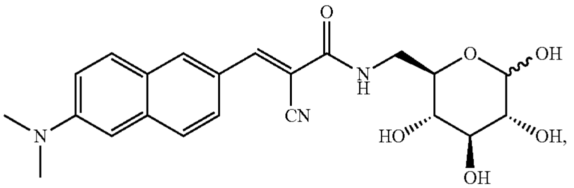
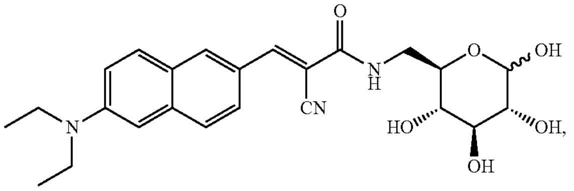
-continued
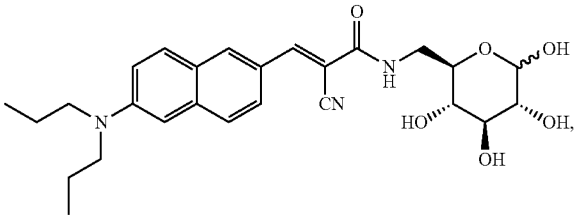
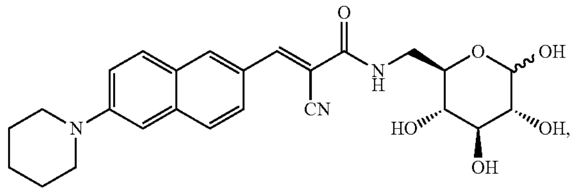
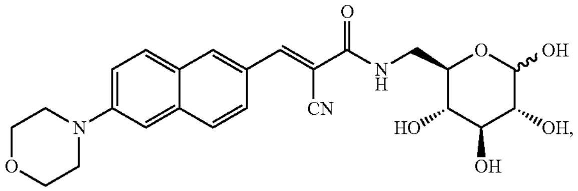
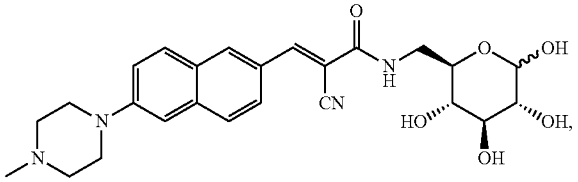
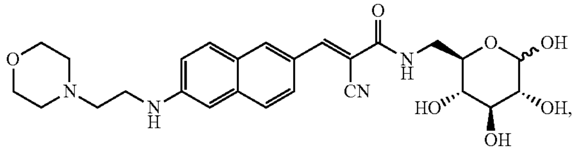
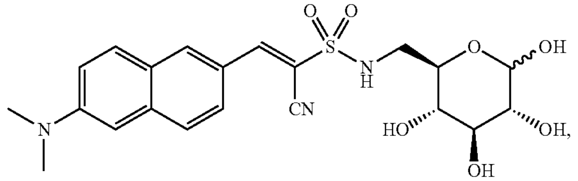
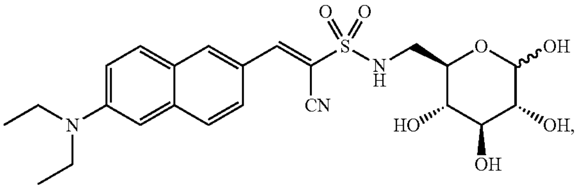
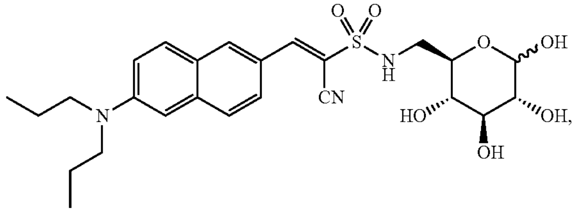
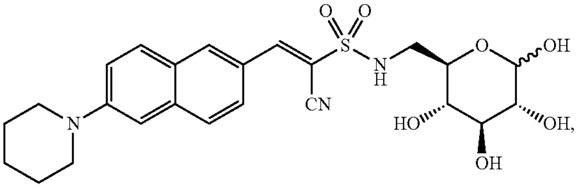

-continued
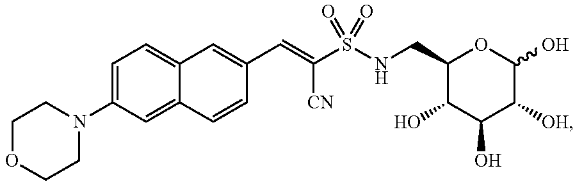
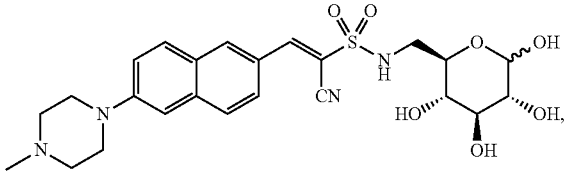
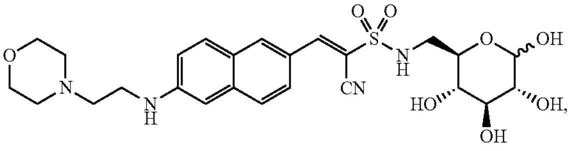
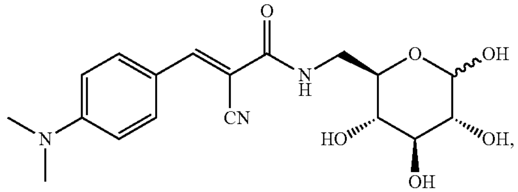
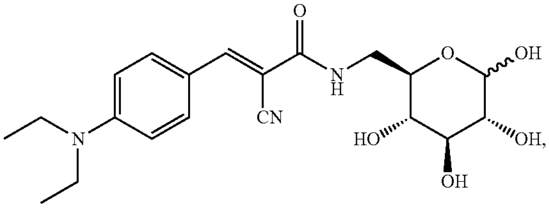
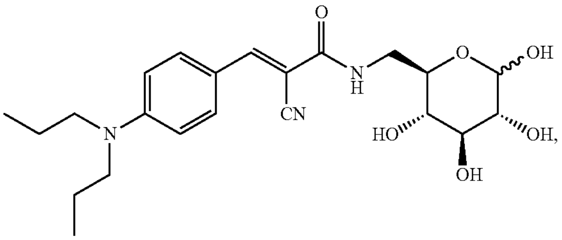
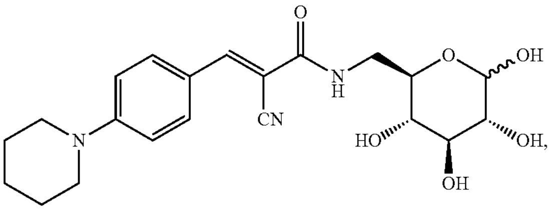
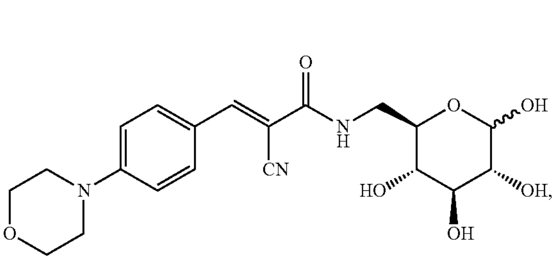
-continued
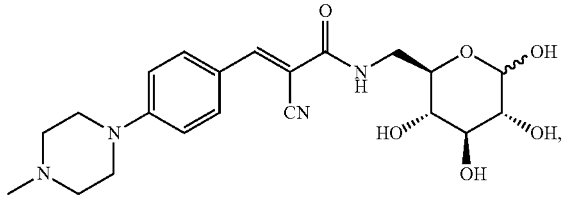
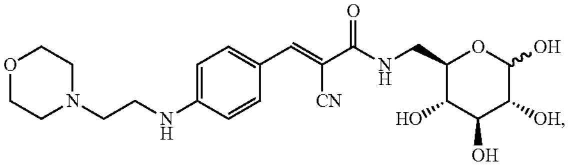
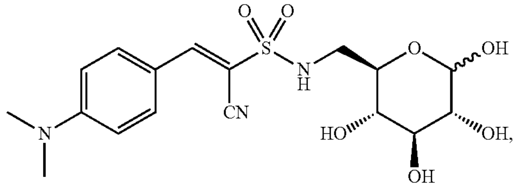
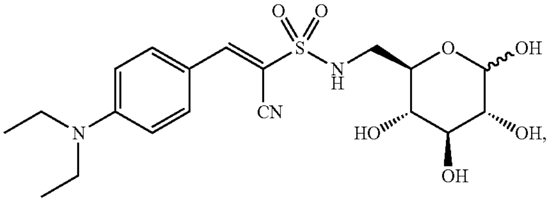
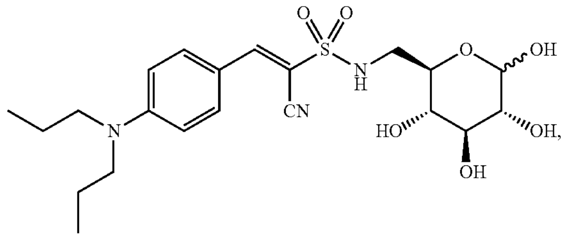
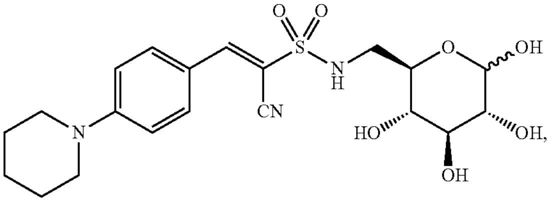
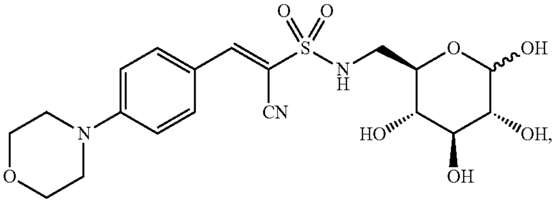
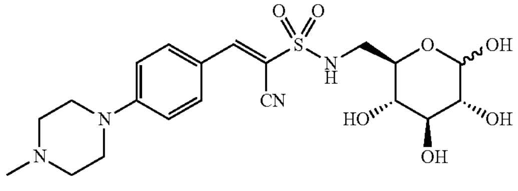
and -continued
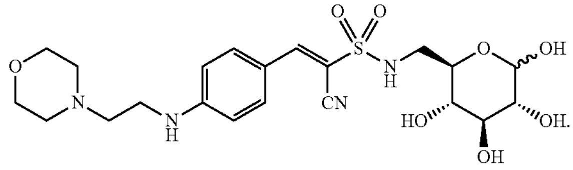
In certain embodiments, the compound is selected from a group consisting of
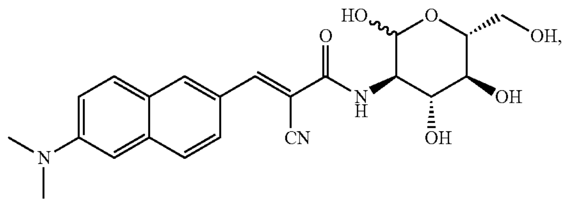
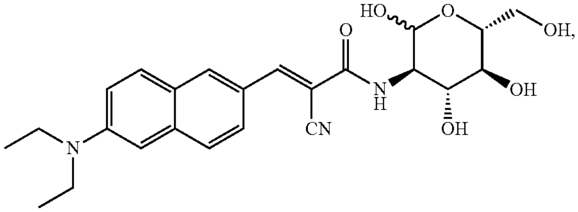
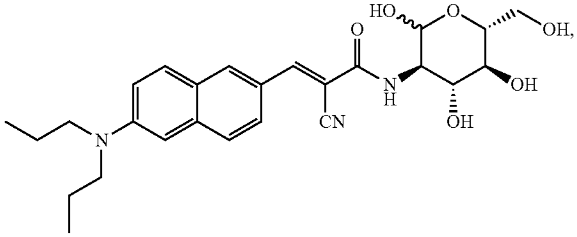
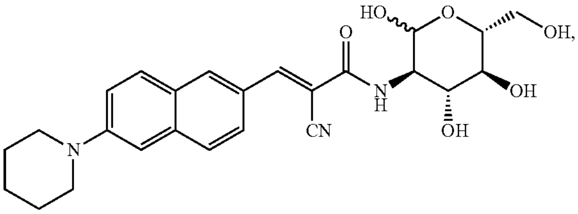
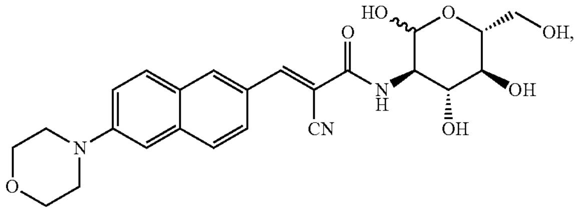
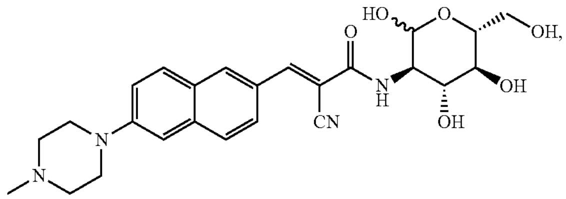
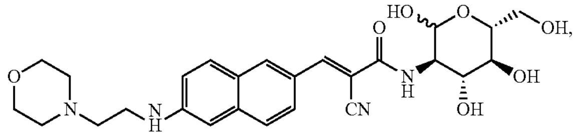
-continued
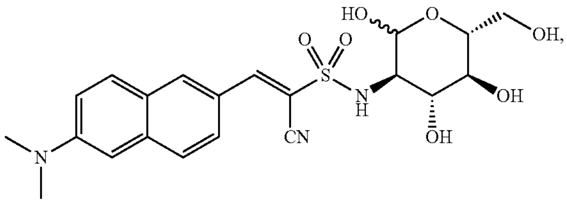
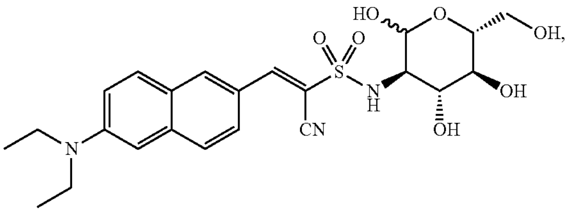
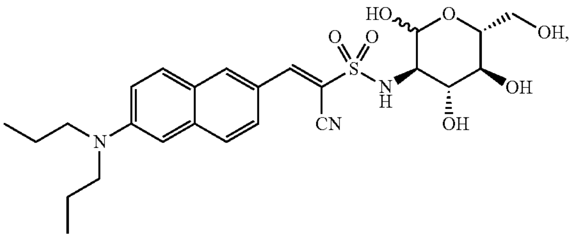
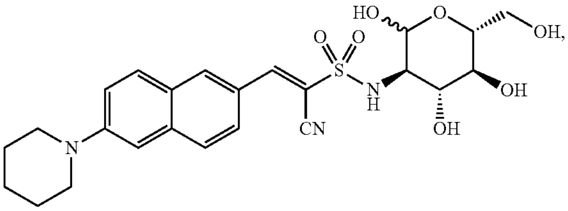
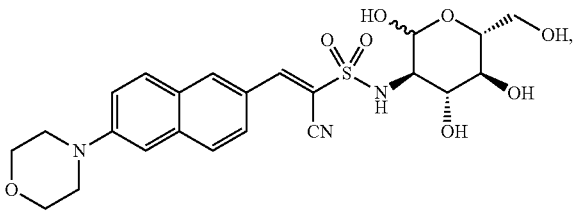
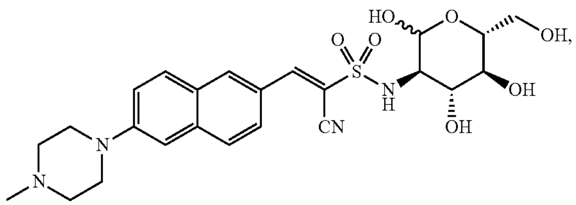
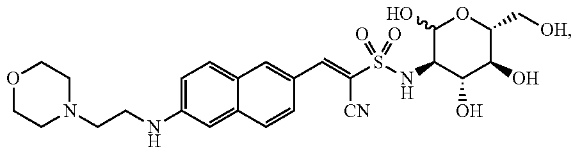
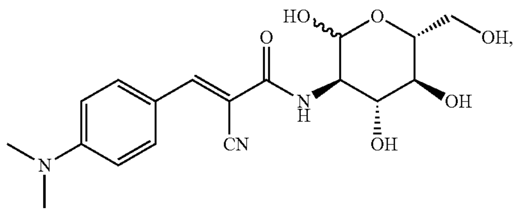

-continued
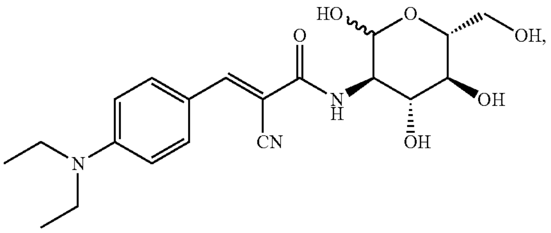
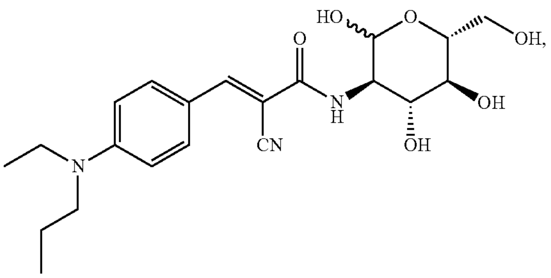
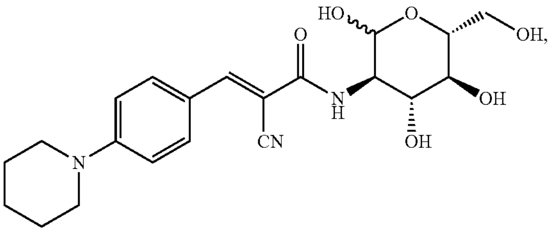
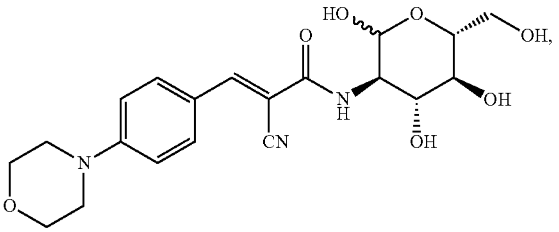
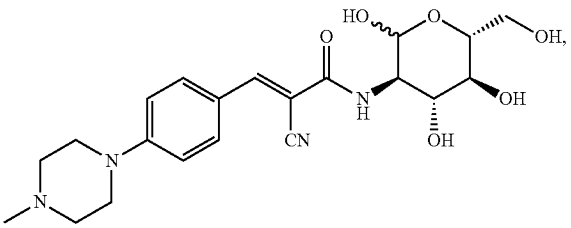
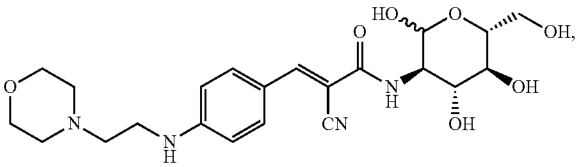
-continued
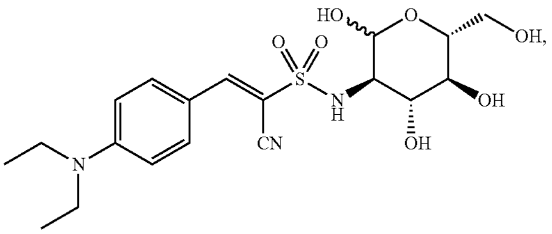
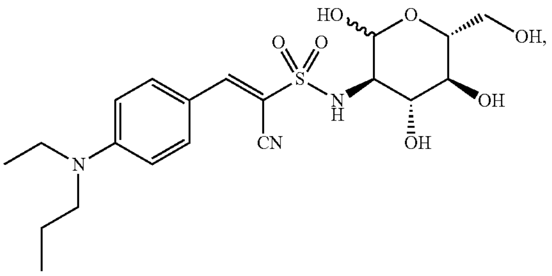
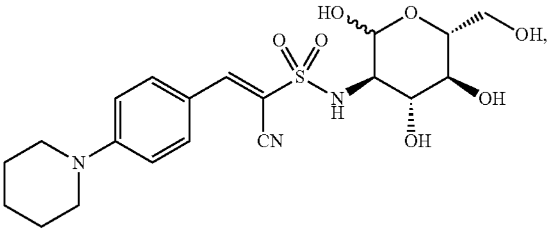
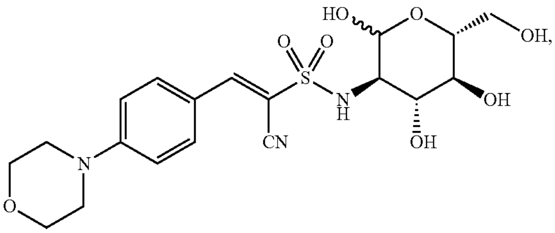
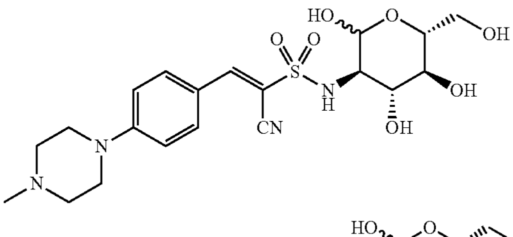
and
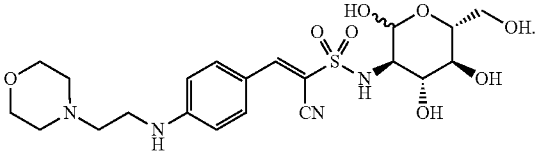
In certain embodiments, the compound is selected from a group consisting of
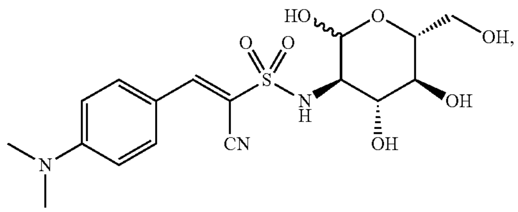
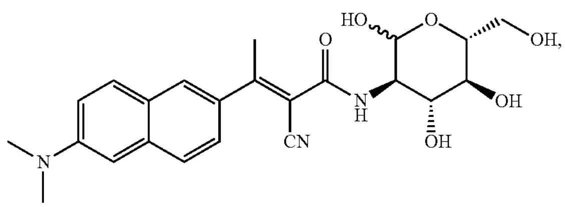

-continued
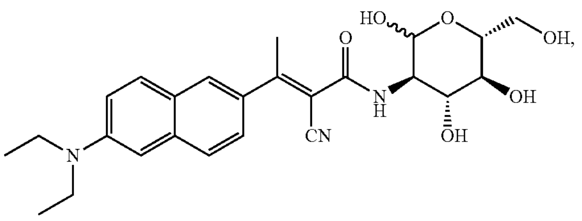
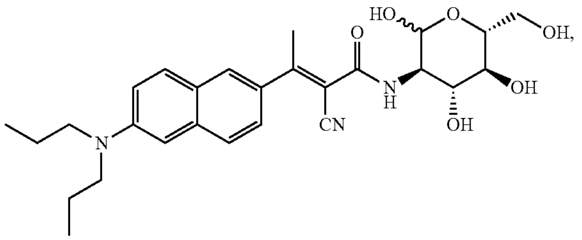
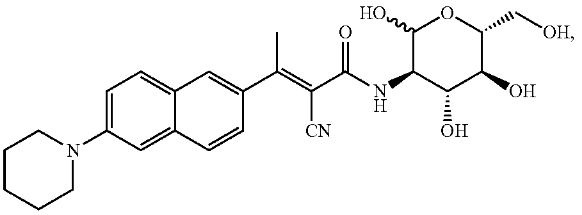
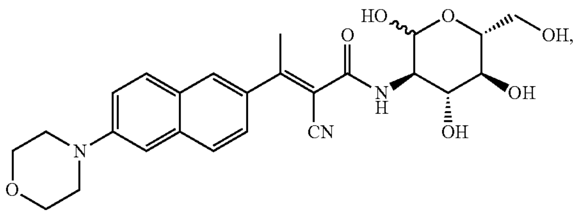
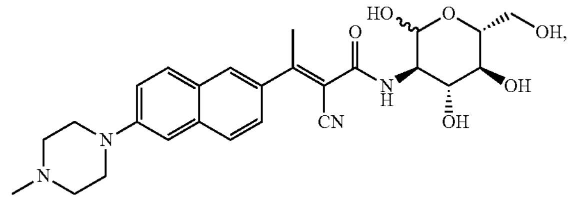
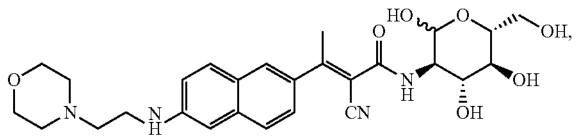
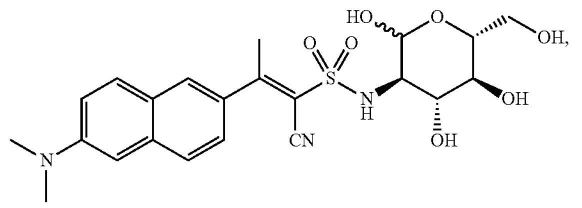
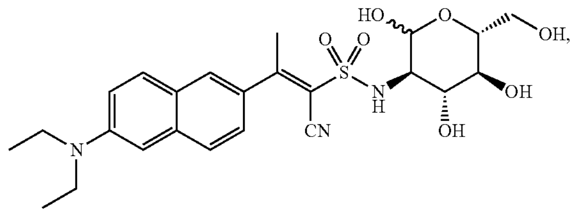
-continued
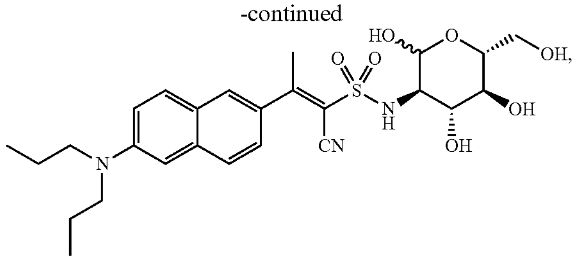
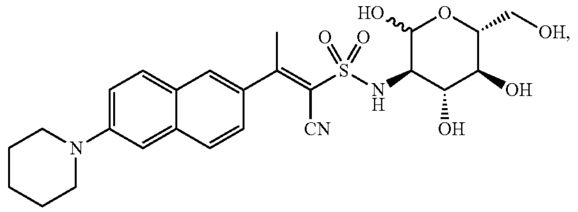
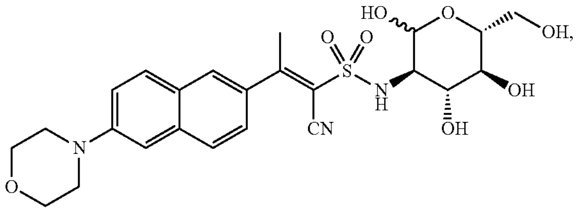
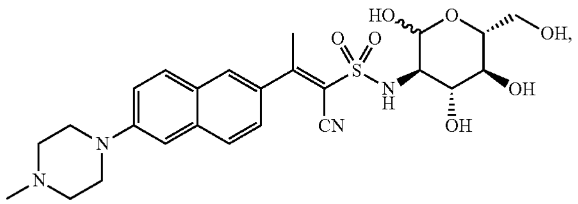
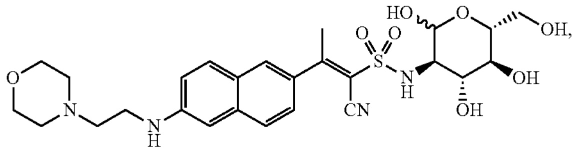
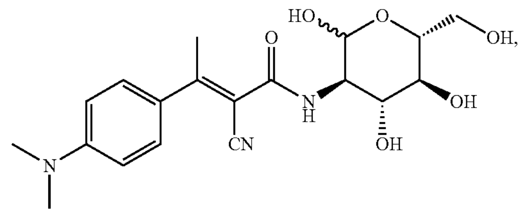
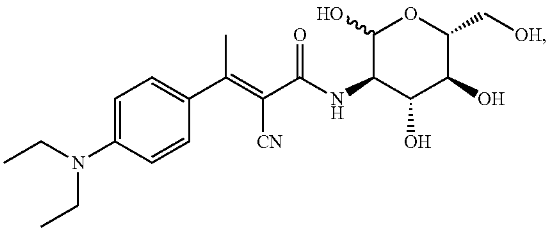
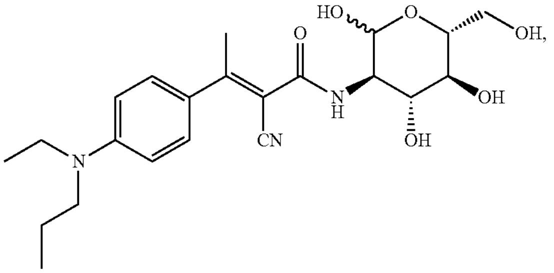

-continued
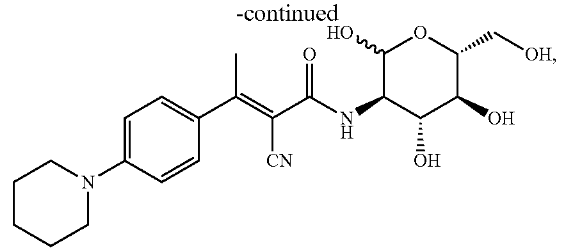
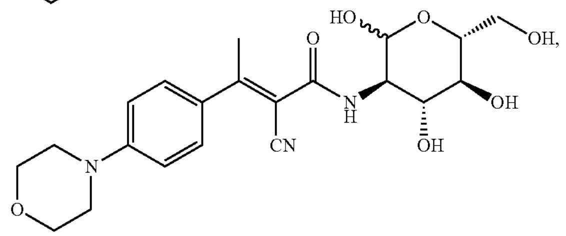
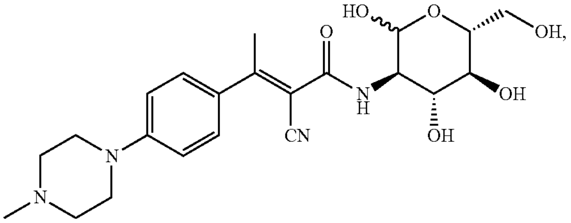
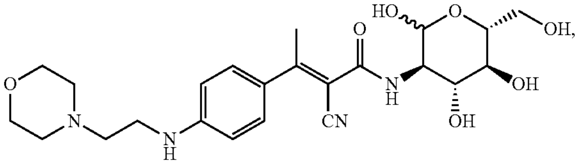
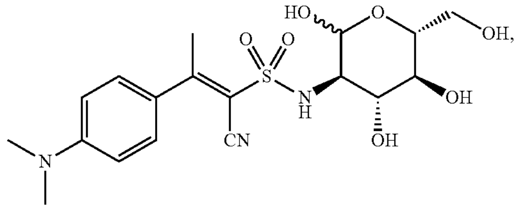
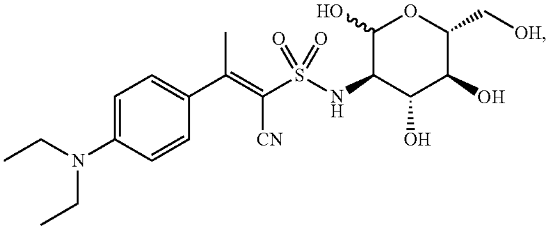
-continued
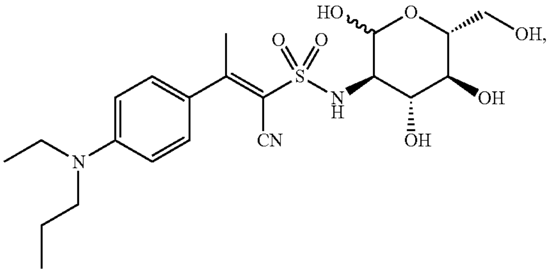
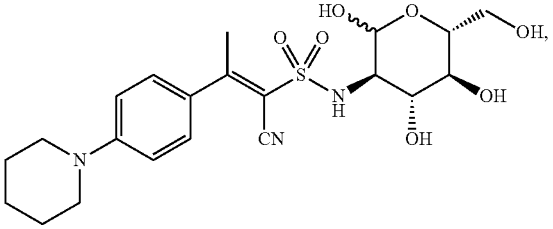
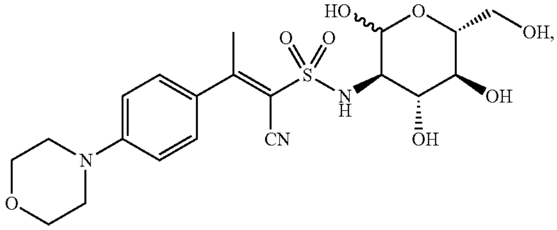
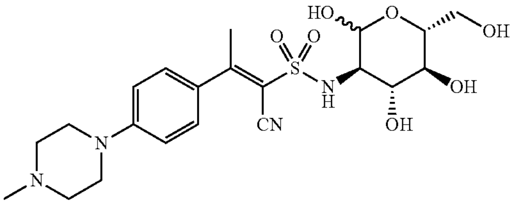
and
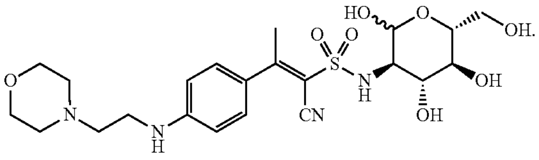
In certain embodiments, the compound is selected from a group consisting of
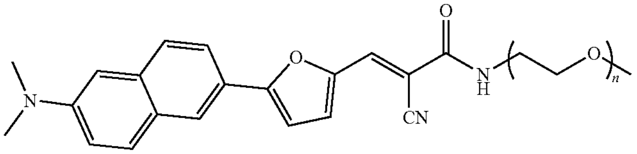
,
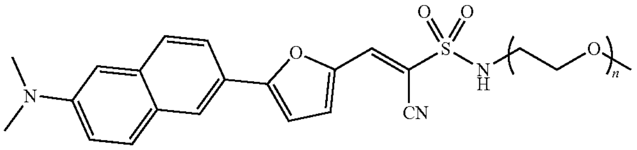
, -continued
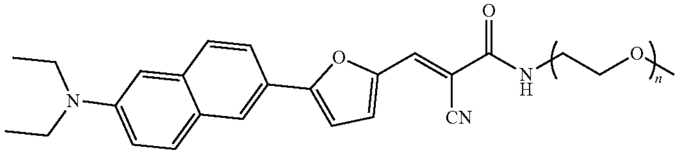
,
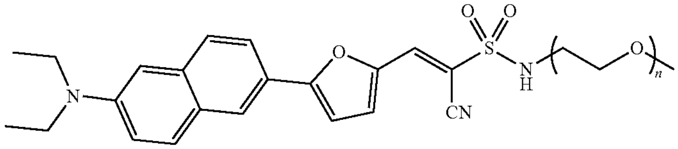
,
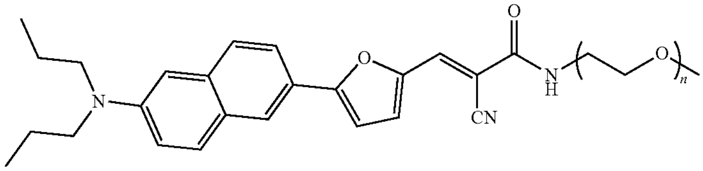
,
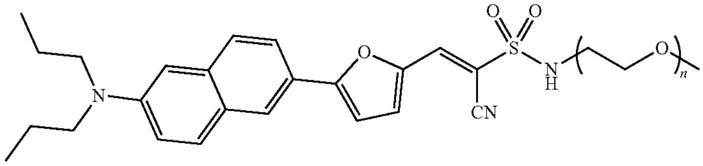
,
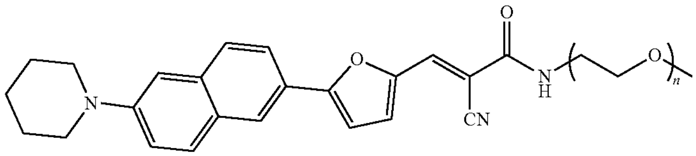
,
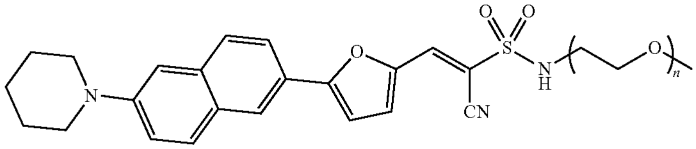
,
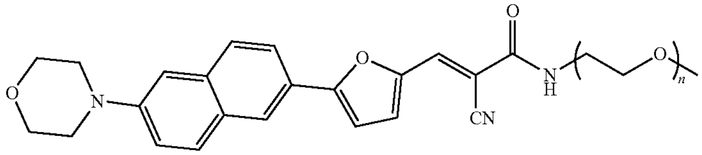
,
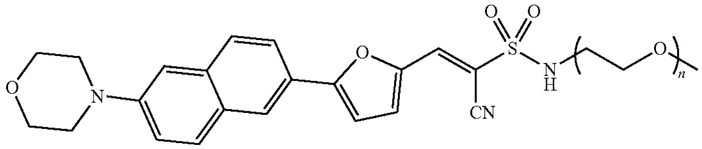
,
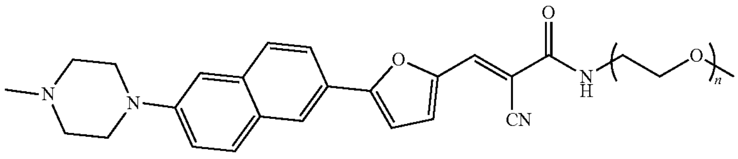
,
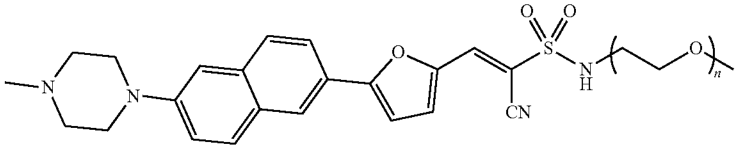
,
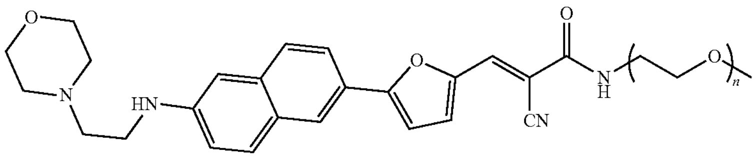
, and -continued
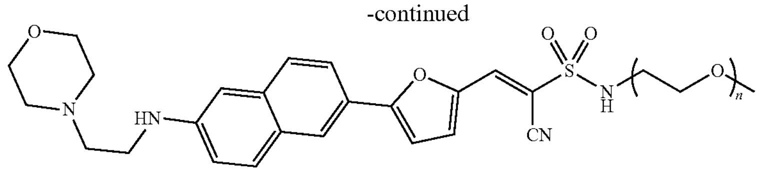
,
wherein n is an integer with value 1-50. In some cases, n is a integer of value 1-10, e.g. n is 1, 2, 3, 4, 5, 6, 7, 8, 9, or 10.
In certain embodiments, the compound is selected from a group consisting of
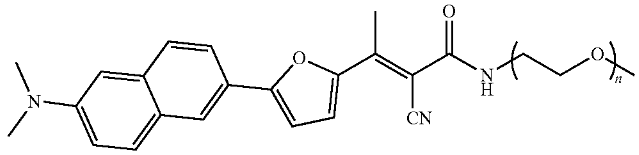
,
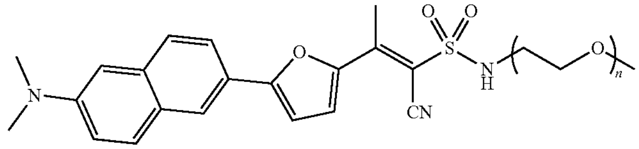
,
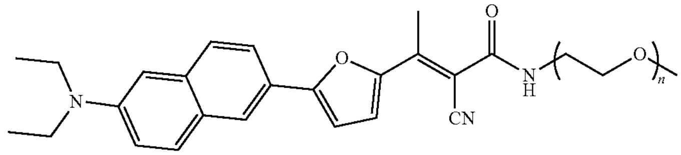
,
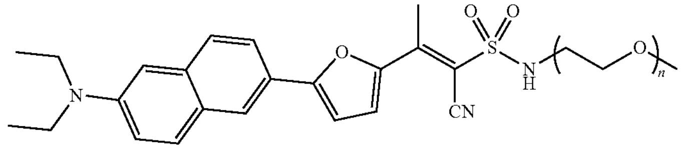
,
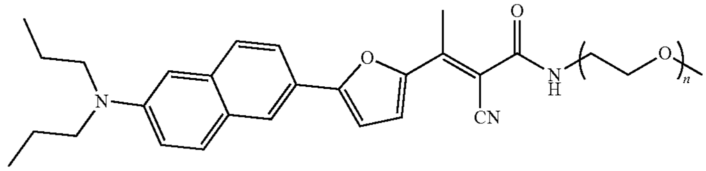
,
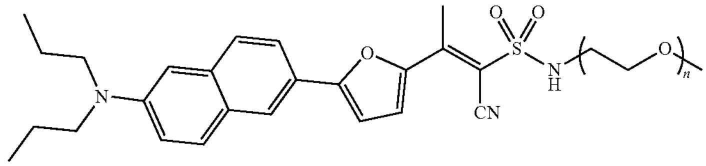
,
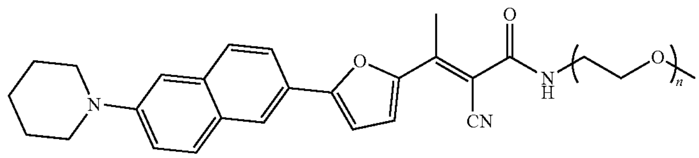
,
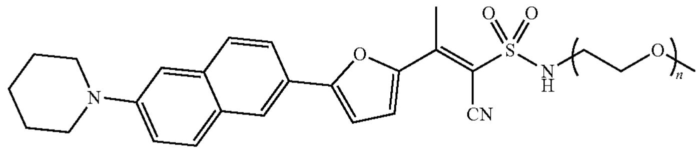
, -continued
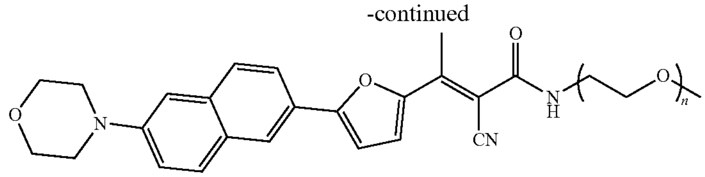
,
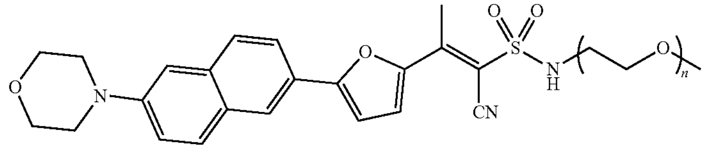
,
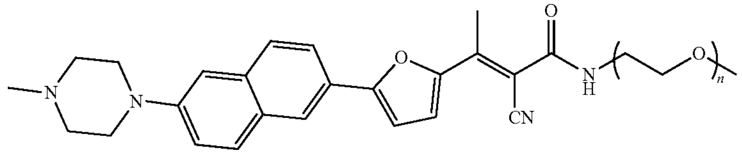
,
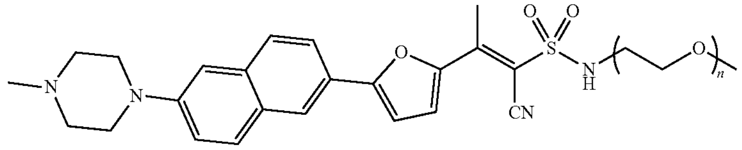
,
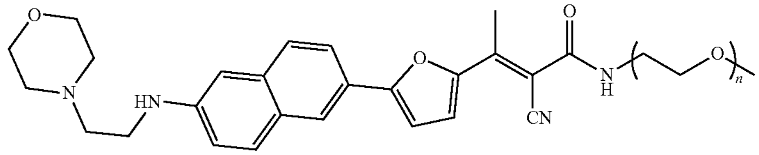
, and
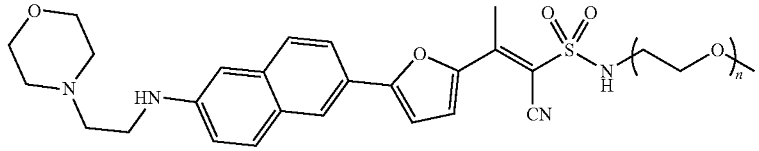
,
wherein n is an integer with value 1-50. In some cases, n is a integer of value 1-10, e.g. n is 1, 2, 3, 4, 5, 6, 7, 8, 9, or 10.
In certain embodiments, the compound is selected from a group consisting of
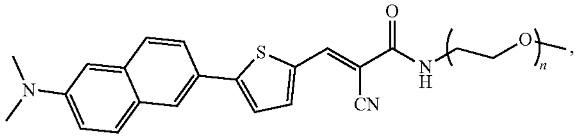
,
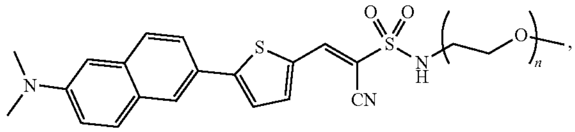
,
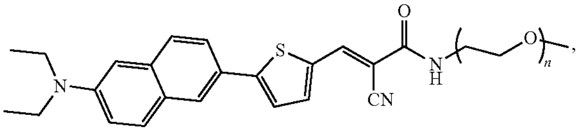
,
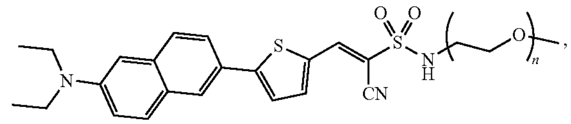
,
-continued
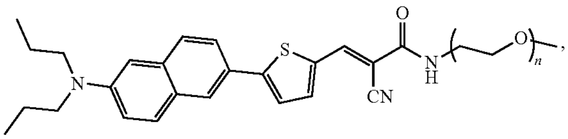
,
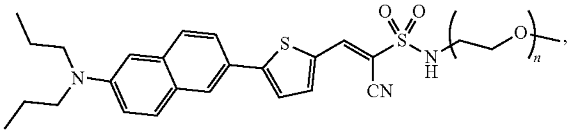
,
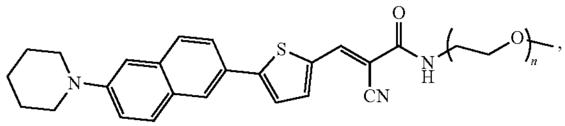
,
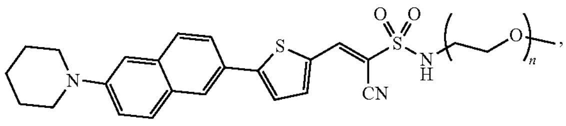
,
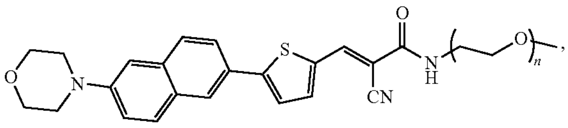
, -continued
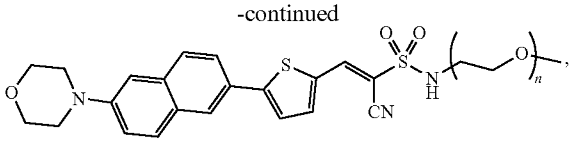
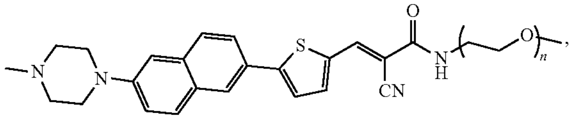
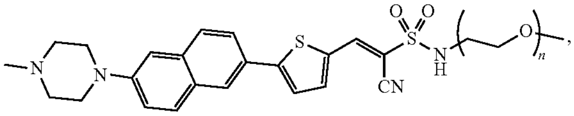
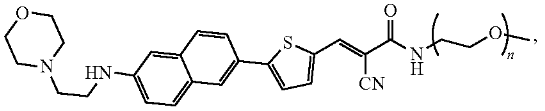
and
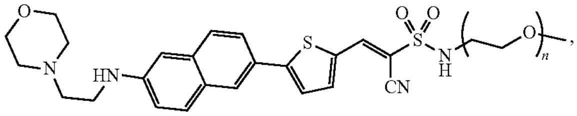
wherein n is an integer with value 1-50. In some cases, n is a integer of value 1-10, e.g. n is 1, 2, 3, 4, 5, 6, 7, 8, 9, or 10.
In certain embodiments, the compound is selected from a group consisting of
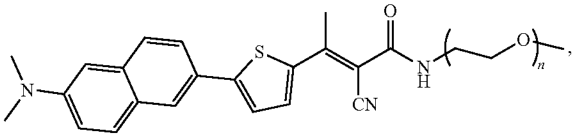
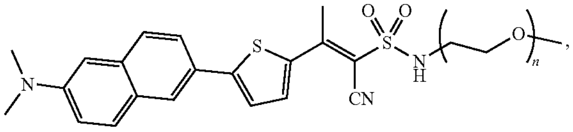
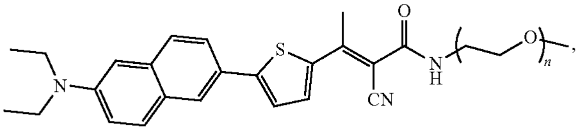
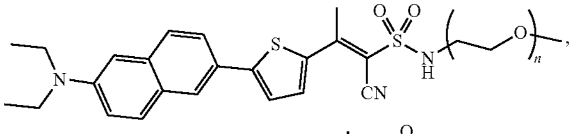
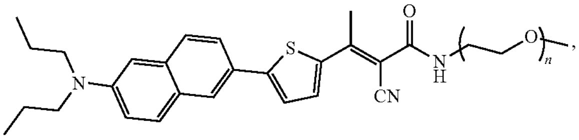
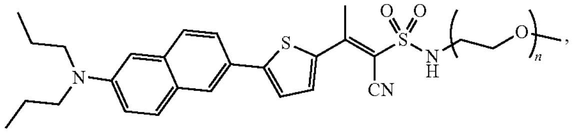
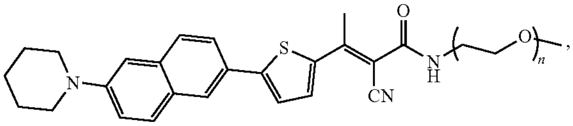
-continued
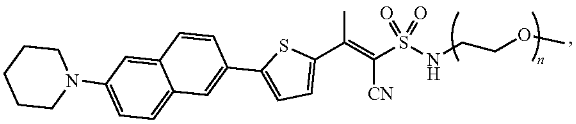
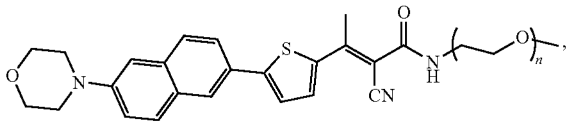
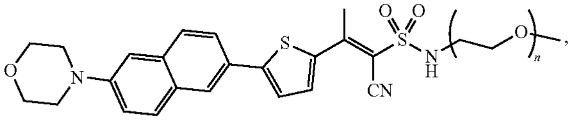
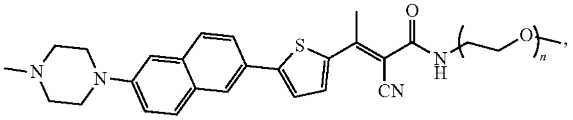
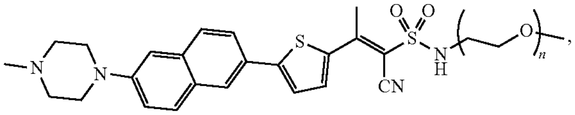
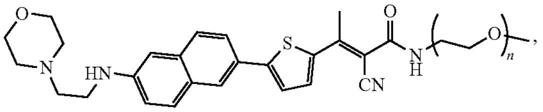
and
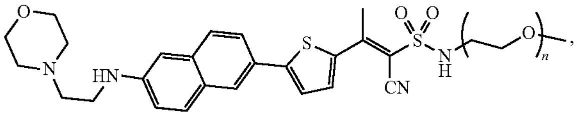
wherein n is an integer with value 1-50. In some cases, n is a integer of value 1-10, e.g. n is 1, 2, 3, 4, 5, 6, 7, 8, 9, or 10.
In certain embodiments, the compound is selected from a group consisting of
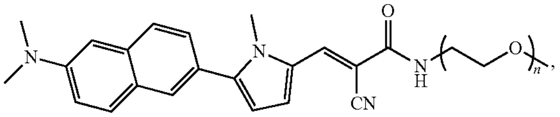
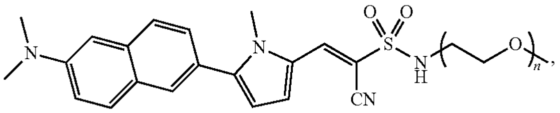
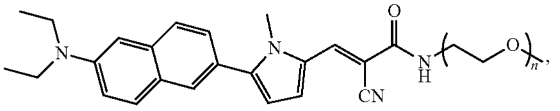
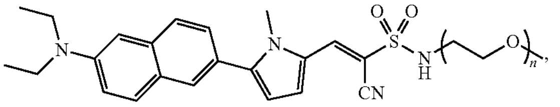
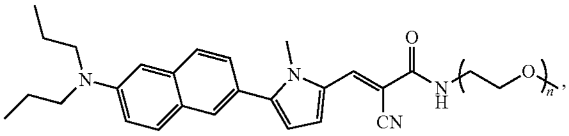

-continued
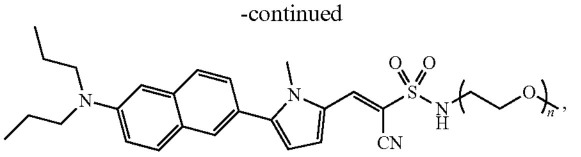
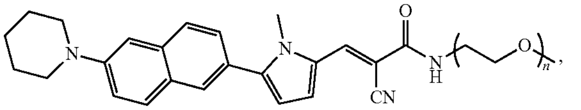
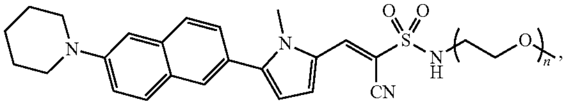
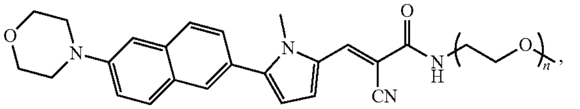
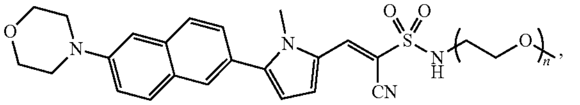
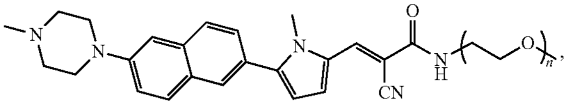
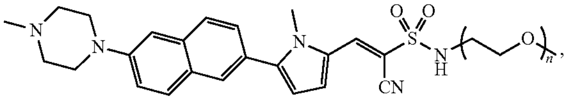
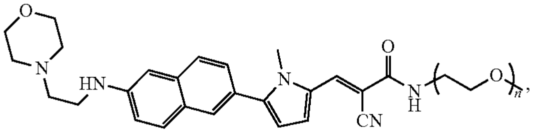
and
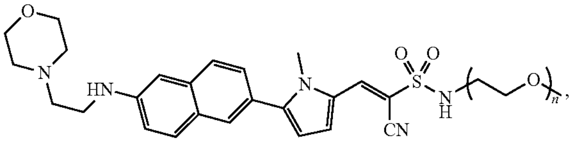
wherein n is an integer with value 1-50. In some cases, n is a integer of value 1-10, e.g. n is 1, 2, 3, 4, 5, 6, 7, 8, 9, or 10.
In certain embodiments, the compound is selected from a group consisting of
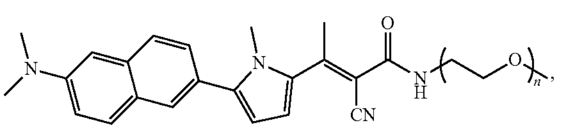
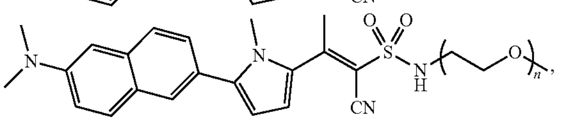
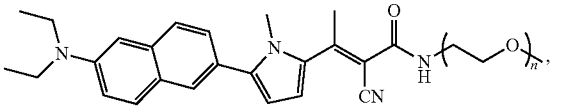
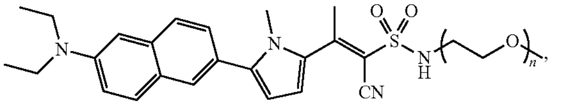
-continued
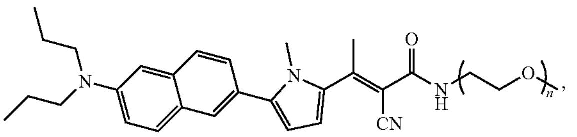
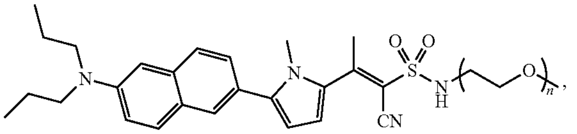
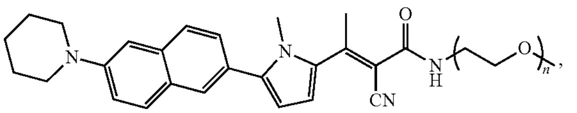
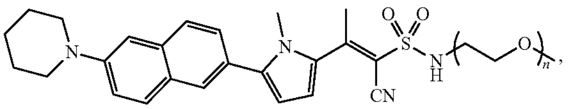
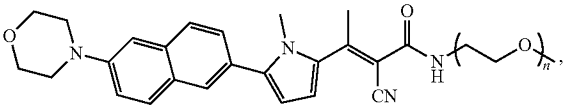
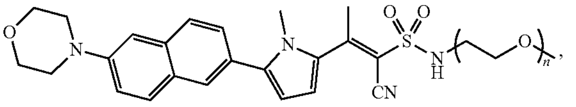
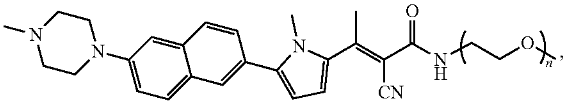
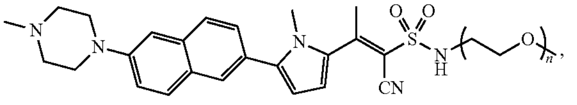
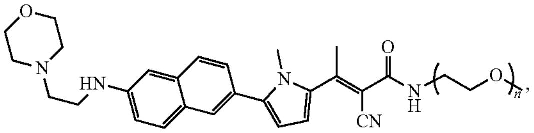
and
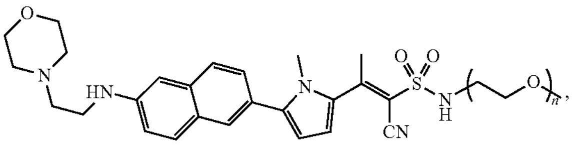
wherein n is an integer with value 1-50. In some cases, n is a integer of value 1-10, e.g. n is 1, 2, 3, 4, 5, 6, 7, 8, 9, or 10.
In certain embodiments, the compound is selected from a group consisting of
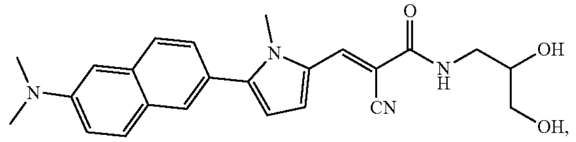
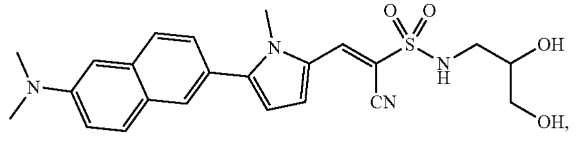

-continued
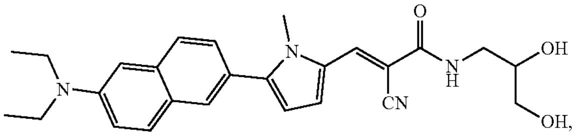
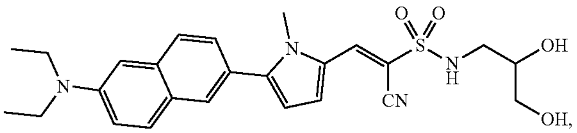
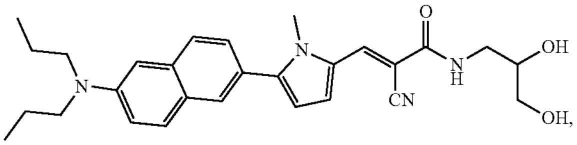
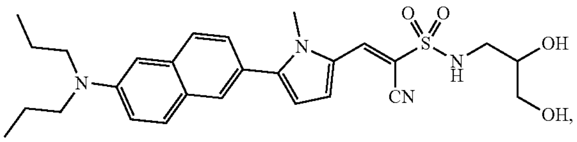
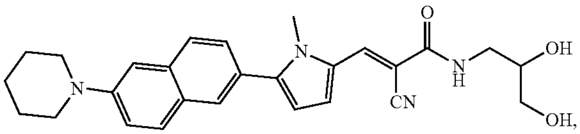
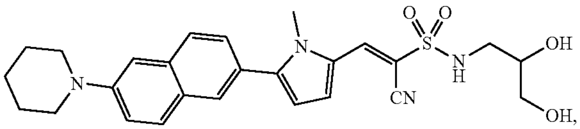
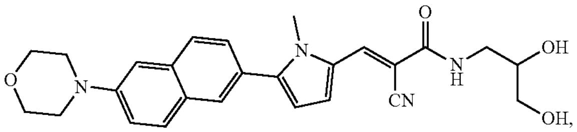
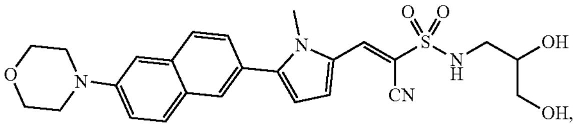
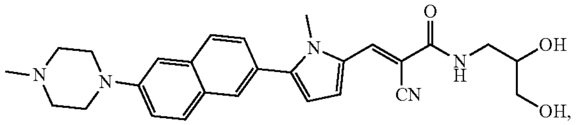
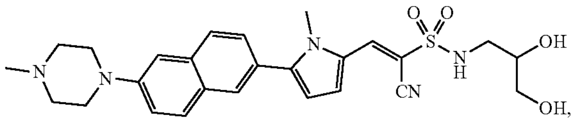
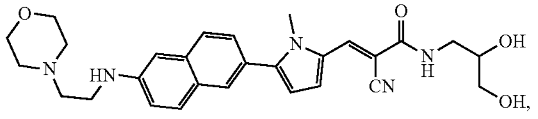
and
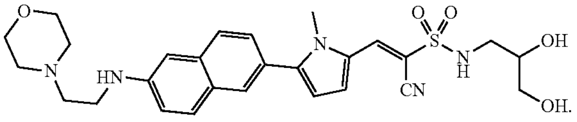
In certain embodiments, the compound is selected from a group consisting of
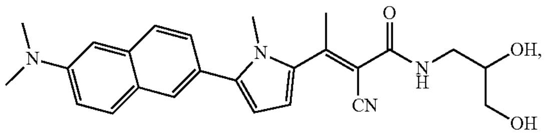
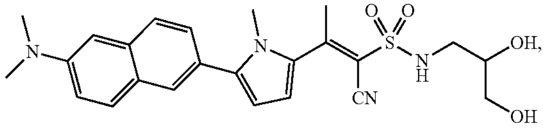
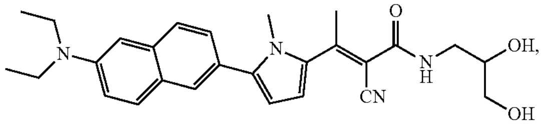
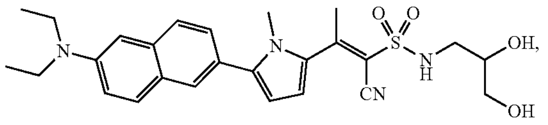
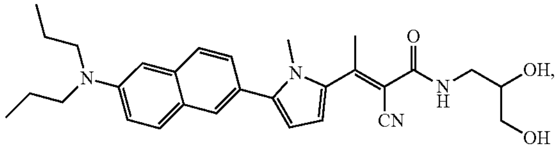
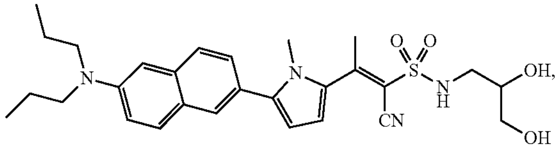
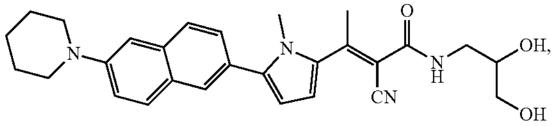
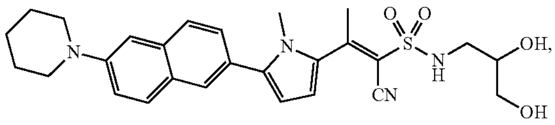
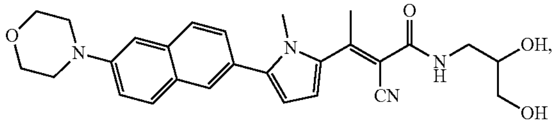
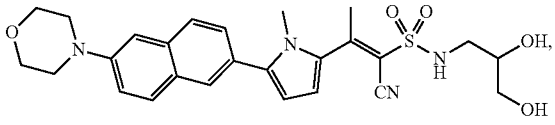
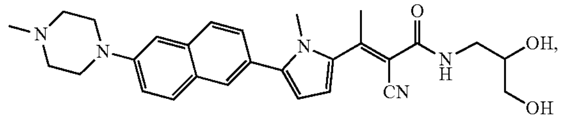
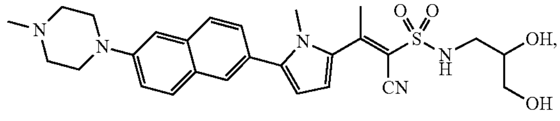
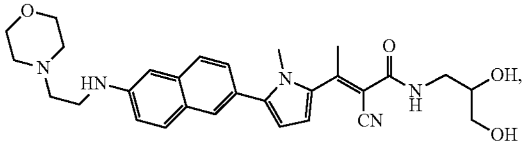
and -continued
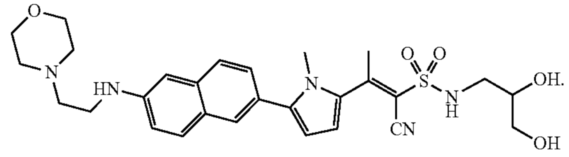 [SMILES: C/C(=C(/C#N)S(=O)(=O)NCC(O)CO)c1ccc(-c2ccc3cc(NCCN4CCOCC4)ccc3c2)n1C]
In certain embodiments, the compound is selected from a group consisting of
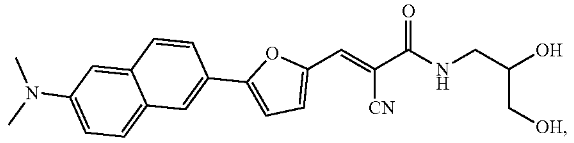
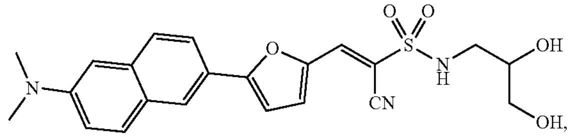
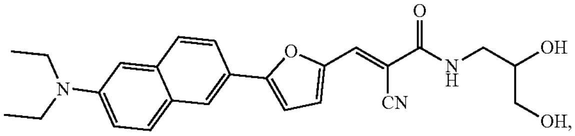
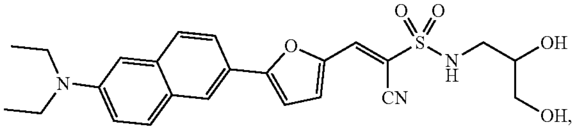
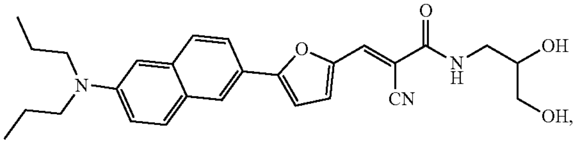
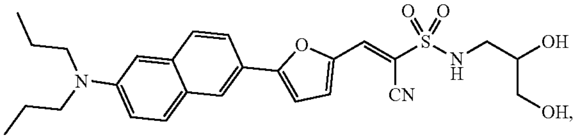
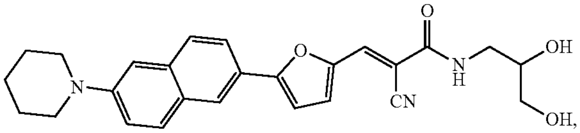
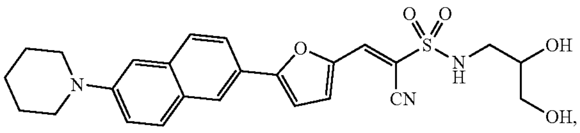
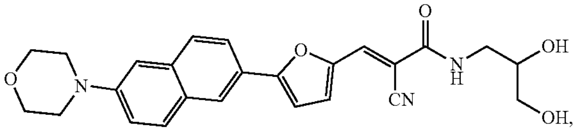
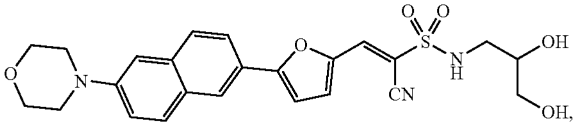
-continued
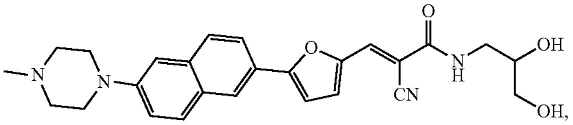
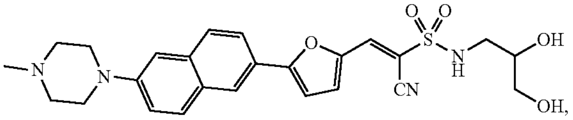
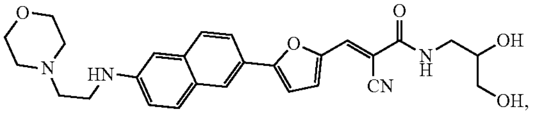
and
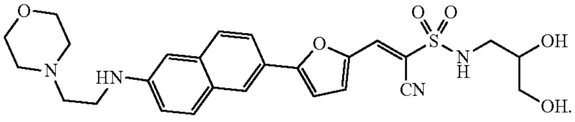
In certain embodiments, the compound is selected from a group consisting of
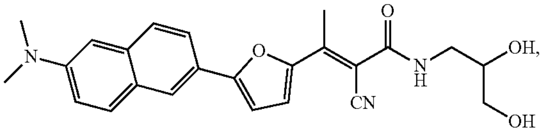
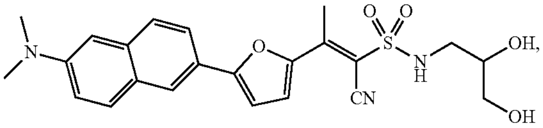
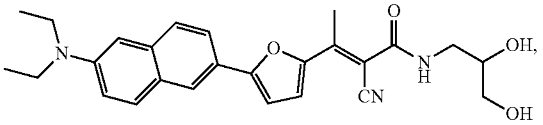
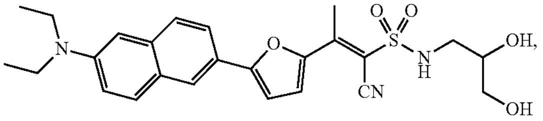
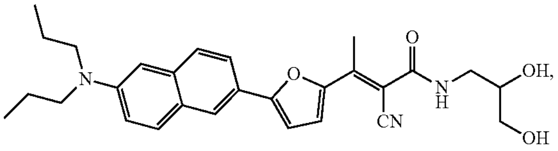
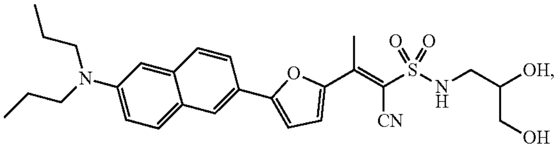
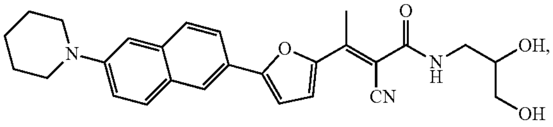
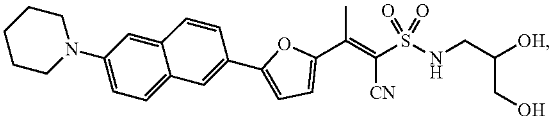

-continued
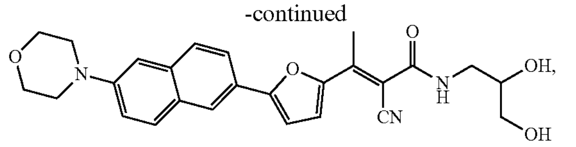
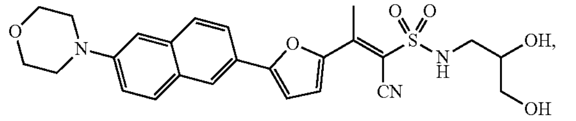
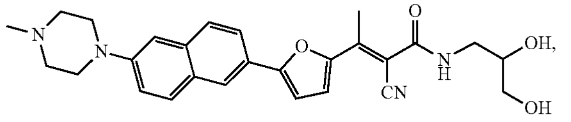
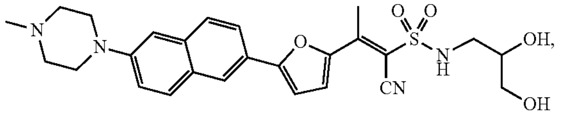
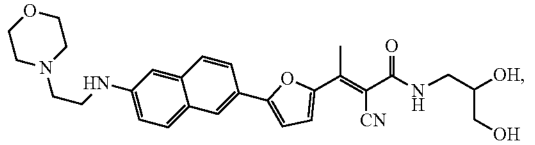
and
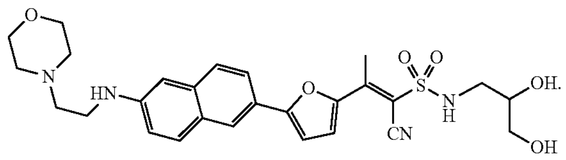 [SMILES: C/C(=C(/C#N)S(=O)(=O)NCC(O)CO)c1ccc(-c2ccc3cc(NCCN4CCOCC4)ccc3c2)o1]
In certain embodiments, the compound is selected from a group consisting of
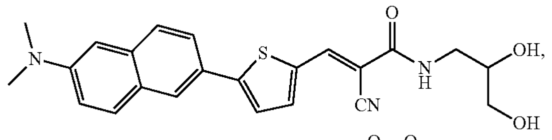
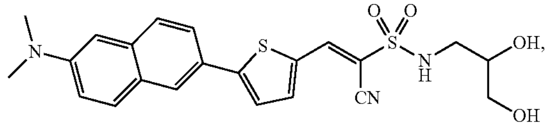
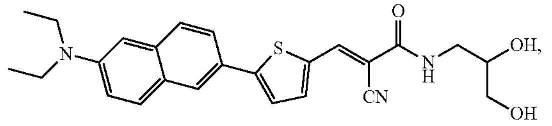
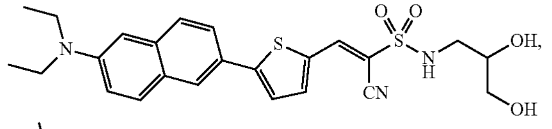
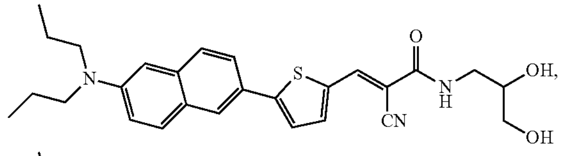
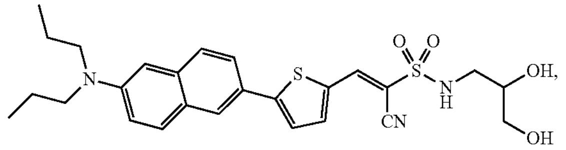
-continued
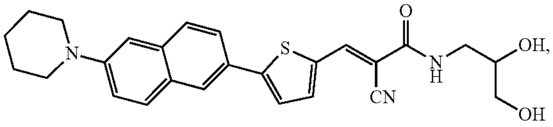
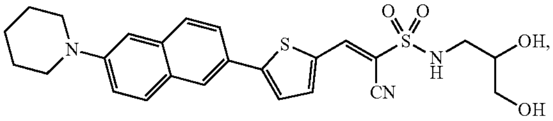
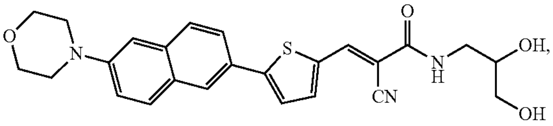
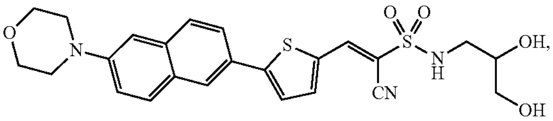
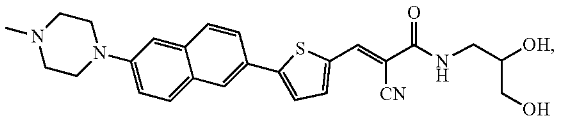
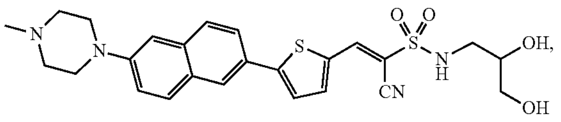
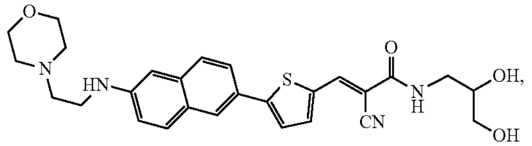
and
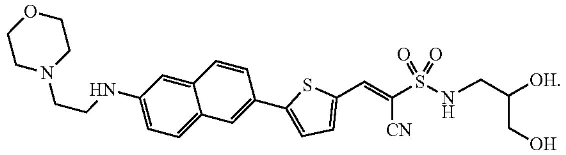 [SMILES: N#C/C(=C\c1ccc(-c2ccc3cc(NCCN4CCOCC4)ccc3c2)s1)S(=O)(=O)NCC(O)CO]
In certain embodiments, the compound is selected from a group consisting of
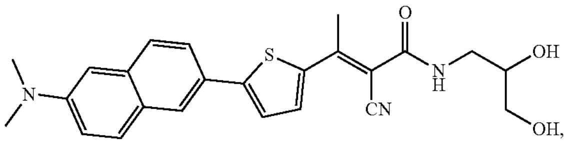
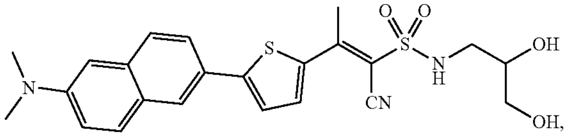
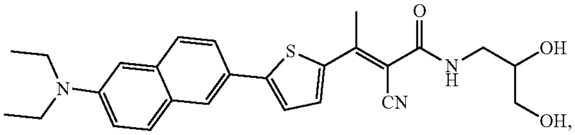
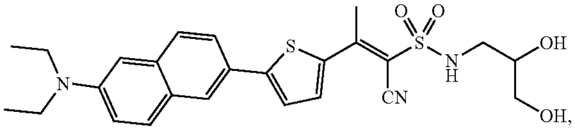

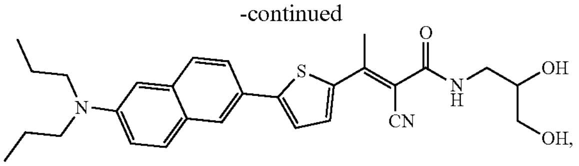
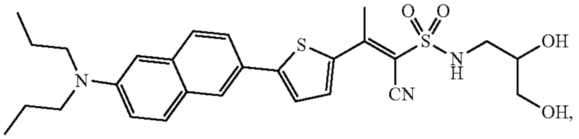
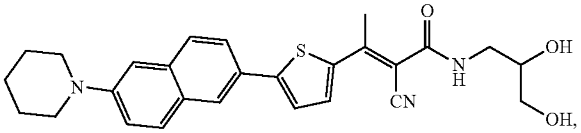
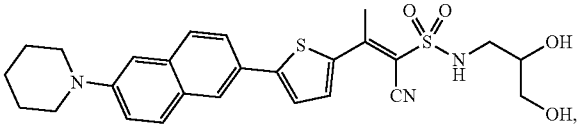
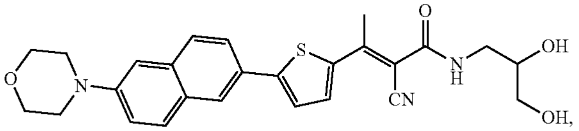
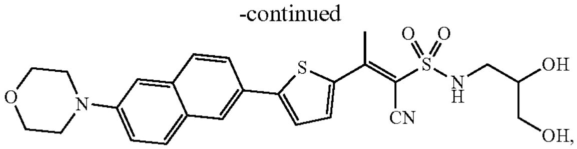
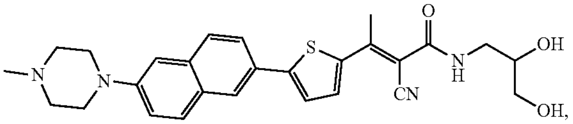
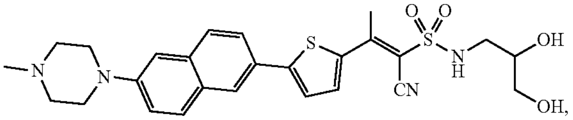
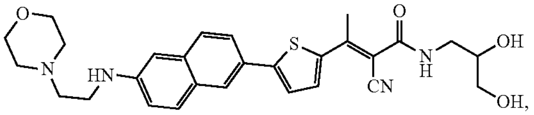
and
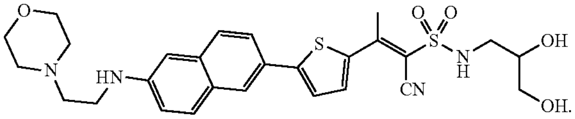
In certain embodiments, the compound is selected from a group consisting of
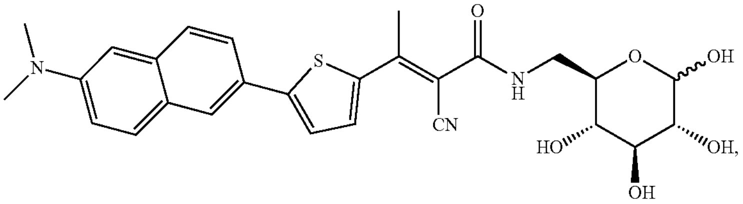
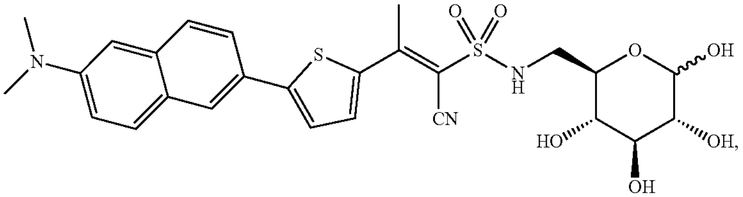
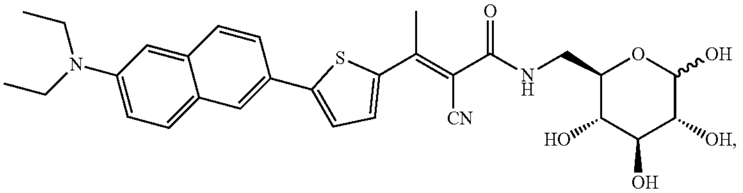
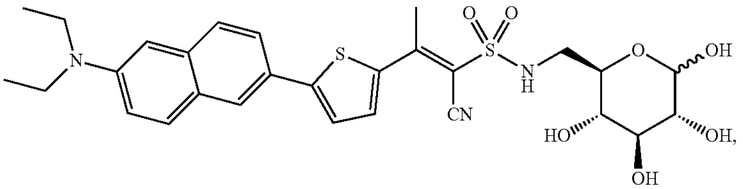

-continued
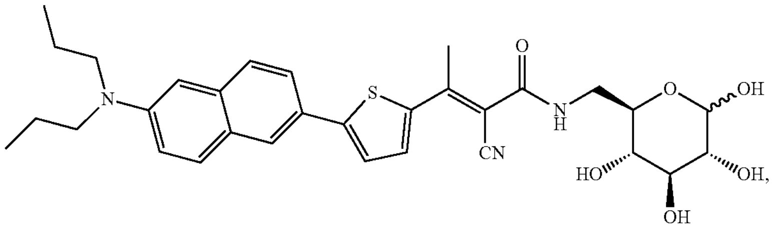
,
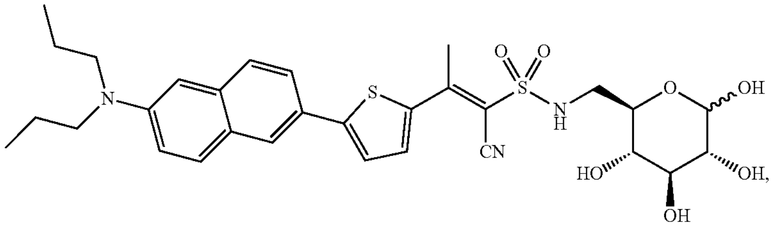
,
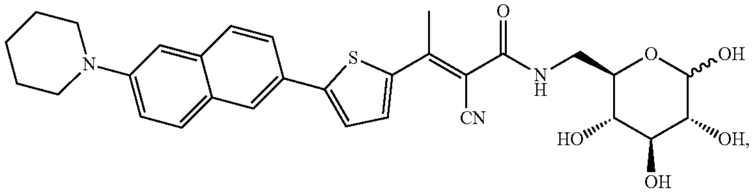
,
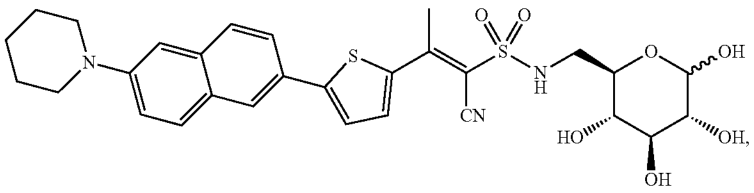
,
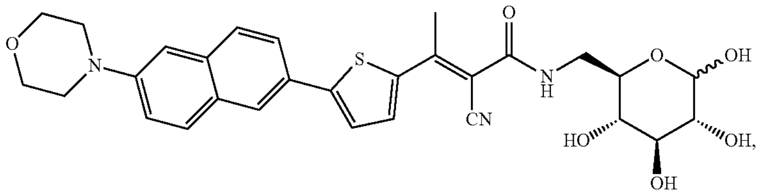
,
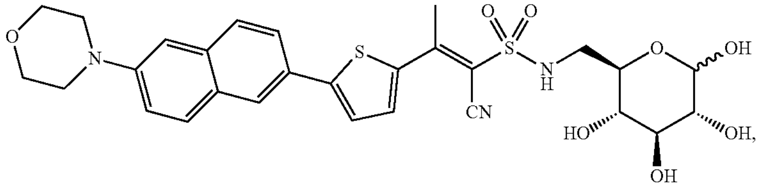
,
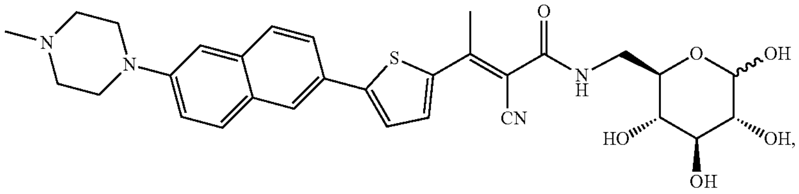
,
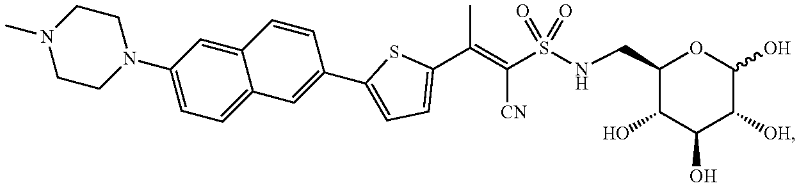
, -continued
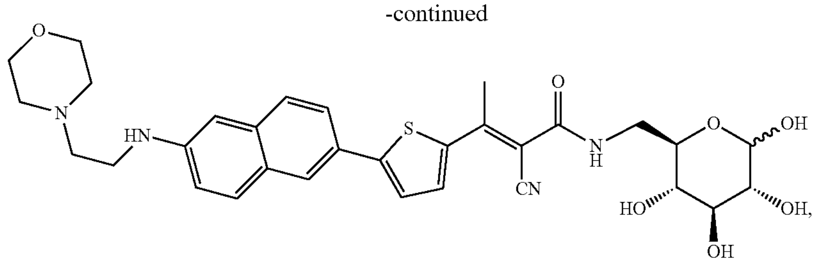
and
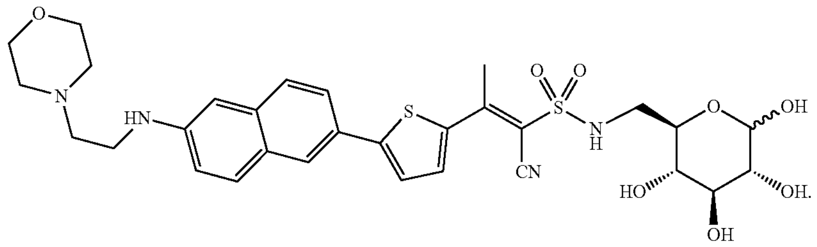
In certain embodiments, the compound is selected from a group consisting of
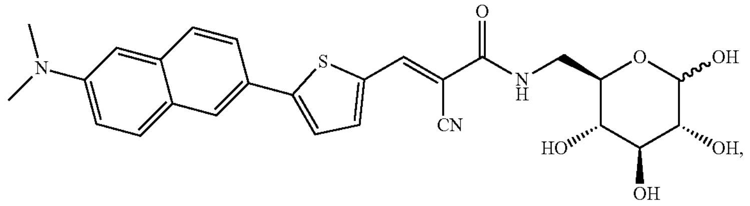
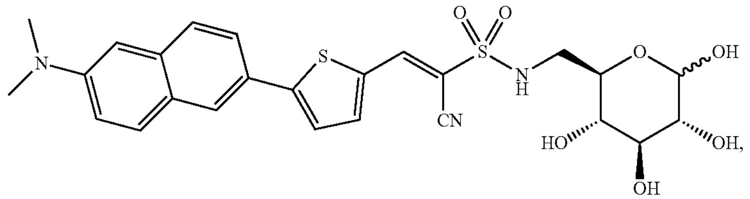
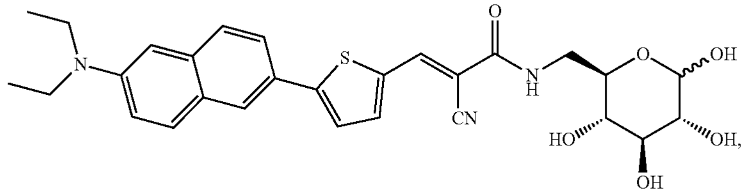
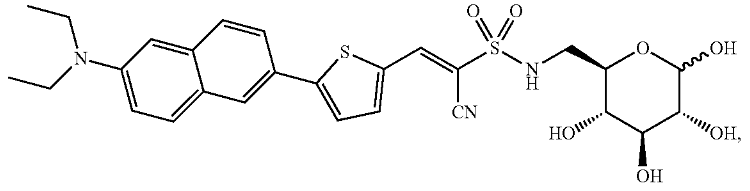
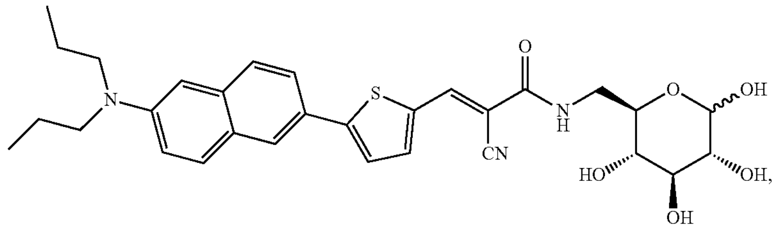

-continued
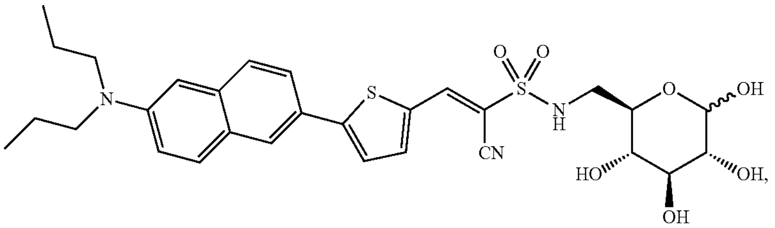
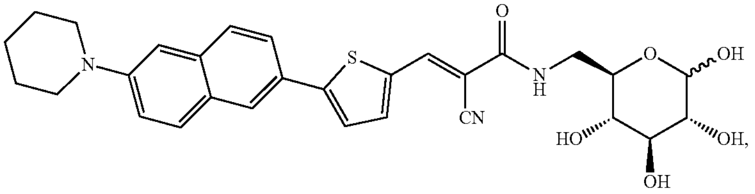
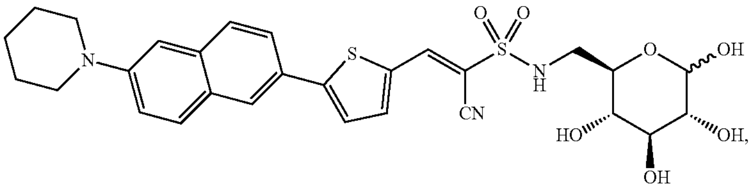
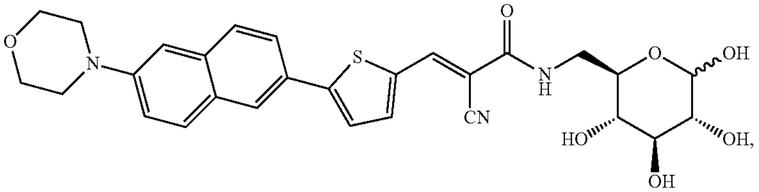
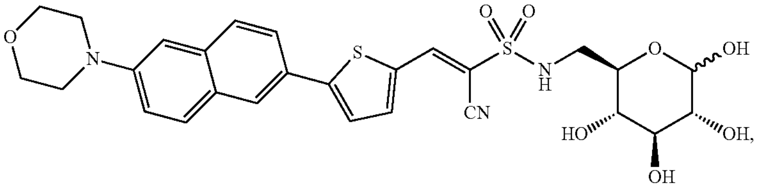
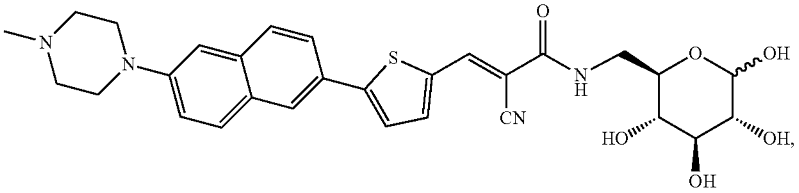
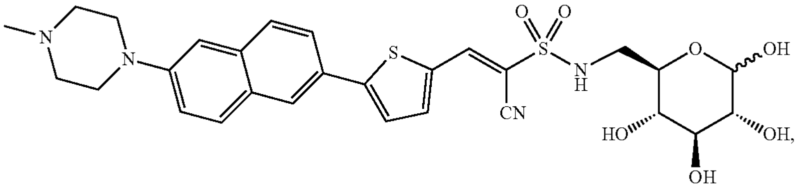
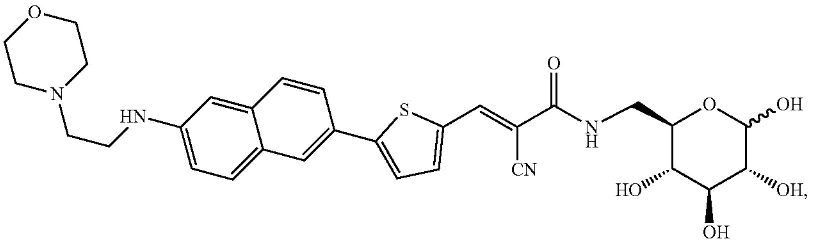
and -continued
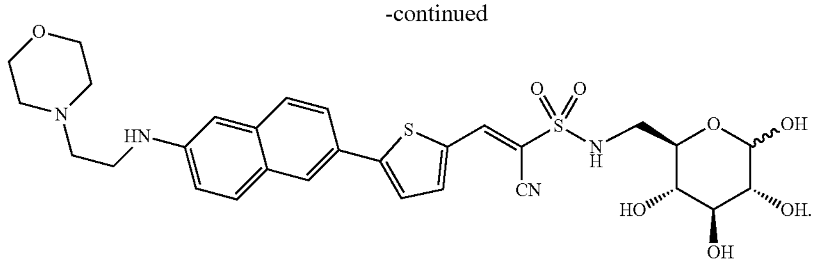
In certain embodiments, is selected from a group consisting of
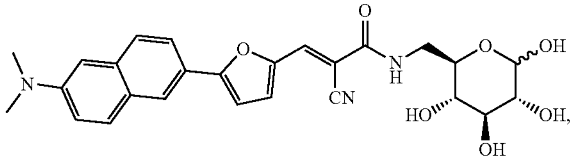
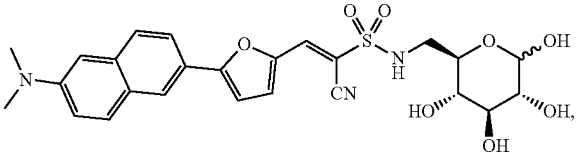
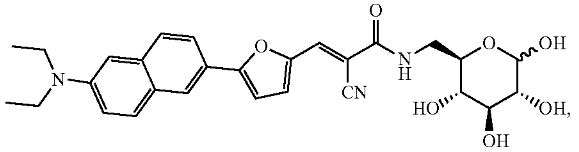
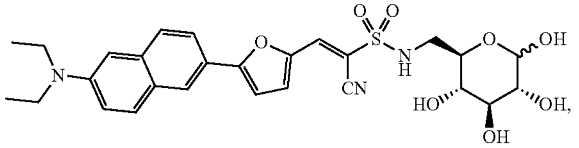
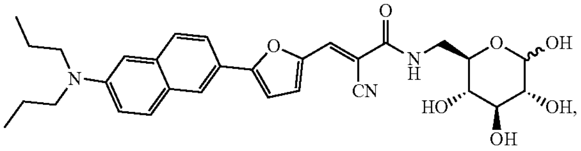
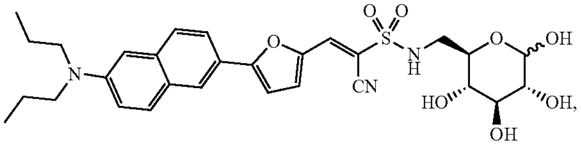
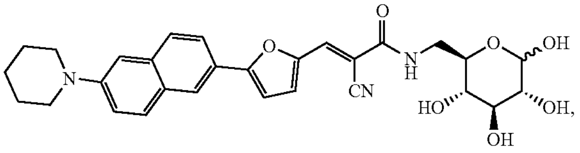
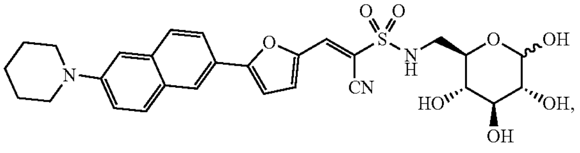
-continued
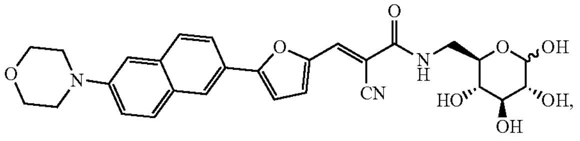
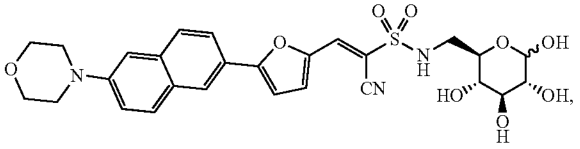
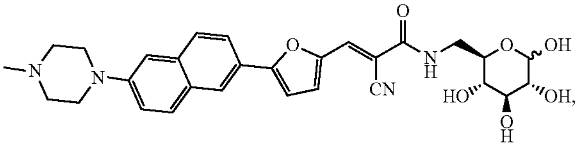
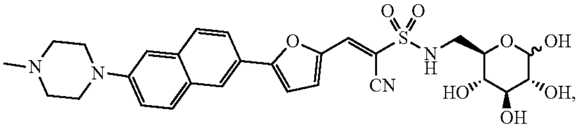
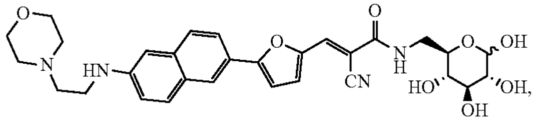
and
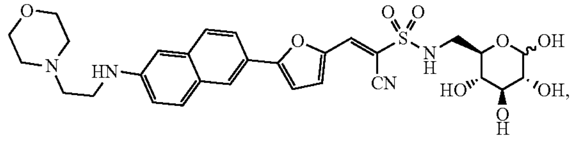
In certain embodiments, the compound is selected from a group consisting of
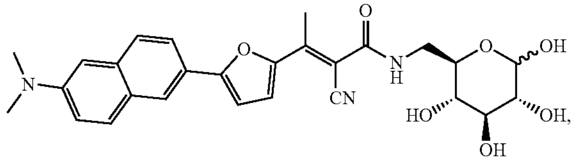
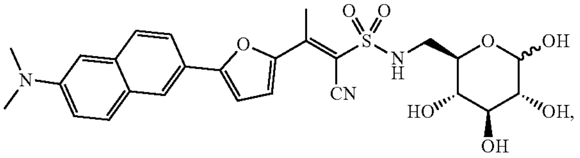

-continued
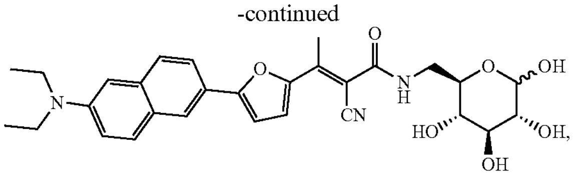
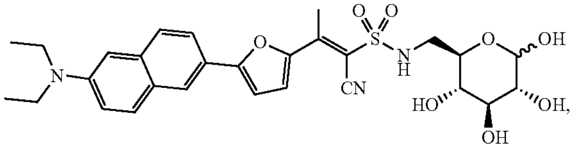
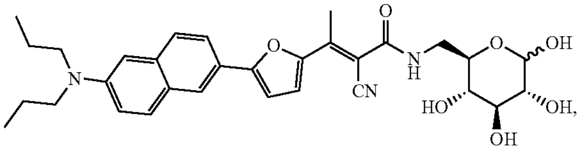
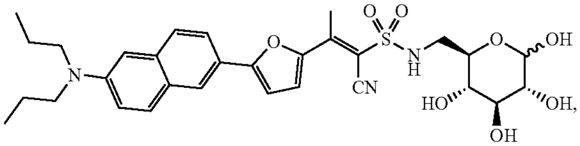
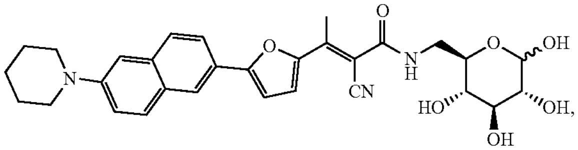
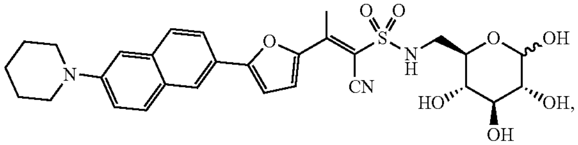
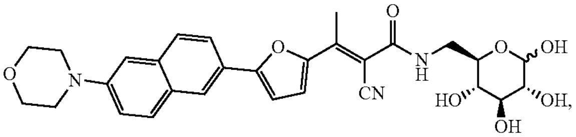
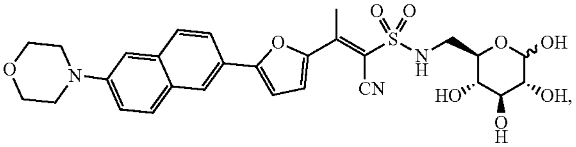
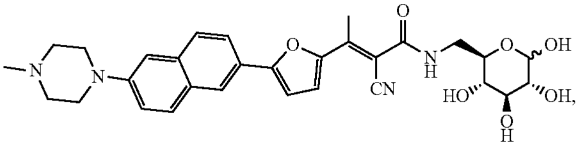
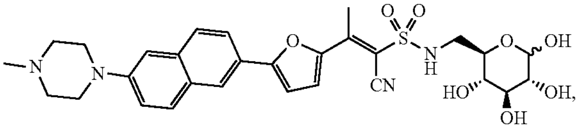
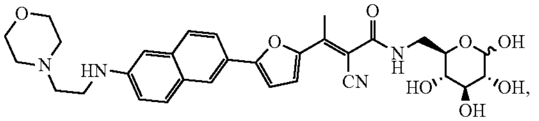
and
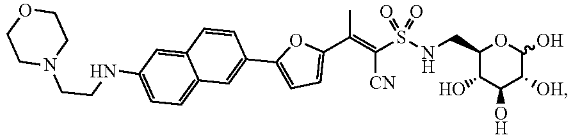
In certain embodiments, the compound is selected from a group consisting of
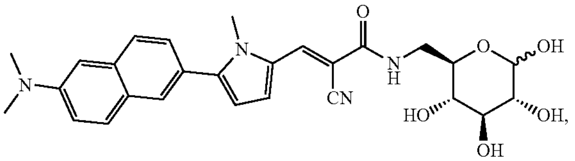
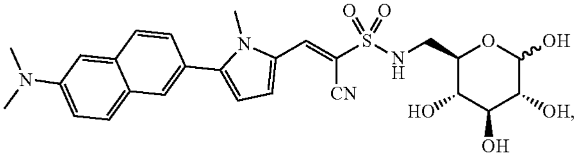
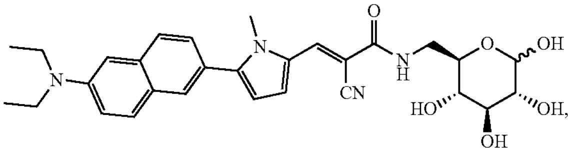
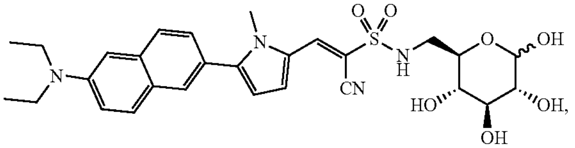
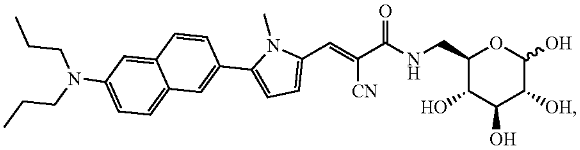
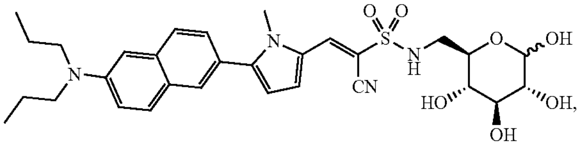
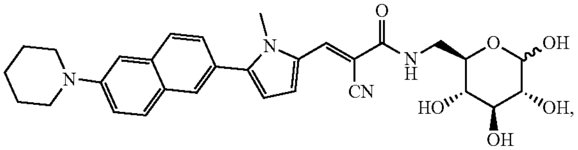
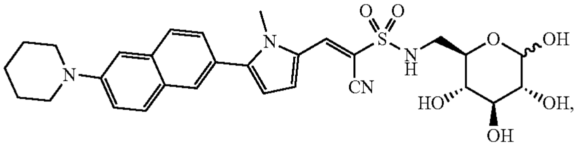
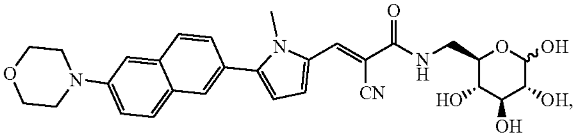
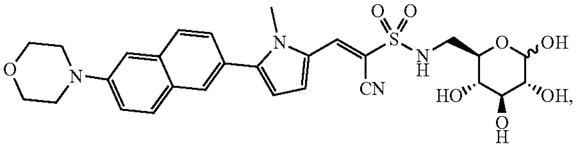
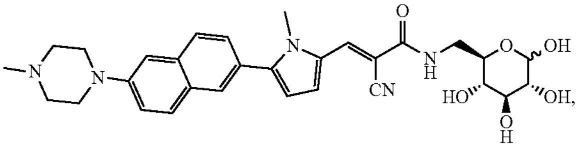

-continued
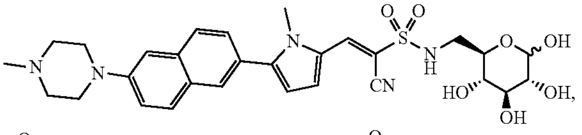
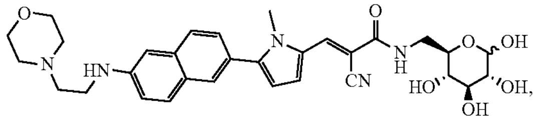
and
-continued
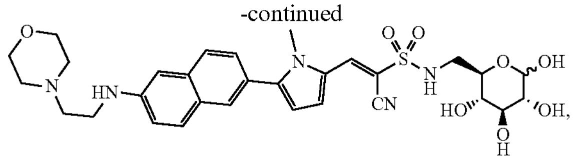
In certain embodiments, the compound is selected from a group consisting of
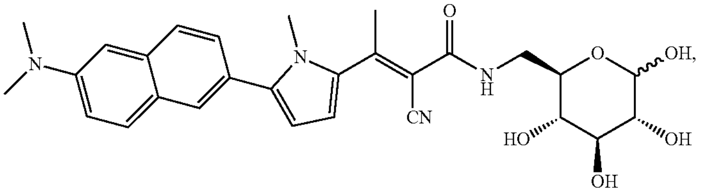
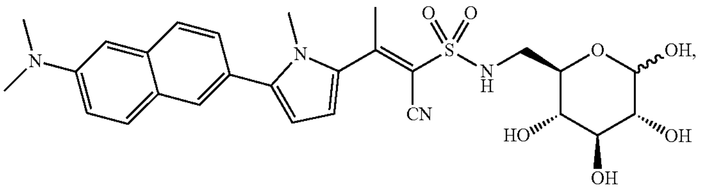
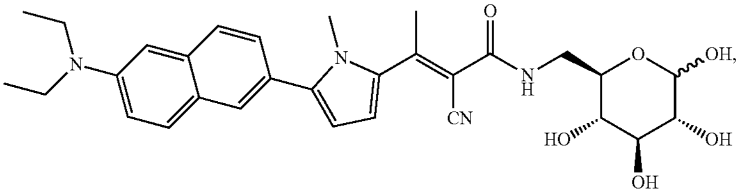
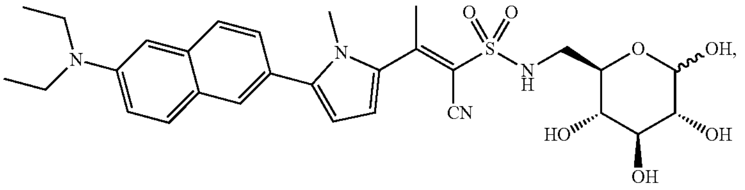
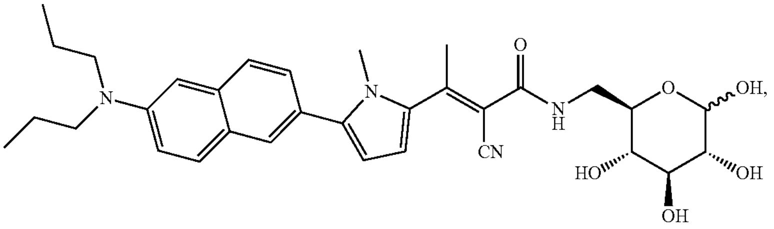
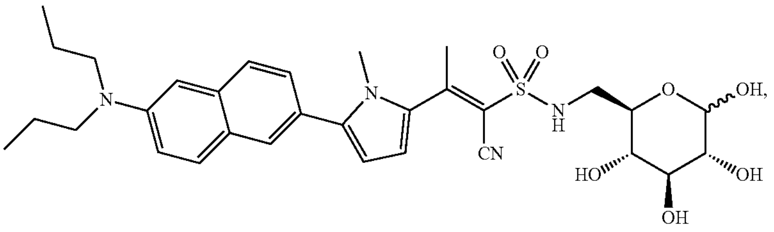

-continued
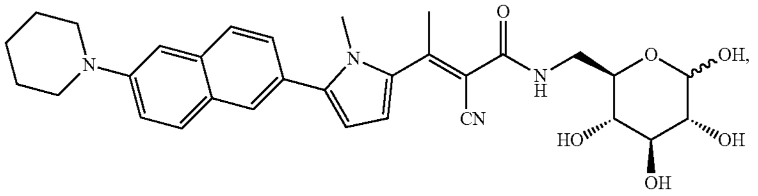
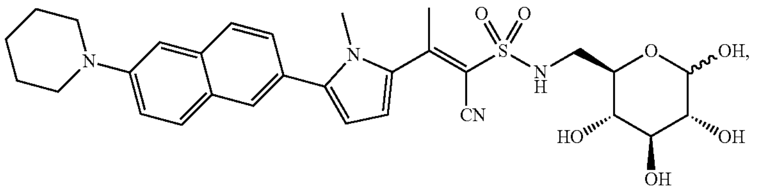
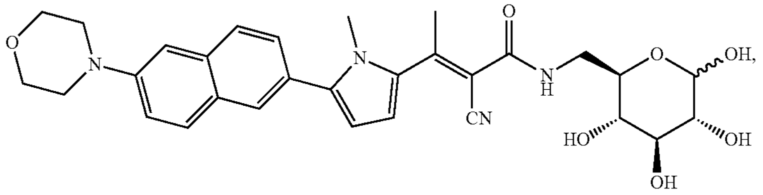
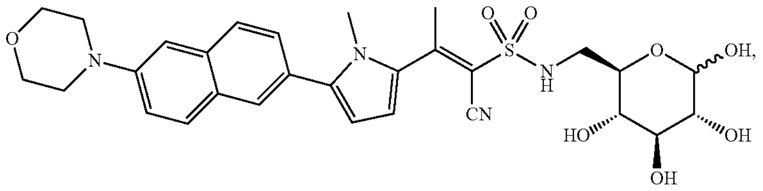
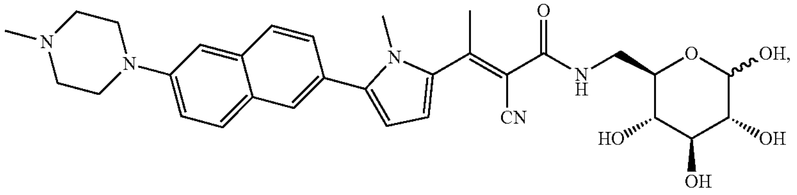
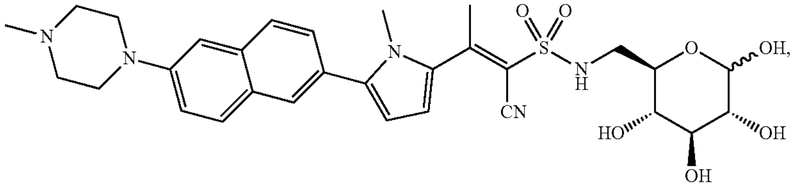
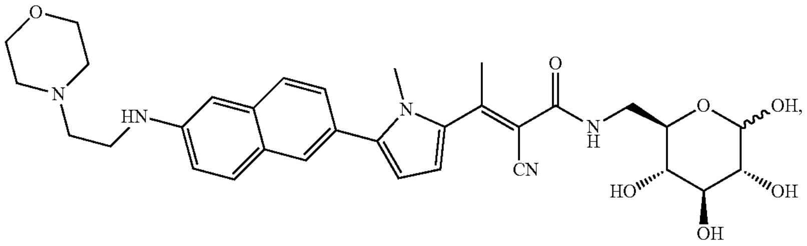
and
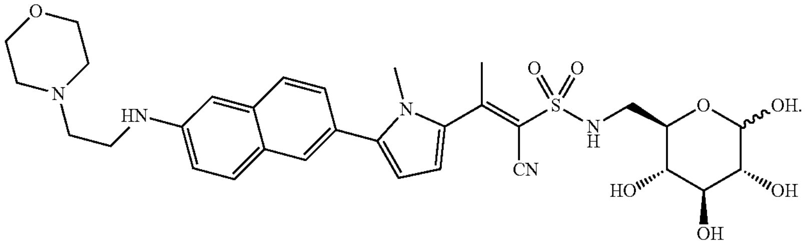

In certain embodiments, the compound is selected from a group consisting of
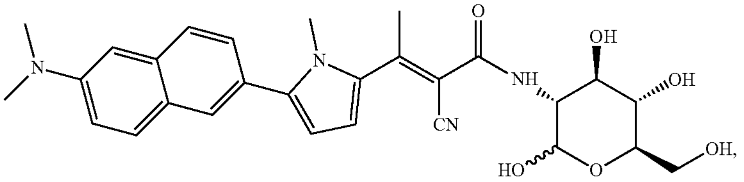
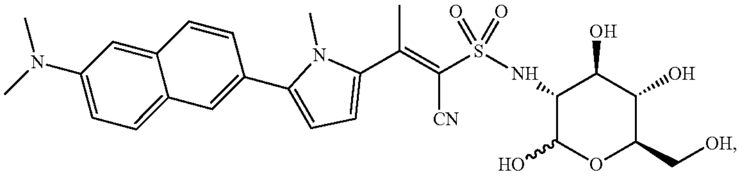
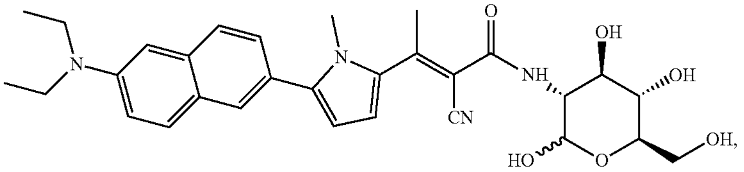
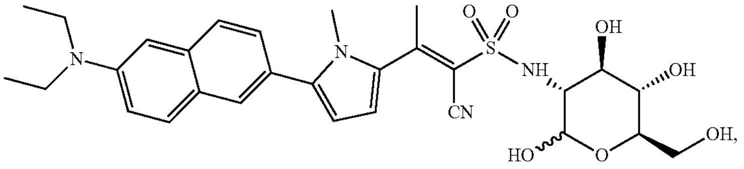
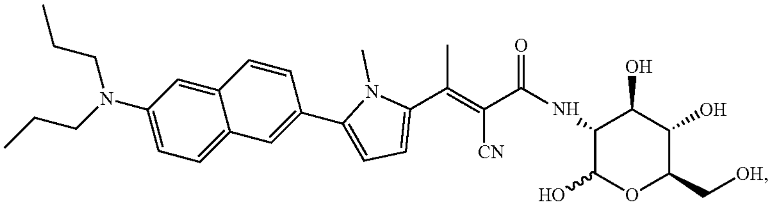
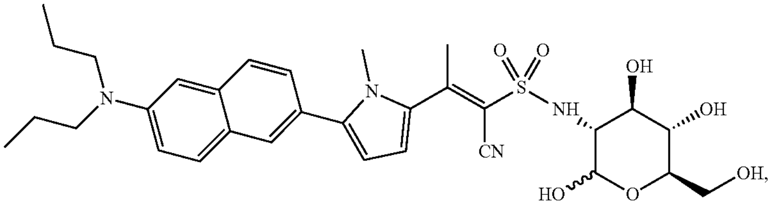
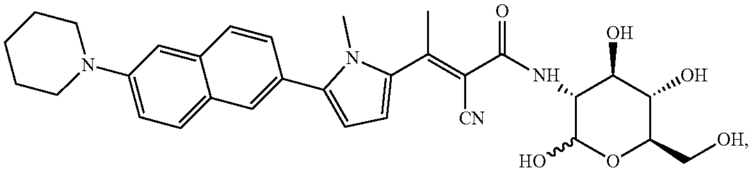
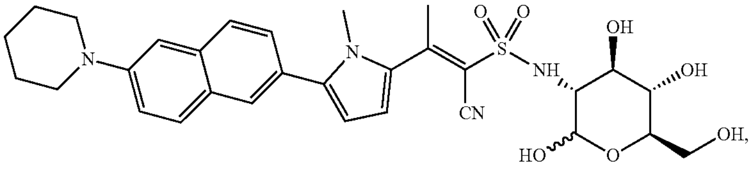
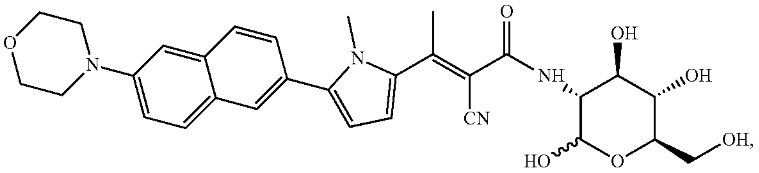

-continued
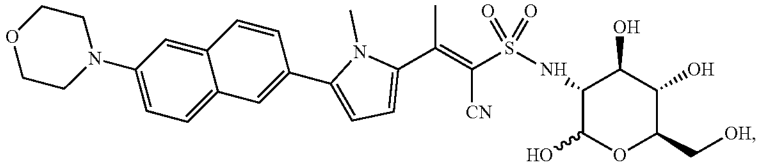
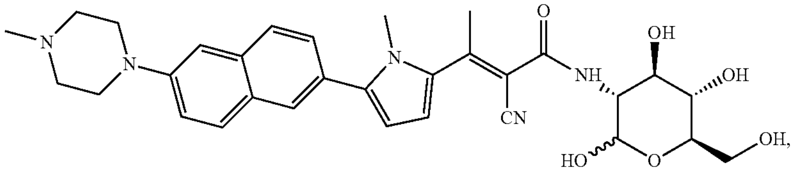
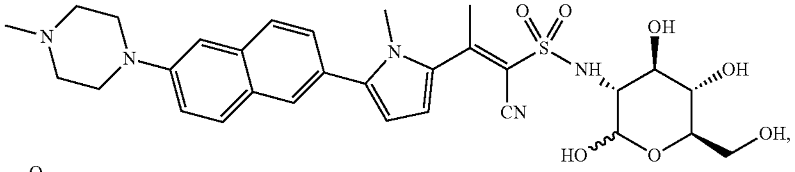
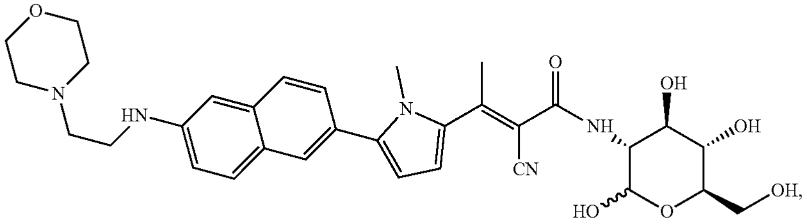
and
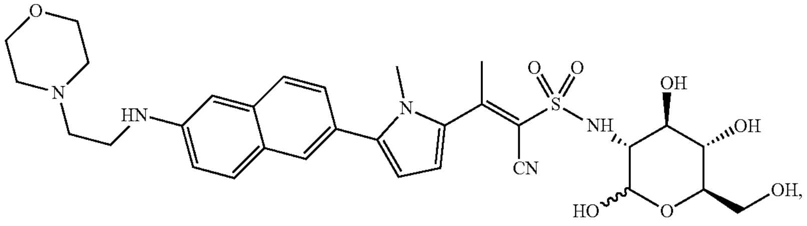
In certain embodiments, the compound is selected from a group consisting of
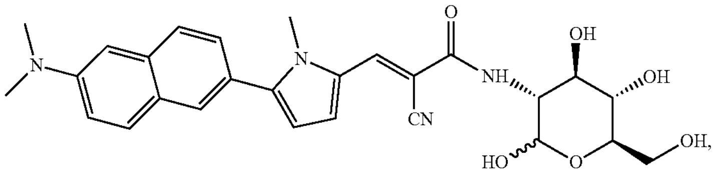
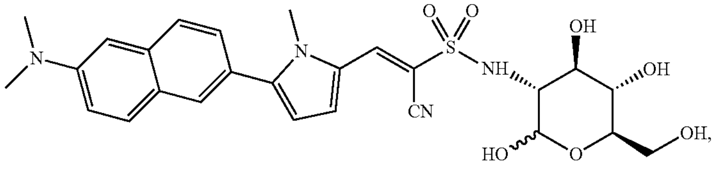
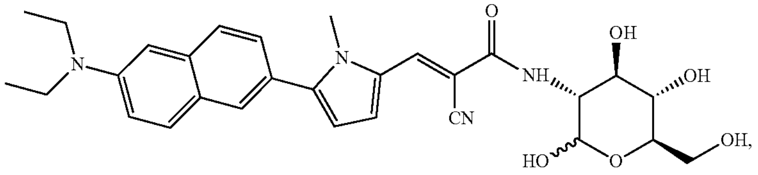

-continued
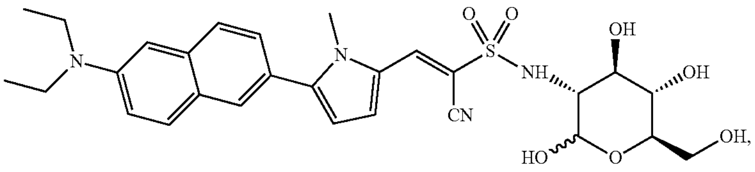
,
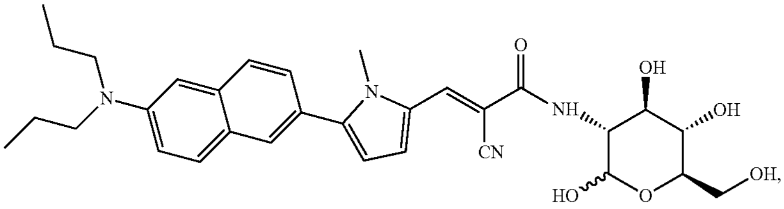
,
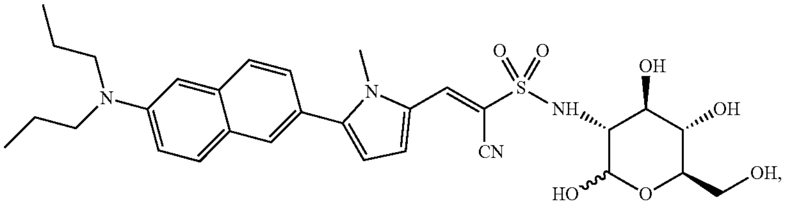
,
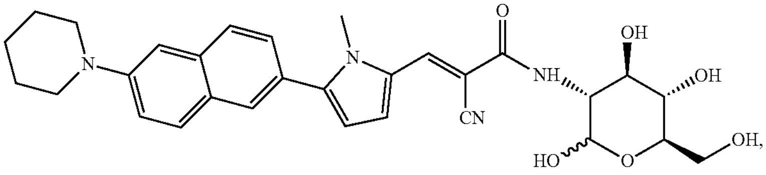
,
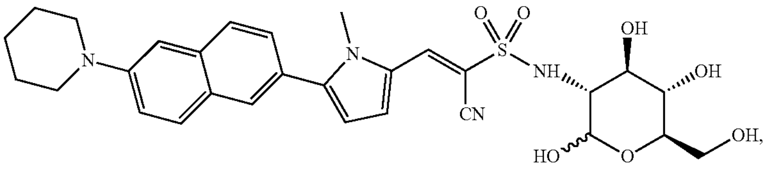
,
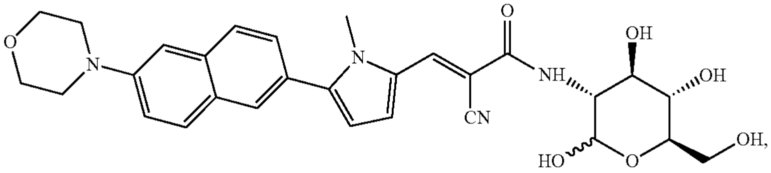
,
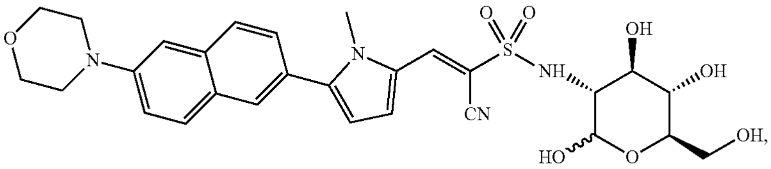
,
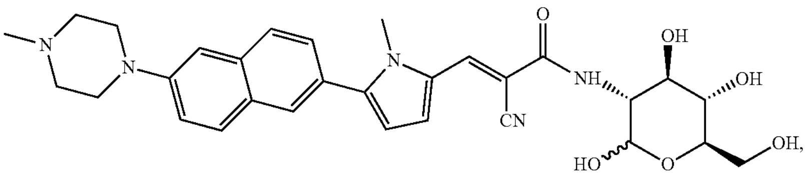
,
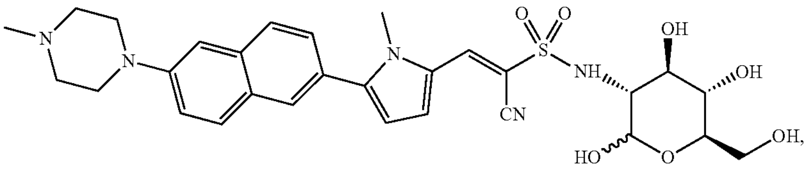
, -continued
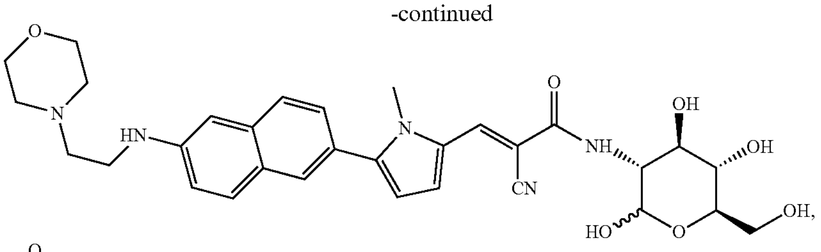
and
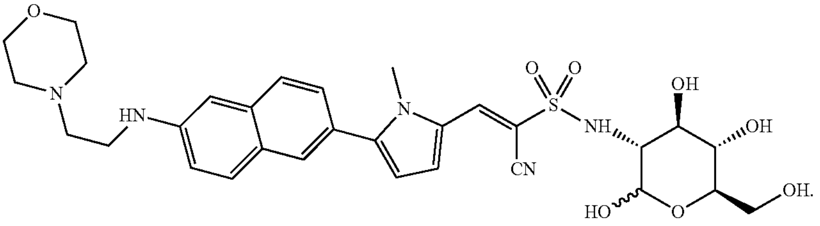
In certain embodiments, the compound is selected from a group consisting of
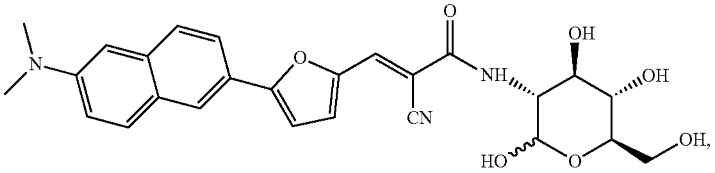
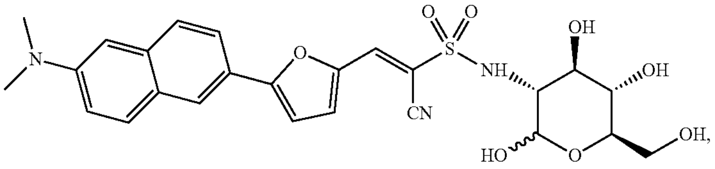
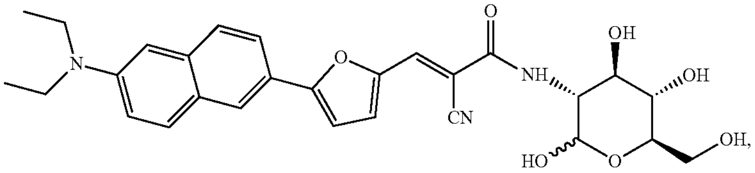
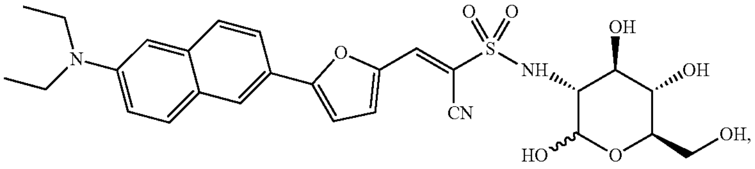
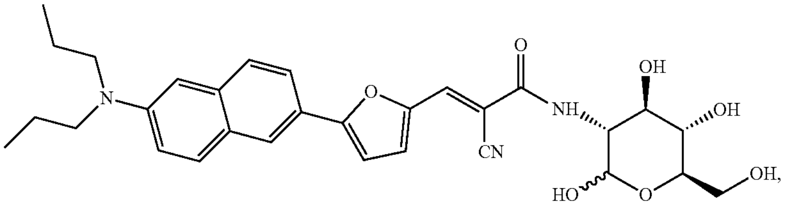
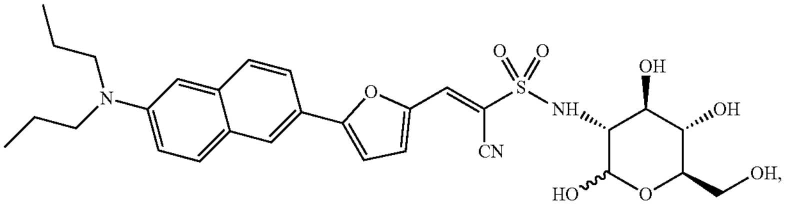

-continued
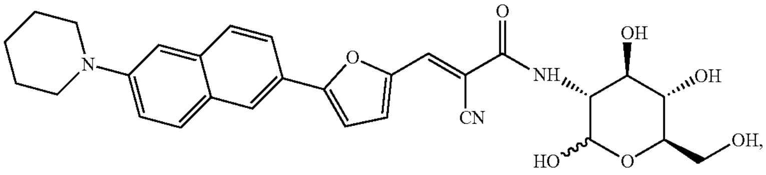
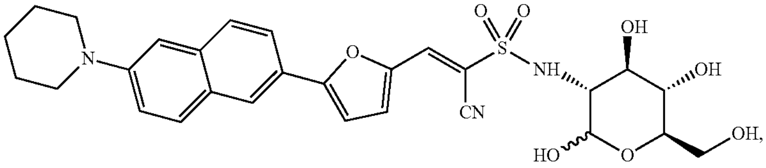
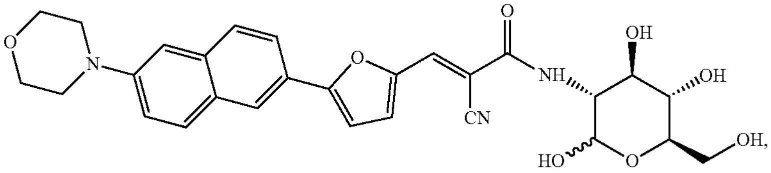
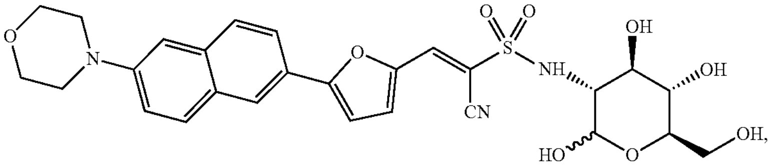
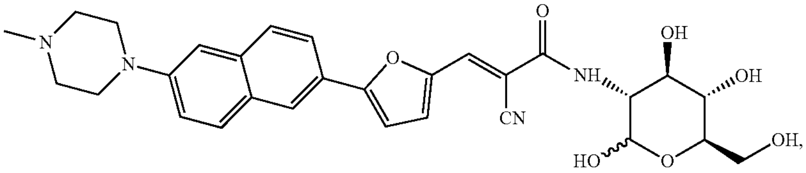
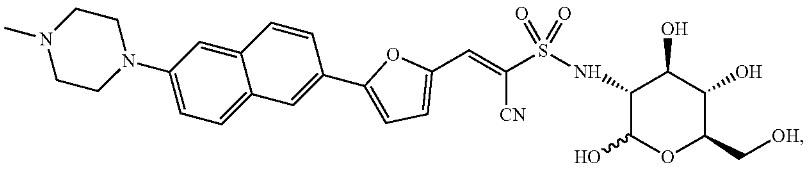
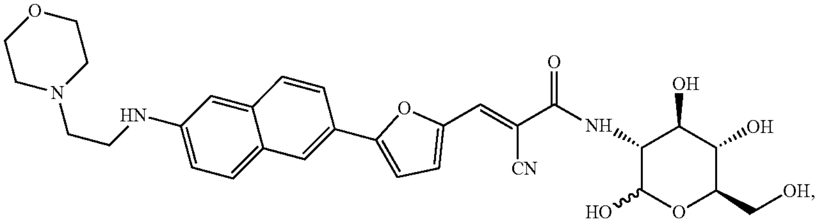
and
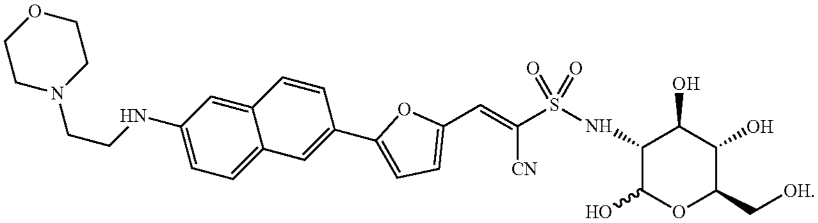

In certain embodiments, the compound is selected from a group consisting of
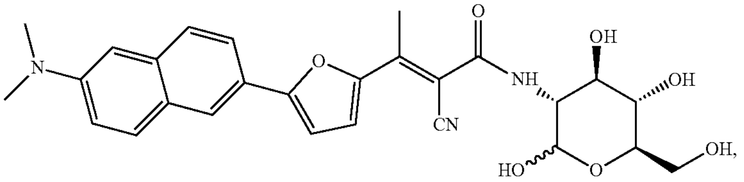
,
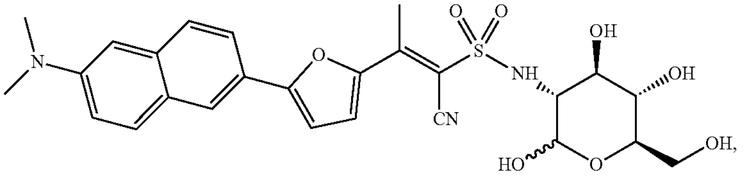
,
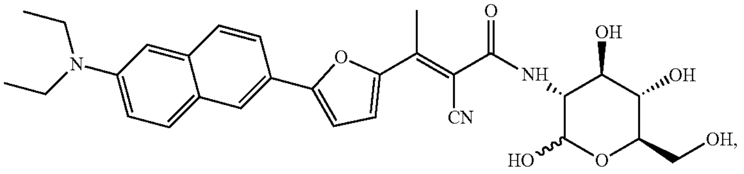
,
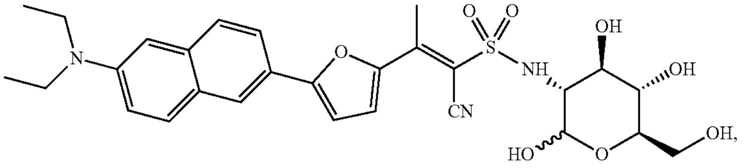
,
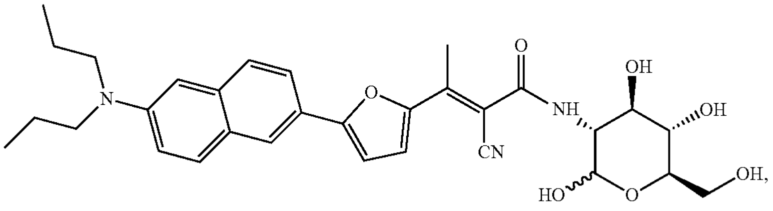
,
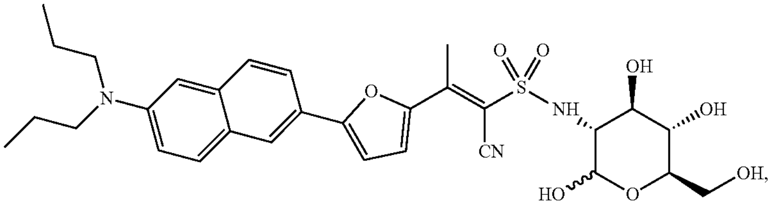
,
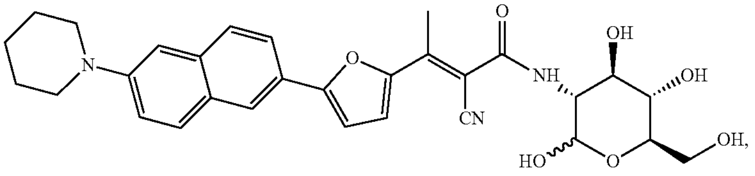
,
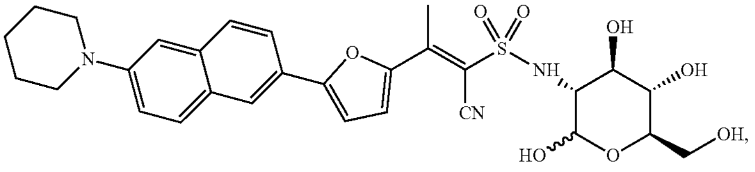
,
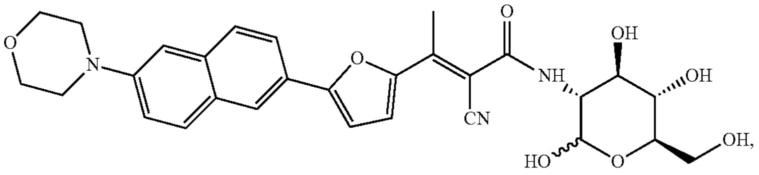
, -continued
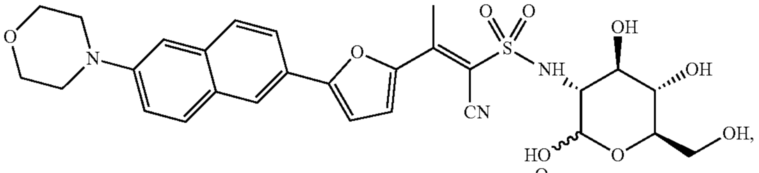
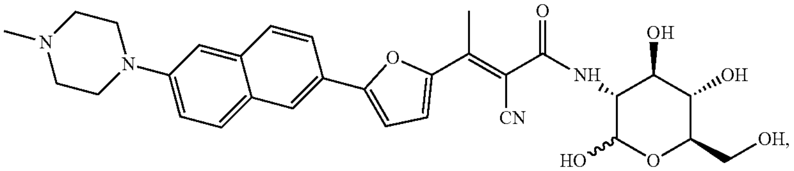
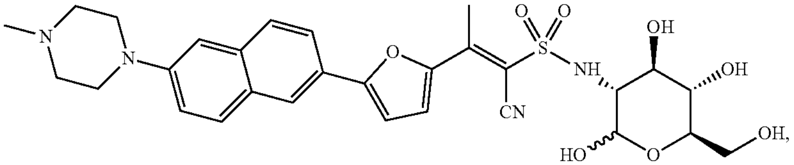
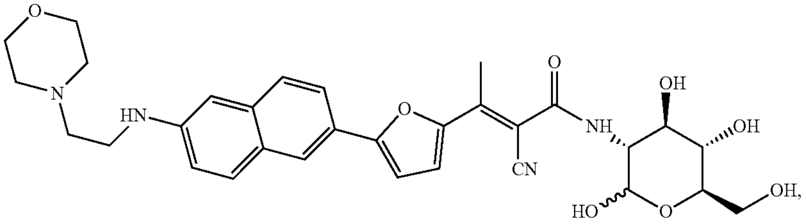
and
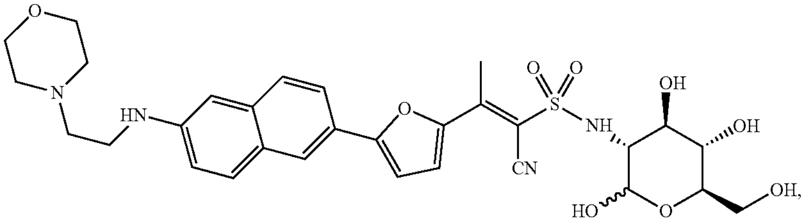
In certain embodiments, the compound is selected from a group consisting of
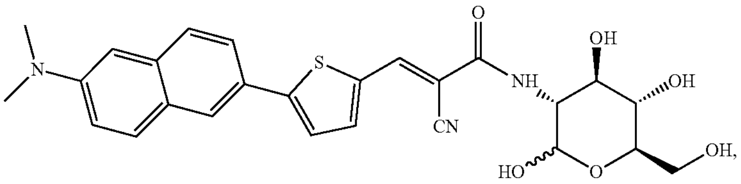
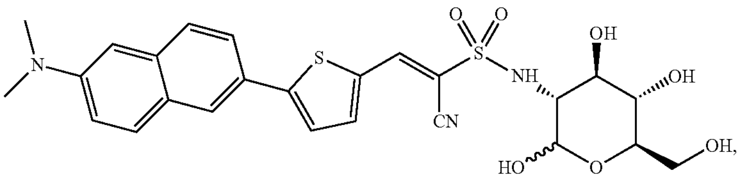
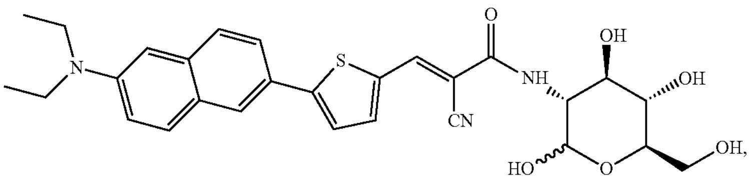

-continued
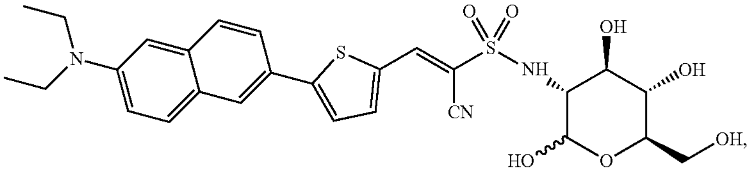
,
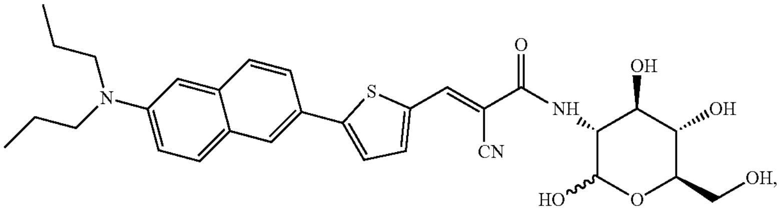
,
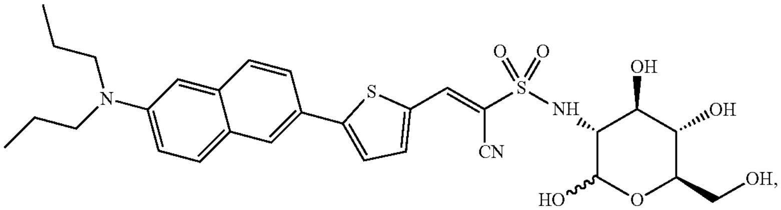
,
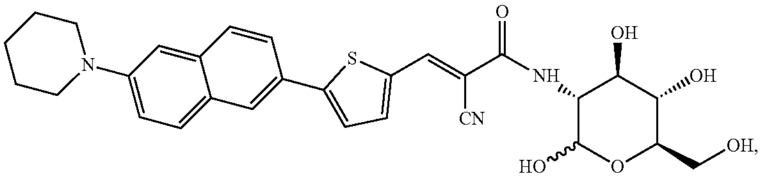
,
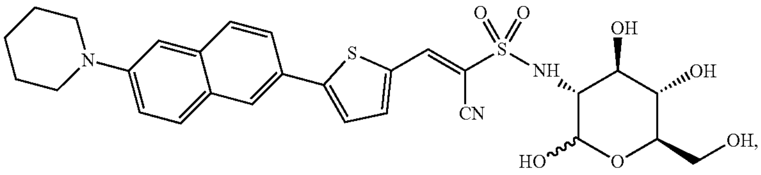
,
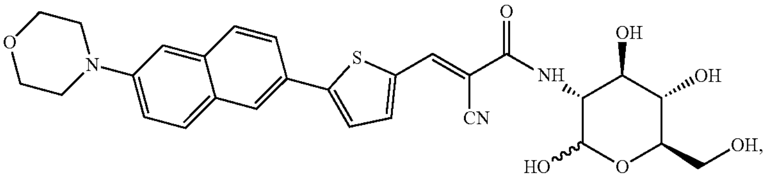
,
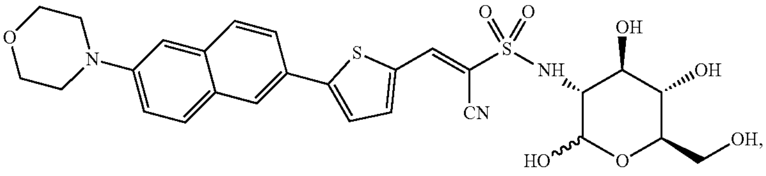
,
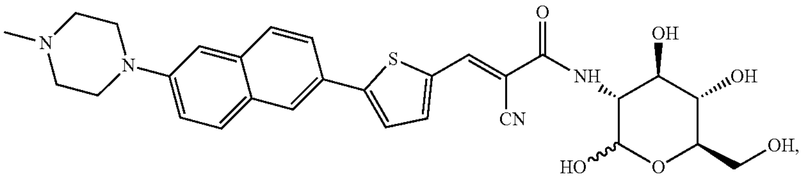
,
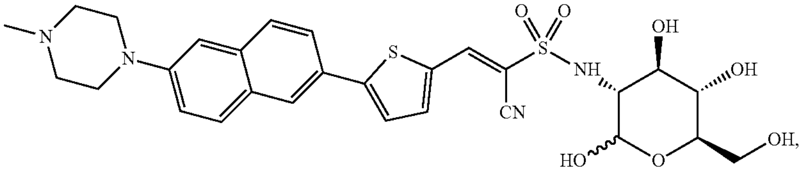
, -continued
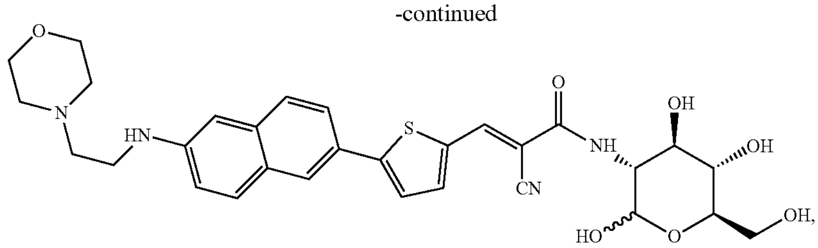
, and
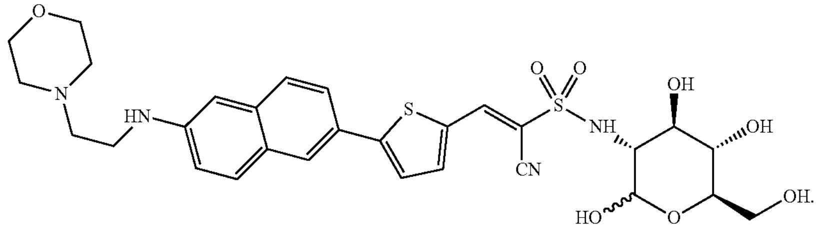
.
In certain embodiments, the compound is selected from a group consisting of
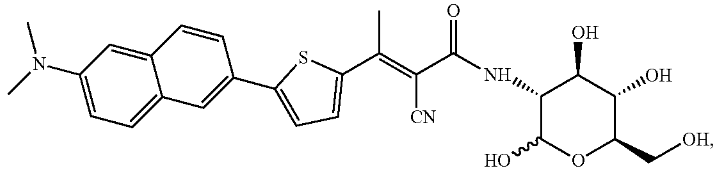
,
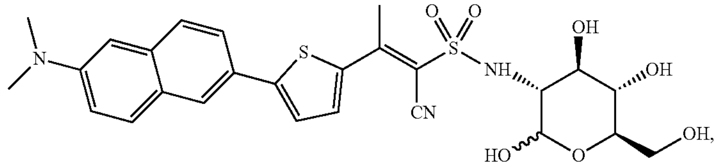
,
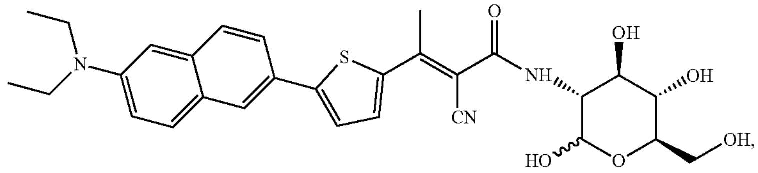
,
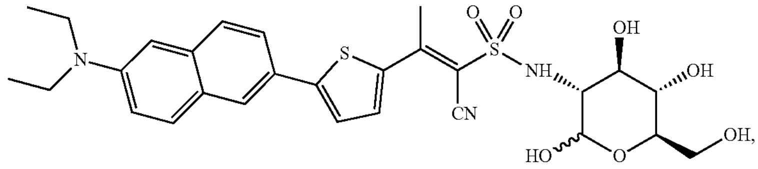
,
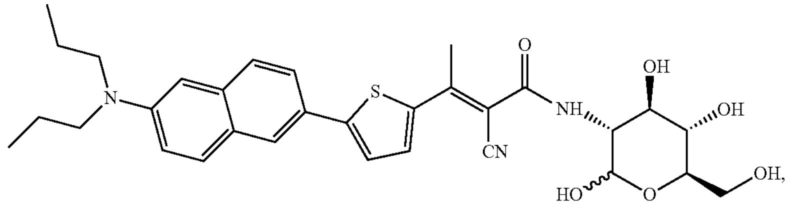
,
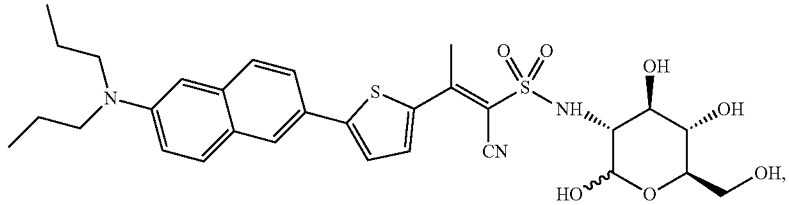
, -continued
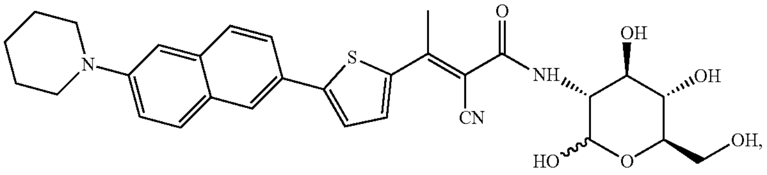
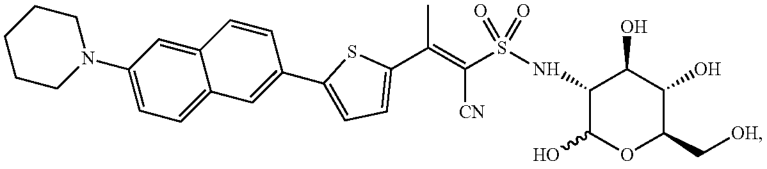
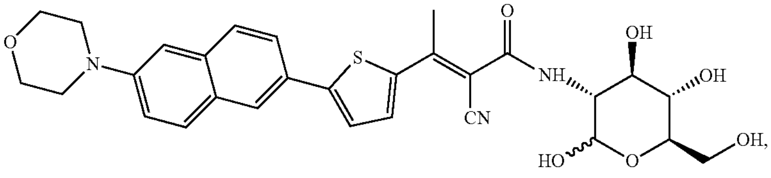
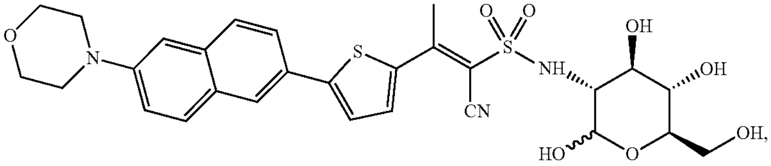
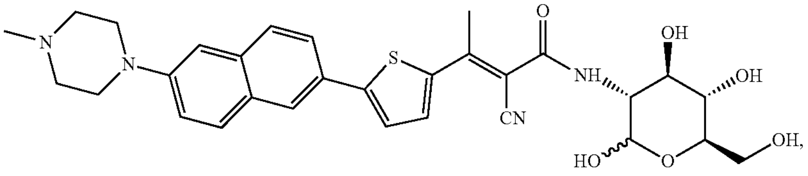
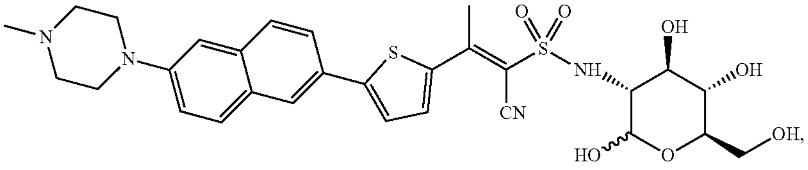
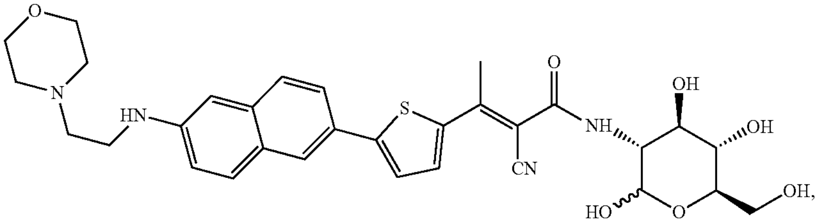
and
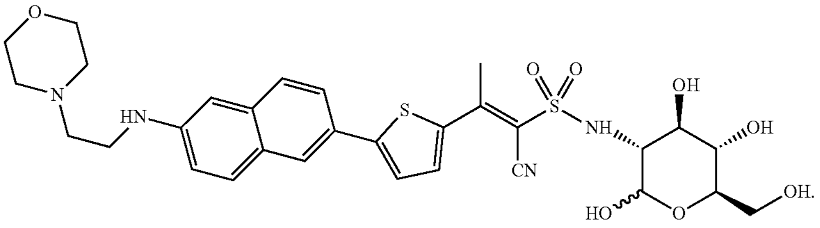

In certain embodiments, the compound is:

(Compound 1)

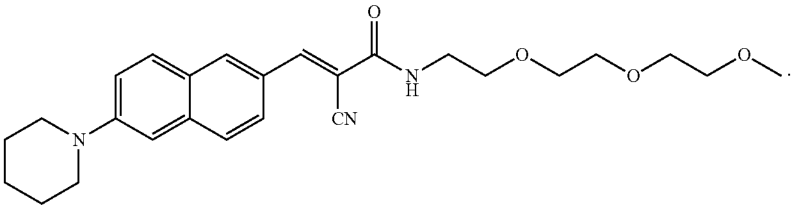

In certain embodiments, the compound is (E)-2-cyano-N-(2-(2-(2-methoxyethoxy)ethoxy)ethyl)-3-(6-(piperidin-11-yl)naphthalen-2-yl)acrylamide. In certain embodiments, the compound is (Z)-2-cyano-N-(2-(2-(2-methoxyethoxy)ethoxy)ethyl)-3-(6-(piperidin-1-yl)naphthalen-2-yl)acrylamide.

In certain embodiments, the compound is:

(Compound 2)

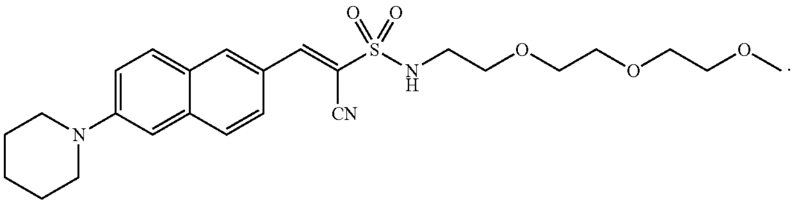

In certain embodiments, the compound is (E)-1-cyano-N-(2-(2-(2-methoxyethoxy)ethoxy)ethyl)-2-(6-(piperidin-1-yl)naphthalen-2-yl)ethene sulfonamide. In certain embodiments, the compound is (Z)-1-cyano-N-(2-(2-(2-methoxyethoxy)ethoxy)ethyl)-2-(6-(piperidin-1-yl)naphthalen-2-yl)ethenesulfonamide.

In certain embodiments, the compound is:

(Compound 3)

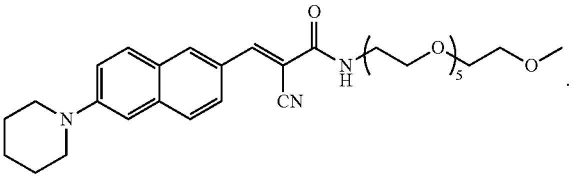

In certain embodiments, the compound is (E)-2-cyano-N-(2,5,8,11,14,17-hexaoxanonadecan-19-yl)-3-(6-(piperidin-1-yl)naphthalen-2-yl)acrylamide. In certain embodiments, the compound is (Z)-2-cyano-N-(2,5,8,11,14,17-hexaoxanonadecan-19-yl)-3-(6-(piperidin-1-yl)naphthalen-2-yl)acrylamide.

In certain embodiments, the compound is:

(Compound 4)

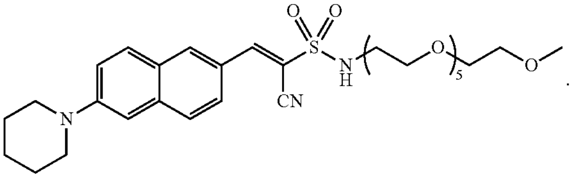

In certain embodiments, the compound is (E)-1-cyano-N-(2,5,8,11,14,17-hexaoxanonadecan-19-yl)-2-(6-(piperidin-1-yl)naphthalen-2-yl)ethenesulfonamide. In certain embodiments, the compound is (Z)-1-cyano-N-(2,5,8,11,14,17-hexaoxanonadecan-19-yl)-2-(6-(piperidin-1-yl)naphthalen-2-yl)ethenesulfonamide.

In certain embodiments, the compound is:

(Compound 5)

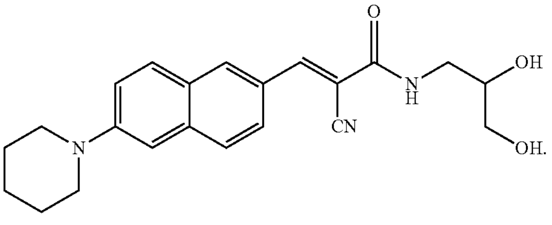

In certain embodiments, the compound is (E)-2-cyano-N-(2,3-dihydroxypropyl)-3-(6-(piperidin-1-yl)naphthalen-2-yl)acrylamide. In certain embodiments, the compound is (Z)-2-cyano-N-(2,3-dihydroxypropyl)-3-(6-(piperidin-1-yl)naphthalen-2-yl)acrylamide.

In certain embodiments, the compound is:

(Compound 6)

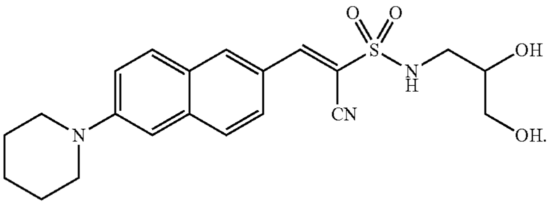

In certain embodiments, the compound is (E)-1-cyano-N-(2,3-dihydroxypropyl)-2-(6-(piperidin-1-yl)naphthalen-2-yl)ethenesulfonamide. In certain embodiments, the compound is (Z)-1-cyano-N-(2,3-dihydroxypropyl)-2-(6-(piperidin-1-yl)naphthalen-2-yl)ethenesulfonamide.

In certain embodiments, the compound is:

(Compound 7)

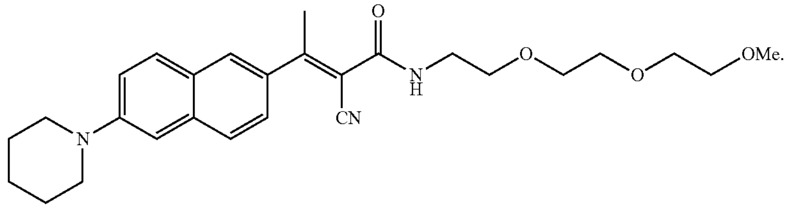

In certain embodiments, the compound is (E)-2-cyano-N-(2-(2-(2-methoxyethoxy)ethoxy)ethyl)-3-(6-(piperidin-1-yl)naphthalen-2-yl)but-2-enamide. In certain embodiments, the compound is (Z)-2-cyano-N-(2-(2-(2-methoxyethoxy)ethoxy)ethyl)-3-(6-(piperidin-1-yl)naphthalen-2-yl)but-2-enamide.

In certain embodiments, the compound is:

(Compound 8)

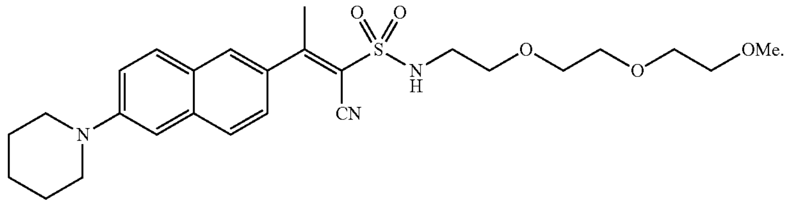

In certain embodiments, the compound is (E)-1-cyano-N-(2-(2-(2-methoxyethoxy)ethoxy)ethyl)-2-(6-(piperidin-1-yl)naphthalen-2-yl)prop-1-ene-1-sulfonamide.

In certain embodiments, the compound is (Z)-1-cyano-N-(2-(2-(2-methoxyethoxy)ethoxy)ethyl)-2-(6-(piperidin-1-yl)naphthalen-2-yl)prop-1-ene-1-sulfonamide.

In certain embodiments, the compound is:

(Compound 9)

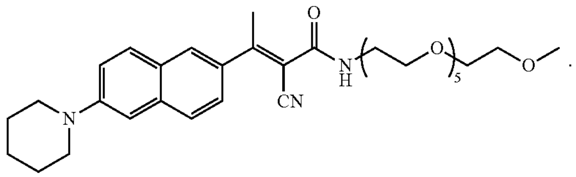

In certain embodiments, the compound is (E)-2-cyano-N-(2,5,8,11,14,17-hexaoxanonadecan-19-yl)-3-(6-(piperidin-1-yl)naphthalen-2-yl)but-2-enamide. In certain embodiments, the compound is (Z)-2-cyano-N-(2,5,8,11,14,17-hexaoxanonadecan-19-yl)-3-(6-(piperidin-1-yl)naphthalen-2-yl)but-2-enamide.

In certain embodiments, the compound is:

(Compound 10)

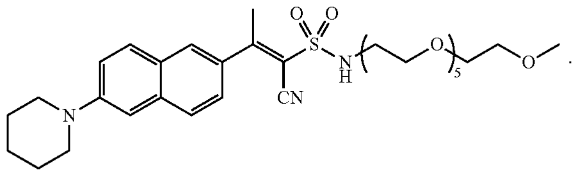

In certain embodiments, the compound is (E)-1-cyano-N-(2,5,8,11,14,17-hexaoxanonadecan-19-yl)-2-(6-(piperidin-1-yl)naphthalen-2-yl)prop-1-ene-1-sulfonamide. In certain embodiments, the compound is (Z)-1-cyano-N-(2,5,8,11,14,17-hexaoxanonadecan-19-yl)-2-(6-(piperidin-1-yl)naphthalen-2-yl)prop-1-ene-1-sulfonamide.

In certain embodiments, the compound is:

(Compound 11)

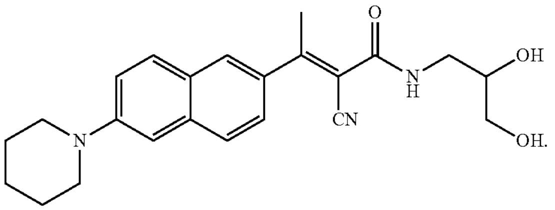

In certain embodiments, the compound is (E)-2-cyano-N-(2,3-dihydroxypropyl)-3-(6-(piperidin-1-yl)naphthalen-2-yl)but-2-enamide. In certain embodiments, the compound is (Z)-2-cyano-N-(2,3-dihydroxypropyl)-3-(6-(piperidin-1-yl)naphthalen-2-yl)but-2-enamide.

In certain embodiments, the compound is:

(Compound 12)

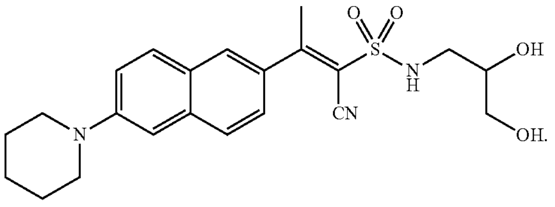

In certain embodiments, the compound is (E)-1-cyano-N-(2,3-dihydroxypropyl)-2-(6-(piperidin-1-yl)naphthalen-2-yl)prop-1-ene-1-sulfonamide. In certain embodiments, the compound is (Z)-1-cyano-N-(2,3-dihydroxypropyl)-2-(6-(piperidin-1-yl)naphthalen-2-yl)prop-1-ene-1-sulfonamide.

In certain embodiments, the compound is:

(Compound 13)

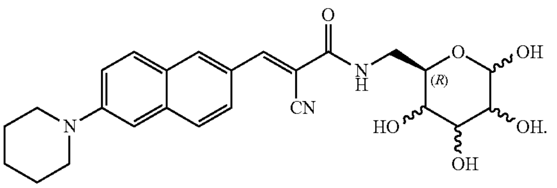

In certain embodiments, the compound is (R,E)-2-cyano-3-(6-(piperidin-1-yl)naphthalen-2-yl)-N-((3,4,5,6-tetrahydroxytetrahydro-2H-pyran-2-yl)methyl)acrylamide. In certain embodiments, the compound is (R,Z)-2-cyano-3-(6-(piperidin-1-yl)naphthalen-2-yl)-N-((3,4,5,6-tetrahydroxytetrahydro-2H-pyran-2-yl)methyl)acrylamide.

In certain embodiments, the compound is:

(Compound 14)

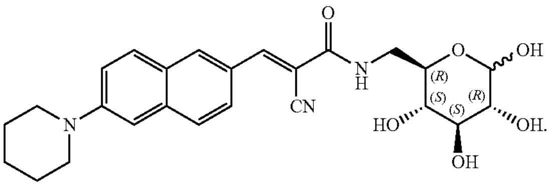

In certain embodiments, the compound is (E)-2-cyano-3-(6-(piperidin-1-yl)naphthalen-2-yl)-N-(((2R,3S,4S,5R)-3,4,5,6-tetrahydroxytetrahydro-2H-pyran-2-yl)methyl)acrylamide. In certain embodiments, the compound is (Z)-2-cyano-3-(6-(piperidin-1-yl)naphthalen-2-yl)-N-(((2R,3S,4S,5R)-3,4,5,6-tetrahydroxytetrahydro-2H-pyran-2-yl)methyl) acrylamide.

In certain embodiments, the compound is:

(Compound 15)

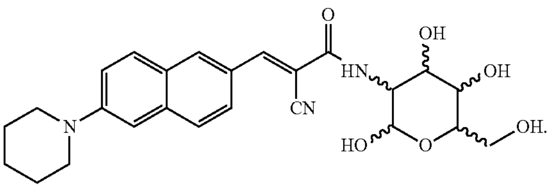

In certain embodiments, the compound is (E)-2-cyano-3-(6-(piperidin-1-yl)naphthalen-2-yl)-N-(2,4,5-trihydroxy-6-(hydroxymethyl)tetrahydro-2H-pyran-3-yl)acrylamide. In certain embodiments, the compound is (Z)-2-cyano-3-(6-(piperidin-1-yl)naphthalen-2-yl)-N-(2,4,5-trihydroxy-6-(hydroxymethyl)tetrahydro-2H-pyran-3-yl)acrylamide.

In certain embodiments, the compound is:

(Compound 16)

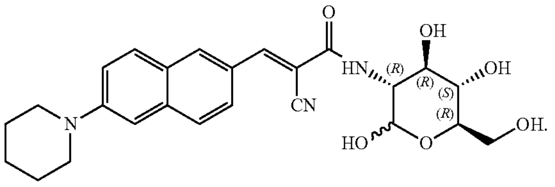

In certain embodiments, the compound is (E)-2-cyano-3-(6-(piperidin-1-yl)naphthalen-2-yl)-N-((3R,4R,5S,6R)-2,4,5-trihydroxy-6-(hydroxymethyl)tetrahydro-2H-pyran-3-yl) acrylamide. In certain embodiments, the compound is (Z)-2-cyano-3-(6-(piperidin-1-yl)naphthalen-2-yl)-N-((3R,4R,5S,6R)-2,4,5-trihydroxy-6-(hydroxymethyl)tetrahydro-2H-pyran-3-yl)acrylamide.

In certain embodiments, the compound is:

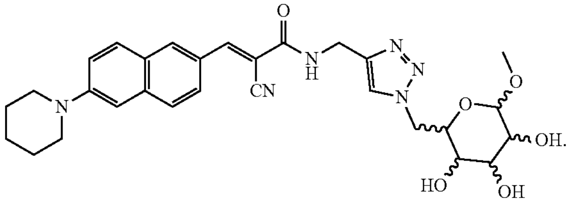 [SMILES: COC1OC(Cn2cc(CNC(=O)/C(C#N)=C/c3ccc4cc(N5CCCCC5)ccc4c3)nn2)C(O)C(O)C1O]

In certain embodiments, the compound is (E)-2-cyano-3-(6-(piperidin-1-yl)naphthalen-2-yl)-N-((1-((3,4,5-trihydroxy-6-methoxytetrahydro-2H-pyran-2-yl)methyl)-1H-1,2,3-triazol-4-yl)methyl)acrylamide. In certain embodiments, the compound is (Z)-2-cyano-3-(6-(piperidin-1-yl)naphthalen-2-yl)-N-((1-((3,4,5-trihydroxy-6-methoxytetrahydro-2H-pyran-2-yl)methyl)-1H-1,2,3-triazol-4-yl)methyl)acrylamide.

In certain embodiments, the compound is:

(Compound 20)

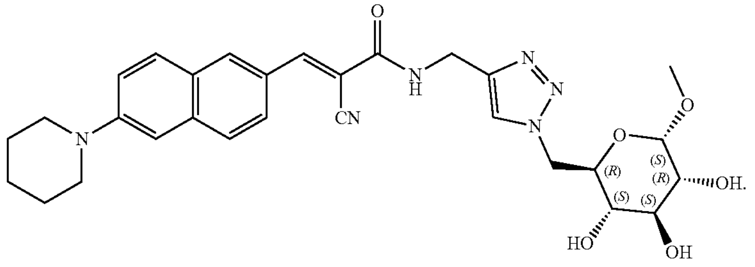

In certain embodiments, the compound is (E)-2-cyano-3-(6-(piperidin-1-yl)naphthalen-2-yl)-N-((1-(((2R,3S,4S,5R,6S)-3,4,5-trihydroxy-6-methoxytetrahydro-2H-pyran-2-yl)methyl)-1H-1,2,3-triazol-4-yl)methyl)acrylamide. In certain embodiments, the compound is (Z)-2-cyano-3-(6-(piperidin-1-yl)naphthalen-2-yl)-N-((1-(((2R,3S,4S,5R,6S)-3,4,5-trihydroxy-6-methoxytetrahydro-2H-pyran-2-yl)methyl)-1H-1,2,3-triazol-4-yl)methyl)acrylamide.

In certain embodiments, the compound is:

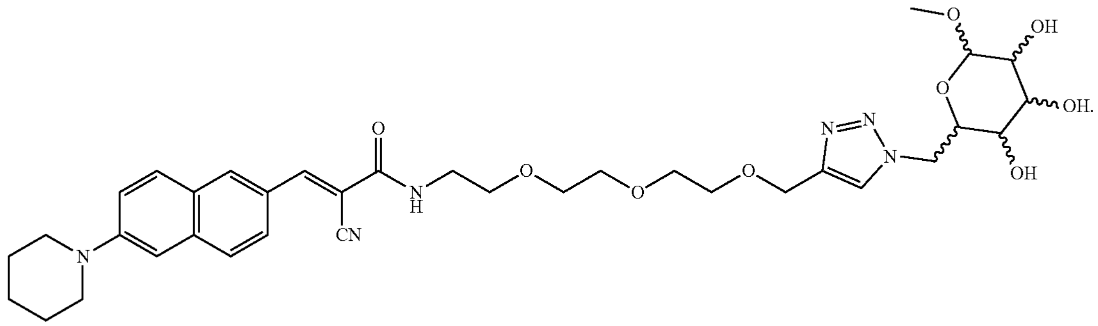 [SMILES: COC1OC(Cn2cc(COCCOCCOCCNC(=O)/C(C#N)=C/c3ccc4cc(N5CCCCC5)ccc4c3)nn2)C(O)C(O)C1O]

In certain embodiments, the compound is (E)-2-cyano-3-(6-(piperidin-1-yl)naphthalen-2-yl)-N-(2-(2-(2-((1-((3,4,5-trihydroxy-6-methoxytetrahydro-2H-pyran-2-yl)methyl)-1H-1,2,3-triazol-4-yl)methoxy)ethoxy)ethoxy)ethyl)acrylamide. In certain embodiments, the compound is (Z)-2-cyano-3-(6-(piperidin-1-yl)naphthalen-2-yl)-N-(2-(2-(2-((1-((3,4,5-trihydroxy-6-methoxytetrahydro-2H-pyran-2-yl)methyl)-1H-1,2,3-triazol-4-yl)methoxy)ethoxy)ethoxy)ethyl)acrylamide.

In certain embodiments, the compound is:

(Compound 19)

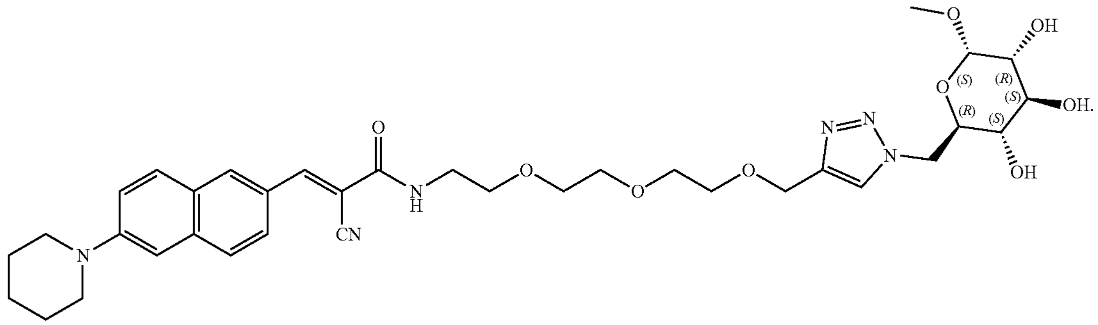

In certain embodiments, the compound is (E)-2-cyano-3-(6-(piperidin-1-yl)naphthalen-2-yl)-N-(2-(2-(2-((1-(((2R,3S,4S,5R,6S)-3,4,5-trihydroxy-6-methoxytetrahydro-2H-pyran-2-yl)methyl)-1H-1,2,3-triazol-4-yl)methoxy)ethoxy)ethoxy)ethyl)acrylamide. In certain embodiments, the compound is (Z)-2-cyano-3-(6-(piperidin-1-yl)naphthalen-2-yl)-N-(2-(2-(2-((1-(((2R,3S,4S,5R,6S)-3,4,5-trihydroxy-6-methoxytetrahydro-2H-pyran-2-yl)methyl)-1H-1,2,3-triazol-4-yl)methoxy)ethoxy)ethoxy)ethyl)acrylamide.

In certain embodiments, the compound is (Compound 21)

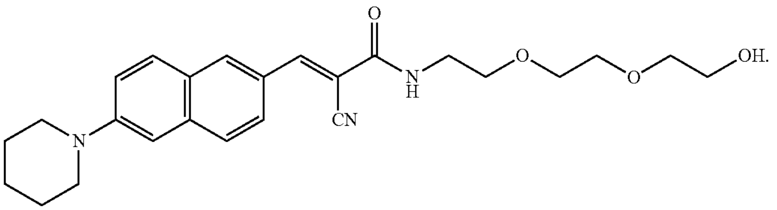

In certain embodiments, the compound is a pharmaceutically acceptable salt or solvate of Compound 21.

In certain embodiments, the compound is (Compound 22)

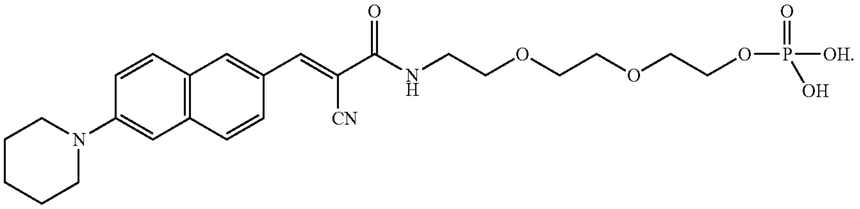

In certain embodiments, the compound is a pharmaceutically acceptable salt or solvate of Compound 22.

In certain embodiments, the compound is (Compound 23)

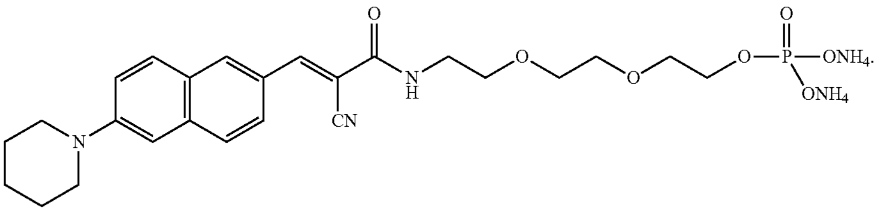

In certain embodiments, each of Ari is independently a substituted or unsubstituted naphthylene or a substituted or unsubstituted phenylene. In certain embodiments, $Ar_2$ is a substituted or unsubstituted naphthylene or a substituted or unsubstituted phenylene. In certain embodiments, $Ar_2$ is a substituted or unsubstituted pyridyl, substituted or unsubstituted pyrimidyl, substituted or unsubstituted pyrazinyl or substituted or unsubstituted pyradizinyl. In certain embodiments, $Ar_2$ is a substituted or unsubstituted pyridyl.

The substituent EDG in Formula II is an electron donating group. In certain embodiments, EDG is any electron donating group known in the art. In some cases, it is any atom or functional group that is capable of donating some of its electron density into a conjugated pi system via resonance or inductive electron withdrawal, thus making the pi system more nucleophilic. In certain embodiments, the EDG is $—OR_{49}$, $—NR_{50}R_{51}$, $—SR_{52}$, $—PR_{53}R_{54}$, $—NR_{55}C(O)R_{56}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{57}$; wherein each $R_{57}$ is independently halogen, $—OR_{58}$, $—NR_{59}R_{60}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene; each of $R_{49}$, $R_{50}$, $R_{51}$, $R_{52}$, $R_{53}$, $R_{54}$, $R_{55}$, $R_{56}$, $R_{58}$, $R_{59}$ and $R_{60}$ is independently hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, each of which except for hydrogen is optionally substituted with one or more $R_{61}$ and wherein $R_{50}$ and $R_{51}$ are optionally joined together to form a heterocycloalkyl or heteroaryl optionally substituted with $R_{61}$; each of $R_{61}$ is independently halogen, $—OR_{62}$, $—NR_{63}R_{64}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{65}$; each of $R_{62}$, $R_{63}$ and $R_{64}$ is independently hydrogen or $C_1$-$C_{10}$ alkyl; and each $R_{65}$ is independently $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene.

In certain embodiments, Y is absent, O, NH, or S. In certain embodiments, Y is absent (i.e. Y is a bond). In certain embodiments, Y is O. In certain embodiments, Y is NH. In certain embodiments, Y is S.

The variable x in Formula II is an integer from 0-10. In certain embodiments, x is 0. In certain embodiments, x is 1. In certain embodiments, x is 2. In certain embodiments, x is 3. In certain embodiments, x is 4. In certain embodiments, x is 5. In certain embodiments, x is 6. In certain embodiments, x is 7. In certain embodiments, x is 8. In certain embodiments, x is 9. In certain embodiments, x is 10.

The variable y in Formula II is an integer from 0-10. In certain embodiments, y is 0. In certain embodiments, y is 1. In certain embodiments, y is 2. In certain embodiments, y is 3. In certain embodiments, y is 4. In certain embodiments, y is 5. In certain embodiments, y is 6. In certain embodiments, y is 7. In certain embodiments, y is 8. In certain embodiments, y is 9. In certain embodiments, y is 10.

The variable z in Formula II is an integer from 1-10. In certain embodiments, z is 1. In certain embodiments, z is 2. In certain embodiments, z is 3. In certain embodiments, z is 4. In certain embodiments, z is 5. In certain embodiments, z is 6. In certain embodiments, z is 7. In certain embodiments, z is 8. In certain embodiments, z is 9. In certain embodiments, z is 10.

In certain embodiments, x is 0, y is 0, z is 1, and Y is O.

In certain embodiments, x is 0, y is 0, z is 1, and Y is S.

In certain embodiments, x is 0, y is 0, z is 1, and Y is NH.

In certain embodiments, x is 0, y is 0, z is 1, and Y is absent.

In certain embodiments, x is 0, y is 0, z is 2, and Y is O.

In certain embodiments, x is 0, y is 0, z is 2, and Y is S.

In certain embodiments, x is 0, y is 0, z is 2, and Y is NH.

In certain embodiments, x is 0, y is 0, z is 2, and Y is absent.

In one aspect the disclosure provides a compound of Formula IIa:

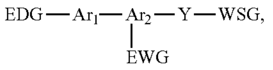

(Formula IIa)

wherein EDG, $Ar_1$, $Ar_2$, Y, EWG, and WSG are defined as above for Formula II.

In one aspect the disclosure provides a compound of Formula IIb:

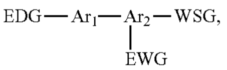

(Formula IIb)

wherein EDG, $Ar_1$, $Ar_2$, EWG, and WSG are defined as above for Formula II.

In some cases, the compound according to Formula II is selected from a group consisting of

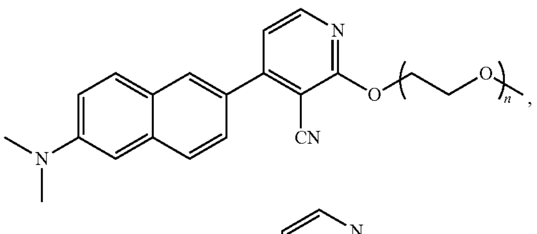

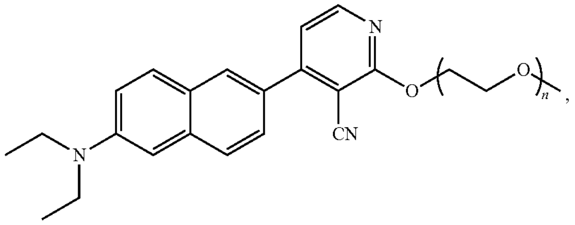

-continued

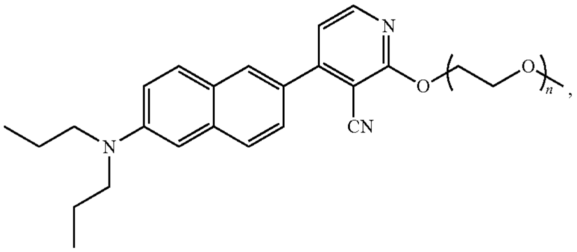

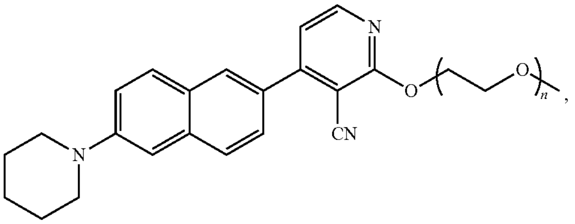

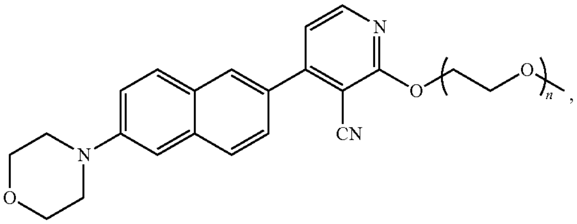

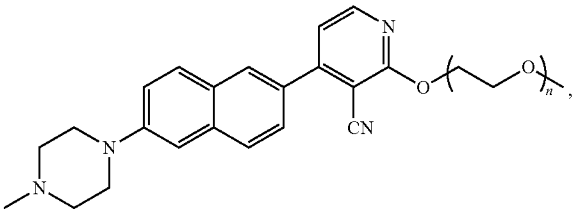

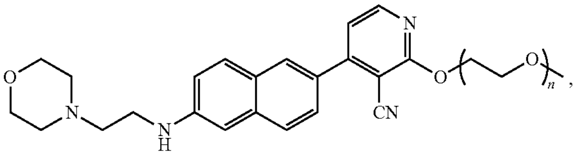

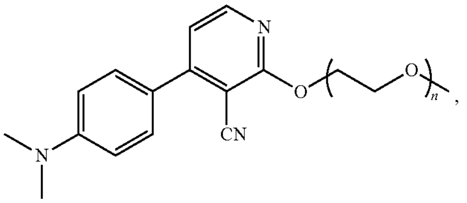

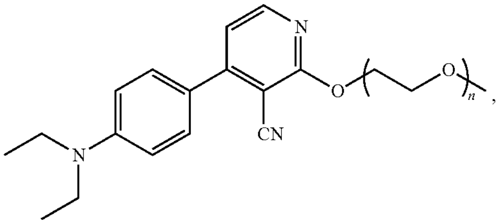

-continued
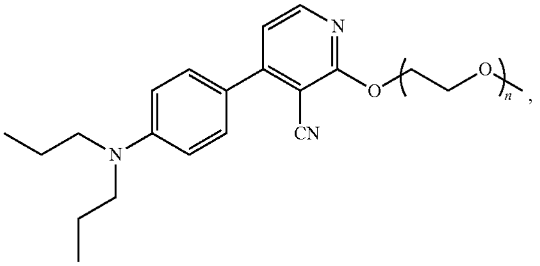
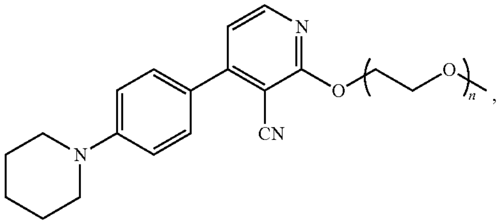
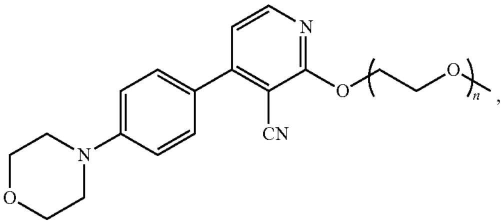
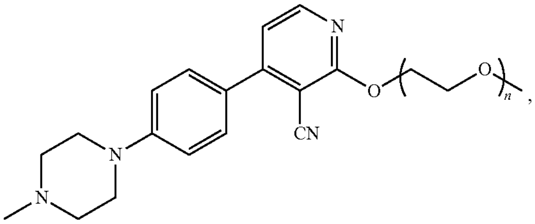
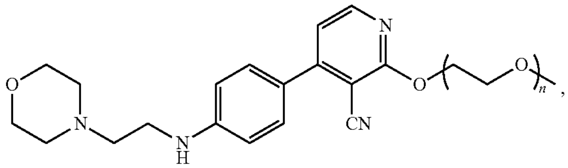
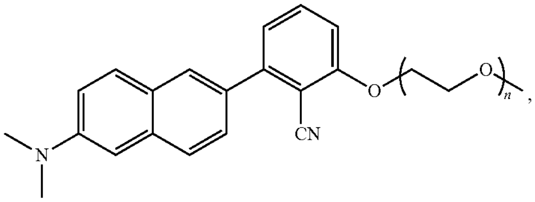
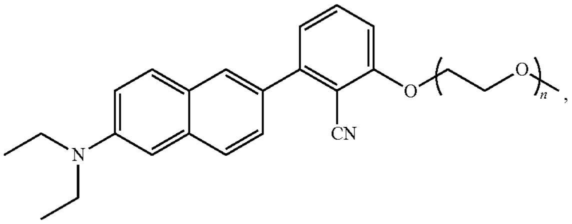
-continued
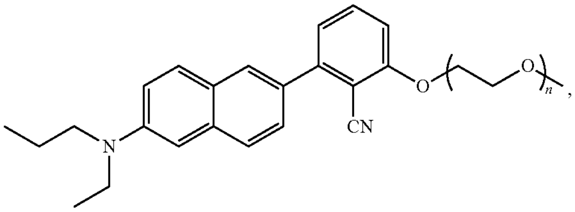
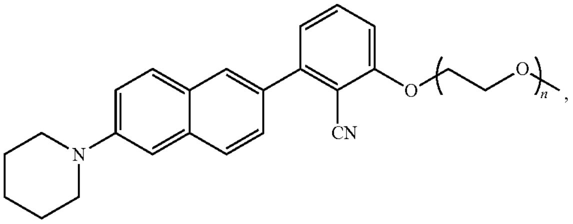
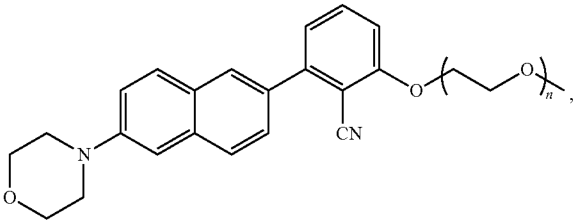
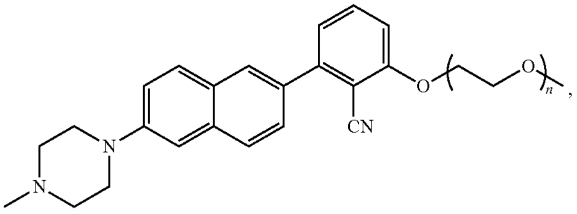
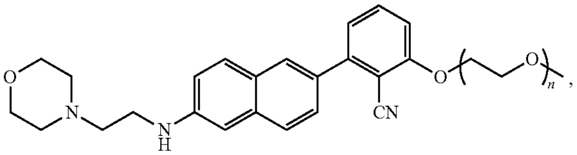
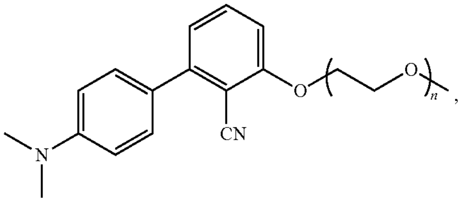
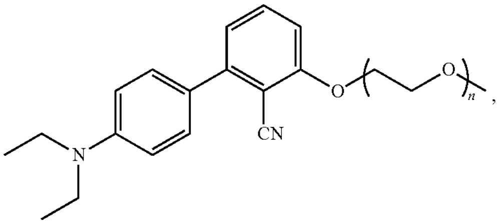
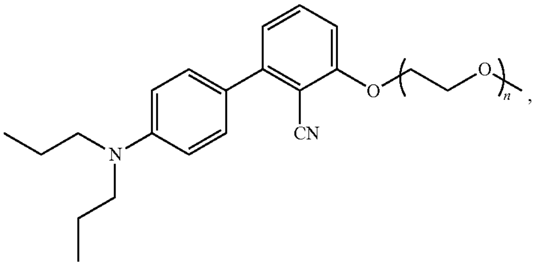

-continued
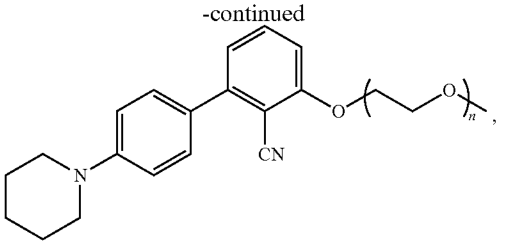
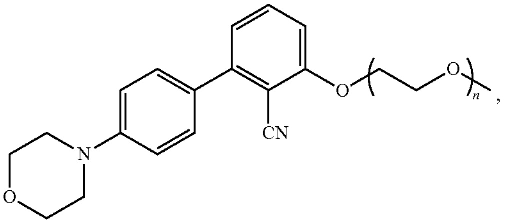
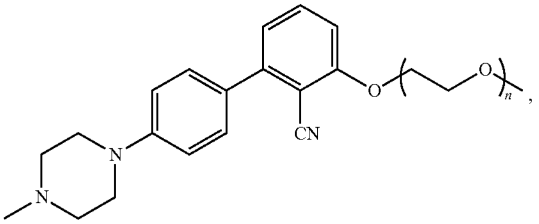
and
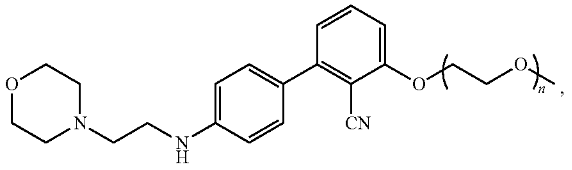
wherein n is an integer with value 0-50. In certain embodiments, n is a integer of value 0-10, e.g. n is 0, 1, 2, 3, 4, 5, 6, 7, 8, 9, or 10.
In certain embodiments, the compound is selected from a group consisting of:
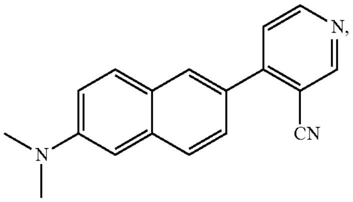
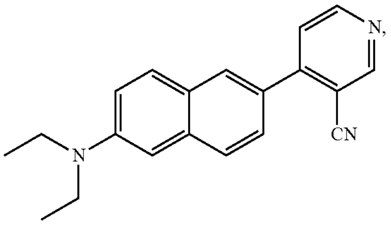
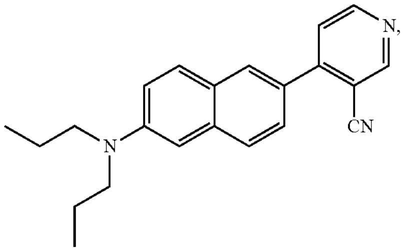
-continued
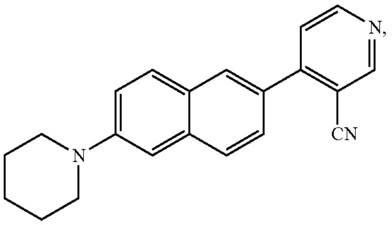
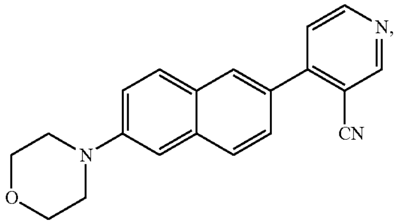
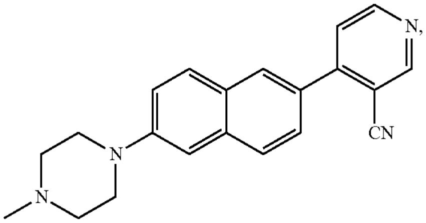
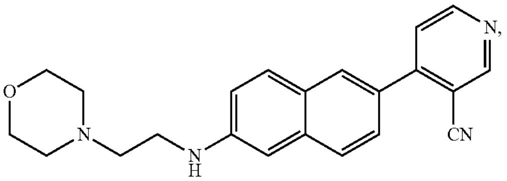
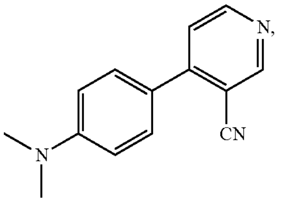
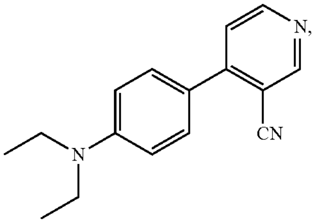
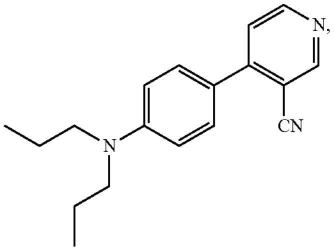

-continued
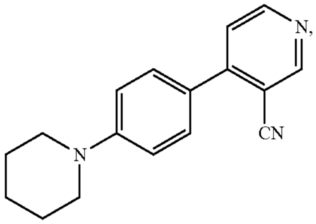,
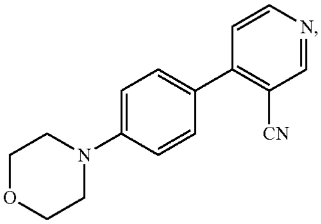,
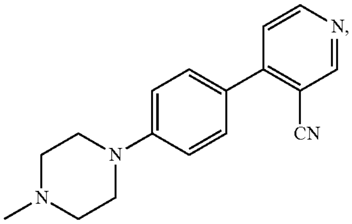,
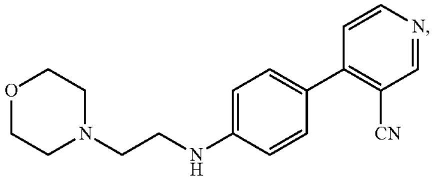,
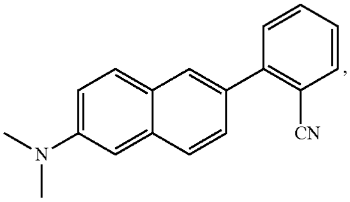,
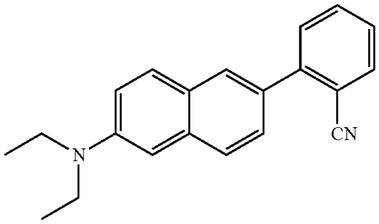,
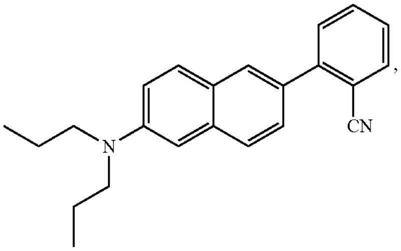,
-continued
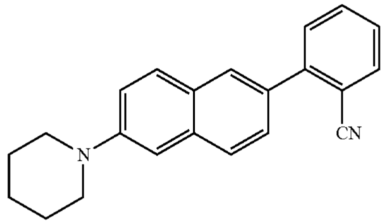,
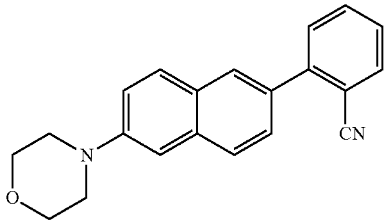,
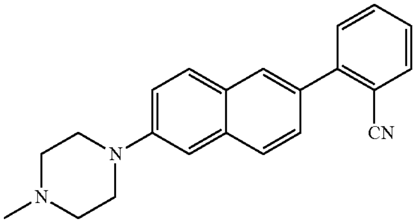,
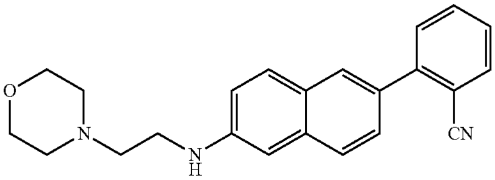,
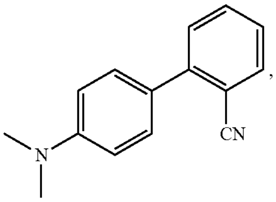,
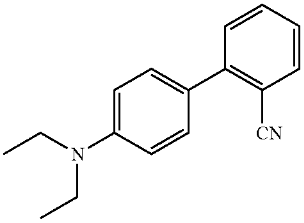,
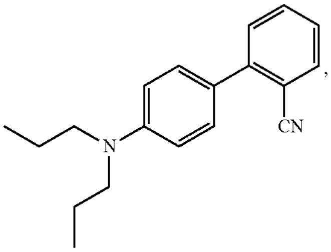, -continued
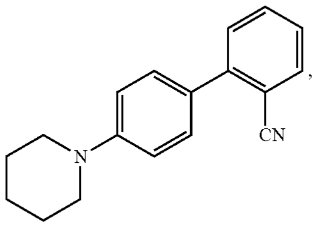
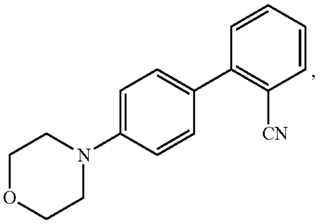
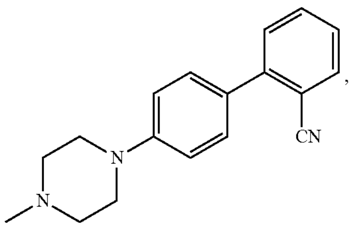
and
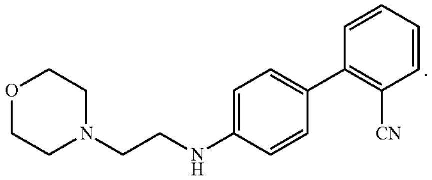
In certain embodiments, the compound is selected from a group consisting of
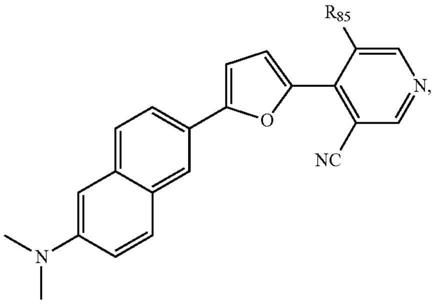
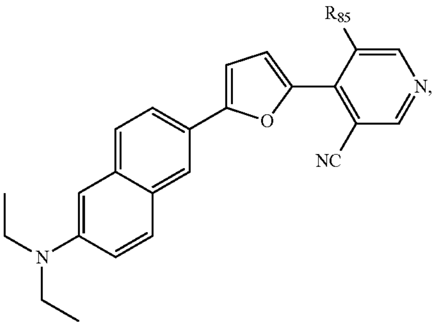
-continued
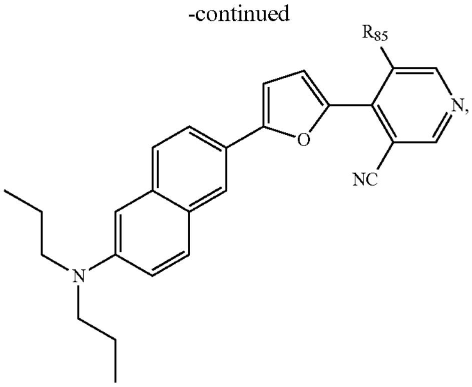
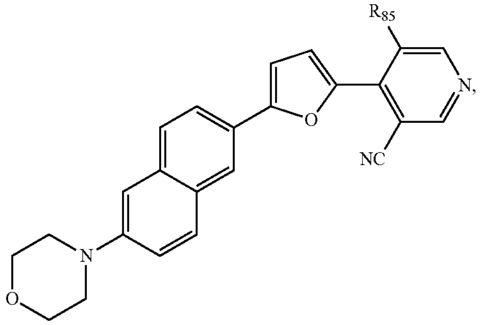
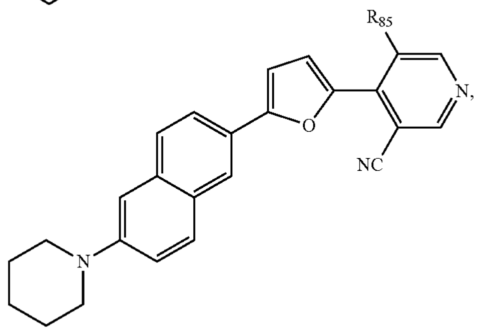
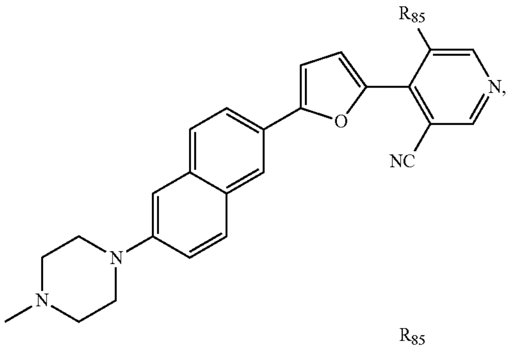
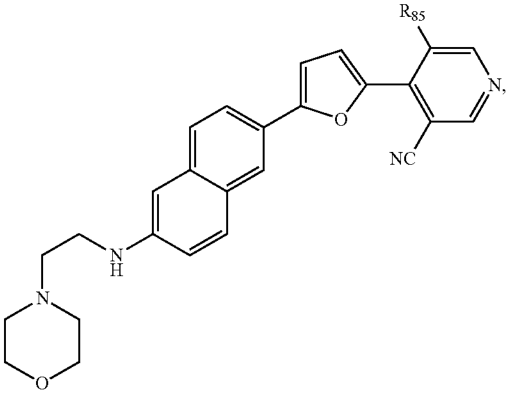

-continued
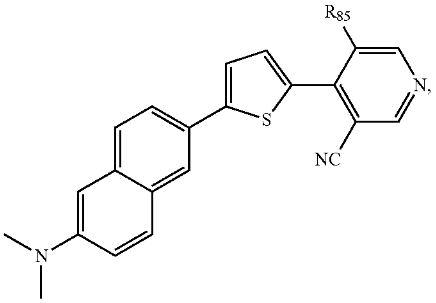
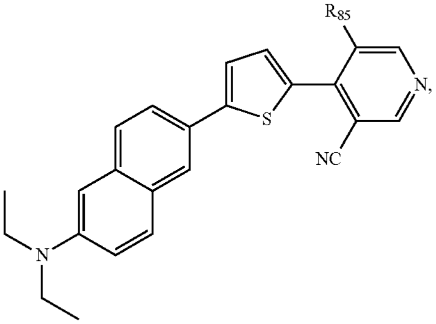
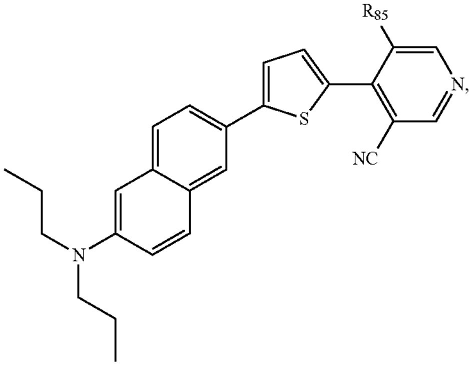
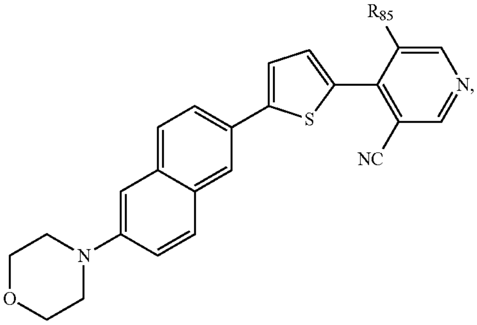
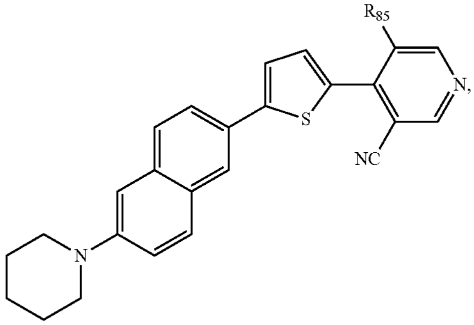
-continued
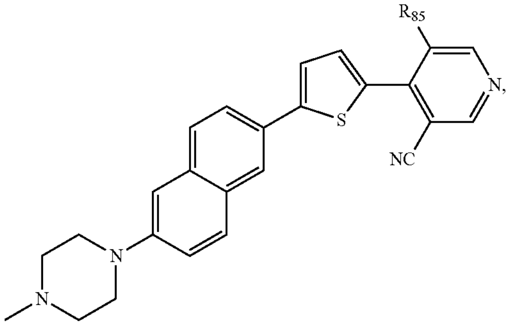
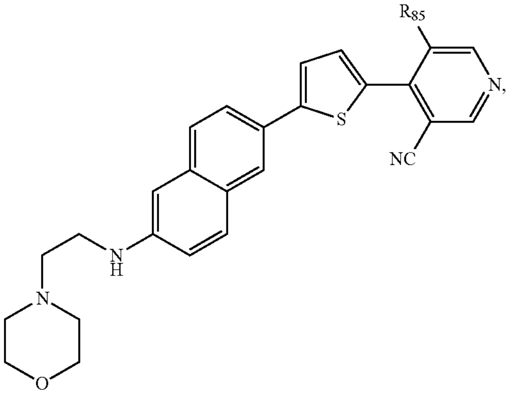
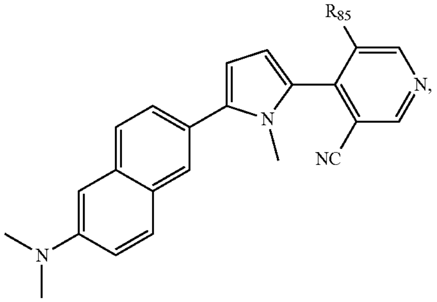
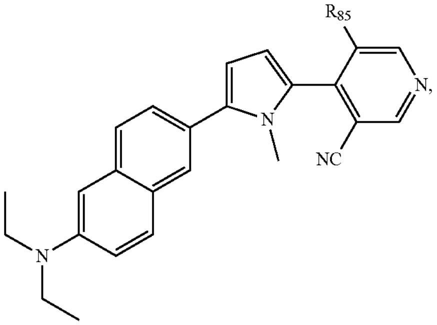
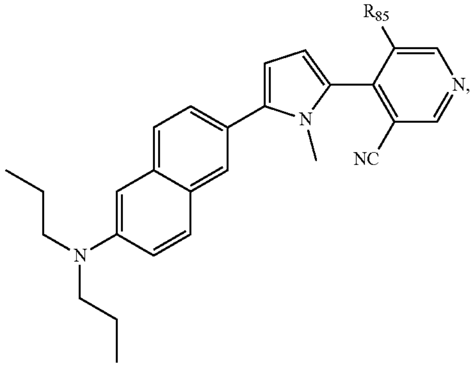

-continued
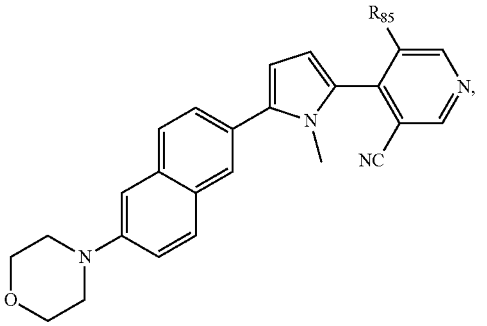
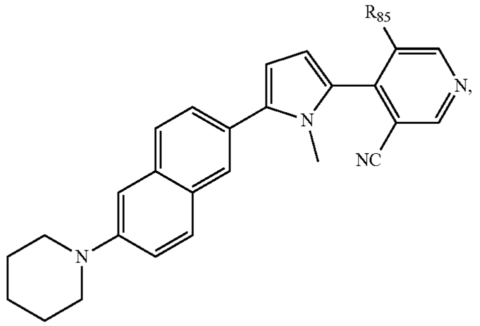
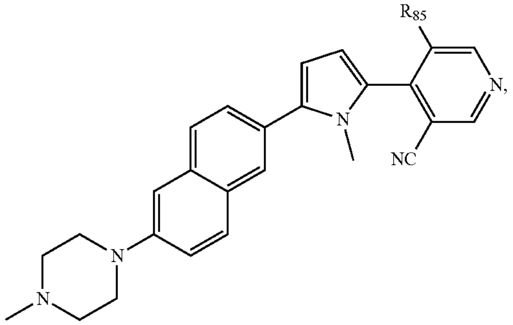
and
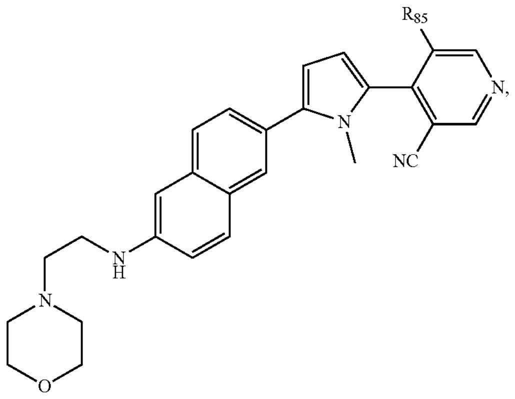
wherein $R_{85}$ is H or CN.
In certain embodiments, the compound is selected from a group consisting of
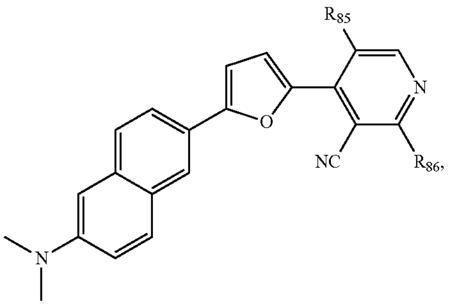
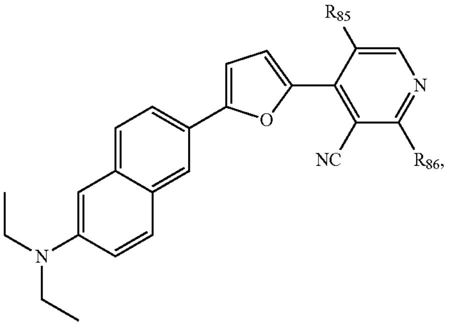
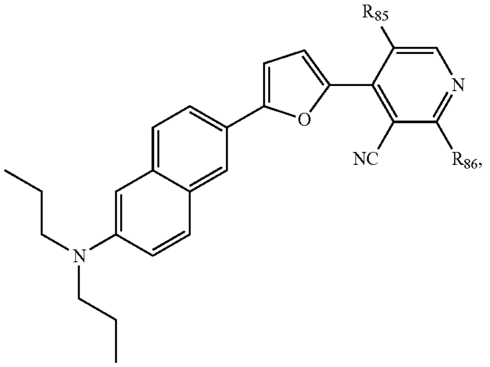
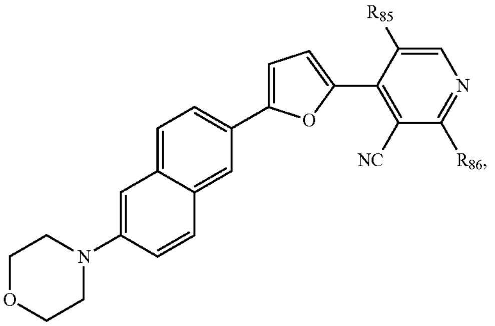
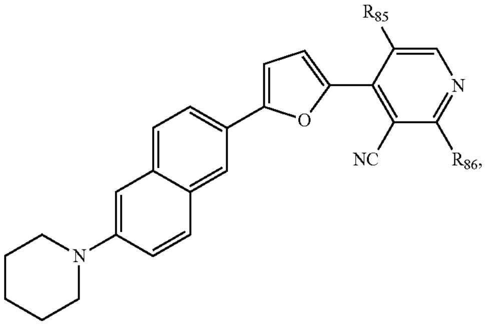

-continued
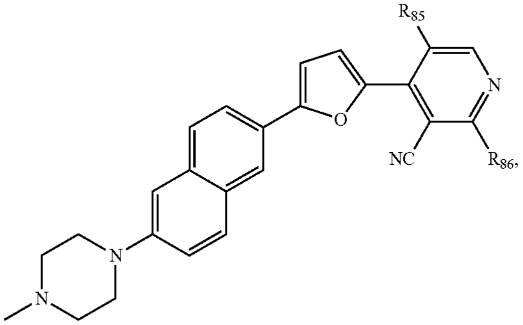
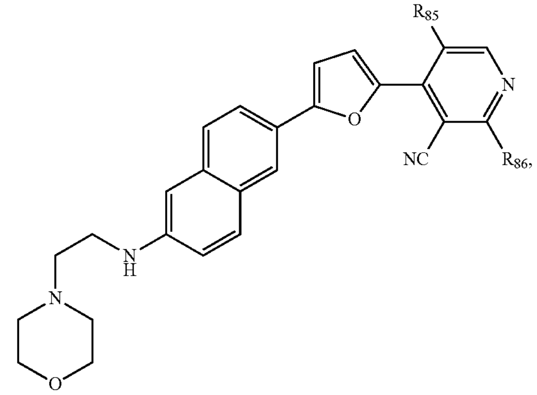
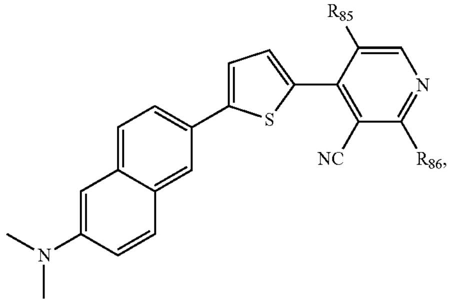
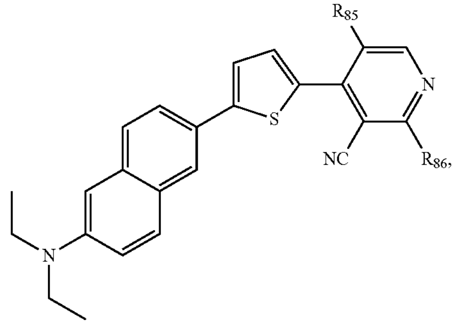
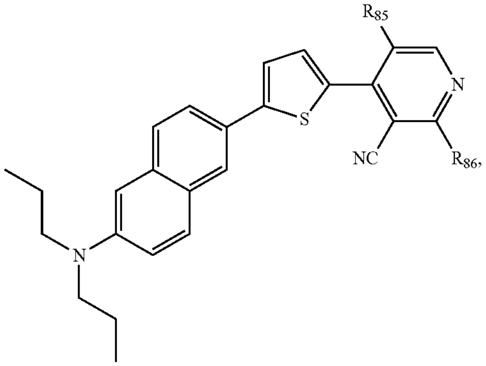
-continued
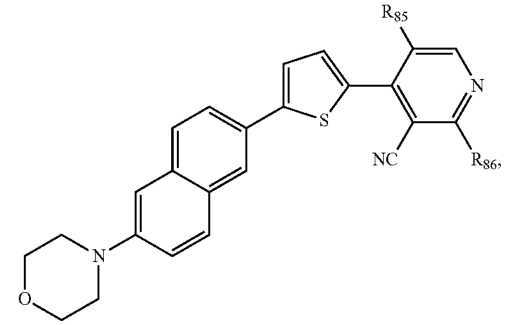
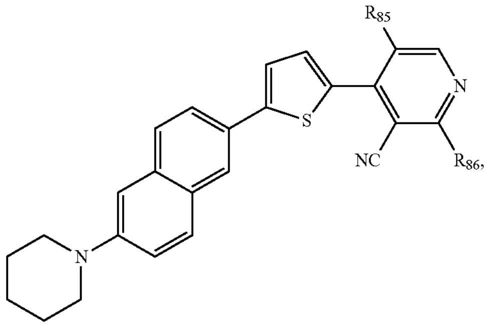
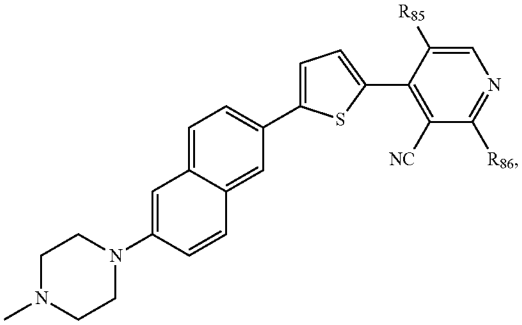
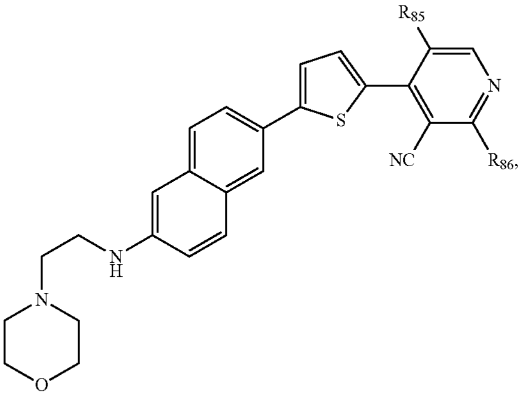
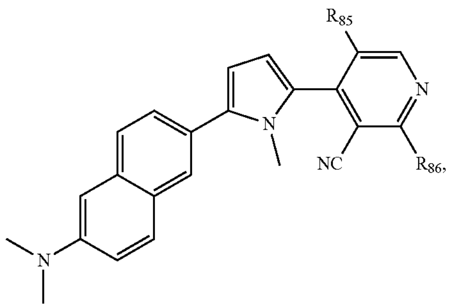

-continued
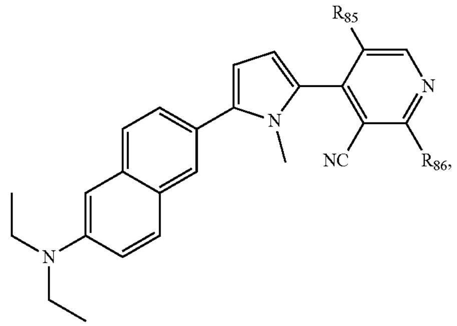
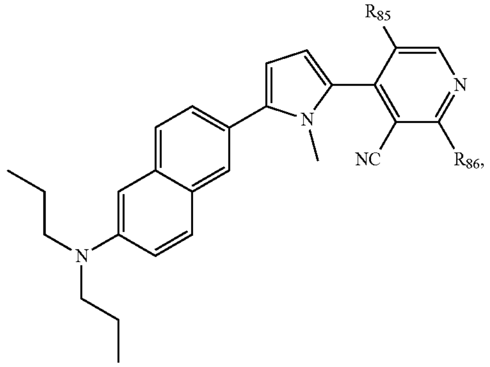
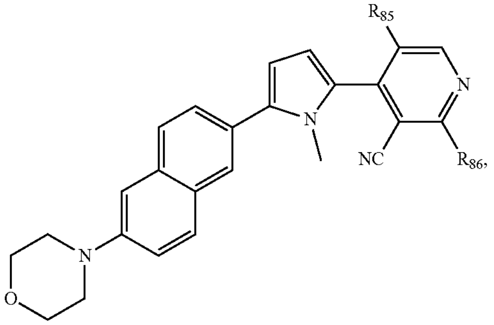
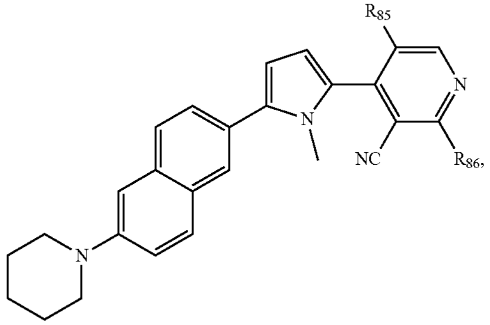
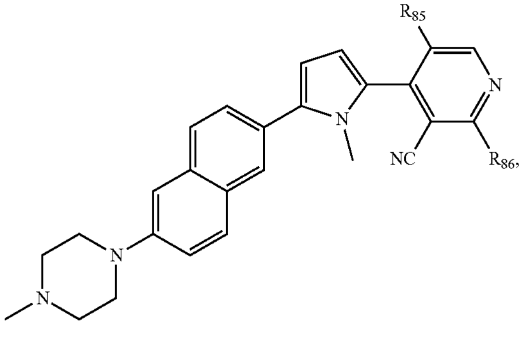
and
-continued
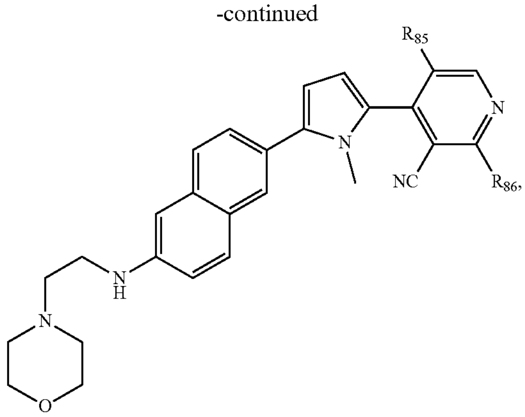
wherein $R_{85}$ is H or CN and $R_{86}$ is
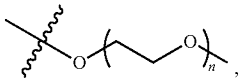
wherein n is an integer with value 0-50. In certain embodiments, n is a integer of value 0-10, e.g. n is 0, 1, 2, 3, 4, 5, 6, 7, 8, 9, or 10.
In certain embodiments, the compound is selected from a group consisting of
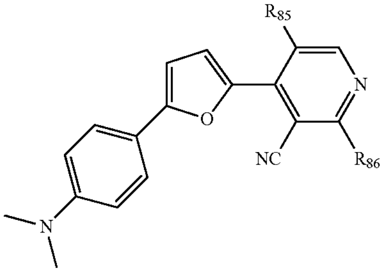
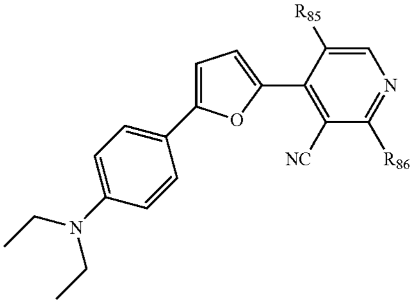
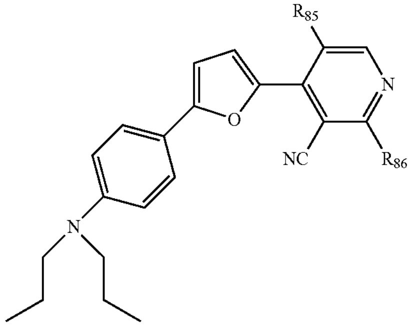

-continued
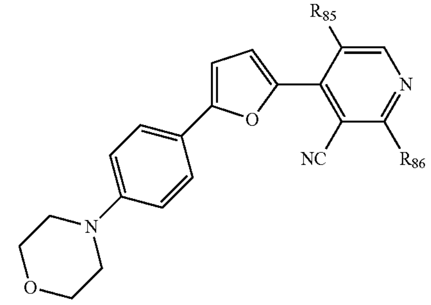
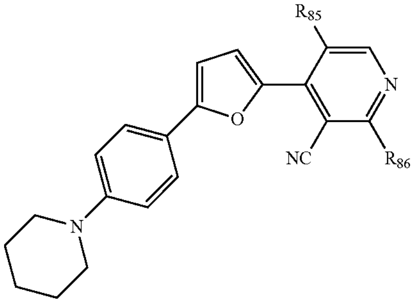
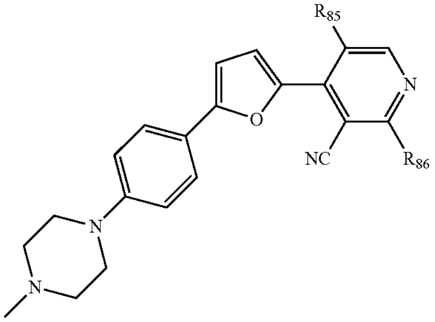
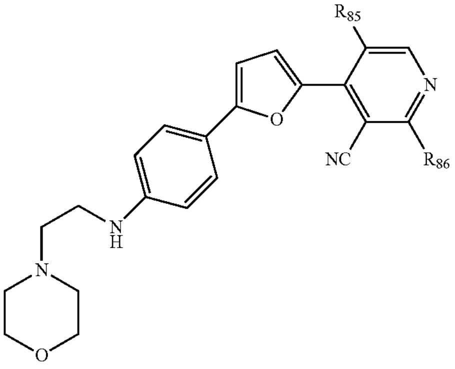
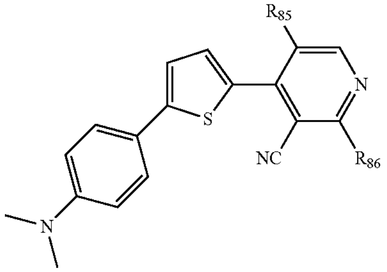
-continued
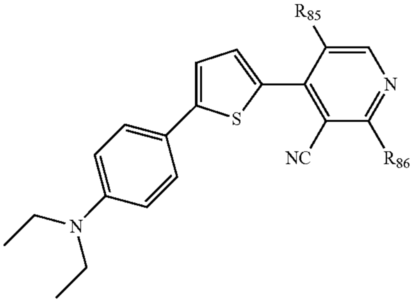
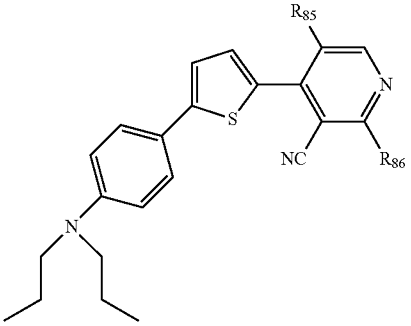
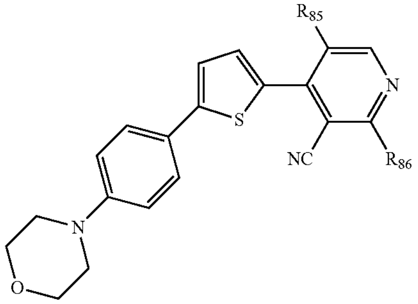
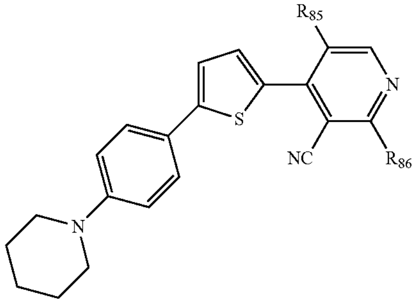
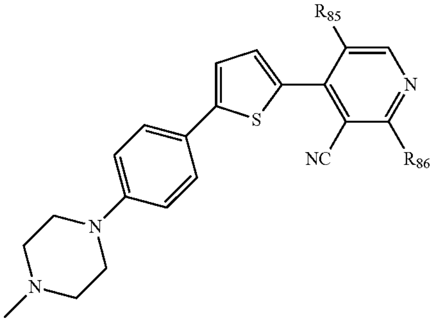

-continued
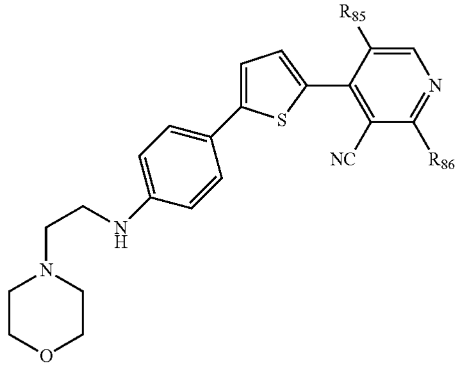
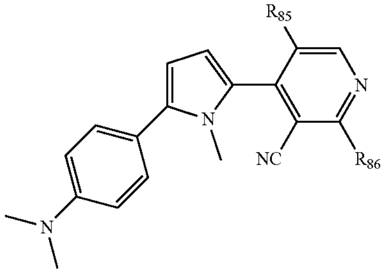
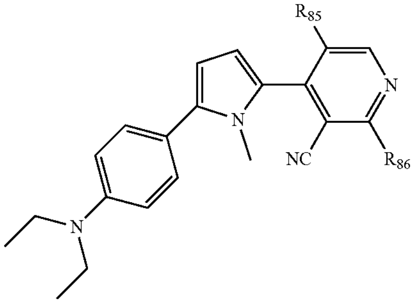
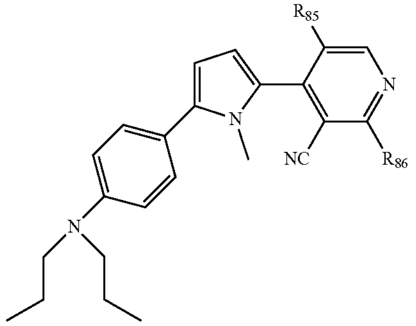
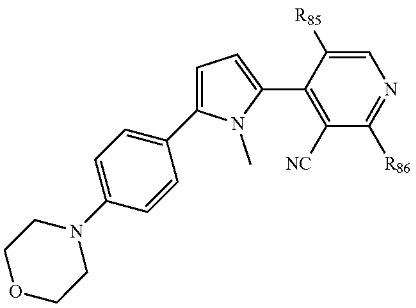
-continued
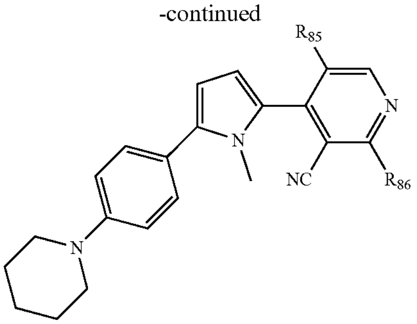
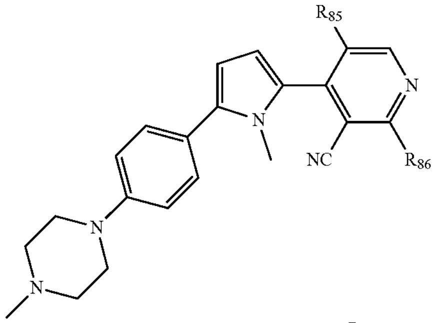
and
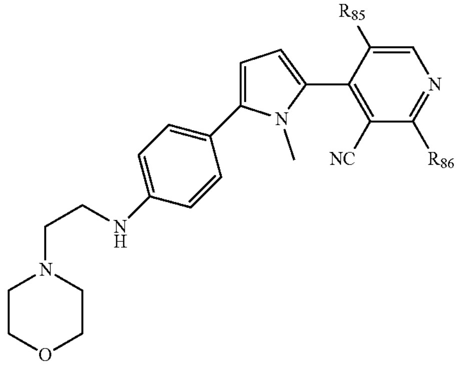
wherein $R_{85}$ is H or CN and $R_{96}$ is H.
In certain embodiments, the compound is selected from a group consisting of
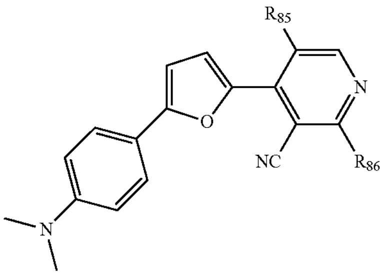
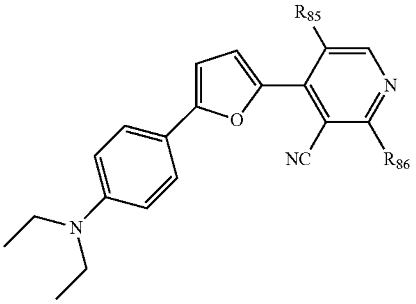

-continued
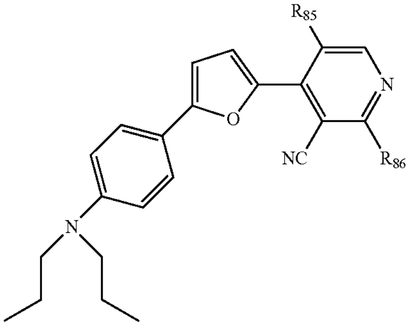
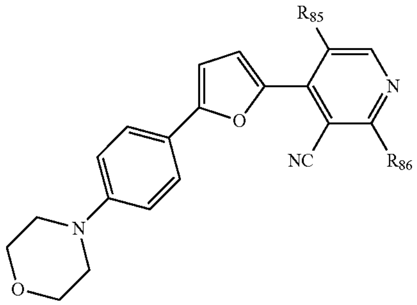
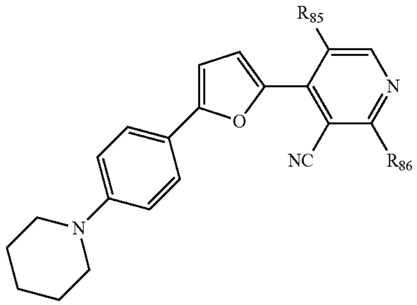
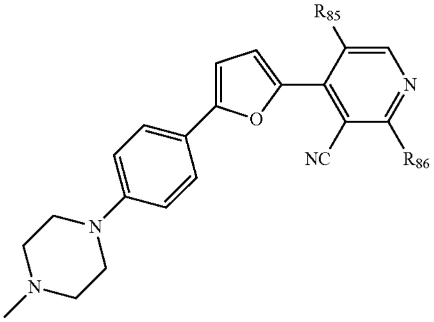
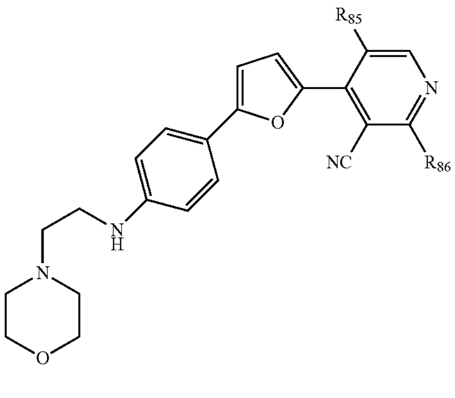
-continued
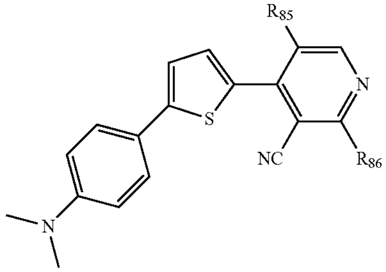
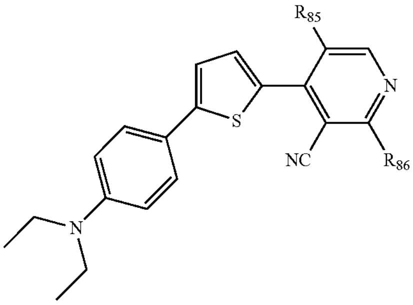
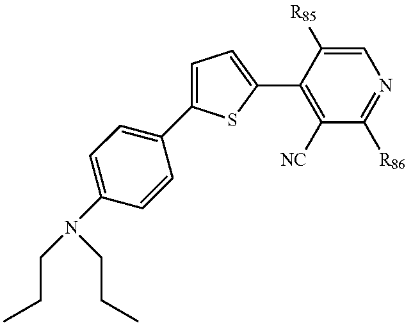
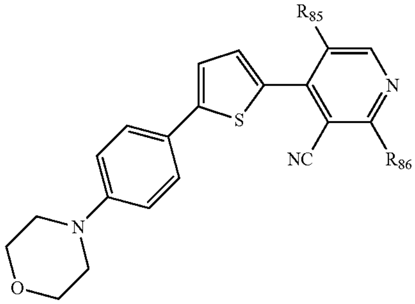
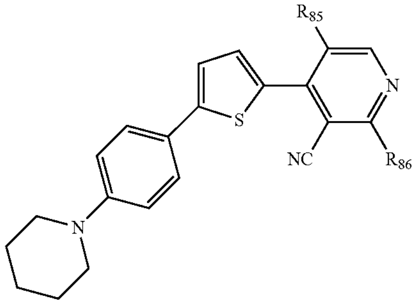

-continued
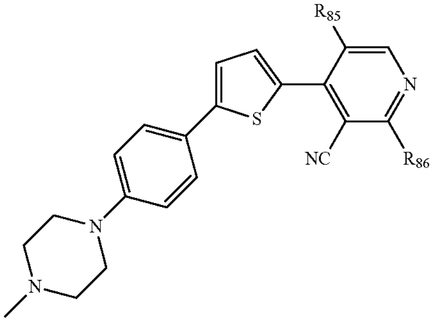
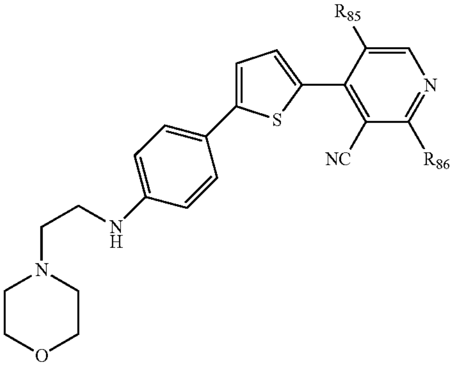
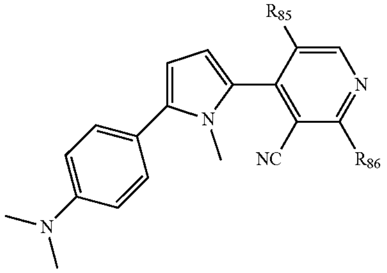
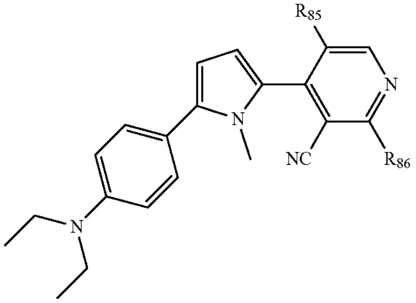
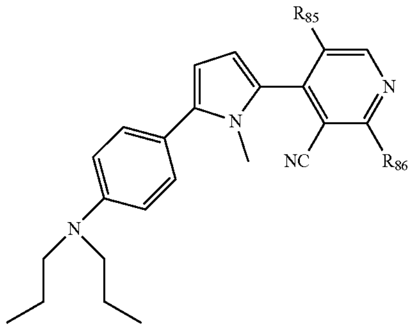
-continued
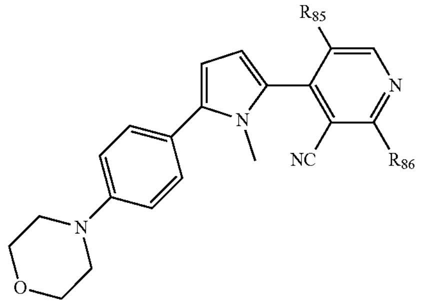
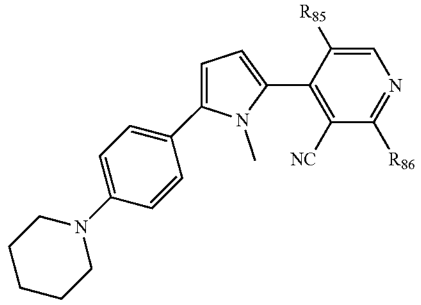
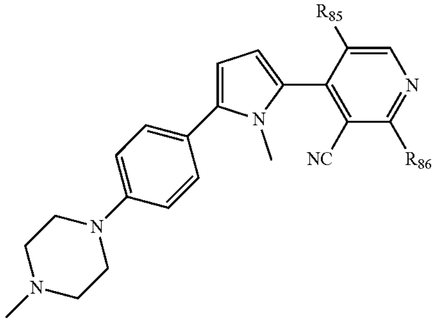
and
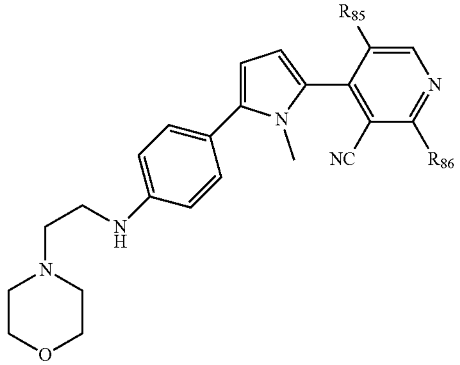
wherein $R_{85}$ is H or CN and $R_{96}$ is
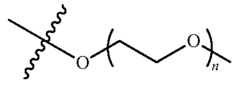
,
wherein n is an integer with value 0-50. In certain embodiments, n is a integer of value 0-10, e.g. n is 0, 1, 2, 3, 4, 5, 6, 7, 8, 9, or 10.

In certain embodiments, the compound is:

(Compound 17)

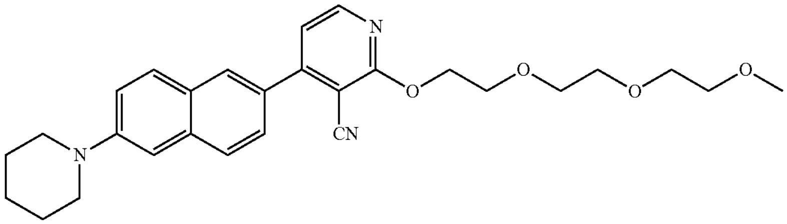

.

In certain embodiments, the compound is 2-(2-(2-(2-methoxyethoxy)ethoxy)ethoxy)-4-(6-(piperidin-1-yl)naphthalen-2-yl)nicotinonitrile.

In certain embodiments, the compound is:

(Compound 18)

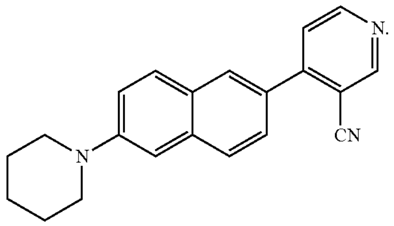

In certain embodiments, the compound is 4-(6-(piperidin-1-yl)naphthalen-2-yl)nicotinonitrile.

In certain embodiments, the compound is selected from the following:

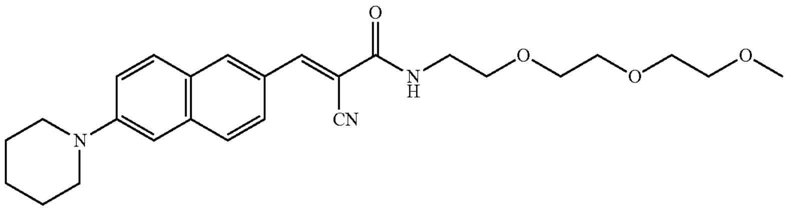

,

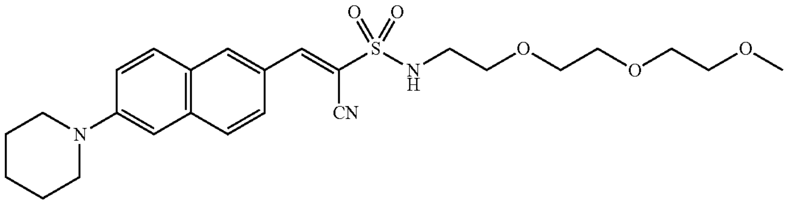

,

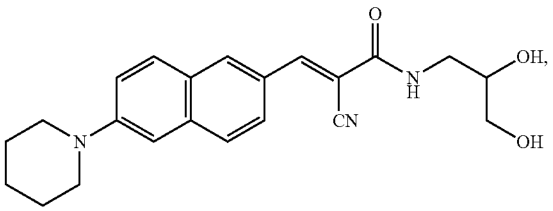

-continued
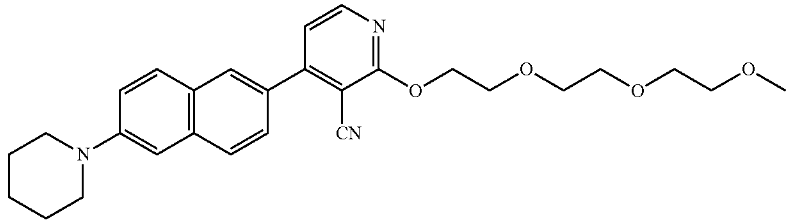
,
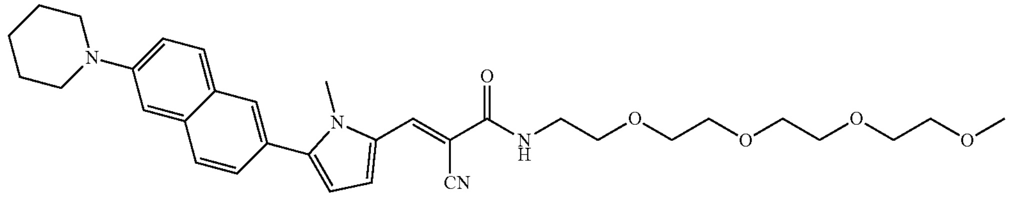
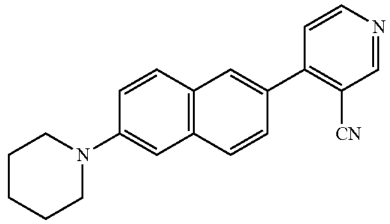
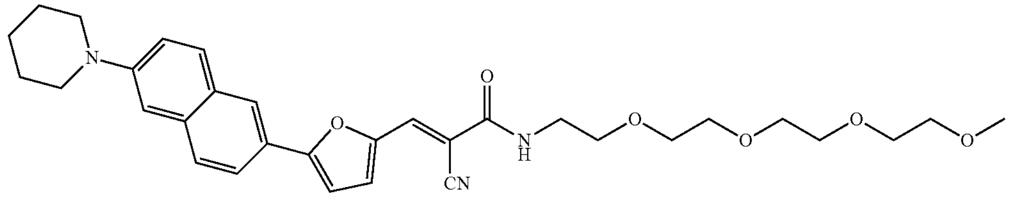
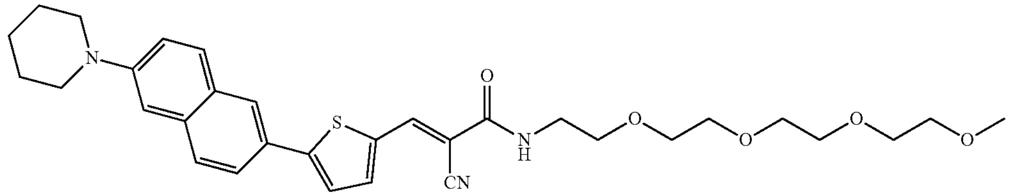
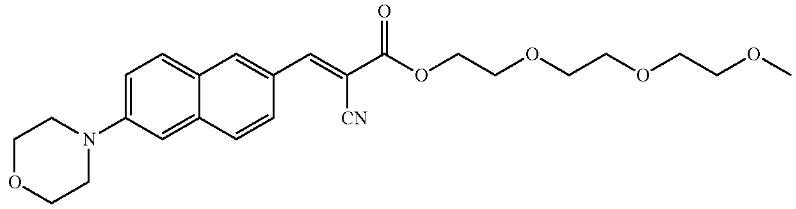
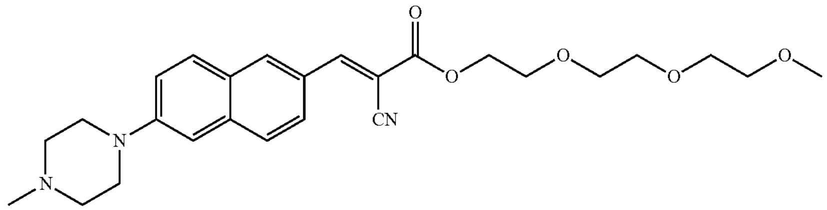
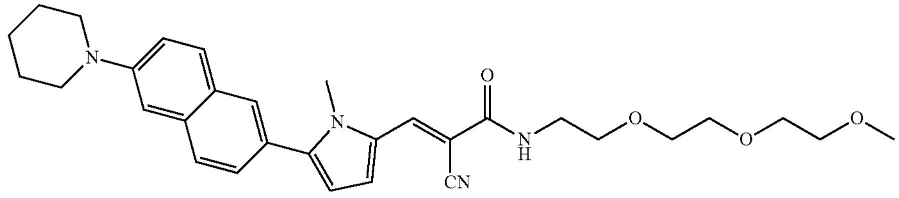

-continued

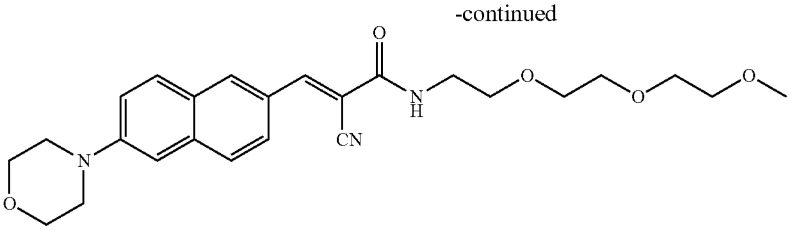

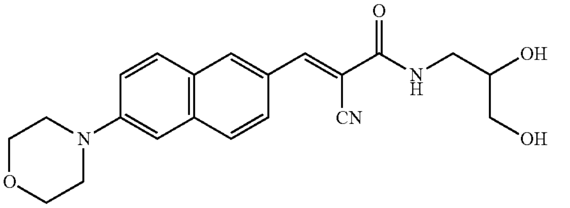

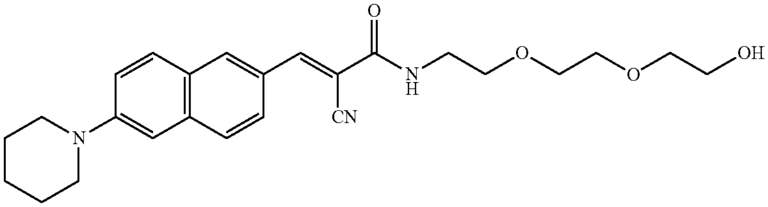

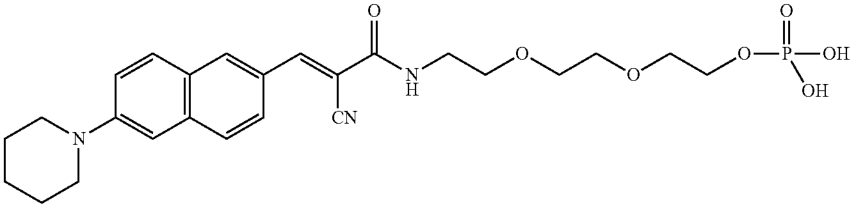

and

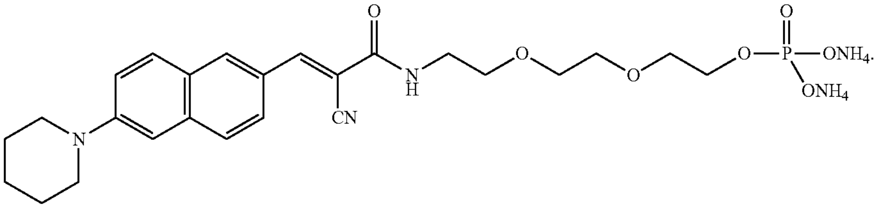

or a salt or solvate thereof.

Treatment Methods and Uses

Upon determination of a traumatic brain injury (TBI) in a patient, certain procedures can be provided to treat or ameliorate the symptoms of the TBI, or to reduce the chance of developing more injuries to the brain. Once a TBI is diagnosed, the progression of the disease may also be monitored by the methods described herein. Once diagnosed, the treating physician may also suggest additional treatments as described herein. In one embodiment, once a TBI is detected or suspected, the patient is instructed to refrain from active physical activities (e.g., sports, military service).

In some embodiments, an agent that treats or ameliorates TBI may be administered to the patient. Examples of treatments (agents) of TBI are provided below.

Medications

Sedation: This can help prevent agitation and excess muscle activity and contribute to pain relief. Examples include profanol.

Pain relief: Opioids may be used.

Diuretics: These increase urine output and reduce the amount of fluid in tissue. These are administered intravenously. Mannitol is the most commonly used diuretic for TBI patients.

Anti-seizure medication: A person who has experienced moderate to severe TBI may have seizures for up to a week after the incident. Medication may help prevent further brain damage that may result from a seizure.

Coma-inducing medications: During a coma, a person needs less oxygen. Sometimes, a coma may be deliberately induced coma if the blood vessels are unable to supply adequate amounts of food and oxygen to the brain.

Surgery

Surgery may be necessary in some cases.

Removing a hematoma: Internal bleeding can cause partly or fully clotted blood to pool in some part of the brain, worsening the pressure on the brain tissue. Emergency surgery can remove a hematoma from between the skull and the brain, reducing pressure inside the skull and preventing further brain damage.

Repairing a skull fracture: Any part of the skull that is fractured and pressing into the brain will need to be surgically repaired. Skull fractures that are not pressing into the brain normally heal on their own. The main concern with a skull fracture is that forces strong enough to cause it may have caused further, underlying damage.

Creating an opening in the skull: This can relieve the pressure inside the skull if other interventions have not worked.

Long-Term Treatments

A person who experiences a severe TBI may need rehabilitation.

Depending on the extent and type of their injury, they may need to relearn how to walk, talk, and carry out other everyday tasks.

This may include treatment in a hospital or in a specialized therapy center. It can involve a physical therapist, an occupational therapist, and others, depending on the type of injury.

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) ameliorating, slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" or "effective amount" of a compound described herein or a pharmaceutically acceptable salt, tautomer, stereoisomer, mixture of stereoisomers, prodrug, or deuterated analog thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition of TBI. The therapeutically effective amount may vary depending on the subject, and disease or condition being treated, the weight and age of the subject, the severity of the disease or condition, and the manner of administering, which can readily be determined by one or ordinary skill in the art.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. In this context, the compounds and compositions described herein may be used for a variety of purposes, including therapeutic and experimental purposes. For example, the compounds and compositions described herein may be used ex vivo to determine the optimal schedule and/or dosing of administration of a compound of the present disclosure for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds may be further characterized to examine the safety or tolerance dosage in human or non-human subjects. Such properties may be examined using commonly known methods to those skilled in the art.

Administration and Pharmaceutical Compositions

In some cases, the probes or compounds are administered to the eye. In some cases, a pharmaceutical composition of the disclosure administered to eye is delivered to the retina, intraocular space, ocular surface, interconnecting innervation, conjunctiva, lacrimal glands, or meibomian glands. In some cases, the compounds are administered topically to the eye. In some cases, the compounds are administered as an eye drop.

The probes or compounds can also be formulated for intravenous and subcutaneous use, without limitation. The intravenous administration can be bolus administration or continuous injection.

The probes are effective over a wide dosage range. In some cases, in the application to adult humans, dosages from 0.01 to 1000 mg, from 0.5 to 100 mg, from 1 to 50 mg per day, and from 5 to 40 mg per day are examples of dosages that are used. An exemplary dosage is 10 to 30 mg per day. In the applications to juveniles, the dosage may be the same or less than the adult dose. In some cases the effective amount of the probe corresponds to about 50-500 mg of compound per adult subject. The exact dosage will depend upon the route of administration, the form in which the compound is administered, the subject to be treated, the body weight of the subject to be treated, and the preference and experience of the attending physician.

In some cases the effective amount of the probe corresponds to about 0.01-1000 mg of compound per human subject per dosage. In some cases, the effective dose of compound is be 50-500 mg per human per dosage. In some cases the effective amount corresponds to about 0.01-100 mg, 0.01-200 mg, 0.01-300 mg, 0.01-400 mg, 0.01-500 mg, 0.01-600 mg, 0.01-700 mg, 0.01-800 mg, 0.01-900 mg, 0.01-1000 mg, 0.1-100 mg, 0.1-200 mg, 0.1-300 mg, 0.1-400, 0.1-500 mg, 0.1-600 mg, 0.1-700 mg, 0.1-800 mg, 0.1-900 mg, 0.1-1000 mg, 1-100 mg, 1-200 mg, 1-300 mg, 1-400 mg, 1-500 mg, 1-600 mg, 1-700 mg, 1-800 mg, 1-900 mg, 100-200 mg, 100-300 mg, 100-400 mg, 100-500 mg, 100-600 mg, 100-700 mg, 100-800 mg, 100-900 mg, 100-1000 mg, 200-300 mg, 200-400 mg, 200-500 mg, 200-600 mg, 200-700 mg, 200-800 mg, 200-900 mg, 200-1000 mg, 300-400 mg, 300-500 mg, 300-600 mg, 300-700 mg, 300-800 mg, 300-900 mg, 300-1000 mg, 400-500 mg, 400-600 mg, 400-700 mg, 400-800 mg, 400-900 mg, 400-1000 mg, 500-600 mg, 500-700 mg, 500-800 mg, 500-900 mg, 500-1000 mg, 600-700 mg, 600-800 mg, 600-900 mg, 600-1000 mg, 700-800 mg, 700-900 mg, 700-1000 mg, 800-900 mg, 800-1000 mg or about 900-1000 mg per human per dosage. In some cases, the effective amount corresponds to about 50-100 mg, 50-400 mg, 50-500 mg, 100-200 mg, 100-300 mg, 100-400 mg, 100-500 mg, 200-300 mg, 200-400 mg, 200-500, 300-400 mg, 300-500 mg, or 400-500 mg per adult human per dosage.

In some cases, the probe is administered in a single dose. In some cases, the probe of the disclosure is administered in multiple doses. In some cases, dosing is about once, twice, three times, four times, five times, six times, or more than six times per day. In some cases, dosing is about once a month, once every two weeks, once a week, or once every other day. In another case the probe and another agent are administered together about once per day to about 6 times per day. In some cases the administration of the probe and an agent continues for less than about 7 days. In yet another case the administration continues for more than about 6, 10, 14, 28 days, two months, six months, or one year. In some cases, continuous dosing is achieved and maintained as long as necessary.

In some cases, the probes are administered one to ten times, one to four times, or once a day. In some cases, the probes are administered 1, 2, 3, 4, 5, 6, 7, 8, 9, or 10 times a day. In some cases, the probes are administered as drops. In some cases, the size of the drop administered is in the range of about 10-100 μL, about 10-90 μL, about 10-80 μL, about 10-70 μL, about 10-60 μL, about 10-50 μL, about 10-40 μL, about 10-30 μL, about 20-100 μL, about 20-90 μL, about 20-80 μL, about 20-70 μL, about 20-60 μL, about 20-50 μL, about 20-40 μL, or about 20-30 μL. One example of the disclosure administers a drop in the range of about 10 to about 30 μL. One example of the disclosure administers a drop in the range of about 10 to about 100 μL. One example of the disclosure administers a drop in the range of about 20 to about 50 μL. One example of the disclosure administers a drop in the range of about 20 to about 40 μL. One example of the disclosure administers a drop in the range of about 10 to about 60 μL. In some cases, the eye formulations of the disclosure is administered several drops per time, for example 1-3 drops per time, 1-3 drops per time, 1-4 drops per time, 1-5 drops per time, 1-6 drops per time, 1-7 drops per time, 1-8 drops per time, 1-9 drops per time, 1-10 drops per time, 3-4 drops per time, 3-5 drops per time, 3-6 drops per time, 3-7 drops per time, 3-8 drops per time, 3-9 drops per time, 3-10 drops per time, 5-6 drops per time, 5-7 drops per time, 5-8 drops per time, 5-9 drops per time, 5-10 drops per time, 7-8 drops per time, 7-9 drops per time or 9-10 drops per time. In one example, the formulations of the disclosure are administered about one drop per time and 1-6 times per day.

Pharmaceutical Compositions/Formulations

In some cases, the probes described herein are formulated into pharmaceutical compositions. In some cases, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: *Remington: The Science and Practice of Pharmacy*, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and* Drug Delivery Systems, Seventh Ed. (Lippincott Williams & Wilkins1999).

Provided herein are pharmaceutical compositions comprising a probe as described herein and a pharmaceutically acceptable diluent(s), excipient(s), or carrier(s). In certain cases, the compounds described are administered as pharmaceutical compositions in which one or more probes, are mixed with other active ingredients, as in combination therapy. In specific cases, the pharmaceutical compositions include one or more probes as described herein.

A pharmaceutical composition, as used herein, refers to a mixture of a compound of any probe described herein, with other chemical components, such as carriers, stabilizers, diluents, dispersing agents, suspending agents, thickening agents, and/or excipients. In certain cases, the pharmaceutical composition facilitates administration of the compound to an organism. In some cases for practicing the methods of treatment or use provided herein, therapeutically effective amounts of one or more probes provided herein are administered in a pharmaceutical composition to a mammal having a disease or condition to be detected, diagnosed or treated. In specific cases, the mammal is a human. In certain cases, therapeutically effective amounts vary depending on the severity of the disease, the age and relative health of the subject, the potency of the compound used and other factors. The compounds described herein are used singly or in combination with one or more therapeutic agents as components of mixtures.

In some cases, the one or more probe is formulated in an aqueous solution. In specific cases, the aqueous solution is selected from, by way of example only, a physiologically compatible buffer, such as Hank's solution, Ringer's solution, aqueous acetate buffer, aqueous citrate buffer, aqueous carbonate buffer, aqueous phosphate buffer or physiological saline buffer.

In some cases, the compounds described herein are formulated for ocular administration. In some cases, the ocular formulations is liquid (in form of solutions, suspensions, powder for reconstitution, sol to gel systems), semi solids (ointments and gels), solids (ocular inserts), and intraocular dosage forms (injections, irrigating solutions and implants).

Provided herein are ophthalmic formulations comprising the compounds described herein and an ophthalmologically acceptable component. The ophthalmic formulation may be administered in any form suitable for ocular drug administration, e.g., as a solution, suspension, ointment, gel, liposomal dispersion, colloidal microparticle suspension, or the like, or in an ocular insert, e.g., in an optionally biodegradable controlled release polymeric matrix. Significantly, at least one component of the formulation, and preferably two or more formulation components, are "multifunction al" in that they are useful in preventing or treating multiple conditions and disorders, or have more than one mechanism of action, or both.

By a "pharmaceutically acceptable" or "ophthalmologically acceptable" component is meant a component that is not biologically or otherwise undesirable, i.e., the component may be incorporated into an ophthalmic formulation of the invention and administered topically to a patient's eye without causing any undesirable biological effects or interacting in a deleterious manner with any of the other components of the formulation composition in which it is contained. When the term "pharmaceutically acceptable" is used to refer to a component other than a pharmacologically active agent, it is implied that the component has met the required standards of toxicological and manufacturing testing or that it is included on the Inactive Ingredient Guide prepared by the U.S. Food and Drug Administration.

The formulation also includes an effective amount of a permeation enhancer that facilitates penetration of the formulation components through cell membranes, tissues, and extra-cellular matrices, including the cornea. The "effective amount" of the permeation enhancer represents a concentration that is sufficient to provide a measurable increase in penetration of one or more of the formulation components through membranes, tissues, and extracellular matrices as just described. Suitable permeation enhancers include, by way of example, methylsulfonylmethane (MSM; also referred to as methyl sulfone), combinations of MSM with dimethylsulfoxide (DMSO), or a combination of MSM and, in a less preferred embodiment, DMSO, with MSM particularly preferred.

Kits and Packages

Provided herein are also kits and packages that include a probe of the disclosure, a retinal imaging device, and optionally suitable packaging. In one embodiment, a kit further includes instructions for use.

The retinal imaging device may include lens(es) and image sensors (thus forming a suitable retina scanner) for detecting a signal emitted from the probe used. In some embodiments, the retinal imaging device detects a fluorescent signal. In some embodiments, the retinal imaging device further includes a laser light source which can be used to activate the fluorescent signal from the probe.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

Example 1: Ex Vivo Analysis of Probes with Human AD Tissue

Post-mortem retinal tissue and brains of humans with confirmed or probable Alzheimer's disease (AD) were obtained and examined by staining amyloid-beta (A3) with a test amyloid sensitive fluorescent probe (ASF), Compound 1. This example was conducted to determine if the ASF could identify patients with amyloid burden in the brain through fluorescence inspection of retinas stained with the ASF.

As shown in FIG. 1, dense deposits that were 5-10 μm in diameter could be fluorescently visualized in flat mounted retina samples that were stained with the ASF. While this example could observe these deposits in both AD (panels A-B) and cognitively normal patients (panels C-D), there is a qualitative correlation between the density of these deposits in the retina and the degree of amyloidosis in the brain (as estimated by immunohistochemistry (IHC) with anti-Aβ antibodies).

IHC staining of retinal cryosections provided further evidence for the existence of Aβ in retinal deposits with similar location, size, and morphology as the deposits found in retinal flat mounts stained with the ASF. This provides promising evidence that ASF is capable of binding to amyloid deposits in ex vivo human retinal tissue.

Example 2: Eye Test with TBI Blast Mouse Model

This example was conducted to determine whether the ASF Compound 1 could detect AR in the retina of a TBI mouse model after injury.

Figure 2:
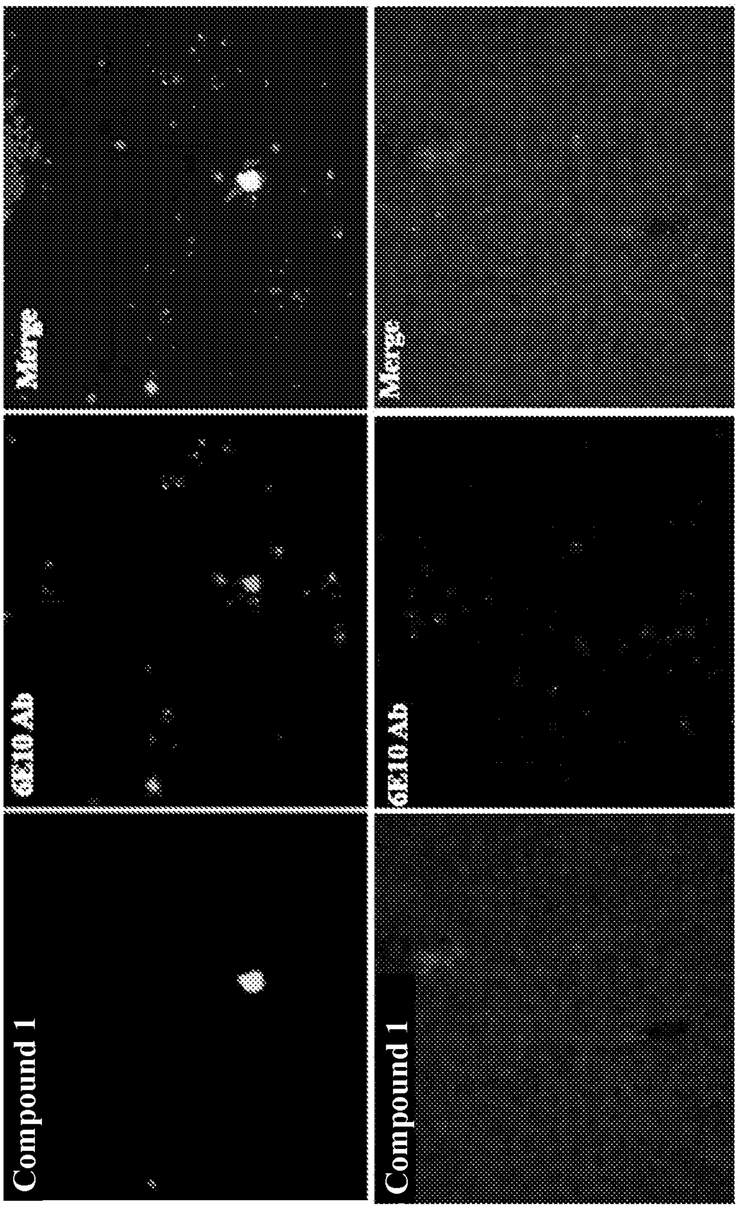
FIG. 2, in a top row, presents image shows Compound 1 fluoresces amyloid beta in retinal tissue of TBI blast mouse model. Bottom row: No visible fluorescence in normal mouse. Staining is as follows: green=Compound 1 stained, red=stained with 6E10 antibody, an antibody specific for amyloid beta.

Retinal tissue of a blast mouse model 24 hours after injury and a non-injured mouse were stained with the ASF and co-stained with an anti-AD antibody (6E10). As demonstrated in FIG. 2, the mouse that had received a blast injury displayed immunoreactivity to Aβ in the retinal tissue where the uninjured mouse displayed no reactivity to 6E10. More importantly, the ASF fluorescently labels these retinal deposits (FIG. 2, top row) but does not display any fluorescent enhancement in the uninjured mouse (FIG. 2, bottom row).

Figure 3:
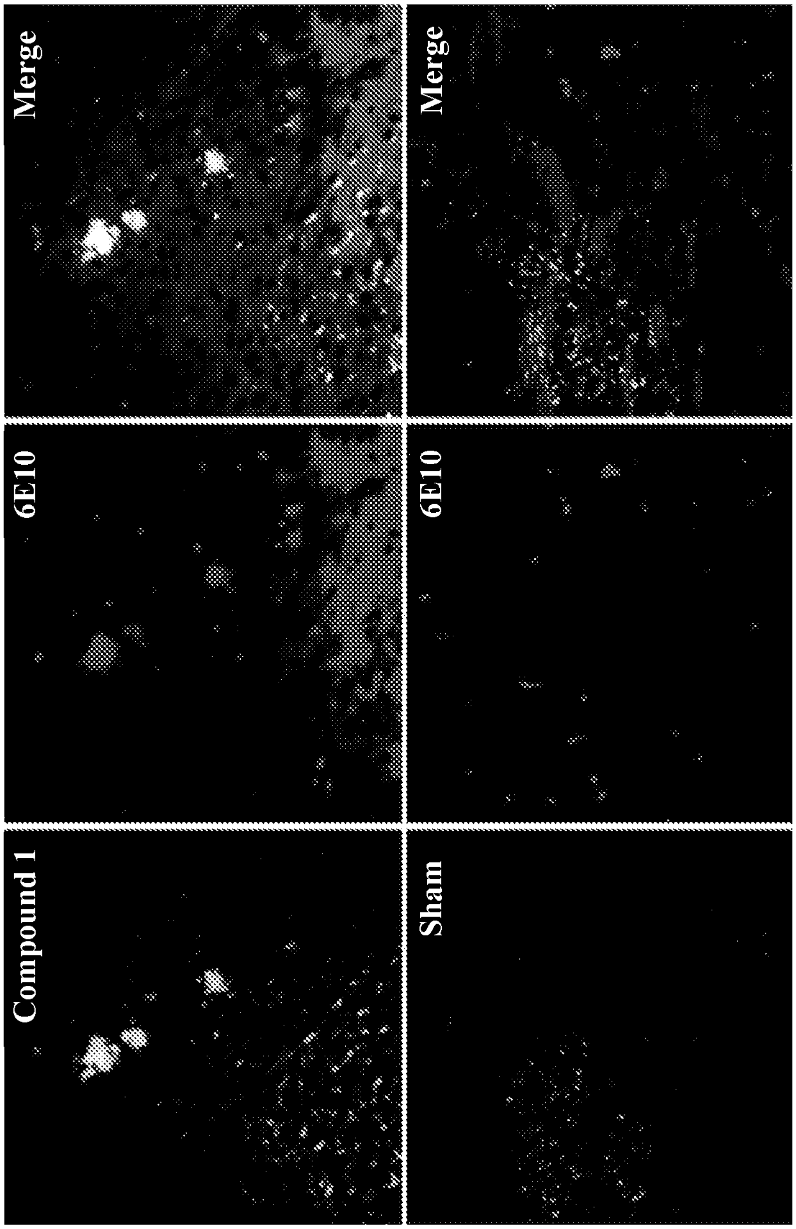
FIG. 3, in top row, presents image showing Compound 1 fluoresces amyloid beta in brain tissue of TBI blast mouse model. Bottom row: No visible fluorescence in normal mouse. Staining is as follows: green=Compound 1 stained, red=stained with 6E10 antibody, an antibody specific for amyloid beta.
Figure 4:
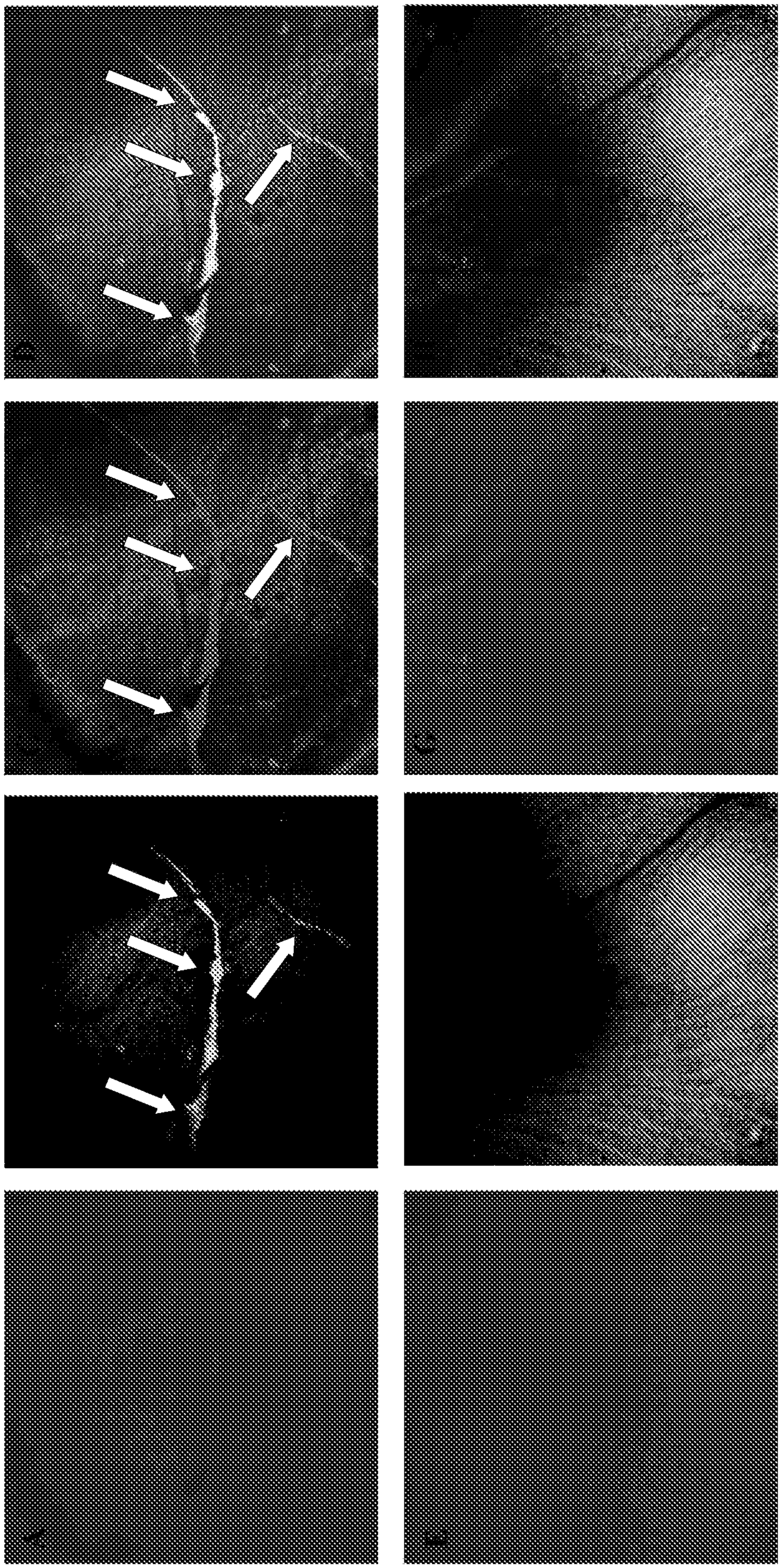
FIG. 4, in top row, presents images showing retinal tissue of C5BL mice subjected to controlled cortical impact (CCI) stained with A) DAPI B) Compound 1 C) 6E10 antibody D) Merged image of three stains. Bottom row: E) Retinal tissue of C5BL/6 mice subjected to craniotomy stained with DAPI, Compound 1, and 6E10 antibody. The fluorescent spectra of F) DAPI G) Compound 1 H) 6E10 antibody. Arrows indicate visible aggregated proteins.
Figure 5:
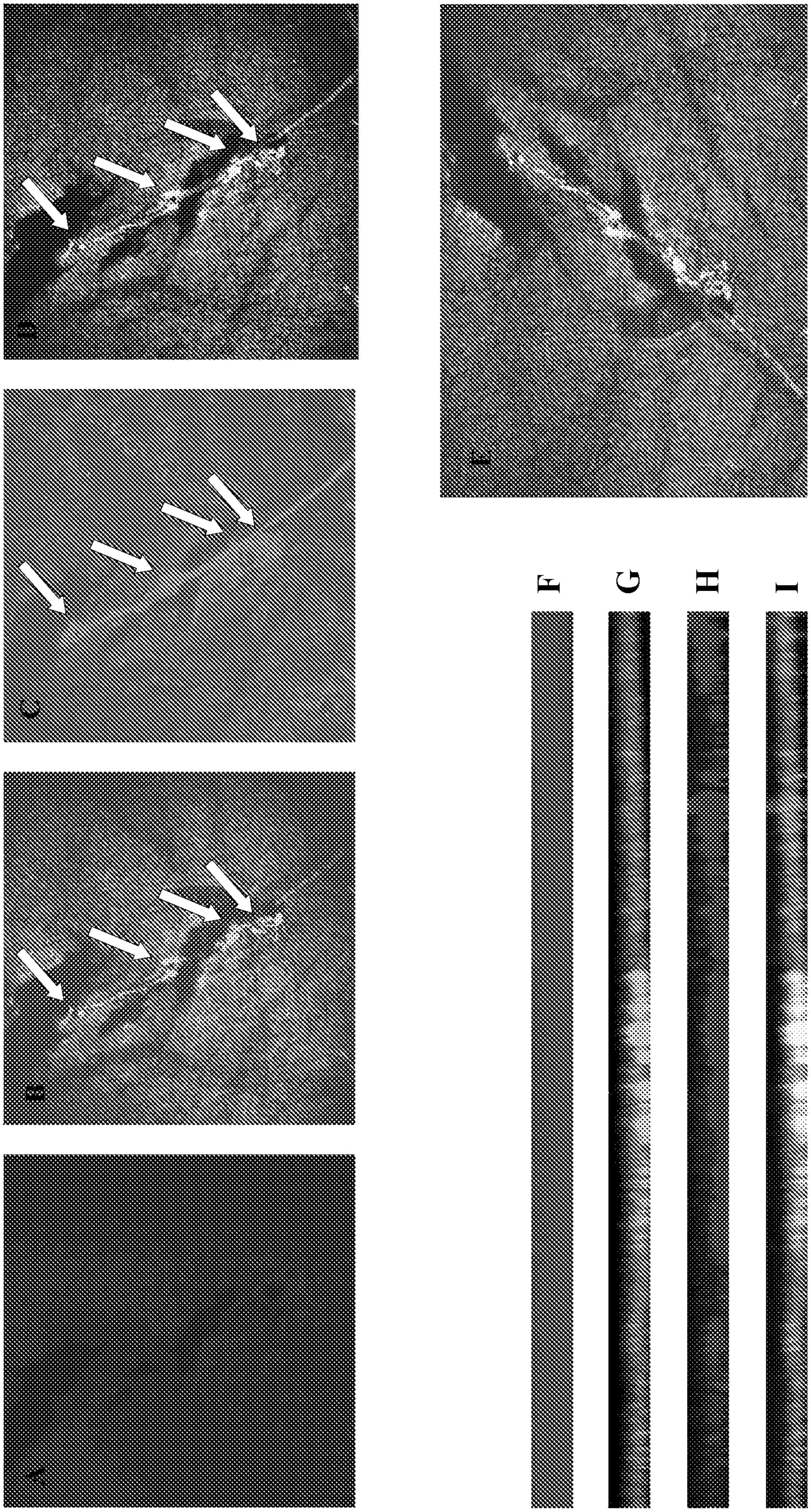
FIG. 5, in top row, presents images showing retinal tissue of C5BL/6 mice subjected to CCI stained with A) DAPI B) Compound 1 C) 6E10 antibody D) Merged image of three stains. Bottom row: E) Merged image of the three stains F) fluorescent spectrum of DAPI G) fluorescent spectrum of Compound 1 H) fluorescent spectrum of 6E10 antibody I) merged fluorescent spectrum of all three stains.
Figure 6:
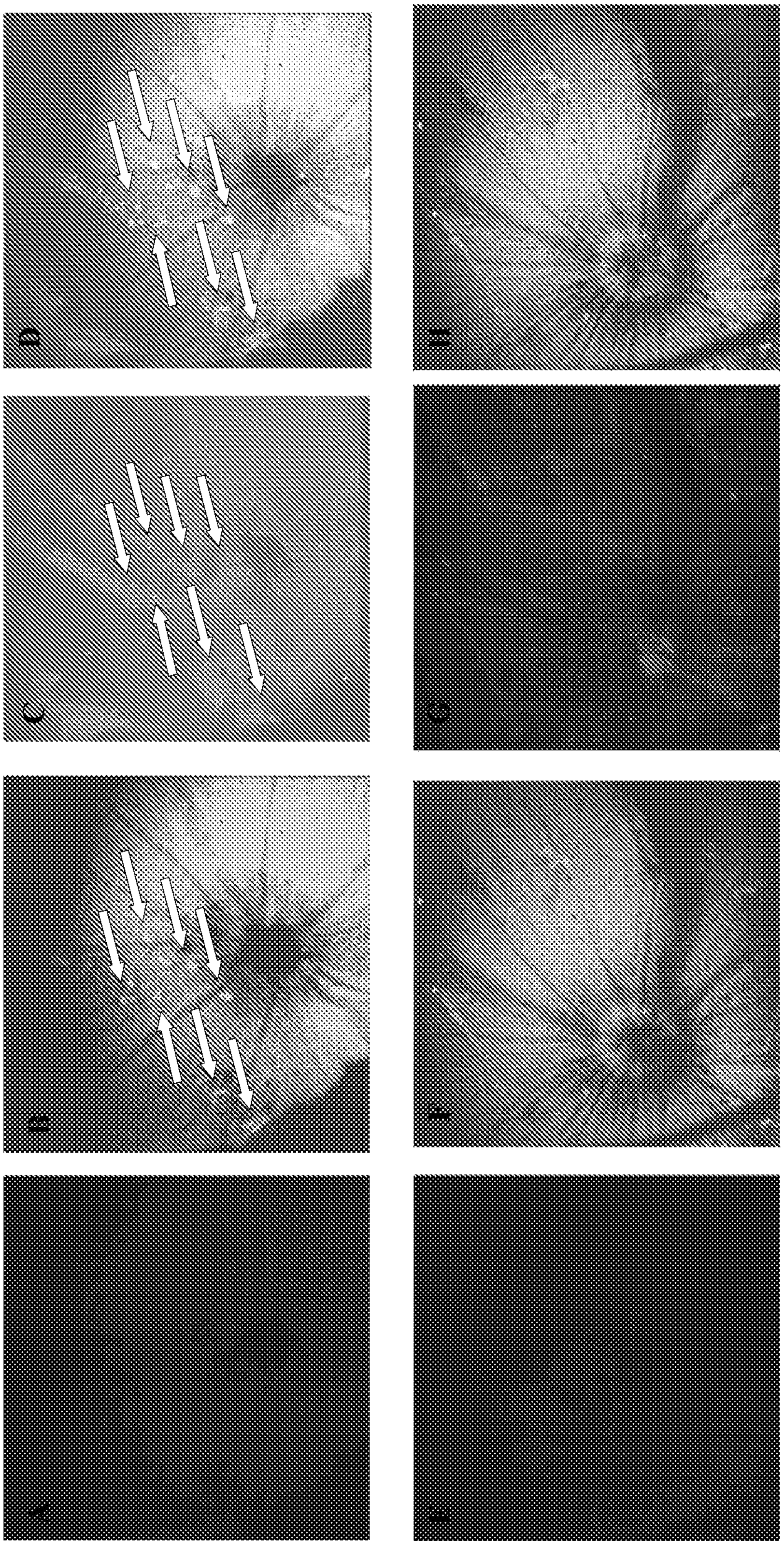
FIG. 6, in top row, presents images showing retinal tissue of C5BL/6 mice subjected to CCI stained with A) DAPI B) Compound 1 C) 6E10 antibody D) Merged image of three stains. Bottom row: Retinal tissue of C5BL/6 mice subjected to craniotomy stained with E) DAPI F) Compound 1 G) 6E10 antibody H) Merged image of three stains. Arrows indicate visible aggregated proteins.
Figure 7:
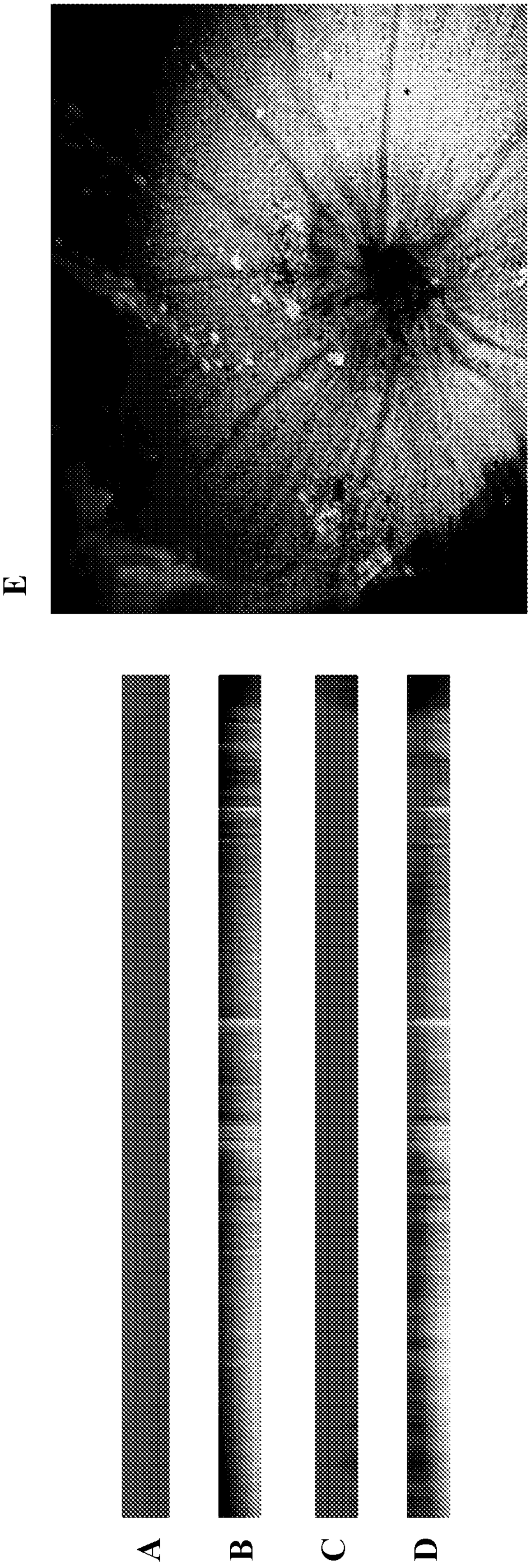
FIG. 7 presents A) fluorescent spectrum of DAPI B) fluorescent spectrum of Compound 1 C) fluorescent spectrum of 6E10 antibody D) merged fluorescent spectrum of all three stains E) merged image showing retinal tissue of C5BL/6 mice subjected to CCI and stained with DAPI, Compound 1, and 6E10 antibody.

This provides evidence that the ASF probe Compound 1 has the ability to detect retinal amyloids present in a TBI mouse model. Based on this evidence, this example further attempted to confirm that AD was also detected in the brain tissue of the same TBI blast mouse model. As demonstrated in FIG. 3, the mouse that had received a blast injury displayed immunoreactivity to Aβ in the brain tissue where the uninjured mouse displayed no reactivity to 6E10. The evidence of Aβ in the brain tissue complements what was found in the retinal tissue of the same injured mouse. It also supports previous studies of the correlation between the brain and retina in the accumulation of Aβ.

Example 3: Controlled Cortical Impact of C5BL/6 Mice 3 month old C5BL/6 mice were briefly anesthetized with isoflurane and placed in a stereotaxic frame. Mice were subjected to craniotomy over the right primary and secondary motor cortex and parietal-temporal cortex (+1 to −4 anterior-posterior from the bregma, 4 mm laterally from the sagittal suture). Half of the mice were not further injured to use as control specimen. For the remaining mice a 3 mm diameter piston was centered over the motor cortex approximately +0.5 to −2.5 mm from the bregma and 3 mm lateral to the sagittal suture. Using a stereotaxic impactor (Impact One, myNeuroLab.com), the piston was accelerated at a speed of 3 m/sec to an impact depth of 1 mm below the cortical surface. After 24 h, mice were euthanized and brain and eyes were collected. Retinas were extracted, stained with DAPI, Compound 1, and 6E10 antibody, and compared.

Retinas were mounted on slides and washed with phosphate-buffered saline (PBS) two times for five minutes each time. Retinas were exposed to 98% formic acid for one minute then washed two times with distilled water for five minutes each time. The retinas were then equilibrated in 1×PBS for 15 minutes. Retinas were exposed to 10% goat/donkey serum in 1× phosphate-buffered saline with Tween® 20 (PBST) for 1 h. Retinas were then incubated with 610 antibody in 10% goat serum in 1×PBST at 4° C. overnight. Retinas were then rinsed with 1× PBST three times for five minutes each time. Retinas were then incubated with secondary antibody, Alexa Fluor 568 Anti mouse, in 1×PBST for 1 h while removed from light. Retinas were rinsed with 1×PBST three times for five minutes each time. Retinas were then stained with Compound 1 working solution for 30 minutes at room temp. while removed from light. Retinas were then washed with 1x PBS three times for five minutes each time, then stained with DAPI 300 nM or 100 ng/mL in dark for 10 minutes. Retinas were then washed three times with PBS for 10 minutes each time. DAKO mounting medium was applied and samples stored out of light until imaging.

Fluorescent imaging was performed on a Leica DMI 4000B microscope equipped with a TCS SPE camera and Leica 10×, 20×, and 40× objectives. The following lasers were used to visualize fluorescent probes pertaining to DAPI (blue), Compound 1 (green), 6E10 antibody (red): 408, 488, and 568 nm. Z-stacked images were taken at 40× at 0.5 μm increments to visualize the entire thickness of the tissue.

FIG. 4-7 demonstrate that after CCI, 3 month old C5BL/6 mice developed deposition of aggregated proteins, detected by Compound 1 and 6E10 antibody in retina. Aggregated proteins were detected by 6E10 in retina and colocalized by Compound 1.

Example 4: Detection of Retinal Aβ Aggregation in Ex Vivo Mouse Model

This example was conducted to examine whether TBI induced retinal A$ aggregation in a mouse model.

Mice were subjected to a controlled cortical impact (CCI). The CCI model applies a controlled impact to the intact dura after a craniotomy and is a commonly used TBI animal model. Mice were anesthetized, the head was mounted in a stereotaxic frame, and a craniotomy was performed over the right side of the frontal cortex. Using a stereotaxic impactor, mice received an impact on the right side of the frontal cortex using a 3 m/s velocity, 1 mm depth, and 3 mm diameter piston. After injury, the incision was closed with staples, anesthesia was terminated, and the animal was placed in a heated cage to maintain normal core temperature.

Sham injury consisted of exposure to anesthesia, stereotaxic mounting, skin and fascia reflection, and closing of incision with staples. Mice were then euthanized 24 hours after injury and retinal tissue were dissected for further analysis.

Figure 8:
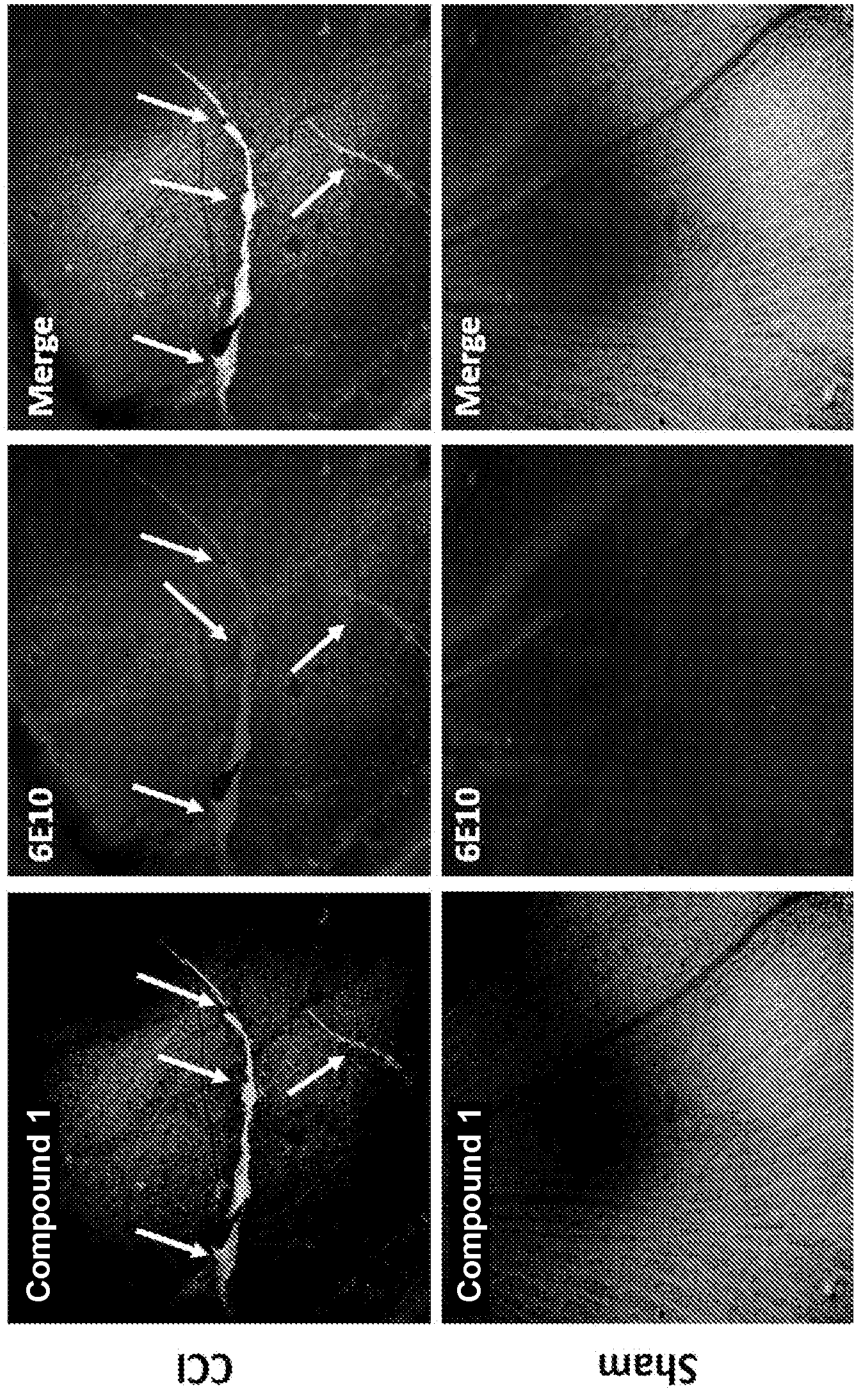
FIG. 8 presents the images of retinal staining of mice that received a controlled cortical impact (CCI) (top row) or Sham mouse (bottom row). Top Row: Flat mount image of a CCI mouse retina stained with Compound 1, 6E10, and merged image. Arrows indicate an area of co-localization with Compound 1 and 6E10. Bottom Row: Sham mouse stained with Compound 1, 6E10, and merged image.

Retina from mice were extracted and stained with Compound 1 along with a 6E10 antibody, a sequence specific antibody for Aβ. As demonstrated in FIG. 8, mice that received a CCI displayed immunoreactivity to Aβ along a vessel in the retina where the uninjured mouse displayed no reactivity to 6E10. More importantly, Compound 1 fluorescently labeled these deposits and co-localized with 6E10 immunoreactivity (FIG. 8 top row, white arrows) but did not display any fluorescence enhancement in the uninjured mouse (FIG. 8, bottom row). This example demonstrates that the compounds of the present disclosure can effectively detect retinal amyloids in a TBI mouse model.

Example 4: Detection of Retinal Aβ Aggregation in Ex Vivo Mouse Model

This example was conducted to examine whether TBI induced retinal A$ aggregation in a mouse model.

Mice were subjected to a controlled cortical impact (CCI). The CCI model applies a controlled impact to the intact dura after a craniotomy and is a commonly used TBI animal model. Mice were anesthetized, the head was mounted in a stereotaxic frame, and a craniotomy was performed over the right side of the frontal cortex. Using a stereotaxic impactor, mice received an impact on the right side of the frontal cortex using a 3 m/s velocity, 1 mm depth, and 3 mm diameter piston. After injury, the incision was closed with staples, anesthesia was terminated, and the animal was placed in a heated cage to maintain normal core temperature. Sham injury consisted of exposure to anesthesia, stereotaxic mounting, skin and fascia reflection, and closing of incision with staples. Mice were then euthanized 24 hours after injury and retinal tissue were dissected for further analysis.

Retina from mice were extracted and stained with Compound 1 along with a 6E10 antibody, a sequence specific antibody for Aβ. As demonstrated in FIG. 8, mice that received a CCI displayed immunoreactivity to Aβ along a vessel in the retina where the uninjured mouse displayed no reactivity to 6E10. More importantly, Compound 1 fluorescently labeled these deposits and co-localized with 6E10 immunoreactivity (FIG. 8 top row, white arrows) but did not display any fluorescence enhancement in the uninjured mouse (FIG. 8, bottom row). This example demonstrates that the compounds of the present disclosure can effectively detect retinal amyloids in a TBI mouse model.

Example 5: Synthesis

Synthesis of Compound 21

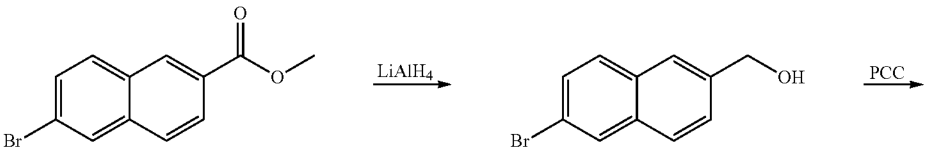

24 25

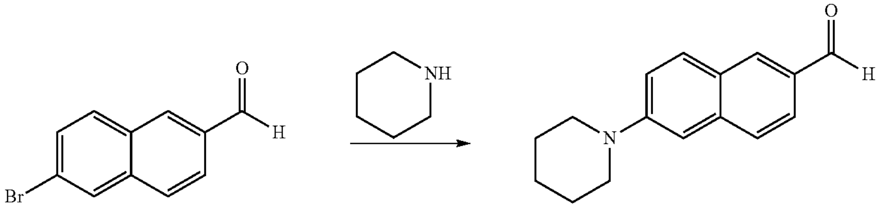

26 27

-continued

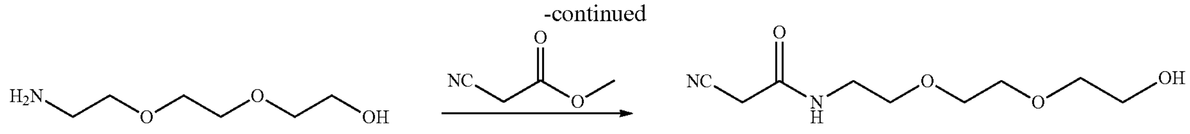

28

29

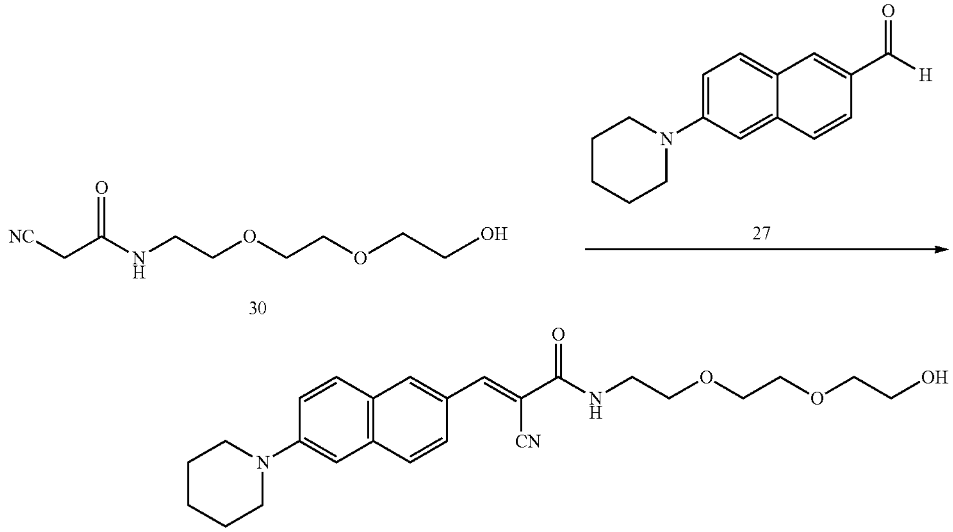

27

30

Compound 21

Synthesis of (6-bromonaphthalen-2-yl)methanol (25) To a solution of $LiAlH_4$ (8.2 g, 217 mmol in 500 mL THF) at 0° C. under $N_2$, a solution of methyl 6-bromo-2-naphthoate (24) (50.0 g, 189 mmol) in 500 mL of anhydrous THF was added dropwise. The reaction mixture was left stirring for 1 h at 0° C. Upon reaction completion monitored by TLC, the mixture was treated with $H_2O$, 15% NaOH, $H_2O$ (1:1:3, v/v/v). After filtration, the filtrate was concentrated and extracted with EA, dried over $NaSO_4$. The crude product was purified from (PE:EA=3:1) to obtain the title compound.

Synthesis of 6-bromo-2-naphthaldehyde (26)

In a suspension of (6-bromonaphthalen-2-yl)methanol (25) (42.0 g, 177 mmol) and silica gel (76.4 g) in DCM (500 mL), was added PCC (76.4 g, 354 mmol). The reaction was stirred at RT (room temperature, 25±5° C.) for 1.5 h. Upon completion, it was filtered through a pad of silica and concentrated under reduced pressure to obtain the title compound.

Synthesis of 6-(piperidin-1-yl)-2-naphthaldehyde (27)

In dry and degassed toluene (300 mL), were added $Pd(OAc)_2$ (1.5 g, 6.3 mmol), BINAP (4.4 g, 7.1 mmol), 6-bromo-2-naphthaldehyde (26) (30.0 g, 127.8 mmol), $Cs_2CO_3$ (60.0 g, 183.9 mmol) and piperidine (12.7 g, 149.5 mmol). The reaction was left stirring for 8 h at 115° C. After cooling, the mixture was filtered and washed with EA, then concentrated to a third of the volume, to which was added 200 ml of 6 N hydrochloric acid with full stirring. Water phase was separated and extracted with DCM three times, then adjusted to alkaline with 5 N NaOH and extracted with EA. The organic phase was concentrated to yield crude material, which was further purified via silica gel chromatography (PE:EA=20:1 to 2:1) to obtain the title compound.

Synthesis of 2-cyano-N-(2-(2-(2-hydroxyethoxy) ethoxy)ethyl)acetamide (29)

In a pear-shaped flask, 28 (6.0 g, 40 mmol) was added to methyl 2-cyanoacetate (4.0 g, 40 mmol) with stirring. The mixture was let stirring overnight at RT and concentrated to a crude material. The crude material was directly used in the next step.

Synthesis of (E)-2-cyano-N-(2-(2-(2-hydroxy-ethoxy)ethoxy)ethyl)-3-(6-(piperidin-1-yl)naphthalen-2-yl)acrylamide (Compound 21)

To a solution of 6-(piperidin-1-yl)-2-naphthaldehyde (27) (7.0 g, 29.3 mmol) and 2-cyano-N-(2-(2-(2-hydroxyethoxy) ethoxy)ethyl)acetamide (29) (7.9 g, 36.5 mmol) in anhydrous THF (250 mL) was added piperidine (0.5 g, 5.9 mmol) and the resulting mixture was refluxed for 12 h. The reaction was then concentrated under reduced pressure to a crude material, which was purified via silica gel chromatography to obtain the title compound. Exact Mass 437.23; m/e 437.23 (100%), 438.23 (28.9%), 439.24 (4.7%); elemental analysis ($C_{25}H_{31}N_3O_4$): C 68.63%, H 7.14%, N 9.60%, O 14.63%.

Synthesis of Compound 22

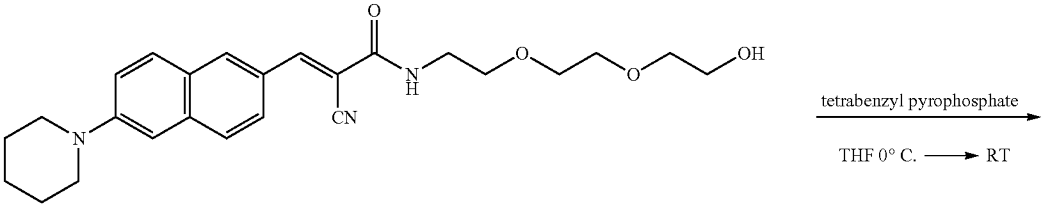

Compound 21

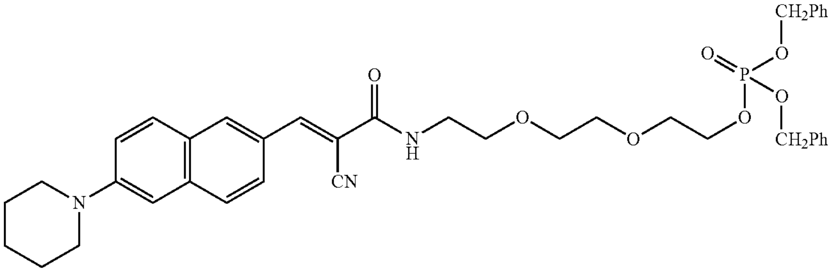

Compound 31

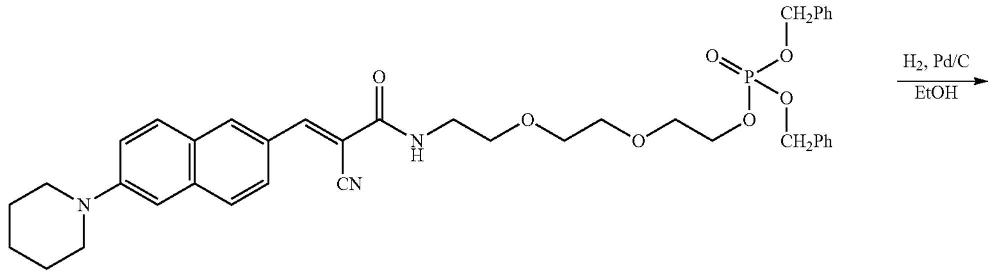

Compound 31

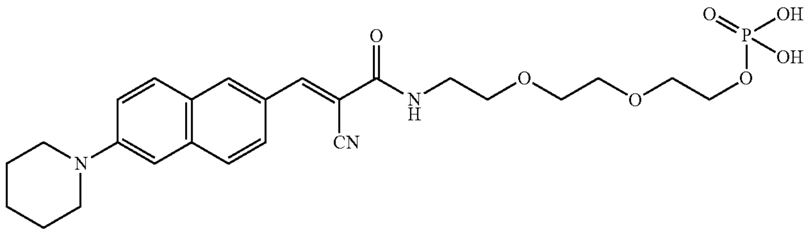

Compound 22

Synthesis of 31

To 1 g (2.3 mM) of Compound 21 in 15 mL of THF at zero degrees was added 1.6 g (3 mM) of tetrabenzyl pyrophosphate prepared using Merck Organic Synthesis preparation, resulting in a deep red solution. Sodium hydride (100 mg, 2.5 mM, 60% in oil) was added. After 15 min and warming to room temperature a solid started precipitating. DMF (5 mL) was added and stirred at RT for 1 hr. Water (200 mL) and ethyl acetate (200 mL) were added. The ethyl acetate layer was dried and evaporated. Purification by ISCO® on an 80 g silica gel cartridge using 0-100% hexane/ethyl acetate afforded the title compound. A $^1H$ NMR spectrum of Compound 8 is presented in FIGS. 1A to 1C. MS (m/z) 701.3 $[M+H]^+$.

Synthesis of Compound 22

To 1 gram of (Compound 31), 95% ethanol (150 mL), degassed with argon was added. 120 mg of 10% Pd/C was added and hydrogen gas was bubbled into reaction mixture for 5 min. The mixture was then stirred under a hydrogen balloon for 3 hrs. Reaction mixture was degassed with argon and evaporated. Purification by prep LC/MS on a C18 column 25×250 mm using 0 to 100% water containing 2 g per liter ammonium acetate. After free drying, Compound 22 was obtained. A $^1H$ NMR spectrum ($D_2O$) of Compound 9 is presented in FIG. 2A and FIG. 2B.

Synthesis of Compound 23

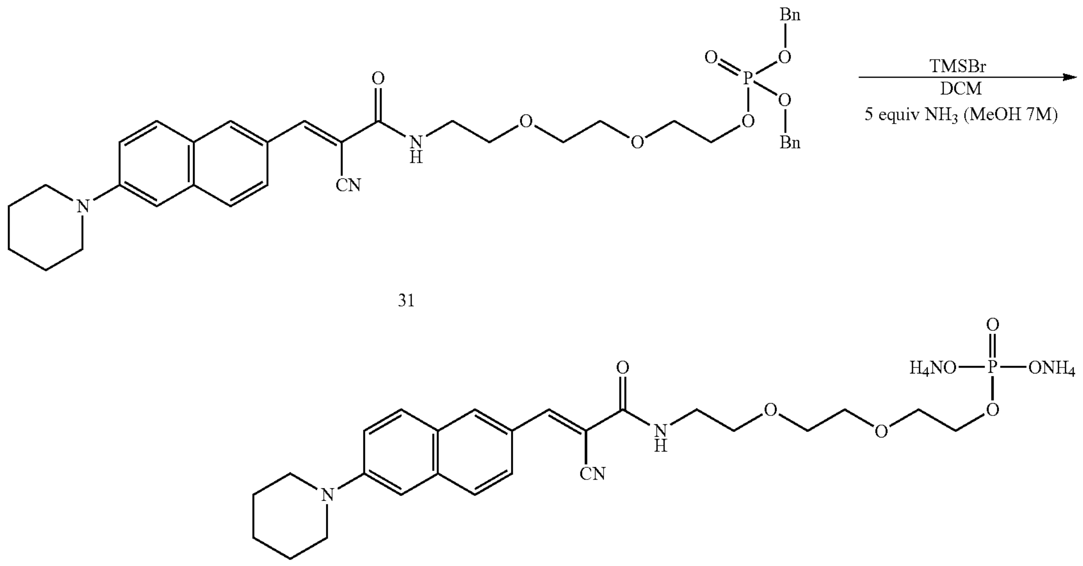

31

Compound 23

A solution of Compound 31 (5 mmol, 3.49 g, 1 equiv) in anhydrous $CH_2C_{12}$ (100 ml) was cooled to 0° C. under Argon, and trimethylsilyl bromide (50 mmol, 6.8 ml, 10 equiv) was added via syringe. The reaction mixture was stirred at 0° C. for 30 mins and completion of conversion was monitored by HPLC. The mixture was then quenched with MeOH (~50 mL) and stirred for 10 minutes. The solution was evaporated to dryness; this step was repeated four times.

The organic solvents were evaporated under vacuum, the residue was suspended in trace amount of MeOH, and EtOAc was added to induce precipitation of the phosphonic acid. The residue was filtered and washed with EtOAc (×2). The residue was then dried under vacuum to give the desired phosphate acid.

Treatment of the phosphonic acid with $NH_4OAc$ (25 mmol, 1.93 g, 5 equiv) and 150 ml water at room temperature and kept stirring for another 15 mins to give a clear red/orange solution. The reaction mixture was then lyophilized to give the final product. LC-MS: (ES, m z) 518 $[M+1]^+$. 1H-NMR: (400 MHz, $CD_3OD$) δ 8.31-8.22 (m, 2H), 8.08 (dd, J=8.8, 1.9 Hz, 1H), 7.81 (d, J=9.2 Hz, 1H), 7.74 (d, J=8.8 Hz, 11H), 7.40 (dd, J=9.2, 2.5 Hz, 1H), 7.18 (d, J=2.5 Hz, 1H), 4.08-3.98 (m, 2H), 3.79-3.65 (m, 8H), 3.58 (t, J=5.5 Hz, 2H), 3.45-3.39 (m, 4H), 1.86-1.63 (m, 6H).

Example 6: Detection of Retinal Aβ Aggregation In Vivo

Following the positive ex vivo experiments in Example 4, an in vivo retinal imaging study was conducted using mice before and after receiving a CCI.

Figure 9:
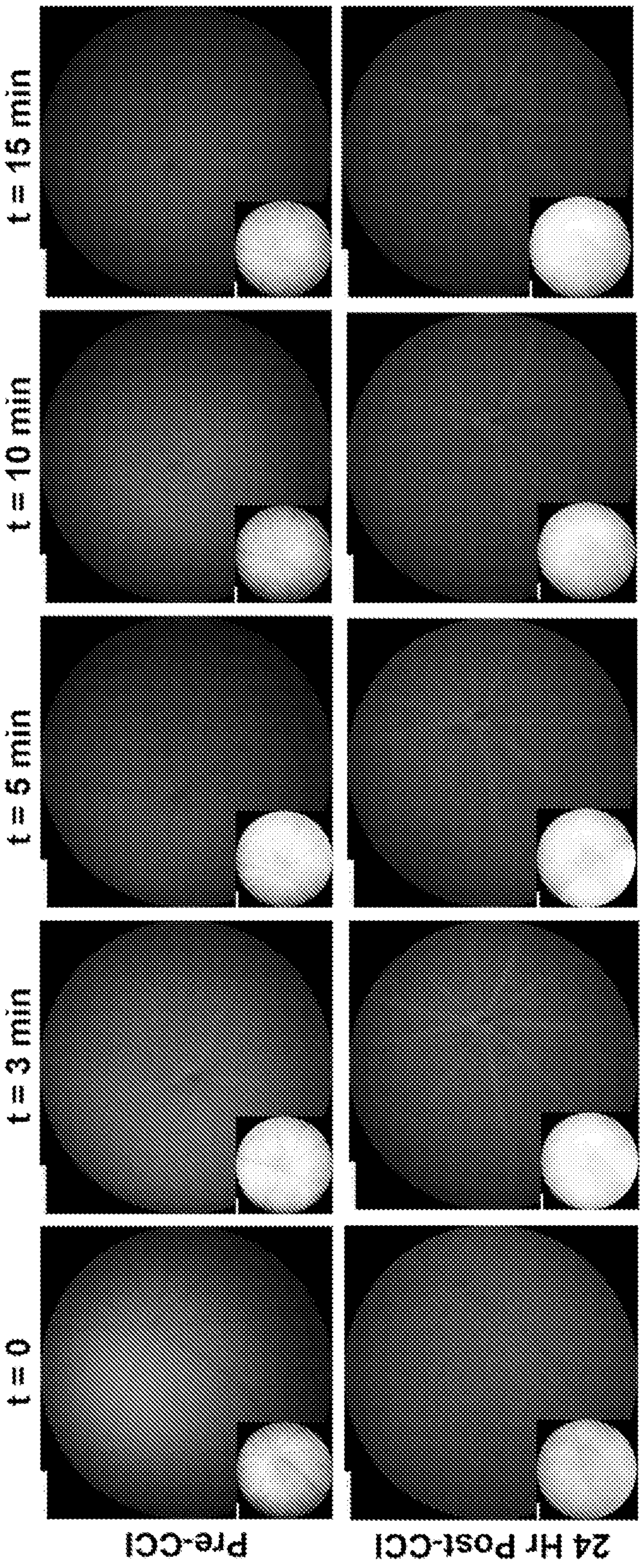
FIG. 9 presents the images of live retinal imaging using Compound 23 with a mouse before and after a CCI. Top Row: Time course retinal imaging of a 3-month-old mouse pre-CCI after iv administration of Compound 23. Time course labeled on the top indicates in vivo retinal imaging time points before (t=0) and after iv administration of Compound 23. Bottom Row: Time course retinal imaging with Compound 23 of the same mouse 24 hours post CCI.

Mice were imaged prior to undergoing a TBI by CCI to obtain baseline retinal images. Anesthetized mice received an iv administration of Compound 23 (15 mg/kg of a 20 mg/mL solution in 0.1 M Phosphate buffer, pH 7.4) before CCI and 24 hours post CCI. As shown in FIG. 9, background fluorescence enhancement was observed in the retinal vasculature 3 minutes after administration of Compound 23 of an uninjured mouse. This enhancement was no longer observed 15 minutes after administration with Compound 23 (FIG. 9, top row).

24 hours after baseline imaging, mice were anesthetized, the head was mounted in a stereotaxic frame, and a craniotomy was performed over the right side of the motor cortex. Using a stereotaxic impactor, mice received an impact on the right side of the motor cortex using a 5 m/s velocity, 2 mm depth, and 3 mm diameter piston. After injury, the incision was closed with stiches, anesthesia was terminated, and the animal was placed on a heating pad to maintain normal core temperature. 24 hours after CCI, live retinal imaging was conducted on anesthetized mice after iv administration of Compound 23. As shown in FIG. 9, the retinal vasculature remained illuminated during the 15-minute imaging period, indicating that Aβ may be present in the vessels (FIG. 9, bottom row). This is in contrast to the pre-CCI imaging where fluorescence enhancement of the vessels was visible 3 minutes post-injection but decreases over the 15-minute imaging period.

This example shows that within 24 hours after a CCI, Compound 23 can be used to detect a change in the retinal vasculature that may be indicative of AP accumulation. This example is consistent with the ex vivo data shown in FIG. 8 where amyloid accumulation appeared along a blood vessel of a mouse 24 hours post-CCI.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The invention claimed is:

1. A method for determining whether a patient who has experienced a head injury suffers from a traumatic brain injury (TBI), comprising detecting the presence of an amyloid beta protein associated with TBI in an eye of the patient, wherein the detection comprises contacting, in vivo, the amyloid beta protein with a probe, wherein the probe comprises a compound of formula:

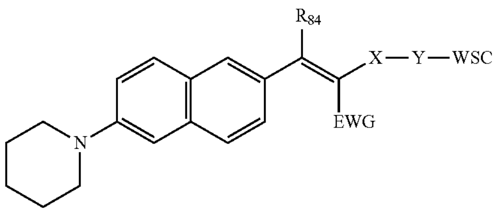

wherein:

EWG is selected from a group consisting of —F, —Cl, —Br, —CH=O, $NO_2$, —$CF_3$, —$CCl_3$, —$SO_3H$ and —CN;

WSG is:

i)

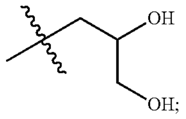 [SMILES: *CC(O)CO]

ii) polyethylene glycol, polypropylene glycol, co-polymer of polyethylene glycol and polypropylene glycol, or alkoxy derivatives thereof;

iii)

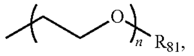

wherein n is an integer from 1-50 and $R_{81}$ is hydrogen, a $C_1$-$C_{10}$ alkyl, a $C_1$-$C_{10}$ alkenyl, or a $C_1$-$C_{10}$ alkynyl, wherein the alkyl, alkenyl, or alkynyl is optionally substituted with one or more $C_1$-$C_{10}$ alkyl, $C_1$-$C_{10}$ heteroalkyl, cycloalkyl of no more than 10 carbons, heterocycloalkyl of no more than 10 carbons, aryl of no more than 10 carbons, or heteroaryl of no more than 10 carbons;

iv)

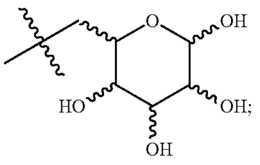 [SMILES: *CC1OC(O)C(O)C(O)C1O]

v)

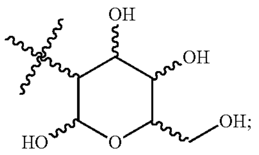

vi)

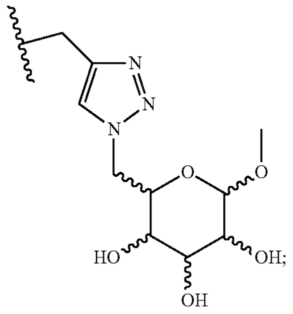 [SMILES: *Cc1cn(CC2OC(OC)C(O)C(O)C2O)nn1]

or vii)

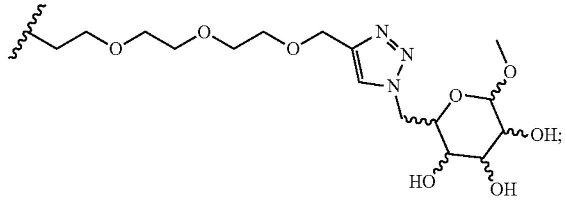 [SMILES: *CCOCCOCCOCc1cn(CC2OC(OC)C(O)C(O)C2O)nn1]

X is C═O or $SO_2$, $R_{84}$ is hydrogen or $C_1$-$C_{10}$ alkyl, or X and $R_{84}$ join to form a pyridinyl;

Y is NH or S; and administration of light to the probe to cause emission of a detectable signal; and evaluating the detectable signal to determine if the patient is suffering from TBI.

2. The method of claim 1, wherein the detection is for the amyloid beta protein in the retina of the eye.

3. The method of claim 1, wherein the patient has been inflicted with a physical impact on the head within 30 days prior to the detection.

4. The method of claim 1, wherein the patient is a human under 40 years of age.

5. The method of claim 1, wherein the detectable signal is a fluorescent or infrared signal.

6. The method of claim 1, further comprising determining that the patient suffers from TBI if an amyloid beta protein is detected in the eye.

7. The method of claim 6, further comprising administering to the patient an agent that treats or ameliorates TBI.

8. The method of claim 1, wherein the probe comprises a compound selected from

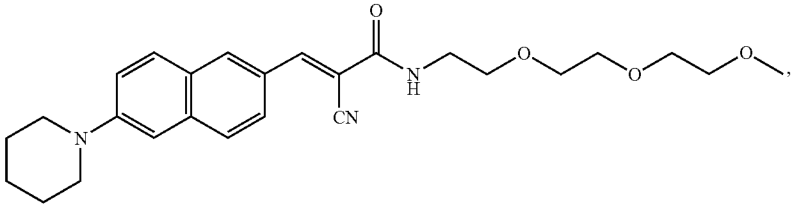

,

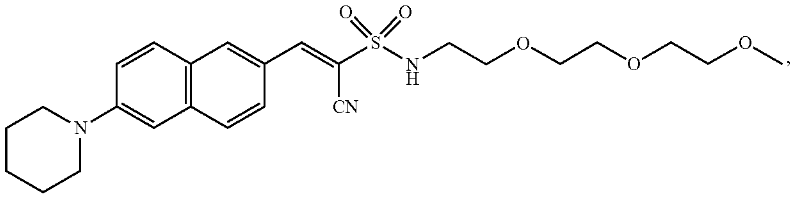

,

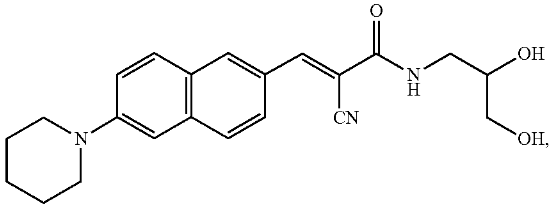

, and

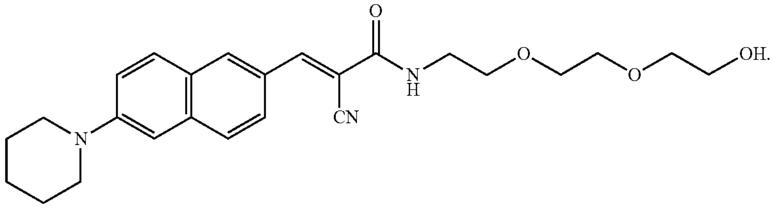

.

9. A method for determining whether a patient who has experienced a head injury suffers from a traumatic brain injury (TBI), comprising detecting the presence of an amyloid beta protein associated with TBI in an eye of the patient, wherein the detection comprises contacting, in vivo, the amyloid beta protein with a probe, wherein the probe comprises a compound selected from:

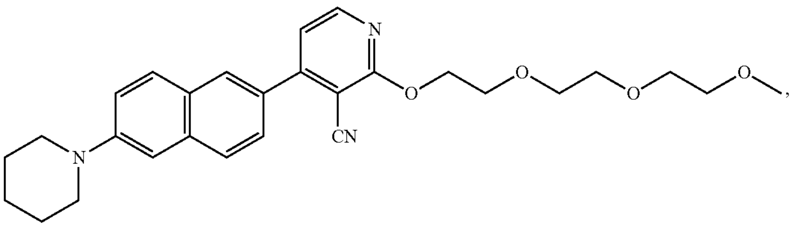

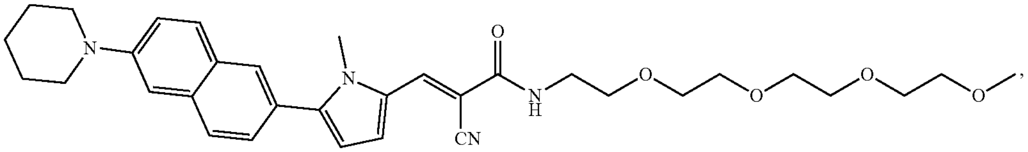

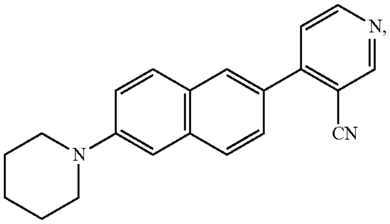

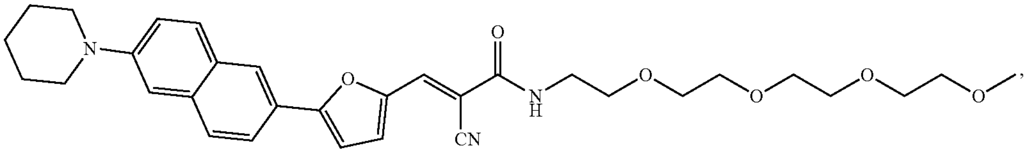

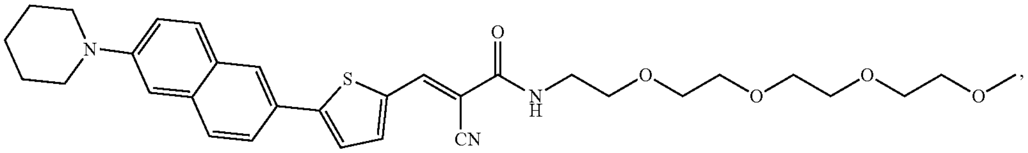

and

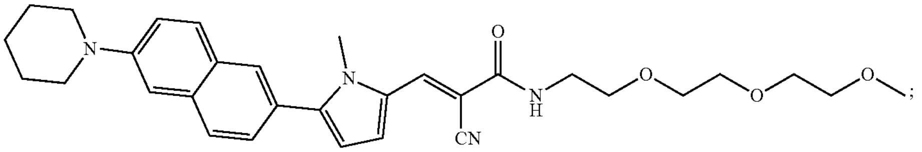

administration of light to the probe to cause emission of a detectable signal; and evaluating the detectable signal to determine if the patient is suffering from TBI.

* * * * *